United States Patent
Martin et al.

(10) Patent No.: US 11,495,328 B2
(45) Date of Patent: Nov. 8, 2022

(54) ARROWLAND: AN ONLINE MULTISCALE INTERACTIVE TOOL FOR -OMICS DATA VISUALIZATION

(71) Applicants: The Regents of the University of California, Oakland, CA (US); National Technology & Engineering Solutions of Sandia, LLC, Albuquerque, NM (US)

(72) Inventors: Hector Garcia Martin, Oakland, CA (US); Garrett W. Birkel, Oakland, CA (US); Ling Liang, Emeryville, CA (US); William Morrell, Oakland, CA (US); Mark Forrer, Oakland, CA (US)

(73) Assignees: The Regents of the University of California, Oakland, CA (US); National Technology & Engineering Solutions of Sandia, LLC, Albuquerque, NM (US)

( * ) Notice: Subject to any disclaimer, the term of this patent is extended or adjusted under 35 U.S.C. 154(b) by 814 days.

(21) Appl. No.: 16/254,477

(22) Filed: Jan. 22, 2019

(65) Prior Publication Data
US 2019/0228841 A1    Jul. 25, 2019

Related U.S. Application Data

(60) Provisional application No. 62/620,949, filed on Jan. 23, 2018.

(51) Int. Cl.
| | |
|---|---|
| G01N 33/48 | (2006.01) |
| G16B 45/00 | (2019.01) |
| G06F 16/56 | (2019.01) |
| G16B 5/00 | (2019.01) |

(52) U.S. Cl.
CPC ............. *G16B 45/00* (2019.02); *G06F 16/56* (2019.01); *G16B 5/00* (2019.02)

(58) Field of Classification Search
None
See application file for complete search history.

(56) References Cited

PUBLICATIONS

Birkel, Garrett, et al. Arrowland v1. 0. No. Arrowland; 004852MLTPL00. Lawrence Berkeley National Lab.(LBNL), Berkeley, CA (United States), 2016.*
Placzek, Sandra, et al. "BRENDA in 2017: new perspectives and new tools in BRENDA." Nucleic acids research vol. 45 (2016) pp. D380-D388.*
Bates et al., "GLAMM: Genome-Linked Application for Metabolic Maps," Nucleic Acids Research 2011, 39, W400-W405.
Bordbar et al., "Constraint-based models predict metabolic and associated cellular functions," Nature Reviews 2014, 1-14.
Bunnik et al., "An Introduction to Functional Genomics and Systems Biology," Advances in Wound Care 2013, 2(9), 490-498.
Caspi et al., "The MetaCyc Database of metabolic pathways and enzymes and the BioCyc collection of Pathway/Genome Databases," Nucleic Acids Research 2008, 36, D623-D631.
Chung et al., "ArrayXPath II: mapping and visualizing microarray gene-expression data with biomedical ontologies and integrated biological pathway resources using Scalable Vector Graphics," Nucleic Acids Research 2005, 33, W621-W626.
Degtyarenko et al., "ChEBI: a database and ontology for chemical entities of biological interest," Nucleic Acids Research 2008, 36, D344-D350.
Demchak et al., "Cytoscape: the network visualization tool for GenomeSpace workflows," F1000Research 2014, 1-12.
Droste et al., "Omix—A Visualization Tool for Metabolic Networks with Highest Usability and Customizability in Focus," Chemie Ingenieur Technik 2013, 85(6), 849-862.
Funahashi et al., "CellDesigner 3.5: A Versatile Modeling Tool for Biochemical Networks," Proceedings of the IEEE 2008, 96(8), 1254-1265.
Gao et al., "The University of Minnesota Biocatalysis/Biodegradation Database: improving public access," Nucleic Acids Research 2010, 38, D488-D491.
Henry et al., "High-throughput generation, optimization and analysis of genome-scale metabolic models," Nature Biotechnology 2010, 28(9), 977-982.
Hu et al., "VisANT 4.0: Integrative network platform to connect genes, drugs, diseases and therapies," Nucleic Acids Research 2013, 41, W225-W223.
Kanehisa et al., "KEGG: Kyoto Encyclopedia of Genes and Genomes," Nucleic Acids Research 2000, 28(1), 27-30.
Kelder et al., "WikiPathways: building research communities on biological pathways," Nucleic Acids Research 2012, 40, D1301-D1307.
King et al., "Escher: A Web Application for Building, Sharing, and Embedding Data-Rich Visualizations of Biological Pathways," PLOS Computational Biology 2015, 1-13.
King et al., "BiGG Models: A platform for integrating, standardizing and sharing genome-scale models," Nucleic Acids Research 2016, 44, D515-D522.
Kitano, "Systems Biology: A Brief Overview," Science 2002, 295(5560), 1662-1664.
Kono et al., "Pathway Projector: Web-Based Zoomable Pathway Browser Using KEGG Atlas and Google Maps API," PLoS ONE 2009, 4(11), e7110.
Krause et al., "Biographer: web-based editing and rendering of SBGN compliant biochemical networks," Bioinformatics 2013, 29(11), 1467-1468.
Kutmon et al., "PathVisio 3: An Extendable Pathway Analysis Toolbox," PLOS Computational Biology 2015, 11(2), 1-13.

(Continued)

*Primary Examiner* — Anna Skibinsky
(74) *Attorney, Agent, or Firm* — Sheppard, Mullin, Richter & Hampton LLP

(57) ABSTRACT

Disclosed herein is Arrowland, a web-based software tool for inputting, managing and viewing multiomics data, such as transcriptomics, proteomics, metabolomics and fluxomics data in an interactive, intuitive and multiscale system.

25 Claims, 202 Drawing Sheets

(56) References Cited

PUBLICATIONS

Latendresse et al., "Web-based metabolic network visualization with a zooming user interface," BMC Bioinformatics 2011, 12(176), 1-9.

Latendresse et al., "Browsing Metabolic and Regulatory Networks with BioCyc," Methods Molecular Biology 2012, 804, 197-216.

Moretti et al., "MetaNetX/MNXref—reconciliation of metabolites and biochemical reactions to bring together genome-scale metabolic networks," Nucleic Acids Research 2016, 44, D523-D526.

Morrell et al., "The Experiment Data Depot: A Web-Based Software Tool for Biological Experimental Data Storage, Sharing, and Visualization," ACS Synthetic Biology 2017, 6, 2248-2259.

Neuweger et al., "Visualizing post genomics data-sets on customized pathway maps by ProMeTra-aeration-dependent gene expression and metabolism of Corynebacterium glutamicum as an example," BMC Systems Biology 2009, 3(82), 1-14.

Perez et al., "IPython: A System for Interactive Scientific Computing," IEEE 2007, 21-29.

Rohn et al., "VANTED v2: a framework for systems biology applications," BMC Systems Biology 2012, 6(139), 1-13.

Rohn et al., "FluxMap: A VANTED add-on for the visual exploration of flux distributions in biological networks," BMC Systems Biology 2012, 6(33), 1-9.

Segrè et al., "Analysis of optimality in natural and perturbed metabolic networks," PNAS 2002, 99(23), 15112-15117.

Shlomi et al., "Regulatory on/off minimization of metabolic flux changes after genetic perturbations," PNAS 2005, 102(21), 7695-7700.

Tang et al., "New Tools for Cost-Effective DNA Synthesis," In Synthetic Biology, Elsevier 2013, 3-21.

Watson et al., Molecular Structure of Nucleic Acids: A Structure for Deoxyribose Nucleic Acid, Nature 1953, 171(4356), 737-738.

Wilson et al., "Best Practices for Scientific Computing," PLOS Biology 2014, 12(1), e1001745.

Winter et al., "Fluxomics—connecting 'omics analysis and phenotypes," Environmental Microbiology 2013, 15(7), 1901-1916.

Wishart et al., "HMDB 3.0—The Human Metabolome Database in 2013," Nucleic Acids Research 2013, 41, D801-D807.

Yamada et al., "iPath2.0: interactive pathway explorer," Nucleic Acids Research 2011, 39, W412-W415.

* cited by examiner

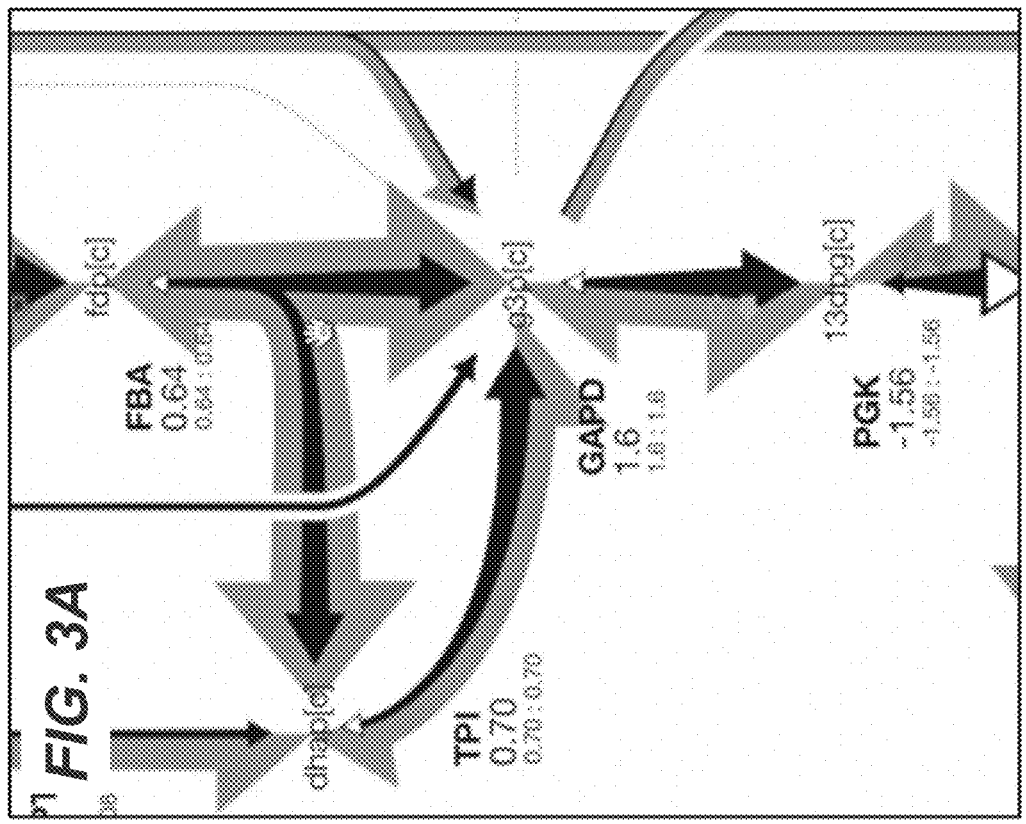
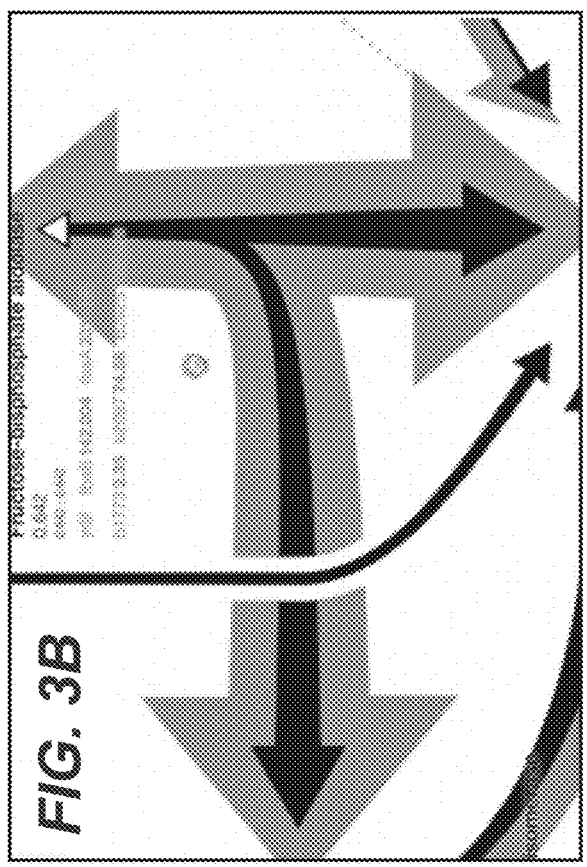
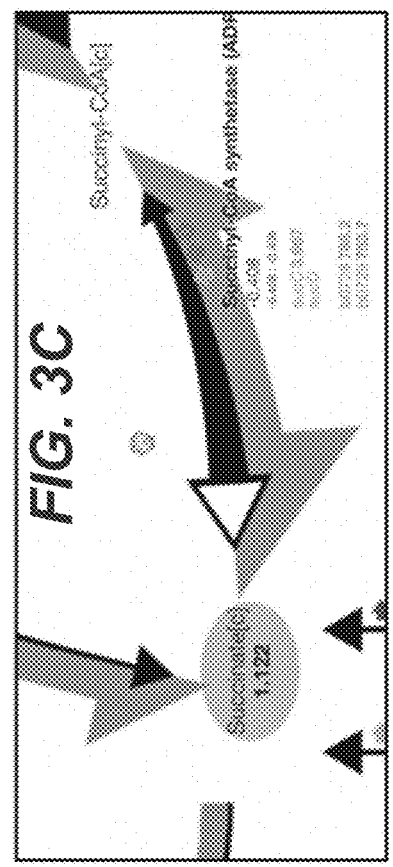

FIG. 6

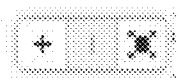
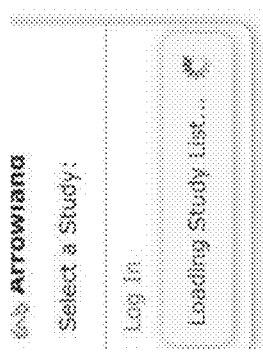
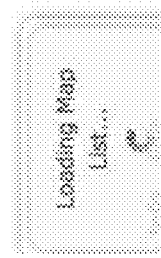
FIG. 10A

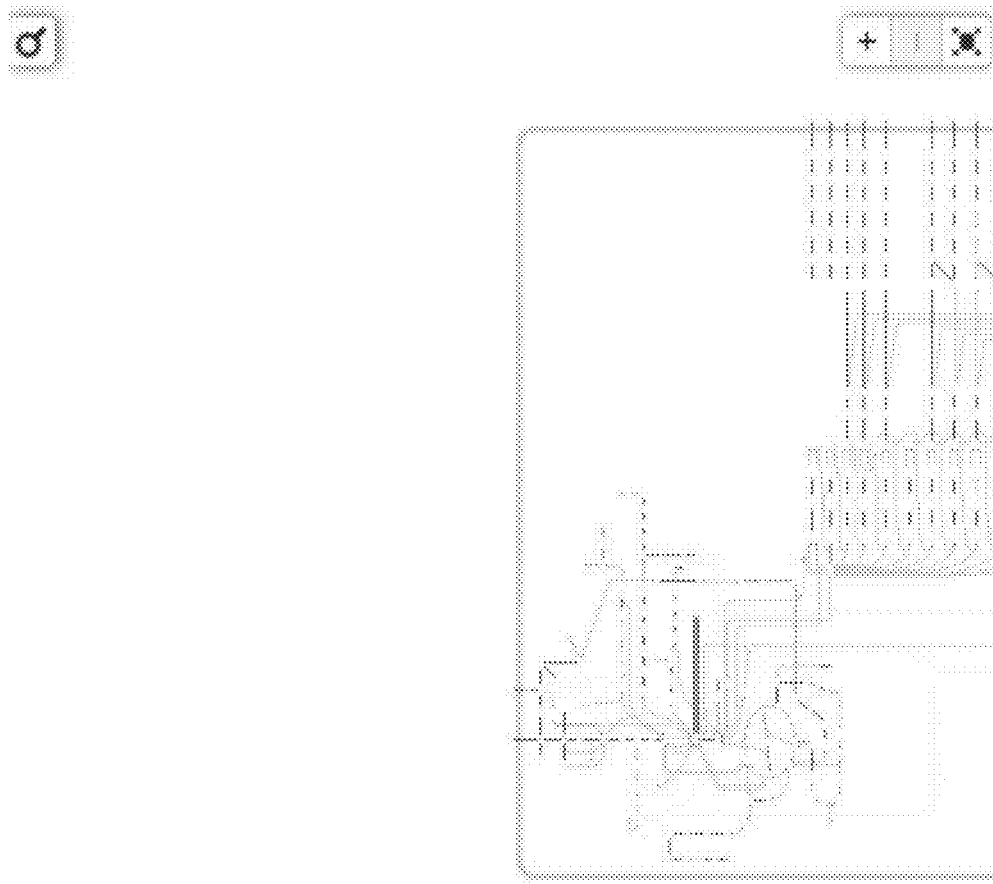
FIG. 10C

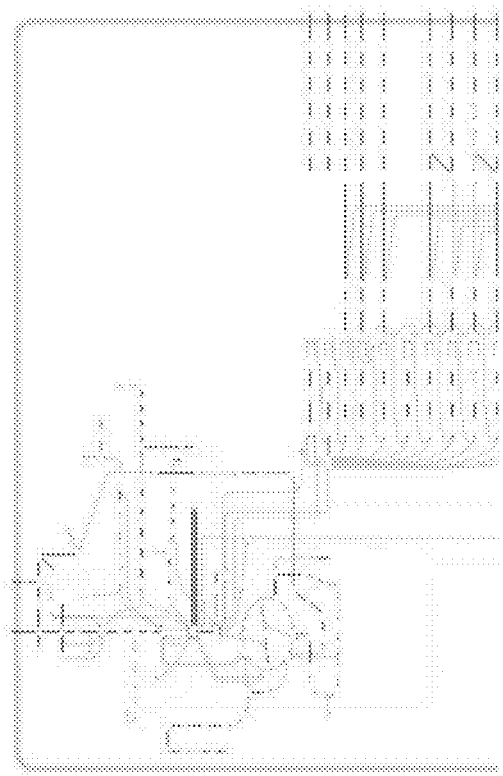
*FIG. 10D*
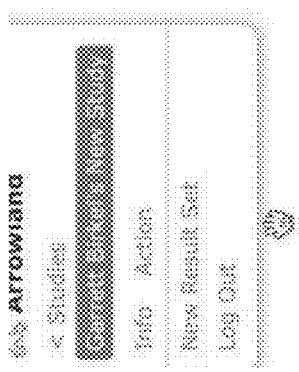
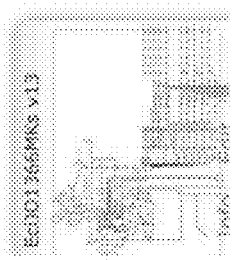

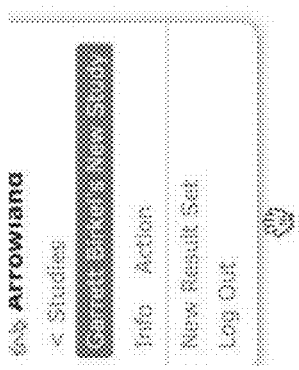
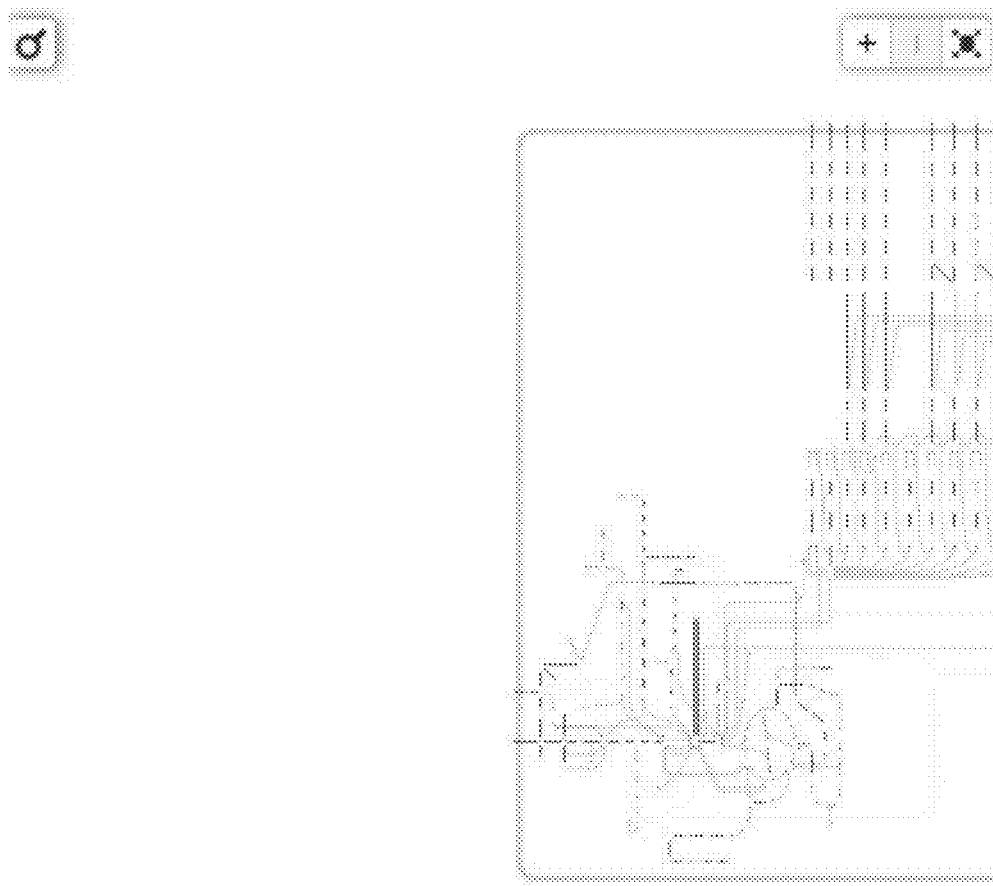
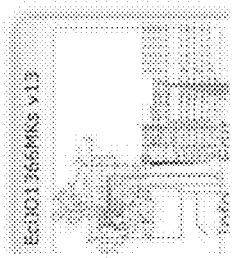
*FIG. 10E*

 
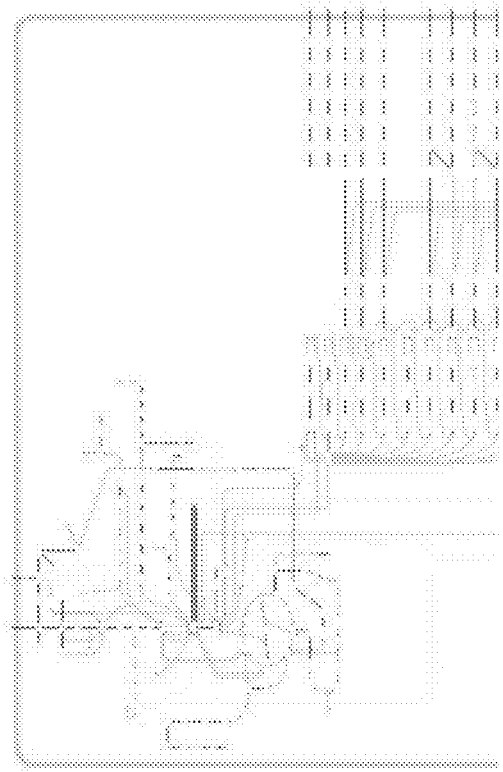
FIG. 10F
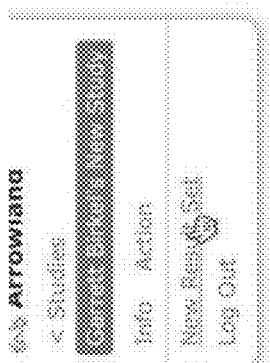 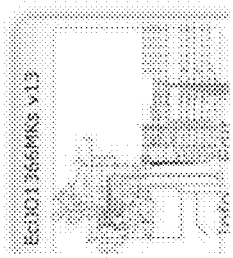

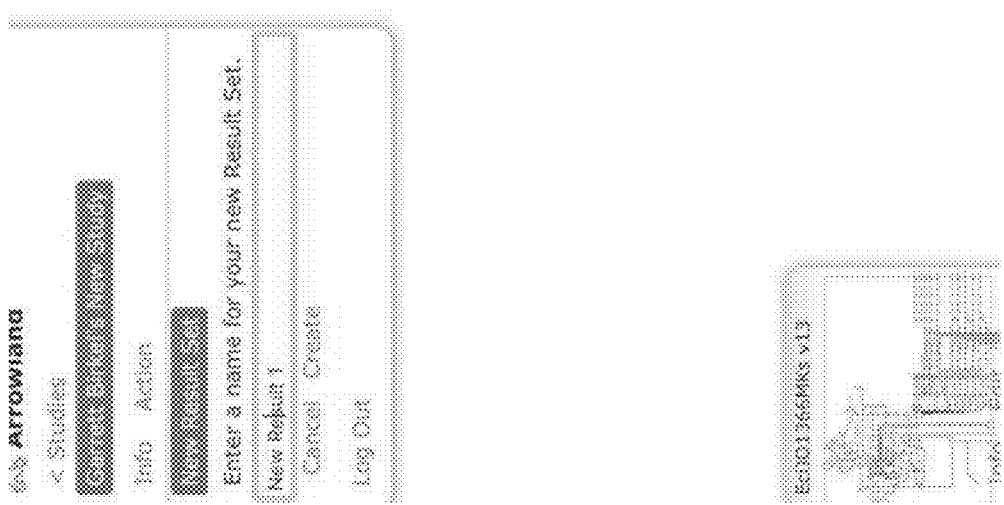
FIG. 10G

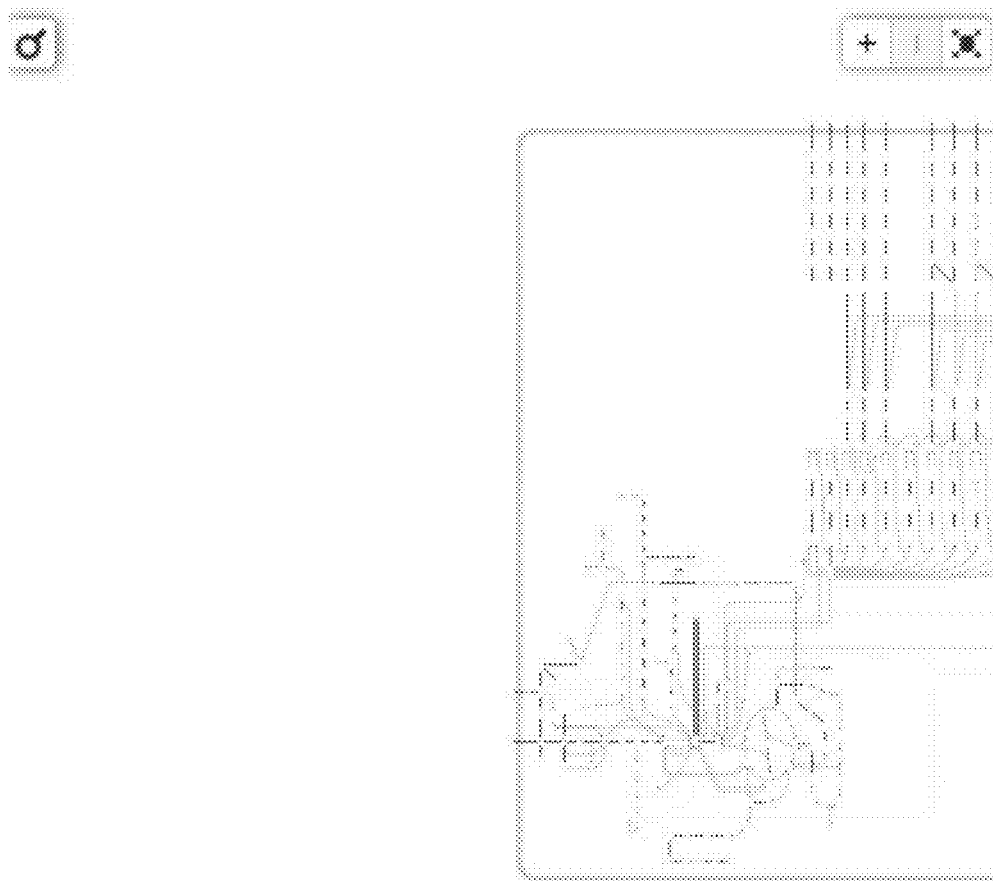
FIG. 10H
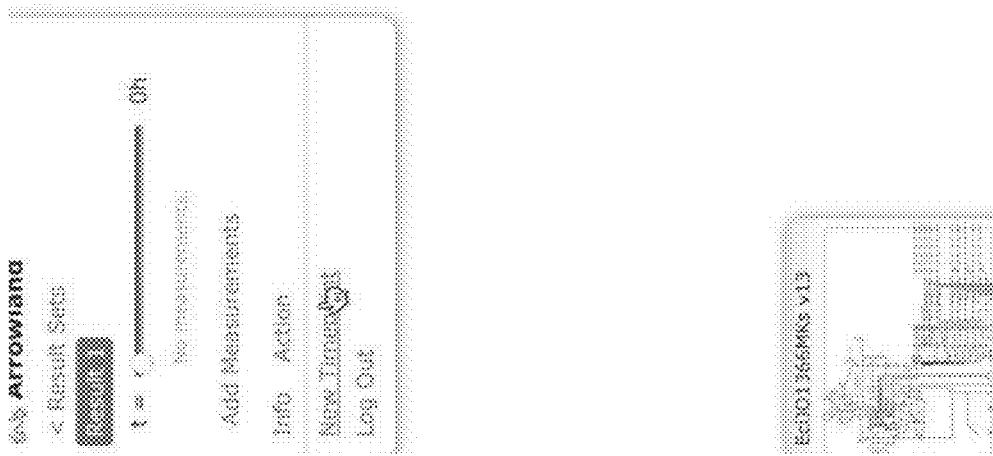

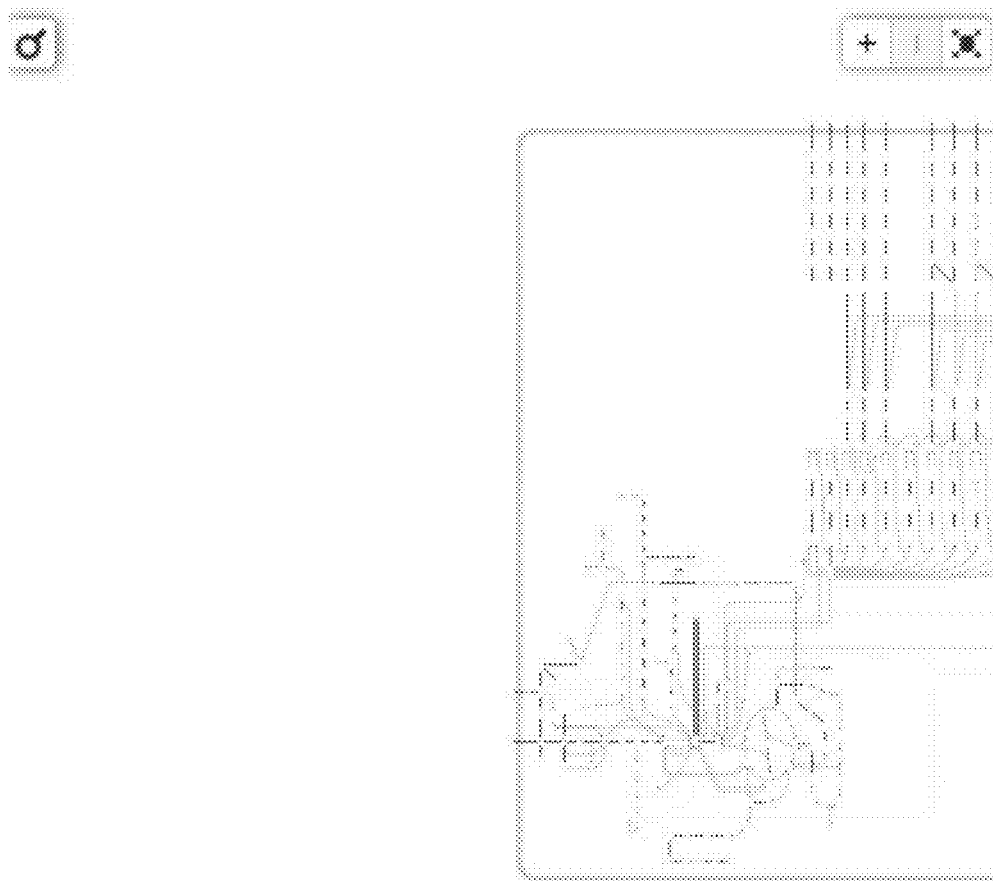
FIG. 10I
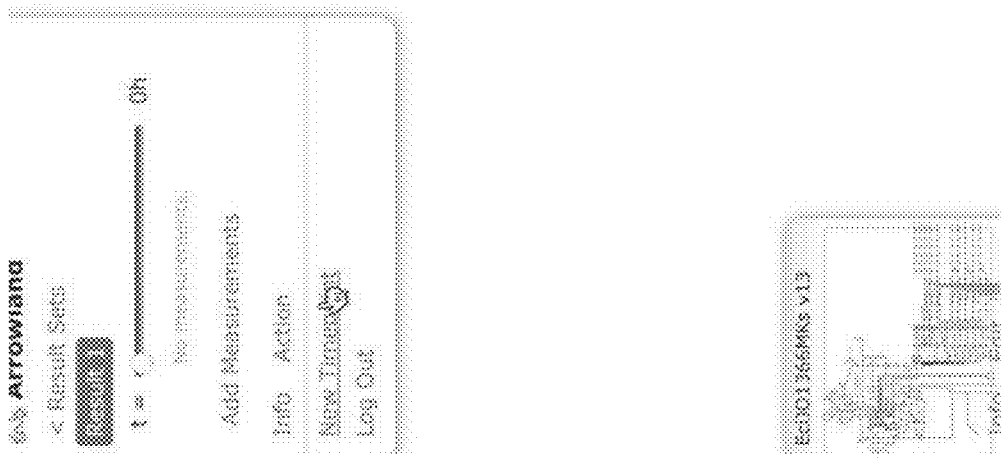

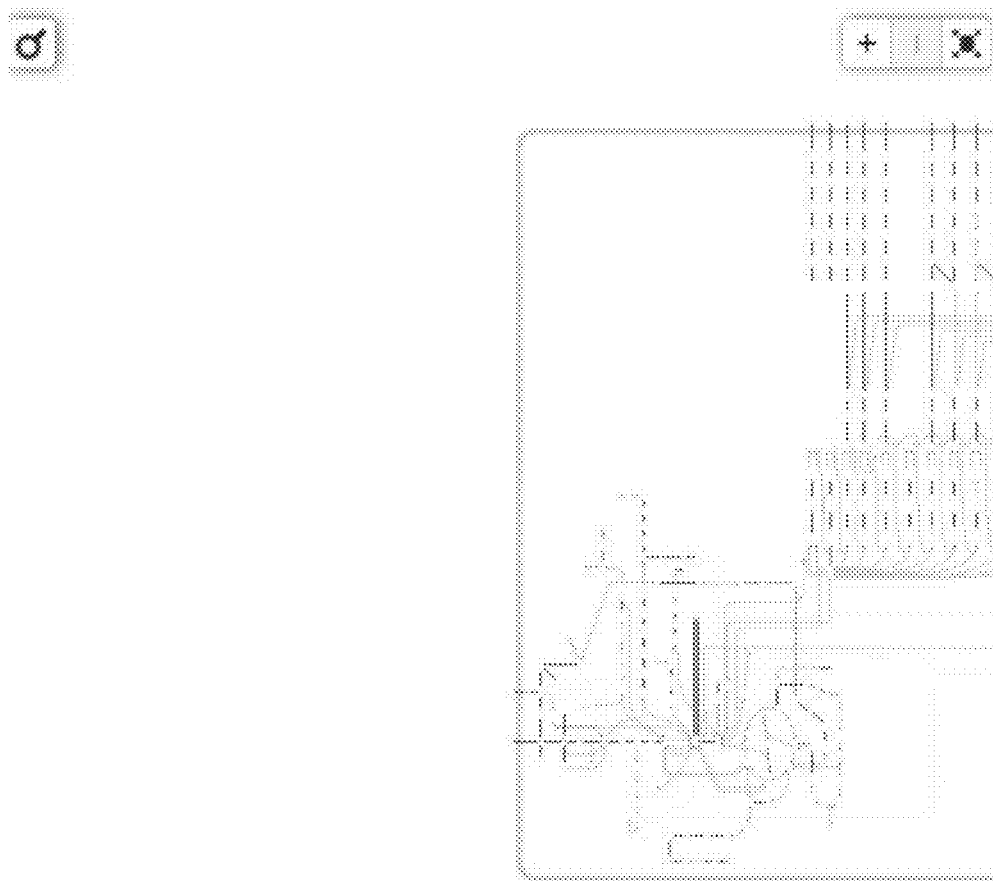
FIG. 10J
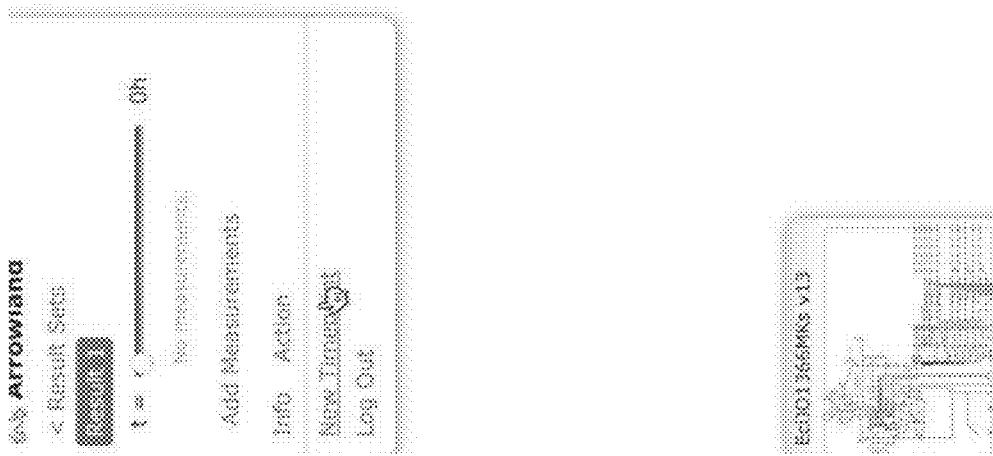

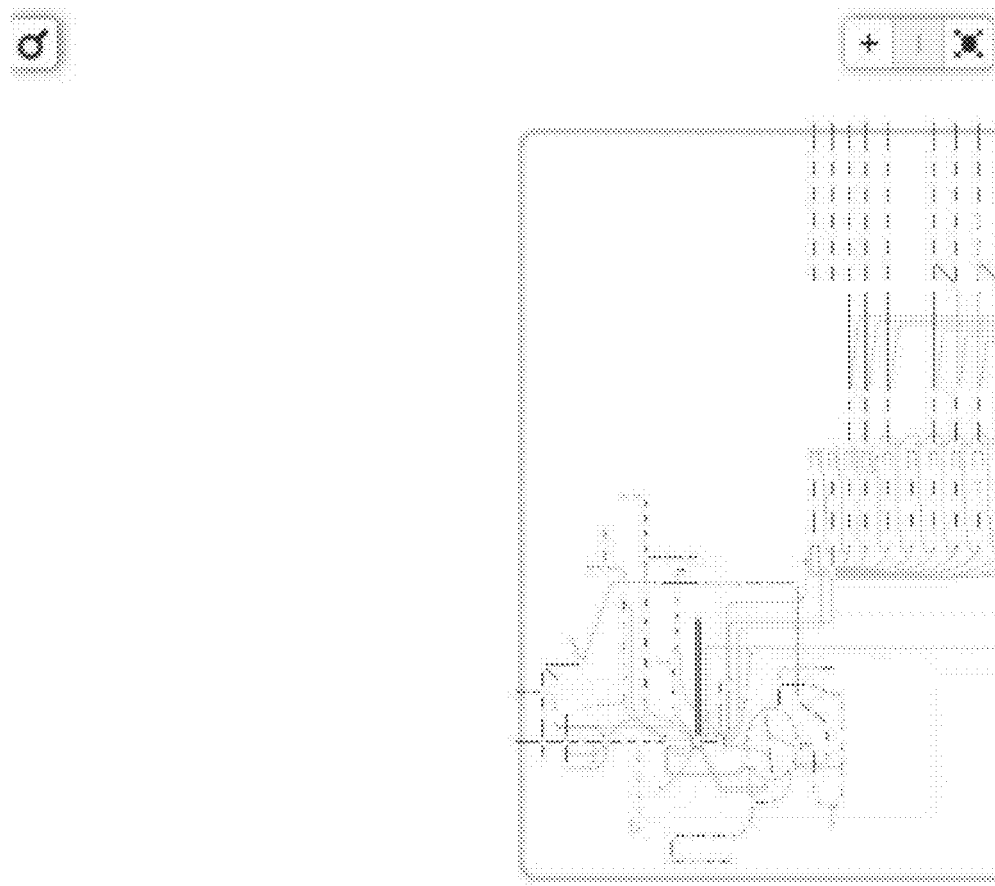
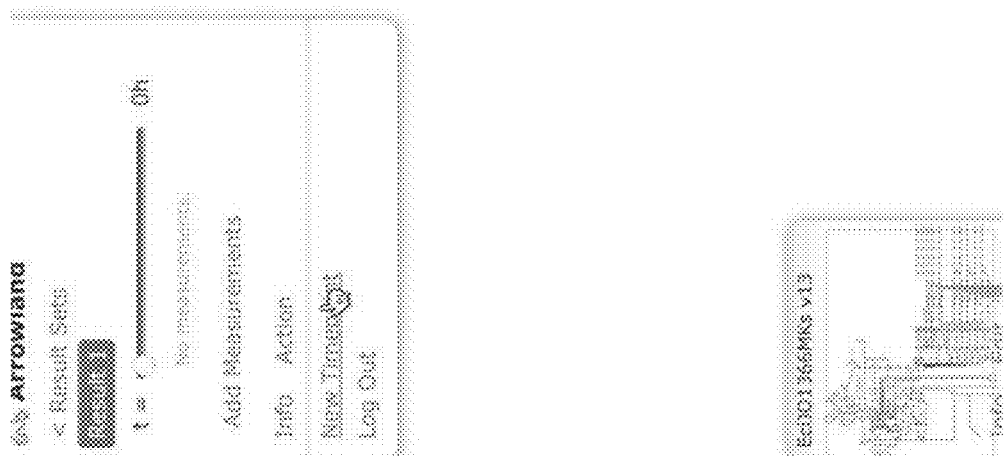
FIG. 10K

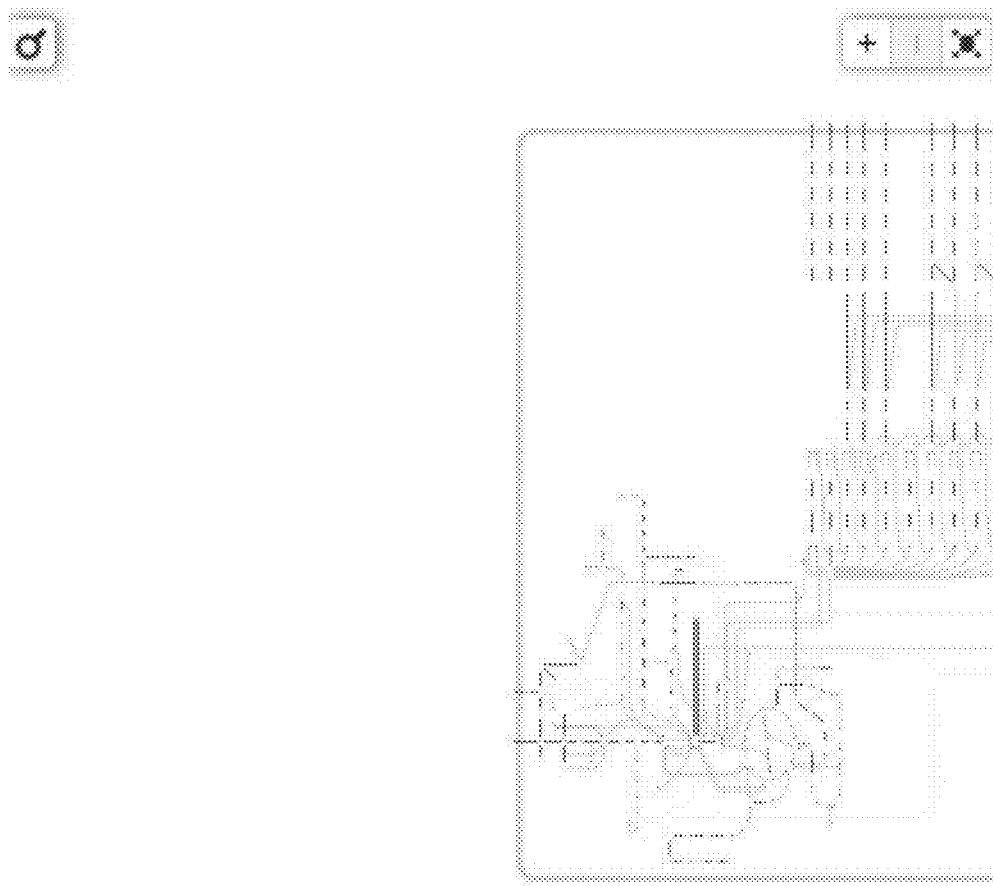
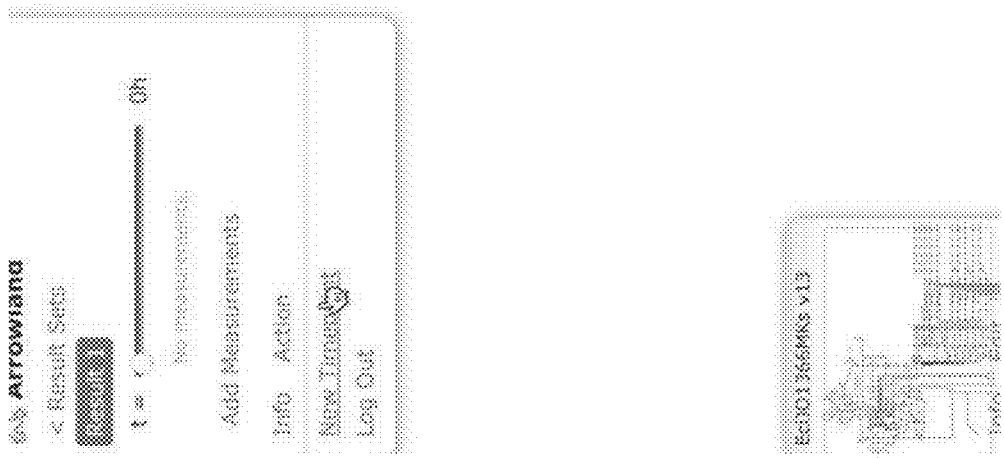
FIG. 10L

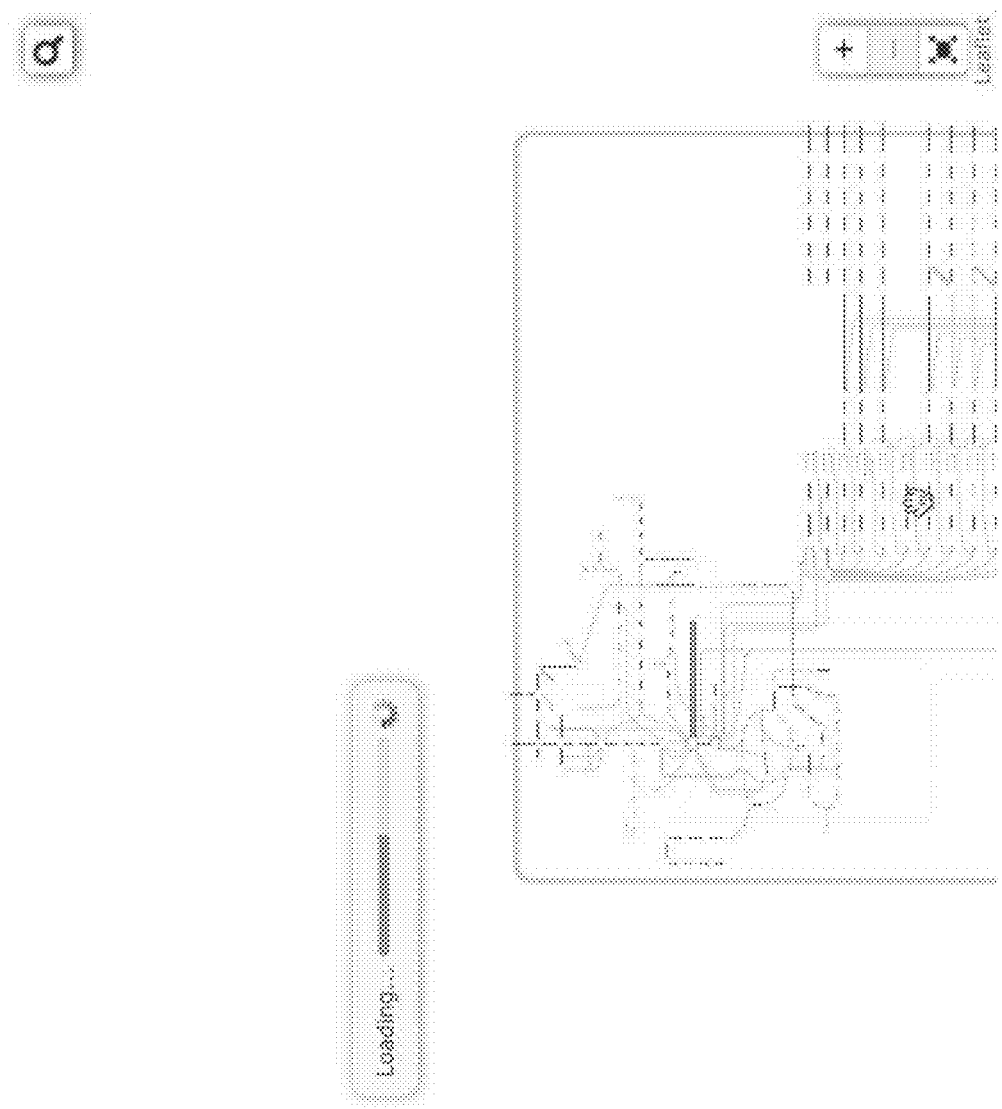
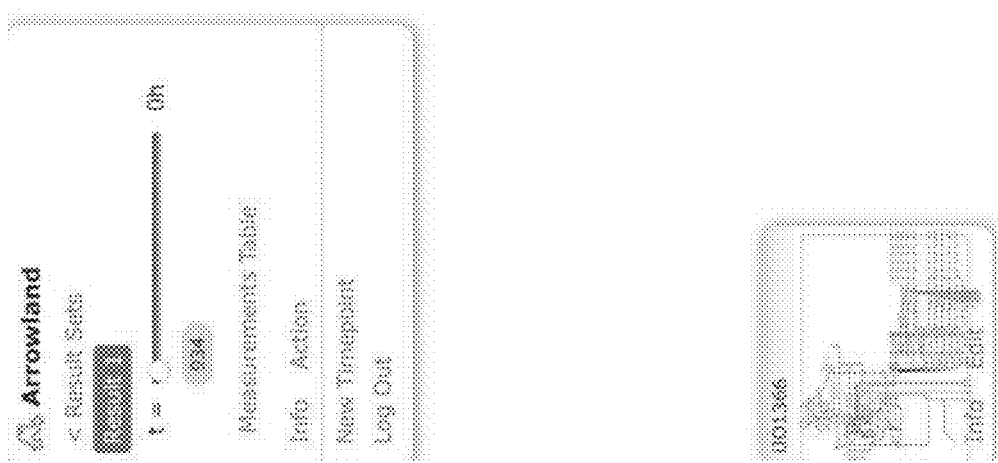
FIG. 10W

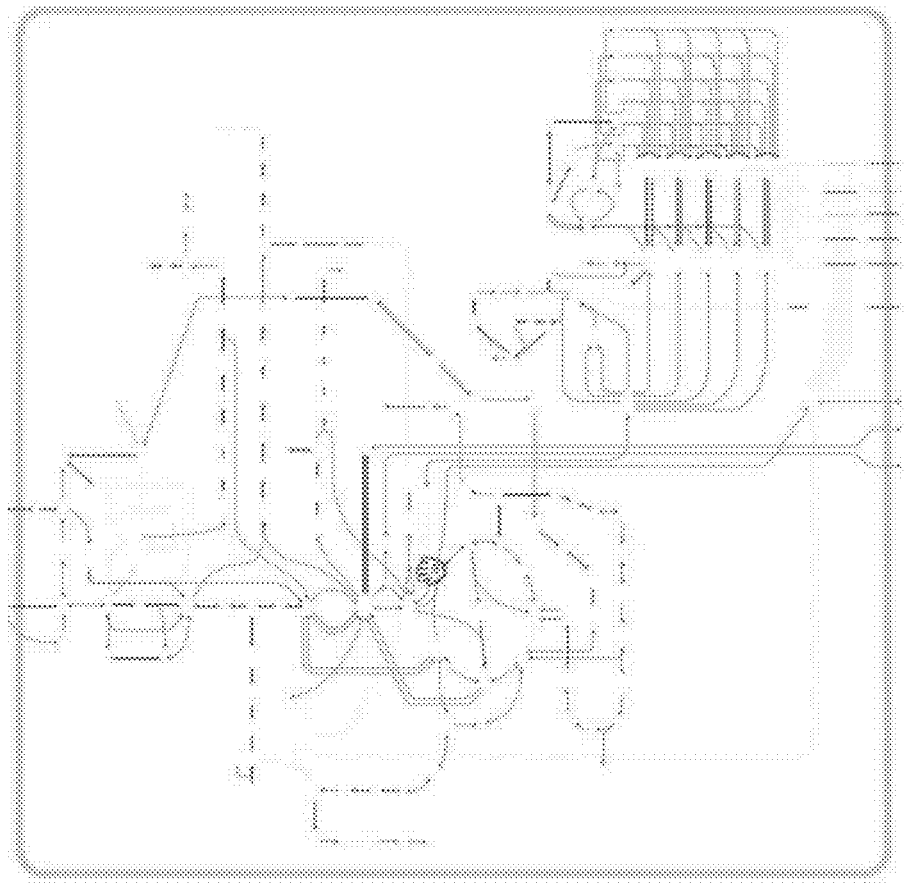
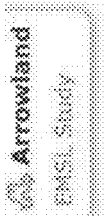
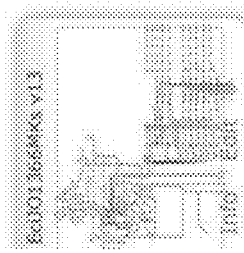
*FIG. 12A*

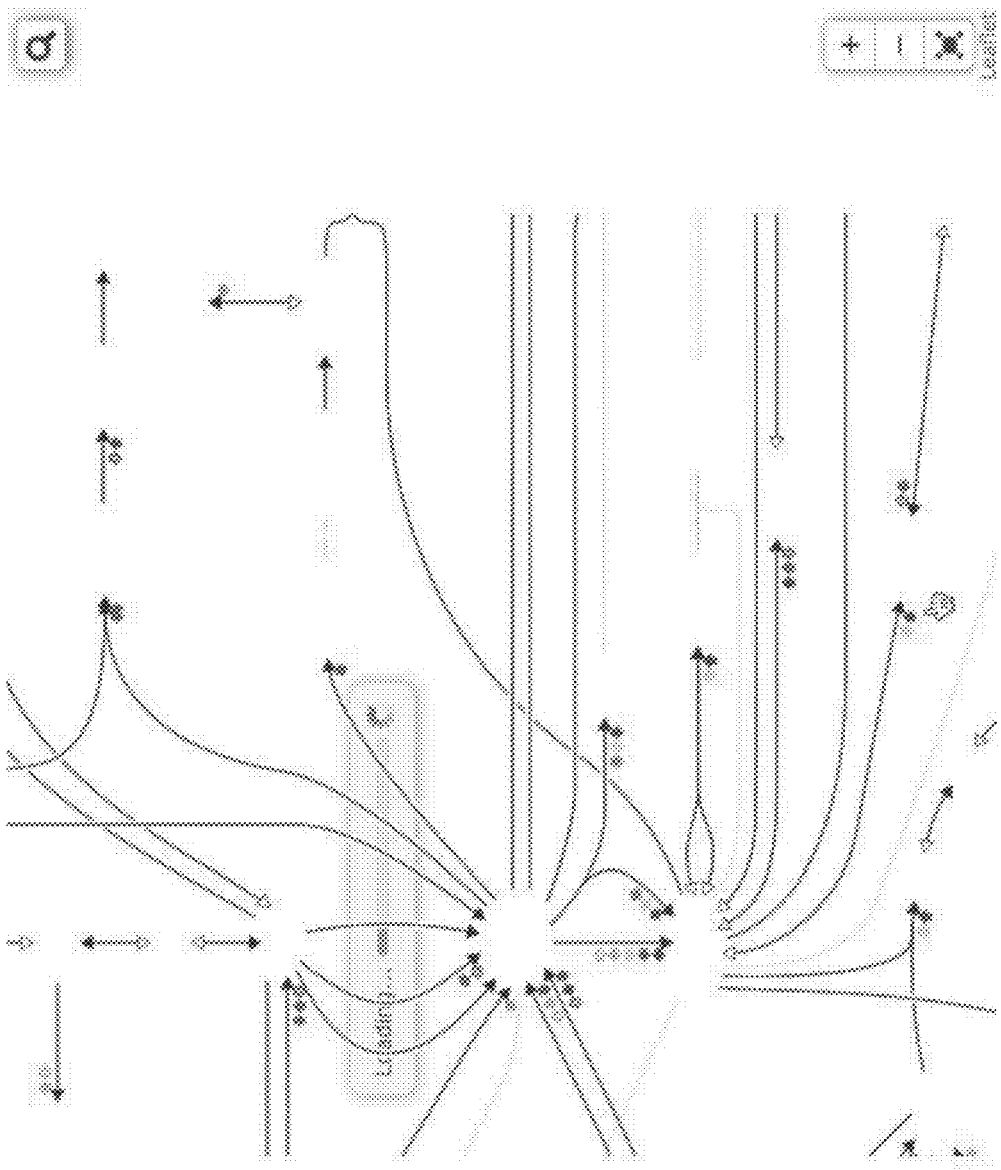
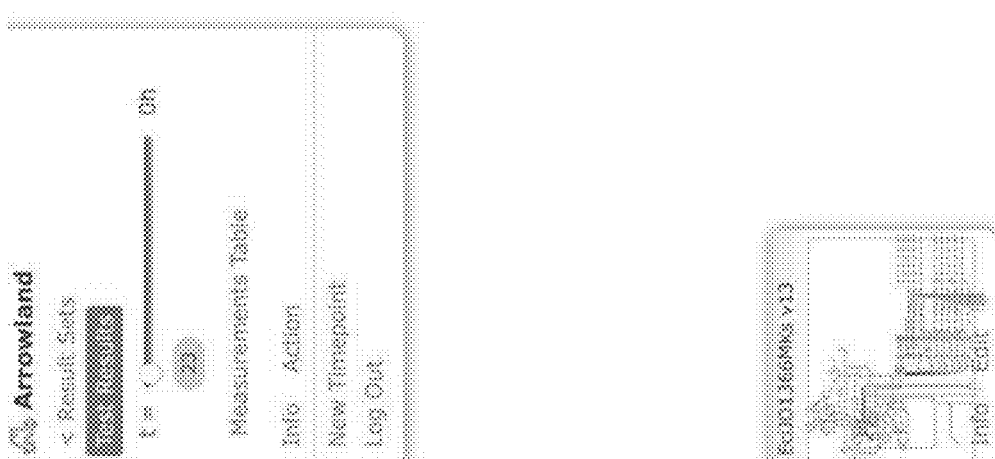
FIG. 12S

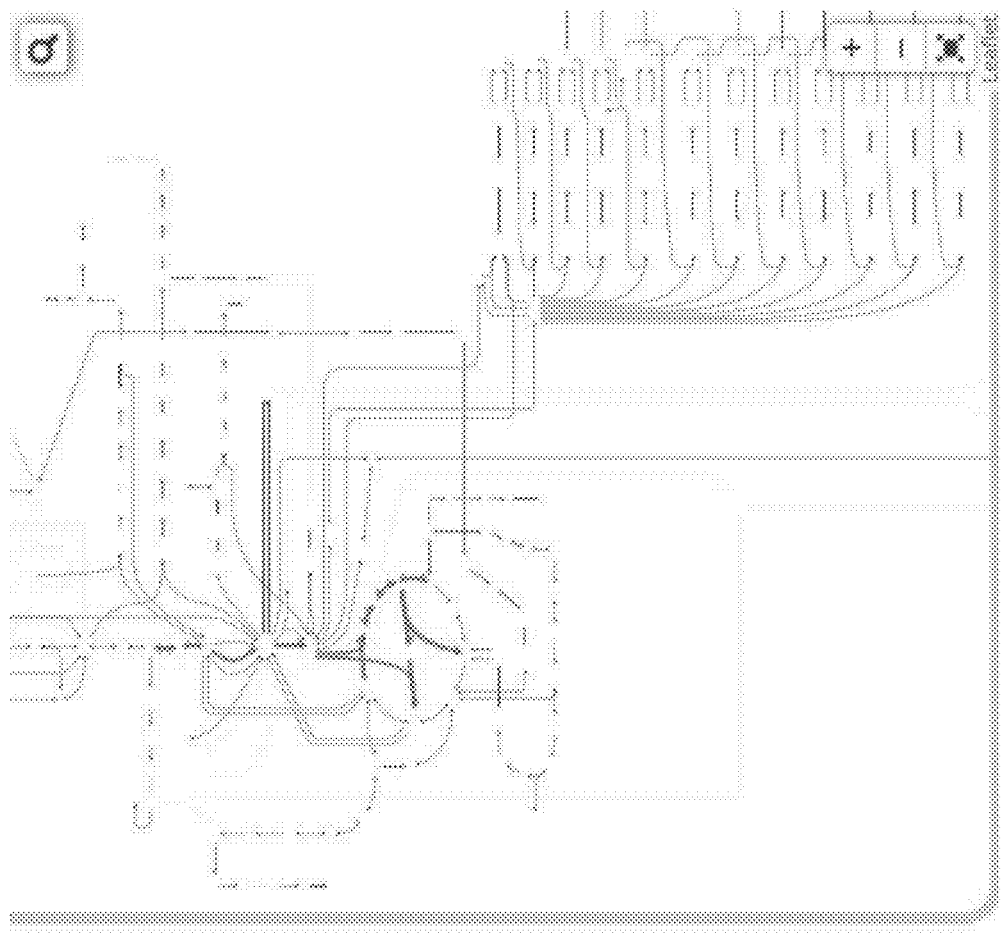
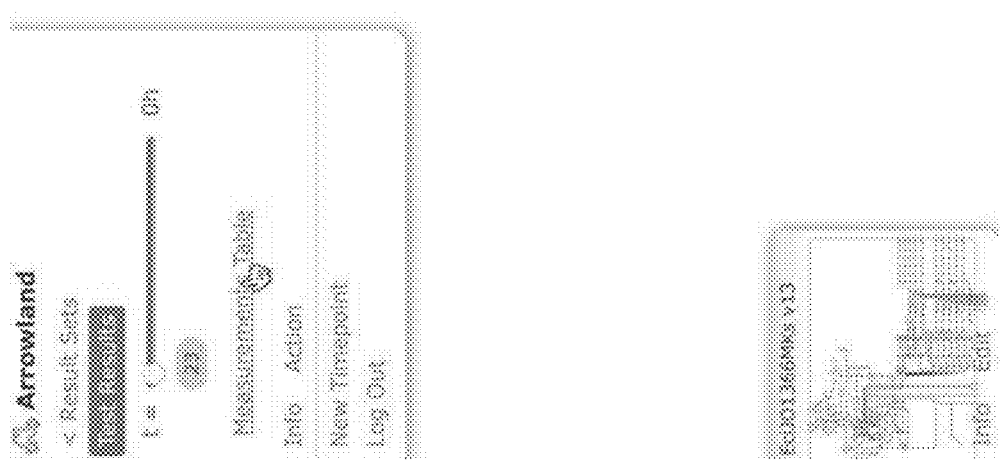
FIG. 12Y

FIG. 13A

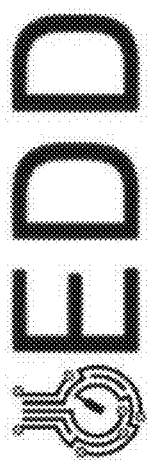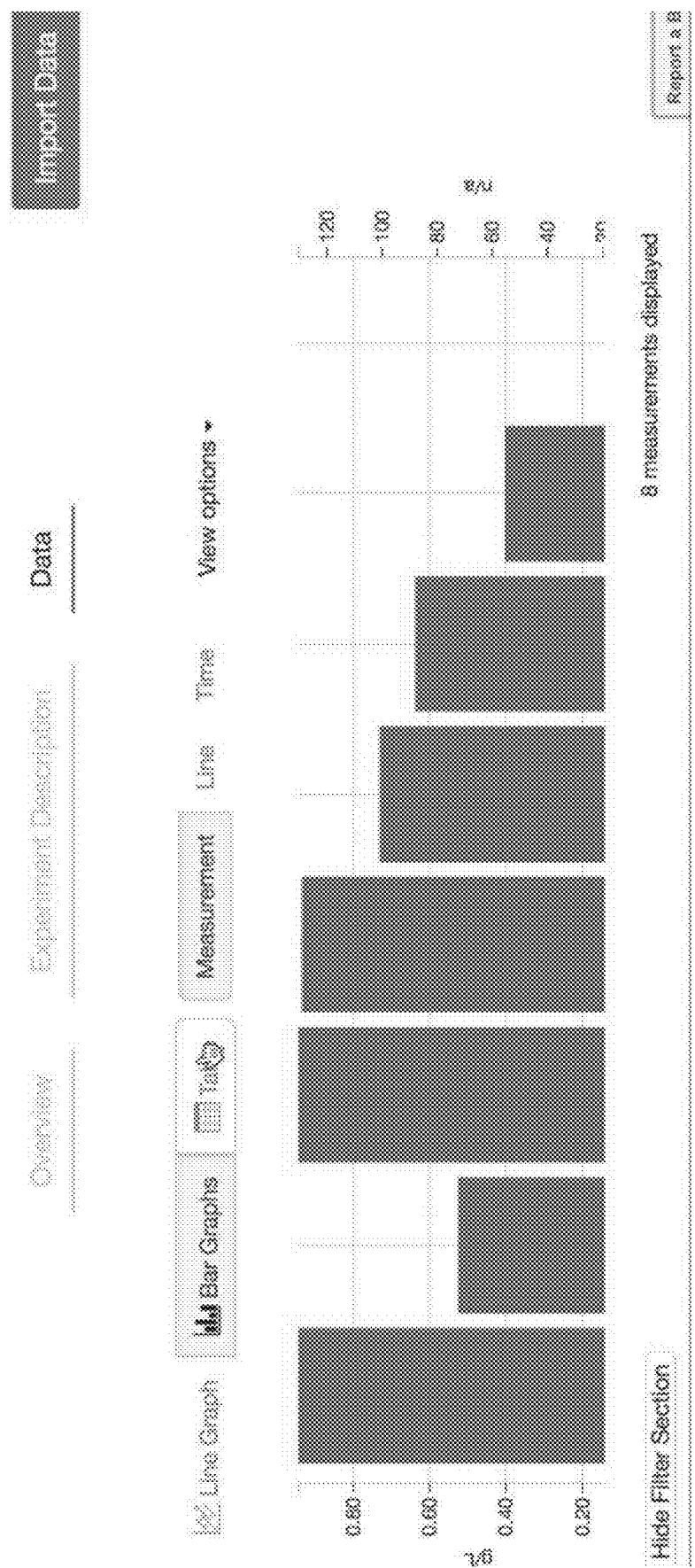
FIG. 13C

FIG. 13F

Include a section for each Protocol
Study fields to include
☐ ID ☐ Name ☐ Contact                                   Select All  Deselect All
Line fields to include
☐ ID ☐ Name ☐ Control ☐ Strain ☐ Carbon Source ☐ Carbon Labeling ☐ Experimenter ☐ Contact   Select All  Deselect All
Protocol fields to include
☐ ID ☐ Name                                              Select All  Deselect All
Assay fields to include
☐ ID ☐ Name                                              Select All  Deselect All
Measurement fields to include
⦿ Measurement Type ☐ Compartment ☐ Measurement Updated ☐ X Units ☐ Y Units
Apply  Download
View the current output here Toggle View

| Measurement Type | 10.0 |
|---|---|
| sp\|P0A9T0\|SERA_ECOLI | 72.45 |
| sp\|P0A799\|PGK_ECOLI | 130.13 |
| sp\|P0A9B2\|G3P1_ECOLI | 129.01 |
| sp\|P0A991\|ALF1_ECOLI | 101.0 |
| sp\|P0A6P9\|PFKB_ECOLI | 88.0 |
| sp\|P0A858\|TPIS_ECOLI | 55.45 |
| sp\|P0A955\|ALKH_ECOLI | 8.323 |

Report a B

*FIG. 13G*

  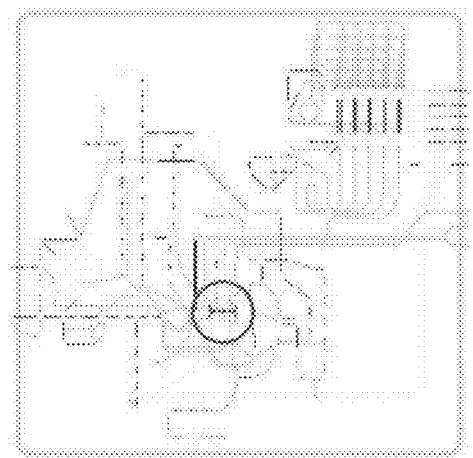
FIG. 14A
 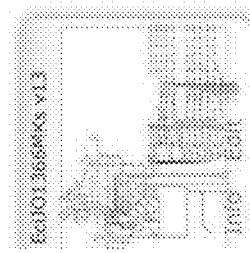

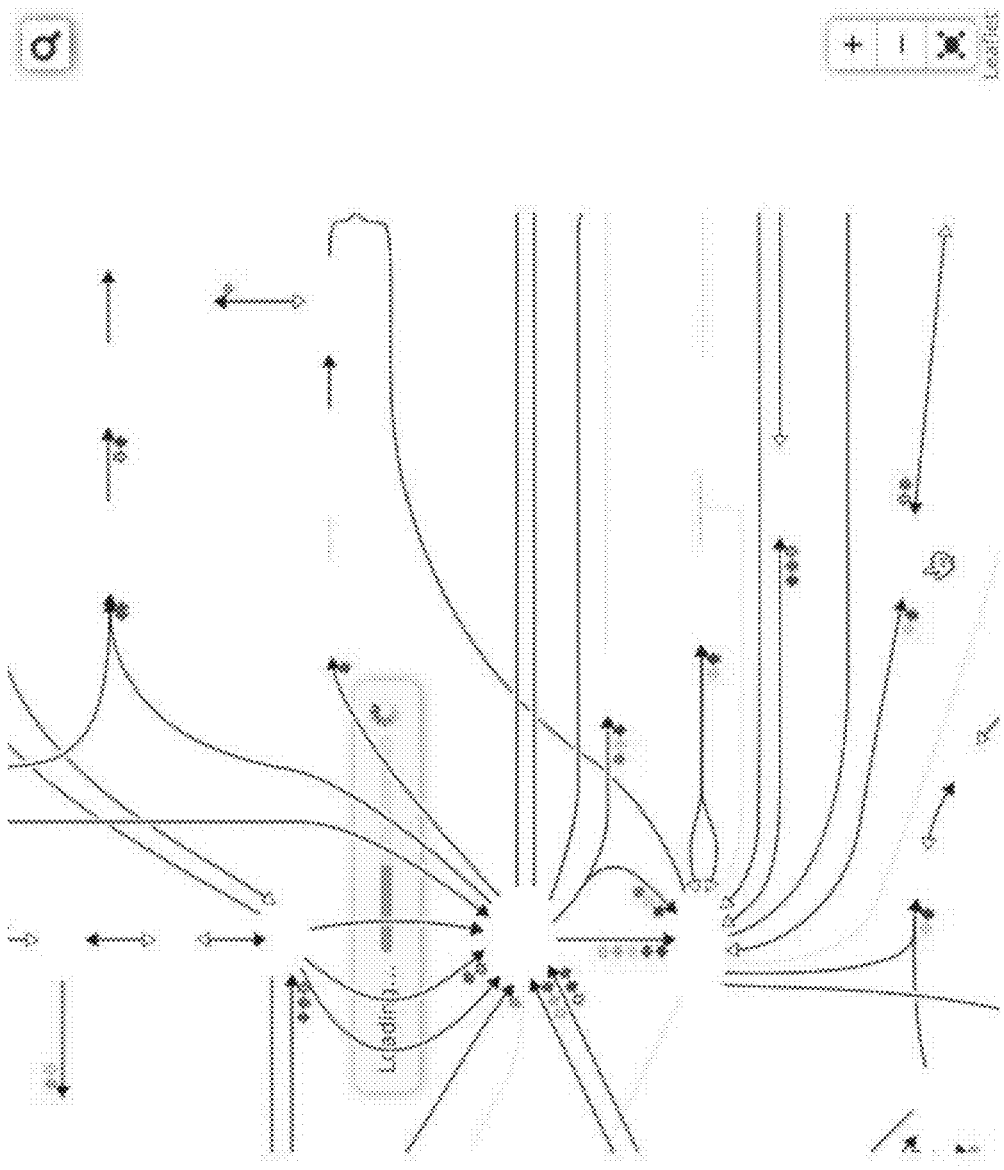
FIG. 14T
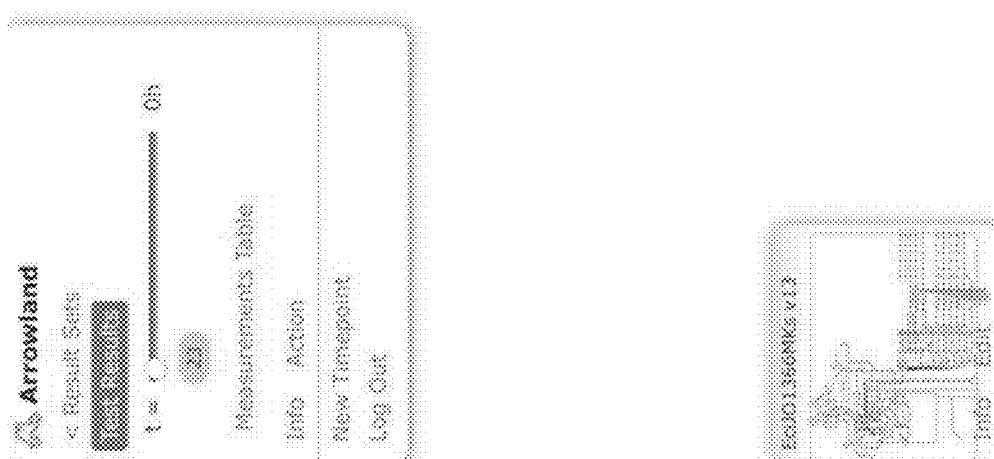

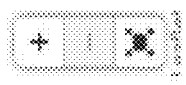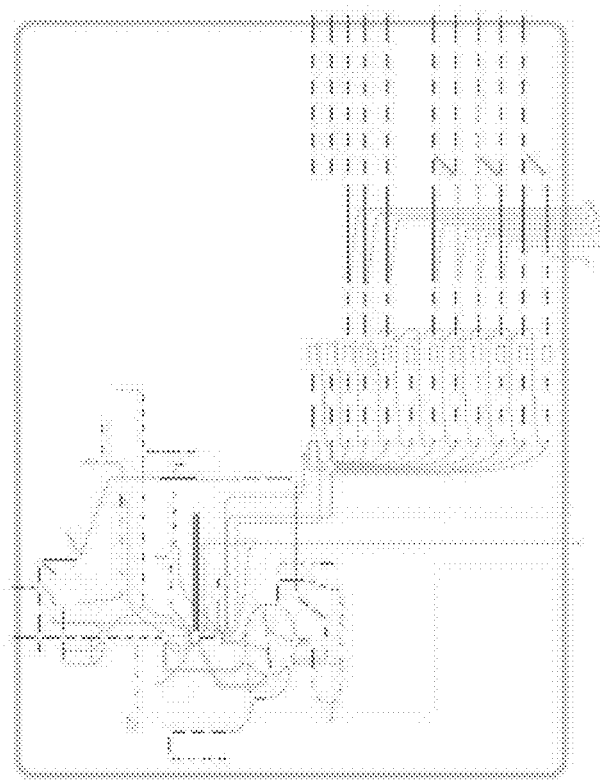
*FIG. 15H*
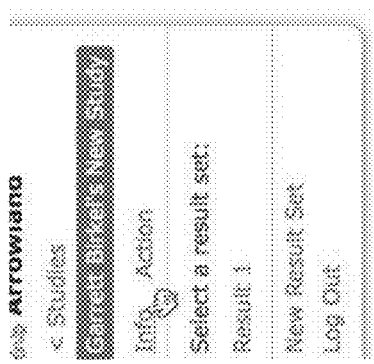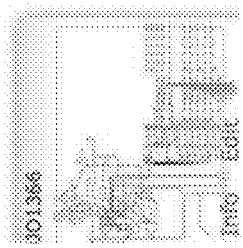

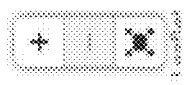
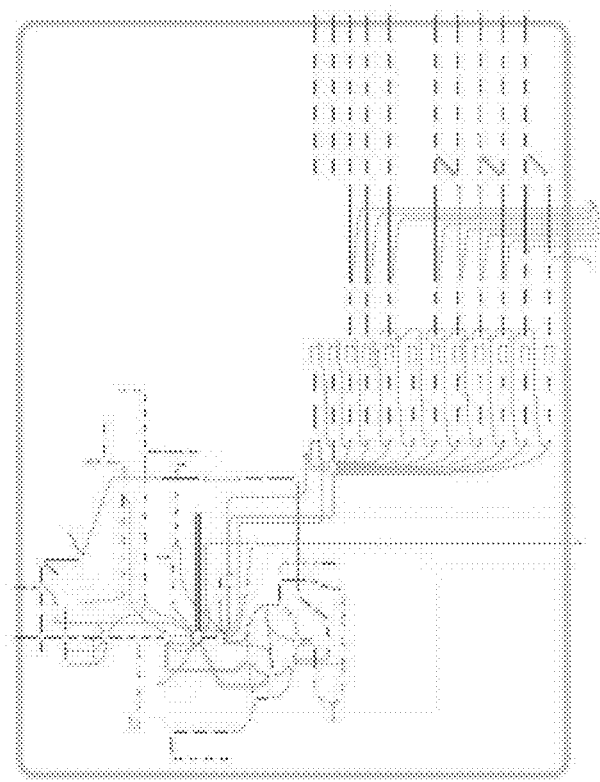
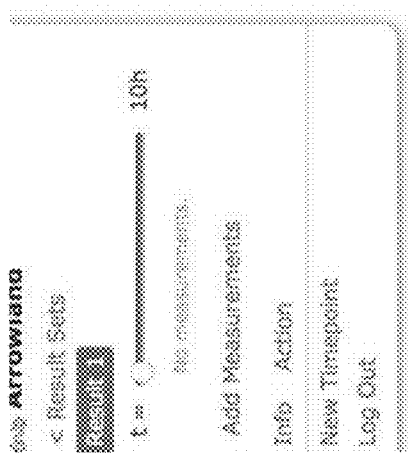
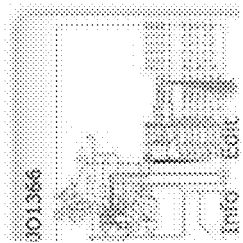
FIG. 15I

FIG. 15M

  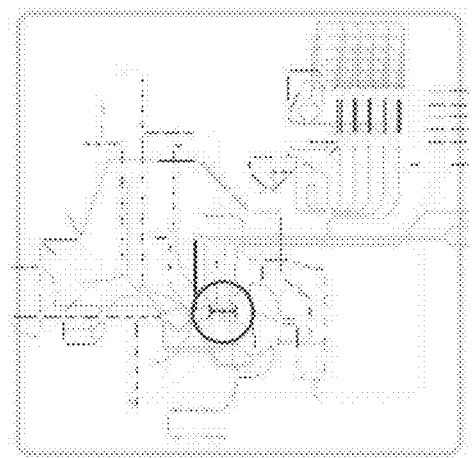  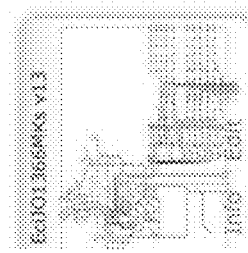
FIG. 16A

FIG. 16S

Jupyter FBA Fluxes in Arrowland (unsaved changes)

File  Edit  View  Insert  Cell  Kernel  Help                    Trusted    |jsapython2 O In [3]: `model = cobra.io.read_sbml_model('BW1.sbml')`

Calculate fluxes through FBA

In [ ]: `solution = model.optimize()`

In [ ]: `solution.objective_value`

In [ ]: `solution.fluxes[['PGI','GND']]`

Display result in Arrowland

1. Create an embedded Arrowland page with a Javascript hook

In [ ]: ```
from IPython.display import HTML, Javascript, display_javascript
import json
```

*FIG. 18C*

Jupyter FBA Fluxes In Arrowland (unsaved changes)

File  Edit  View  Insert  Cell  Kernel  Help

```
In [3]: model = cobra.io.read_sbml_model('BML.sbml')
```

Calculate fluxes through FBA

```
In [4]: solution = model.optimize()

In [5]: solution.objective_value
Out[5]: 0.24872246573675

In [6]: solution.fluxes[['PGI','GND']]
Out[6]: PGI    2.561849
        GND    0.954828
        Name: fluxes, dtype: float64
```

Display result in Arrowland

1. Create an embedded Arrowland page with a Javascript hook

ARROWLAND: AN ONLINE MULTISCALE INTERACTIVE TOOL FOR -OMICS DATA VISUALIZATION

CROSS REFERENCE TO RELATED APPLICATION

The present application is claims the benefit of U.S. Provisional Application No. 62/620,949, filed on Jan. 23, 2018; the content of the related application is incorporated herein by reference in its entirety.

STATEMENT REGARDING FEDERALLY SPONSORED R&D

This invention was made with government support under grant no. DE-AC02-05CH11231 awarded by the U.S. Department of Energy. The government has certain rights in the invention.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

BACKGROUND

Field

The present disclosure relates generally to the field of data visualization and more particularly to -omics and multi-omics data visualization.

Description of the Related Art

The genomic revolution has set the stage for biological research in the 21st century. The discovery of DNA as the repository of genetic heritage during the 20th century and the availability of large-scale affordable sequencing in this century have provided a new framework to interpret biological data. However, the genomic revolution, with its deluge of data, is just the start: while an organism's genome informs as of to what it is capable of doing, functional genomics information describes how it is actually using those capabilities. Functional genomics information encompasses the full central dogma from transcriptomics (study of the comprehensive set of transcripts), proteomics (expressed proteins), metabolomics (present metabolites) and fluxomics (internal metabolic fluxes).

Much of the 21st century's biology will focus around using these genomics and functional genomics data productively. Biological researchers often find themselves buried in a deluge of data orders or magnitude more abundant than they are trained to analyze effectively. There is an acute need for methods able to produce actionable items from that data: methods able to condense all the information into the next action they need to perform in order to obtain their goals, along with a mechanistic explanation. This goal of producing actionable items pervades all fields of biology confronted with genomics and functional genomics data, from metabolic engineering to plant physiology, and is a significant challenge that will engage researchers for much of this century.

However, good tools to visualize these functional genomics data effectively are lacking. There is no single tool available able to simultaneously show multiple -omics data types (e.g., four -omics data types (transcriptomics, proteomics, metabolomics, fluxomics)) in an interactive, multiscale fashion. A good data visualization scheme can often provide an effective way to produce these actionable items from -omics data.

SUMMARY

Disclosed herein are systems and methods for simultaneous visualization of functional genomics data (e.g., transcriptomics, proteomics, metabolomics and fluxomics). The software package is referred to herein as Arrowland.

One embodiment is a system for displaying multiomics data. This embodiment includes a non-transitory memory configured to store executable instructions, a metabolic model, and a metabolic map, wherein the metabolic map comprises a plurality of metabolites and a plurality of associations between the plurality of metabolites, wherein an association between two metabolites is defined by the metabolic model comprising a metabolic flux between the two metabolites, a transcript of a gene, and a protein encoded by the gene capable of catalyzing one of the two metabolites to the other of the two metabolites; and a processor programmed by the executable instructions to perform a method comprising: receiving a selection of the metabolic model and a selection of the metabolic map from a user device; receiving a multiomics data set comprising metabolomics data, fluxomics data, transcriptomics data, and proteomics data; generating a metabolic network comprising (1) a plurality of geometric shapes corresponding to the plurality of metabolites, (2) a plurality of arrows between the geometric shapes corresponding to the plurality of links wherein a size of a geometric shape is determined based on a quantity of the corresponding metabolite in the multiomics data set; and providing the metabolic network to the user device as a plurality of tiles. The metabolic network further comprises (3) a plurality first shading associated with the plurality of arrows, and (4) a plurality of second shading associated with the plurality of arrows from the multiomics and wherein characteristics of an arrow, an associated first half-arrow shading, and an associated second half-arrow shading are determined by quantities of the corresponding metabolic flux, transcript, and protein in first multiomics data. Providing the metabolic network to the user device comprises providing label information of the metabolic network and/or providing external links related to the metabolic network to the user device. The multiomics data set comprises time series multiomics data comprising a first multiomics data set at a first time and a second multiomics data set at a second time, wherein generating the metabolic network comprises generating a first metabolic sub-network from the first multiomics sub-dataset and a second metabolic sub-network from the second multiomics sub-dataset with an offset from the first metabolic sub-network. The processor is programmed by the executable instructions to receive a selection that the first multiomics sub-dataset is used as a baseline in generating the multiomics network. The processor is programmed by the executable instructions to: receive a selection of an area of the metabolic network; determine metabolite(s), metabolic flux(es), transcript(s), and protein(s) in the area, or reactions thereof; determine tiles intersecting the metabolite(s), metabolic flux(es), transcript(s), and protein(s), or reactions thereof; generate updated tiles; and provide the user device with the updated tiles. The metabolic model comprises a first metabolic sub-model and a second metabolic sub-model, wherein the first metabolic sub-model comprises the two metabolites and associated stoichiometry, and wherein the second metabolic sub-model comprises a plurality of genes, transcripts thereof, or proteins thereof, capable of performing the catalysis.

Another embodiment is a system for displaying multiomics data. This embodiment includes non-transitory memory configured to store executable instructions; and a hardware processor programmed by the executable instructions to perform a method comprising: providing a selection of a metabolic model and a selection of a metabolic map to a server device; providing a multiomics data set comprising metabolomics data, fluxomics data, transcriptomics data, and/or proteomics data to the server device; receiving a metabolic network as a first rasterized tile of a first vector graphic of the metabolic network and a second vector graphic of a second rasterized tile from the server device; generating a second rasterized tile of the second vector graphic; providing the first rasterized tile and the second rasterized tile to a display application. The display application is a web browser or a mobile device application. Generating the second rasterized tile of the second vector graphic comprises copying the second vector graphic onto a HTML canvas element. The hardware processor is programmed by the executable instructions to: extract strings from the second vector graphic; and discard the second vector graphic after generating the second rasterized tile of the second vector graphic.

Yet another embodiment is a computer-implemented method for displaying multiomics data, comprising: receiving a selection of a metabolic model and a selection of a metabolic map, wherein the metabolic map comprises a plurality of metabolites and a plurality of associations between the plurality of metabolites, wherein an association between two metabolites is defined by the metabolic model comprising a metabolic flux between the two metabolites, a transcript of a gene, and a protein encoded by the gene capable of performing a catalysis from one of the two metabolites to the other of the two metabolites; receiving a first multiomics data set comprising metabolomics data, fluxomics data, transcriptomics data, and/or proteomics data; generating a metabolic network from the multiomics data, wherein the metabolic network comprises (1) a plurality of geometric shapes corresponding to the plurality of metabolite, (2) a plurality of first arrows between the geometric shapes corresponding to the plurality of links, (3) a plurality first shading associated with the plurality of first arrows, and/or (4) a plurality of second shading associated with the plurality of first arrows, wherein a characteristics of a geometric shape is determined based on a quantity of the corresponding metabolite in the first multiomics data set, and wherein characteristics of a first arrow, an associated first shading, and an associated second shading are determined by quantities of the corresponding metabolic flux, transcript, and protein in first multiomics data. The geometric shapes comprises a circle, an oval, a square, a rectangle, a square, a trapezoid, a parallelogram, or a combination thereof. The characteristics of the geometric shape is a size of the geometric shape, wherein a larger size indicates a larger quantity. The characteristics of the geometric shape is a color of the geometric shape, wherein a darker color indicates a larger quantity. The characteristics of the first arrow is determined by the quantity of the metabolic flux. The characteristics of the first arrow is a size of the first arrow, and wherein a larger size indicates a larger quantity. The characteristics of the first arrow is a color of the first arrow, and wherein a darker color indicates a larger quantity. The characteristics of the first shading is determined by the quantity of the transcript, and wherein the characteristics of the second shading is determined by the quantity of the protein. The characteristics of the first shading is a size of the first shading and/or the characteristics of the second shading is a size of the second shading, and wherein a larger size indicates a larger quantity. The characteristics of the first shading is a color of the first shading and/or the characteristics of the second shading is a color of the second shading, and wherein a darker color indicates a larger quantity. The first shading and/or the second shading is a box, an ellipse, a Bezier curve, or a combination thereof. The Bezier curve is defined by four vectors and two intensity multipliers. The metabolic model comprises a cofactor for the catalysis, wherein the metabolic network comprises a second arrow corresponding to the cofactor, and wherein the second arrow is not parallel to the first arrow. The second arrow is approximately perpendicular to the first arrow.

Details of one or more implementations of the subject matter described in this specification are set forth in the accompanying drawings and the description below. Other features, aspects, and advantages will become apparent from the description, the drawings, and the claims. Neither this summary nor the following detailed description purports to define or limit the scope of the inventive subject matter.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

FIGS. 3A-3C show exemplary multiomics data visualization at different resolution levels. Transcriptomics data is shown in a halo on the arrow left side proportional to the corresponding genes RPKM. Proteomics data is shown as a different halo on the right side proportional to the corresponding protein expression. Metabolites are shown as ellipses of a radius proportional to the metabolites concentration.

FIG. 6 shows a schematic illustration of labeling conventions for constructing Arrowland maps in SVG.

FIGS. 11A-11T are screenshots of an exemplary importing fluxomics data from a CSV file into Arrowland (public-arrowland.jbei.org/static/main/help/fluxomics_csv_import.mp4, the content of which is incorporated herein by reference in its entirety). To view fluxomics in Arrowland, a study is created and a result set is produced inside the study. The study should have a default map and a default model assigned to it. Once a result set is selected, a user may import fluxomics data. Measurements by be selected to show the import window and drop zone. The user can drop in a CSV file containing fluxomics measurements. The file may include reaction names followed by flux values. If the user wants to specify the flux is a range number with the low, high and best, the user can use the bracketed syntax as illustrated. The order of the values inside the brackets may be low, best, and high. The user can instruct Arrowland that it should look for fluxomics measurements in the file and submit the file. The window changes to show all the measurements Arrowland could find in a file. If this import is correct, the user can select an "approve" button. If the user wants to see measurements in tabular format again, the measurements table button may be pressed. The user can edit the measurement values or change which reaction of value belongs to.

Figure 14B:
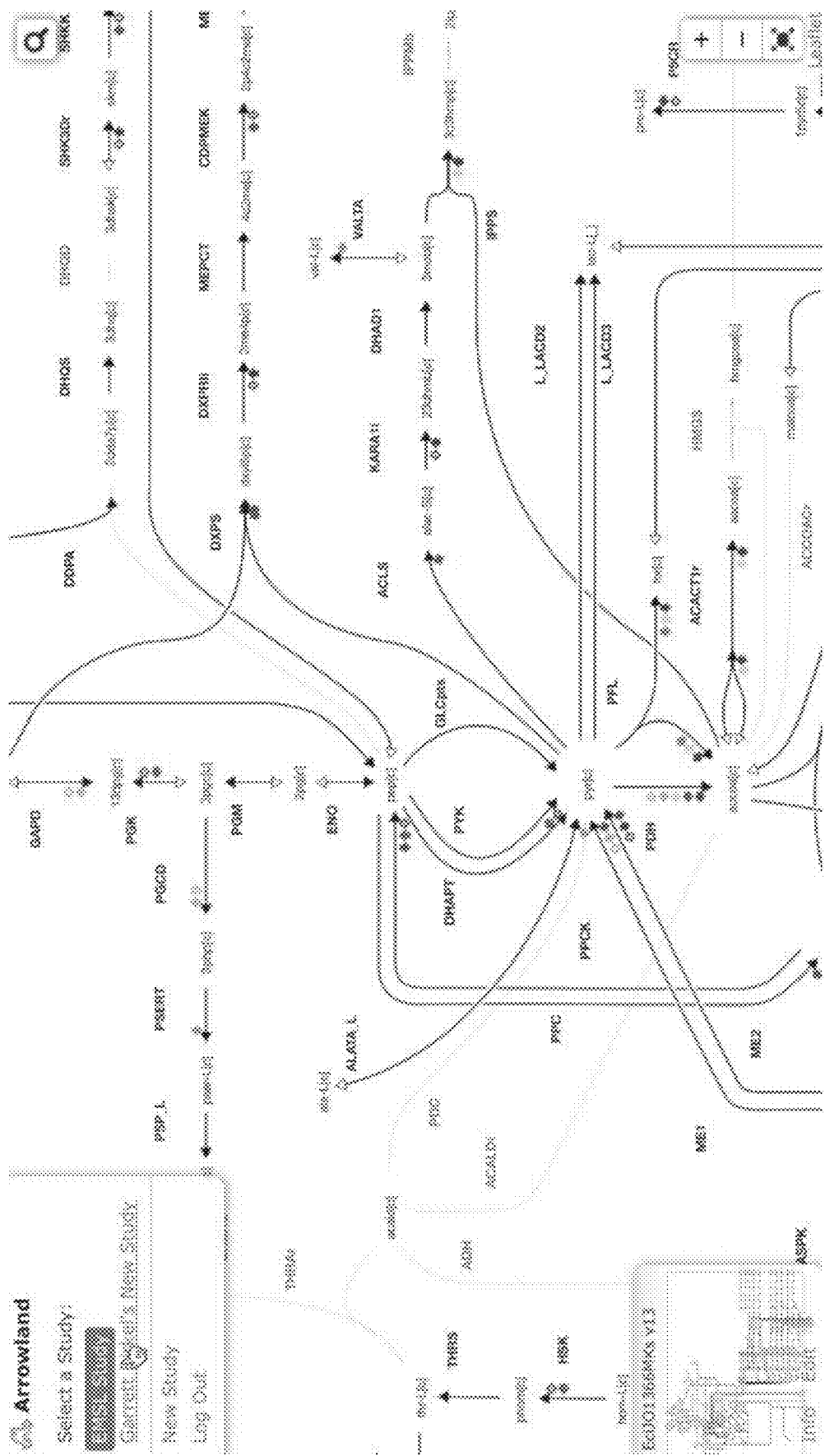
Figure 14C:
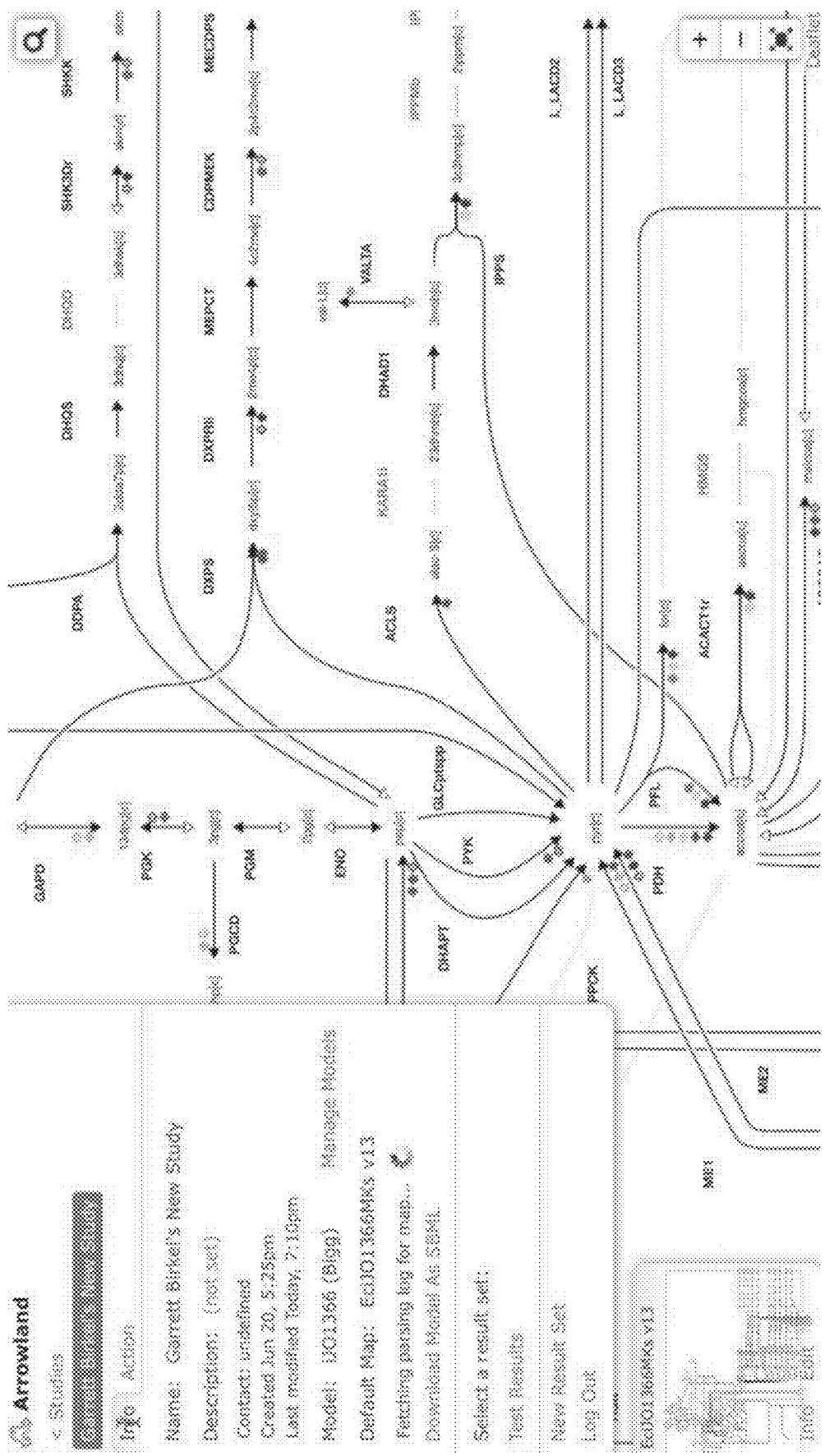
Figure 14D:
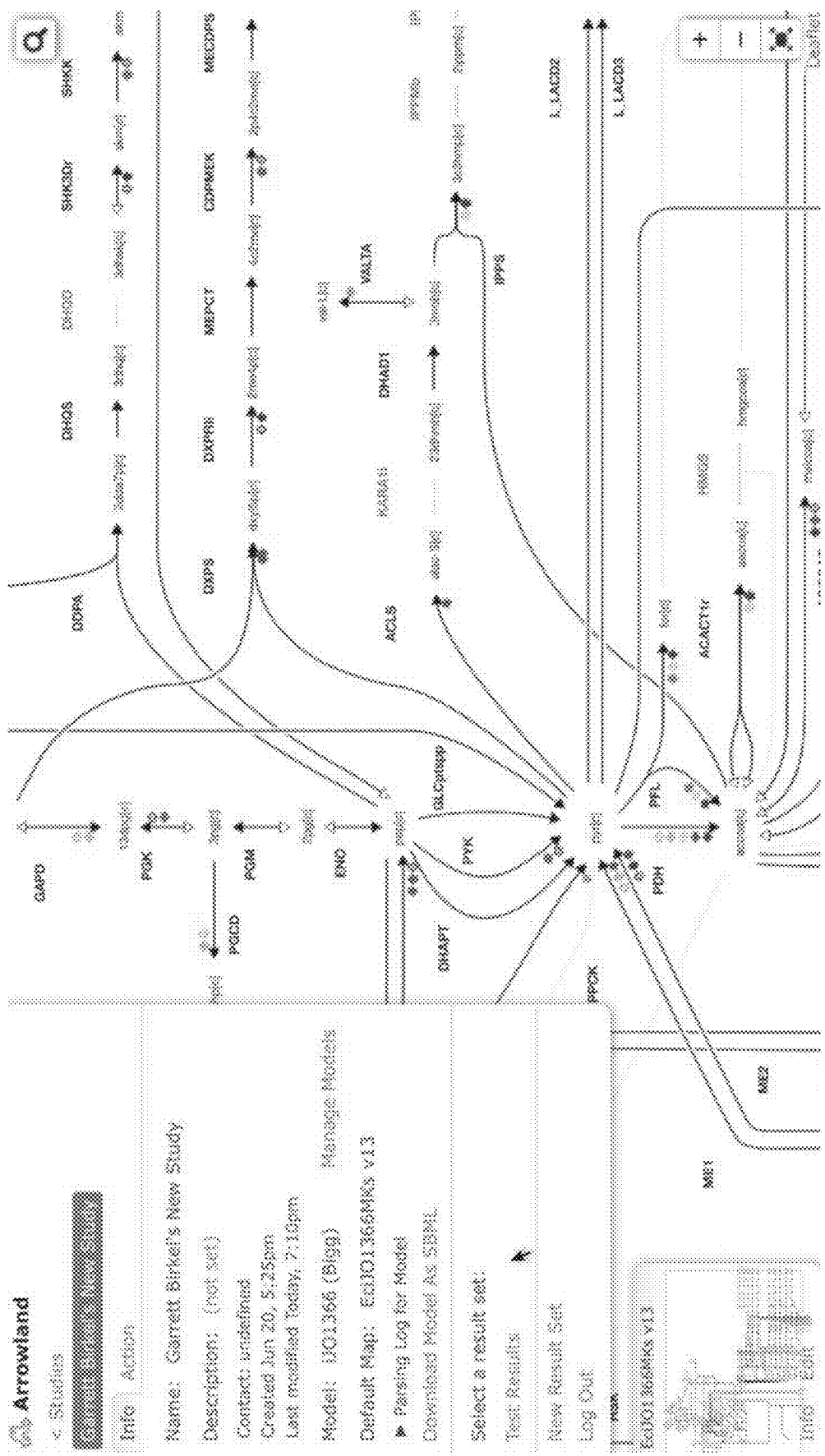
Figure 14E:
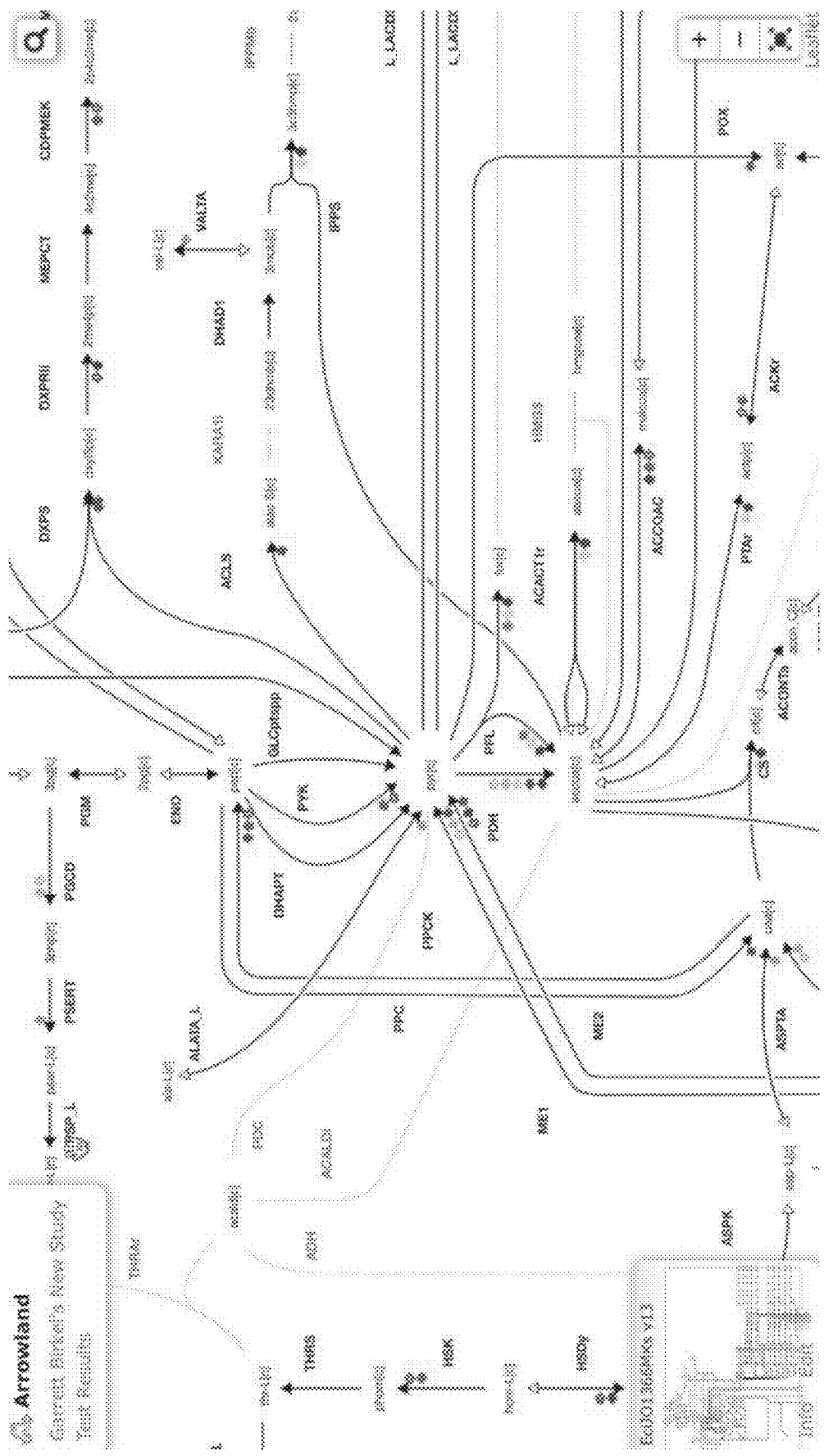
Figure 14F:
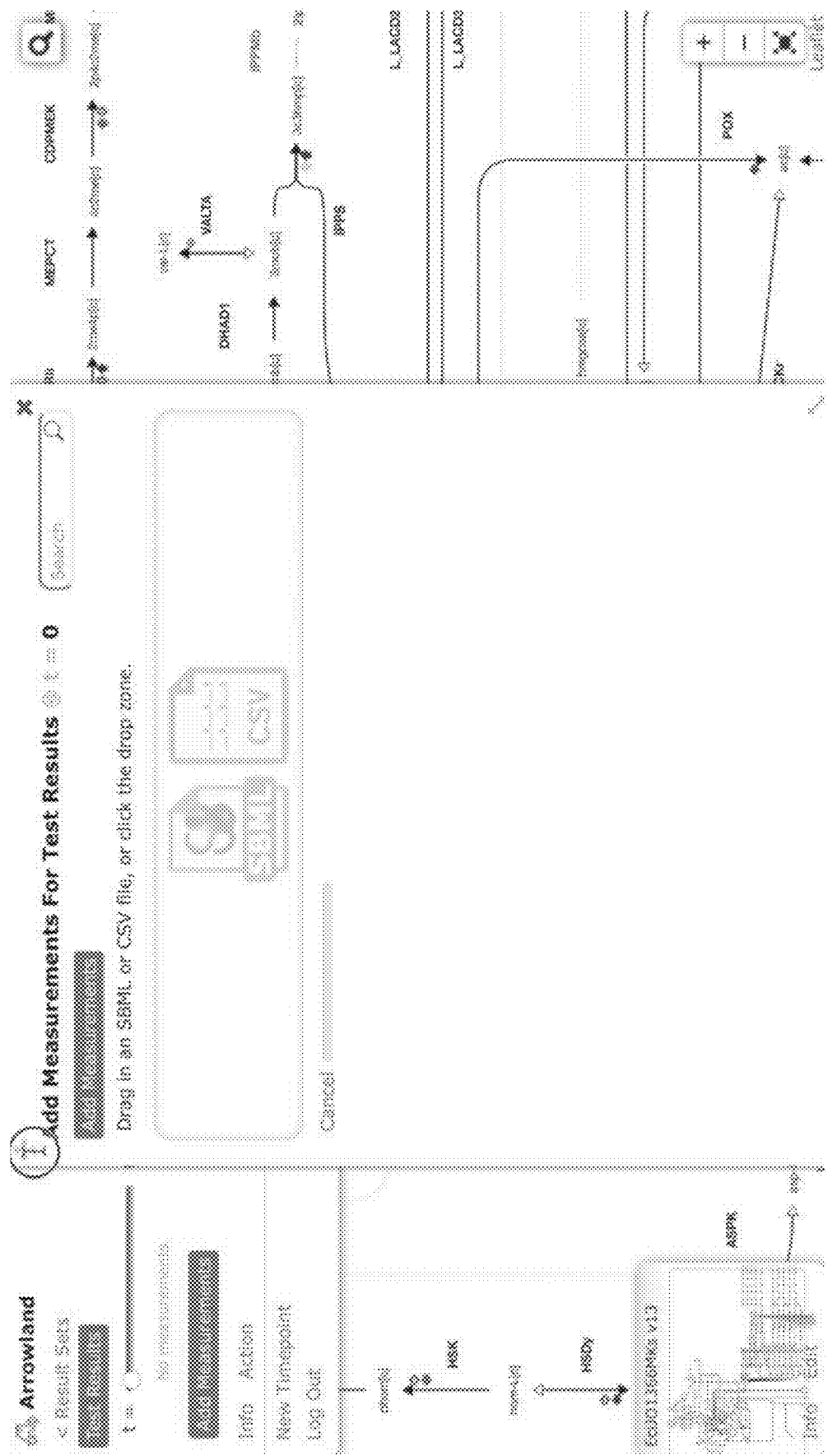
Figure 14G:
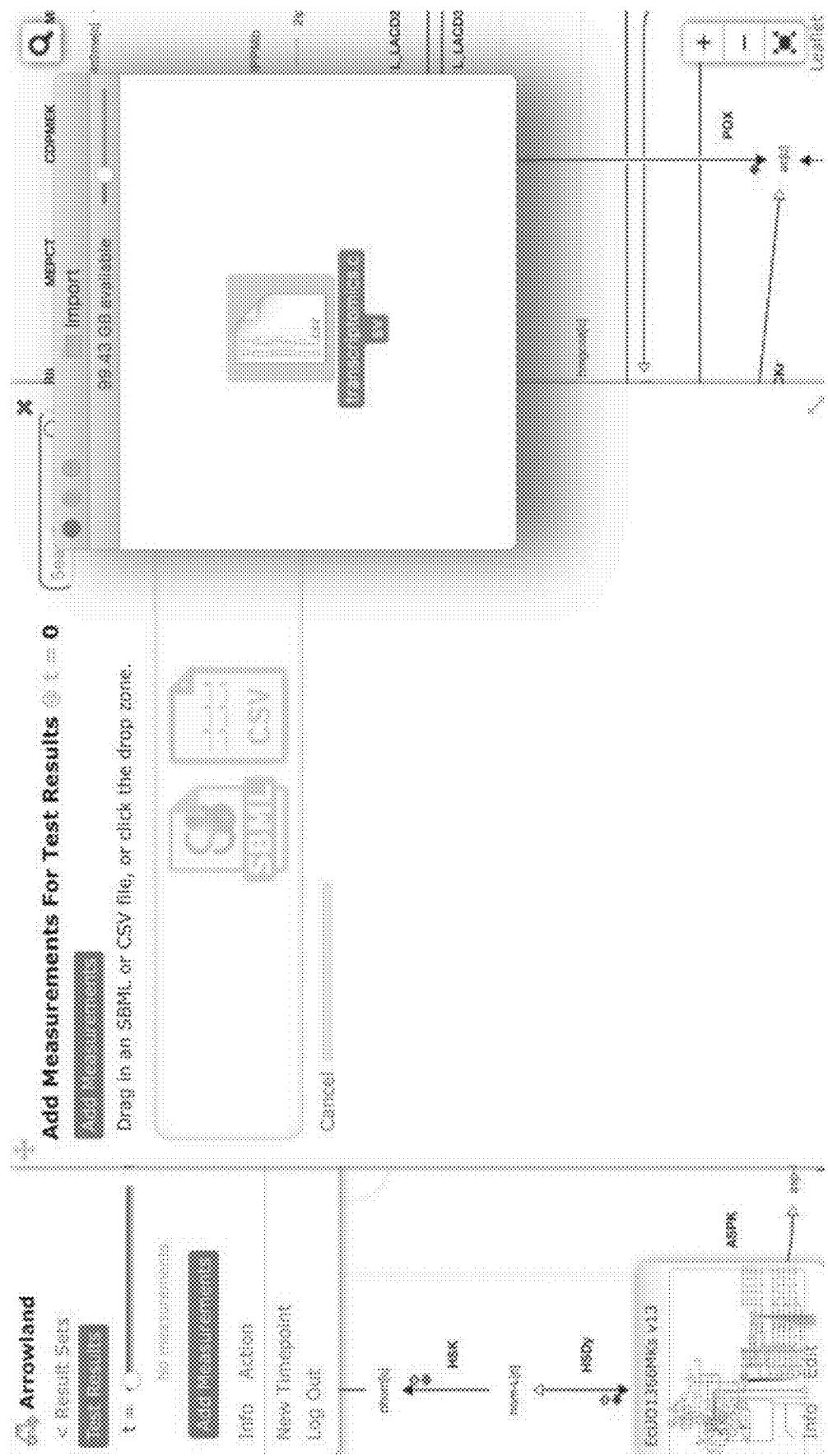
Figure 14H:
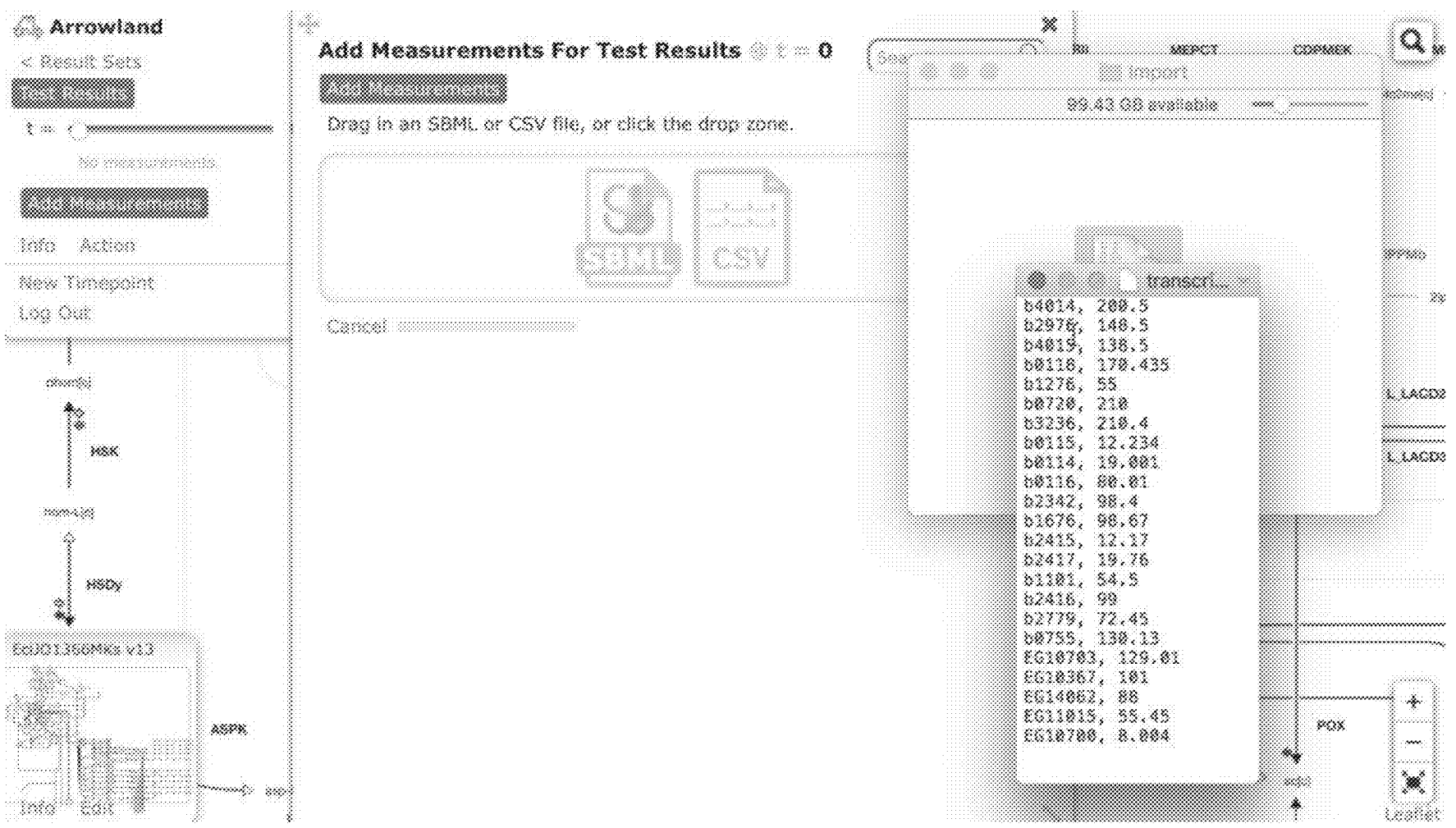
Figure 14I:
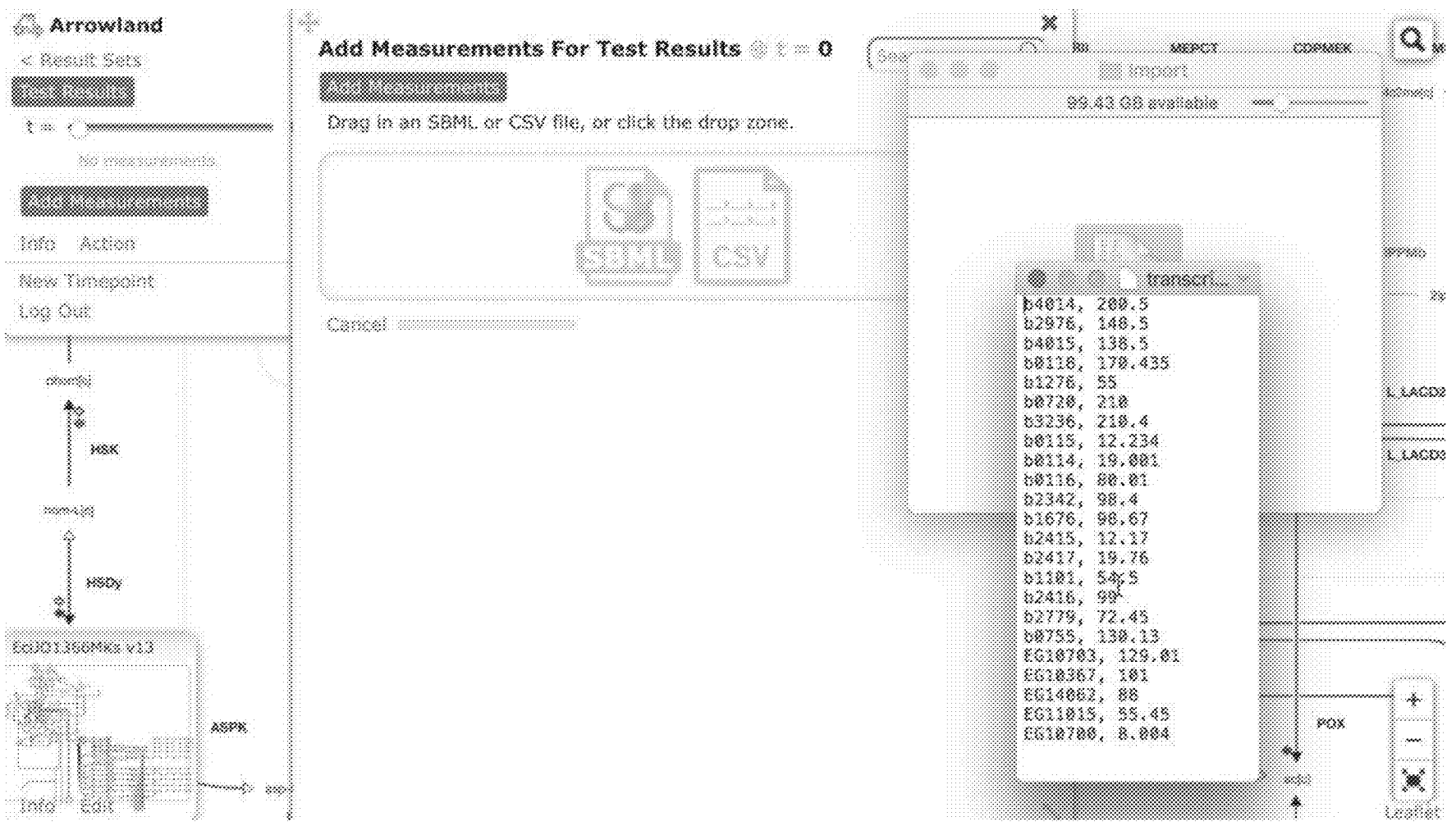
Figure 14J:
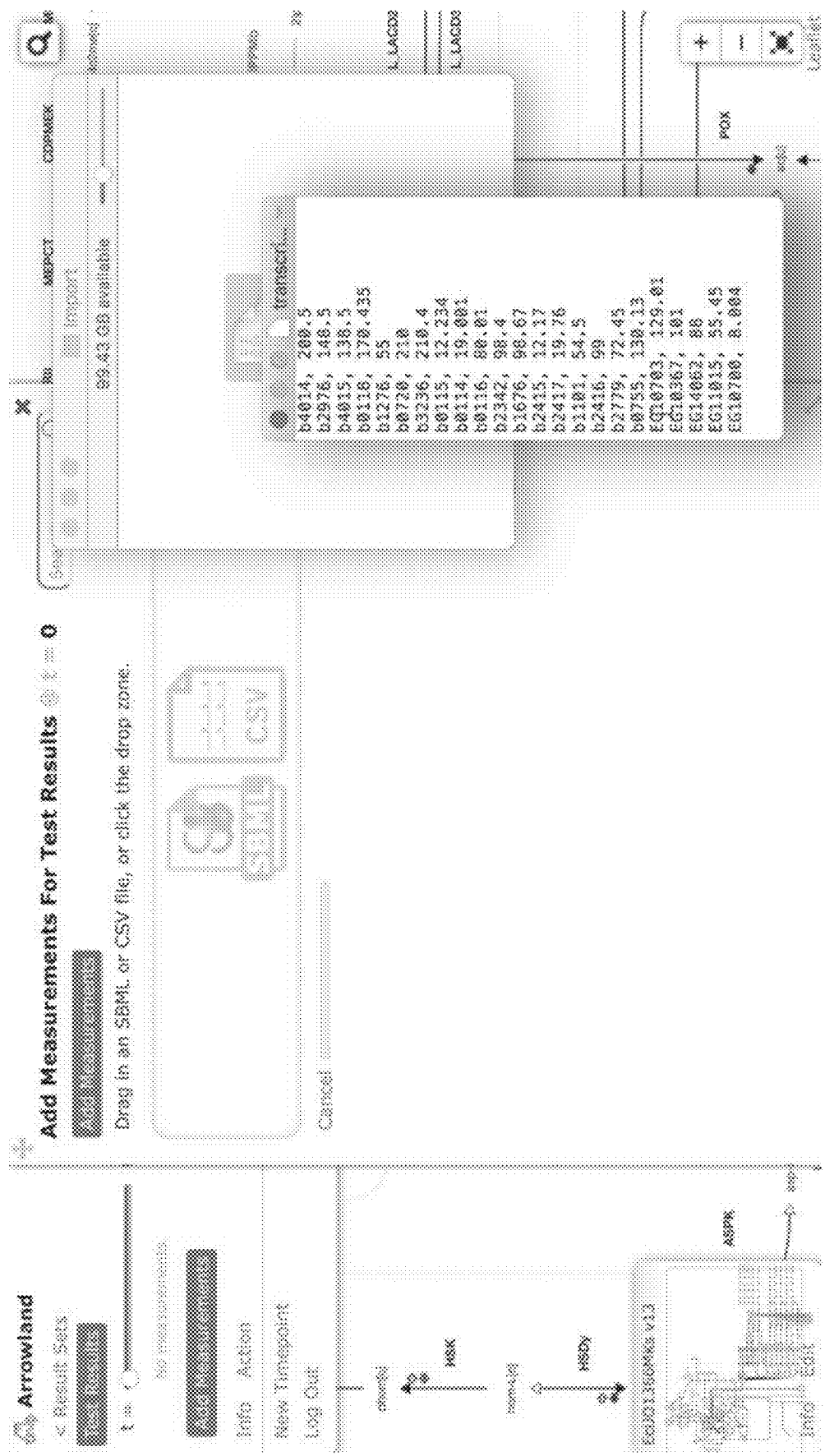
Figure 14K:
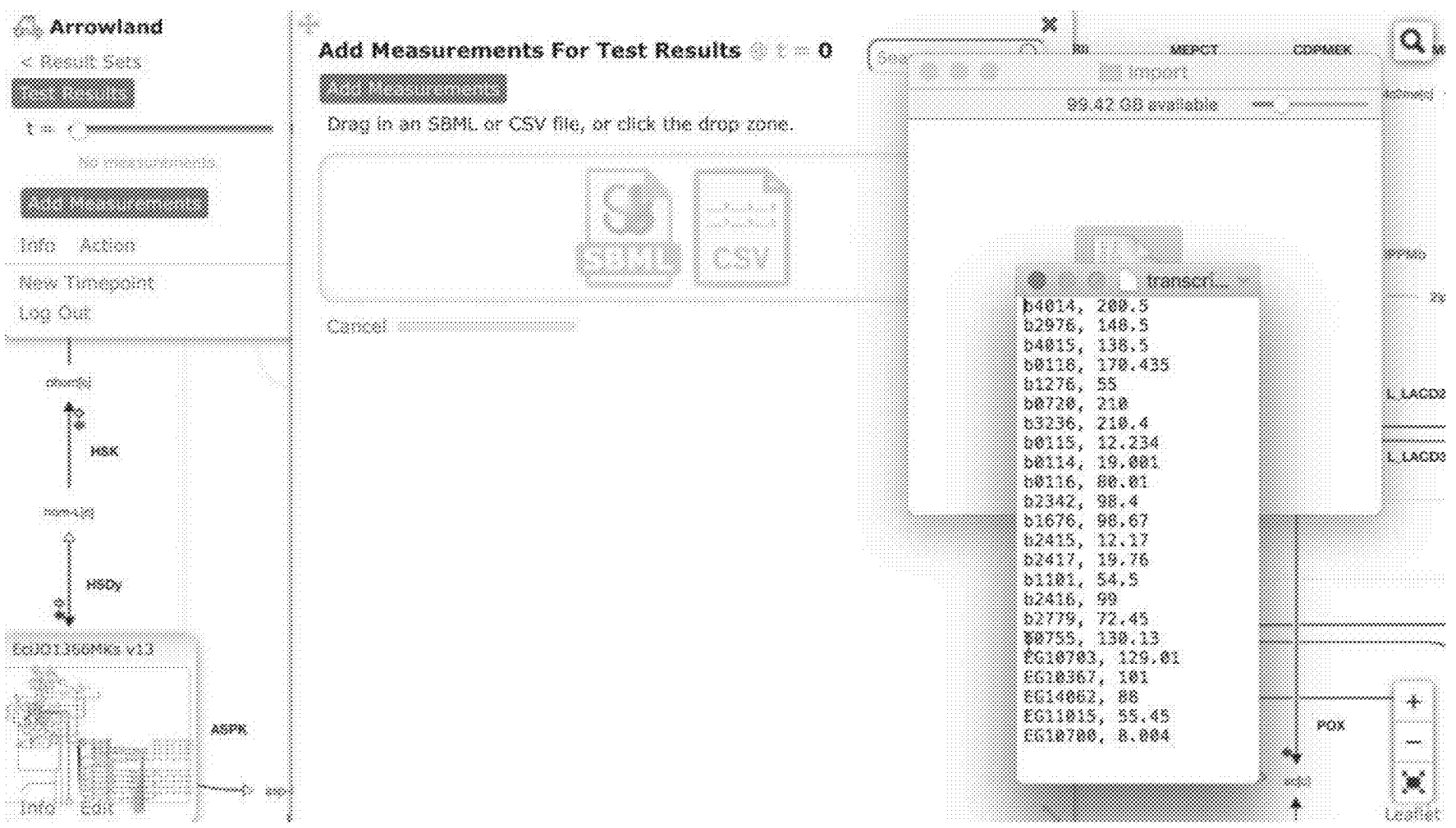
Figure 14L:
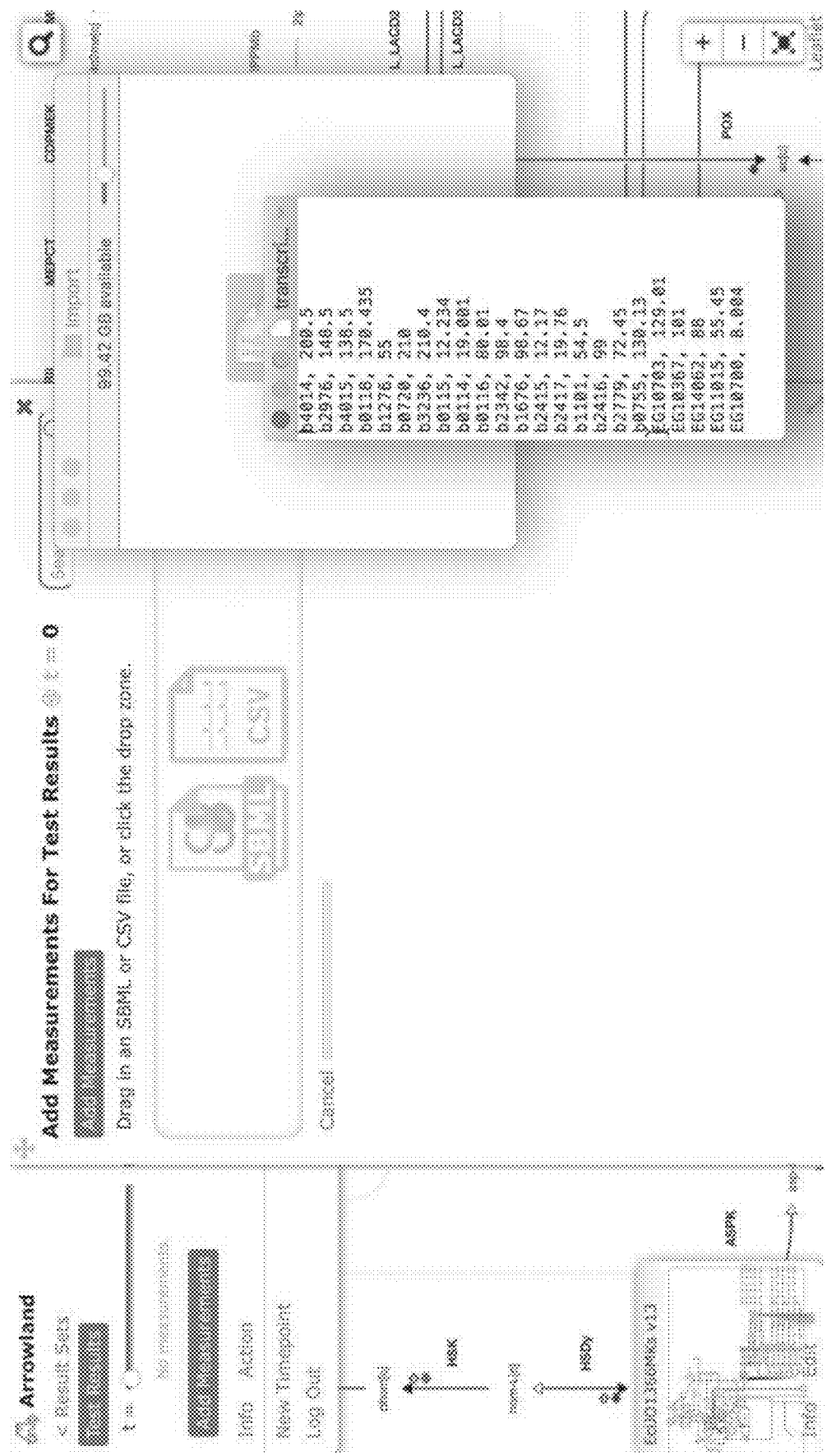
Figure 14M:
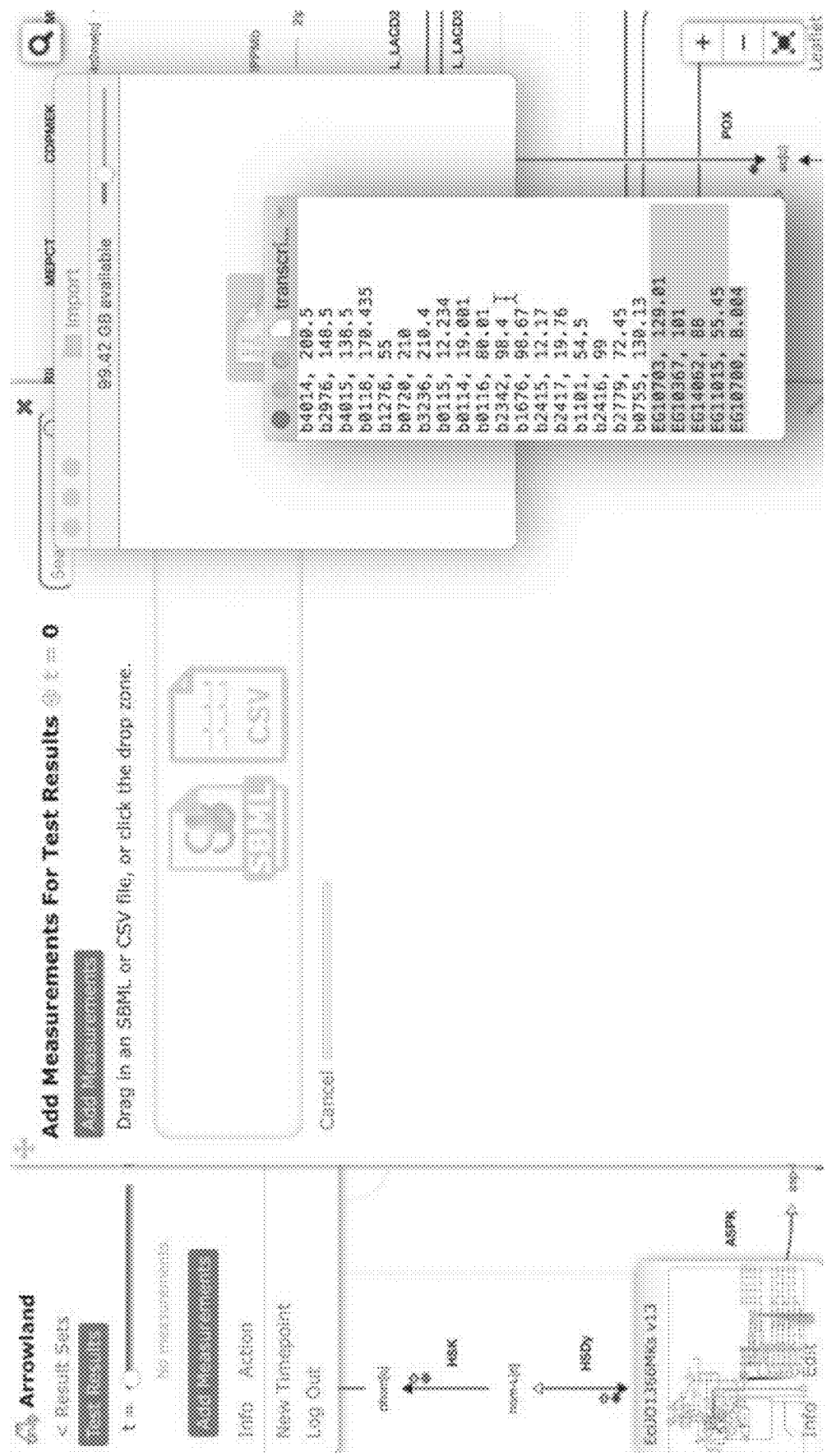
Figure 14N:
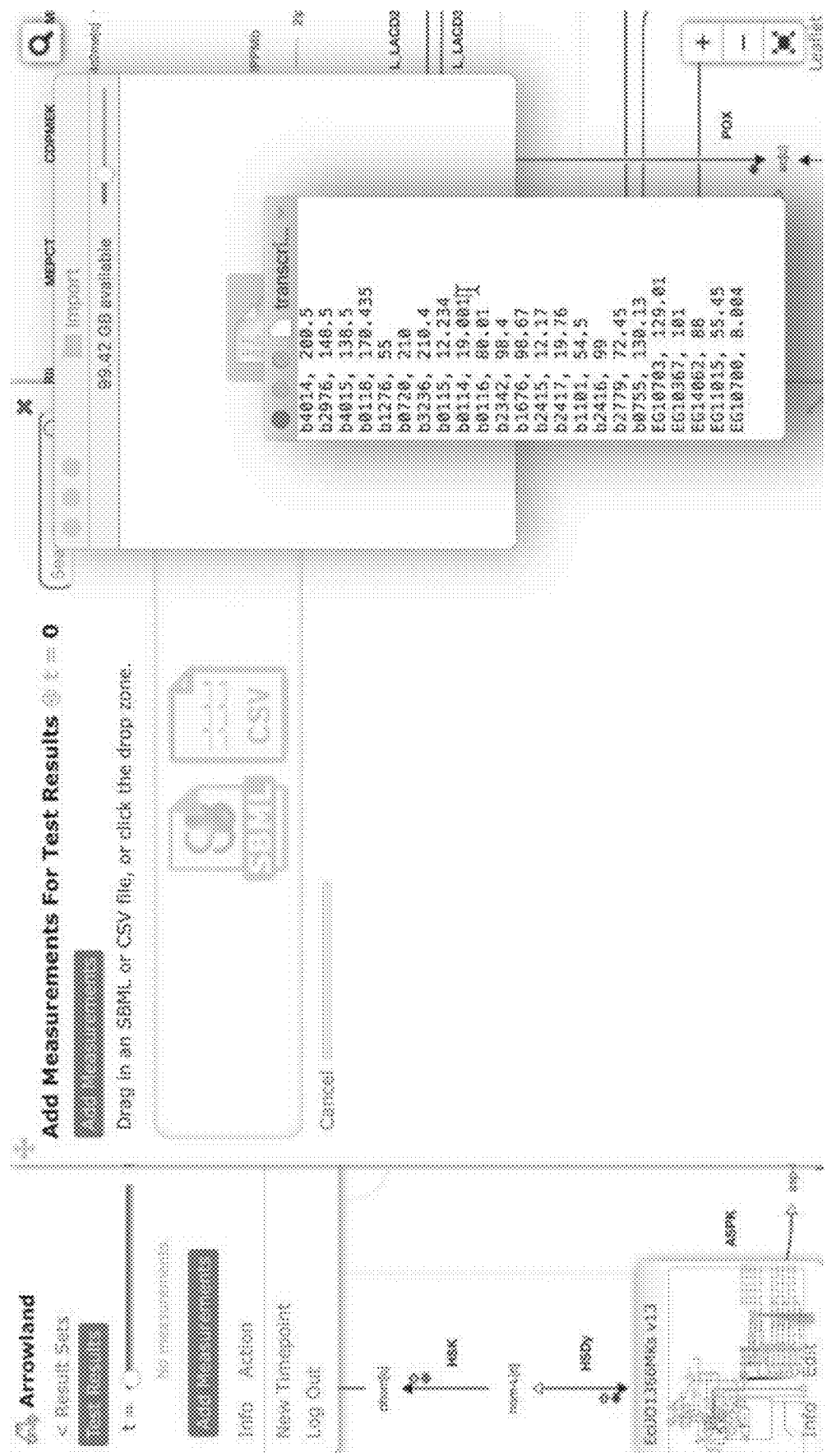
Figure 140:
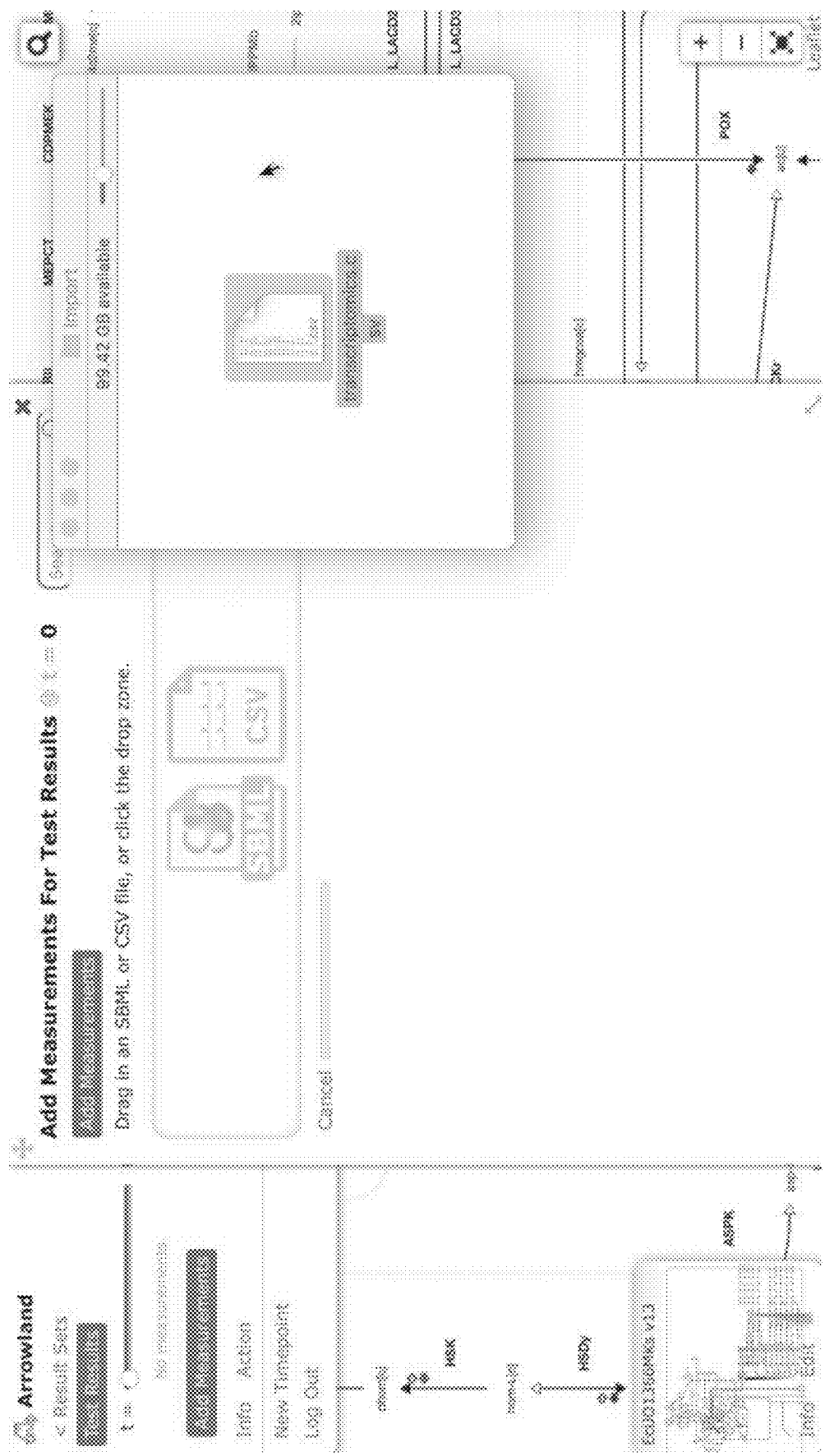
Figure 14P:
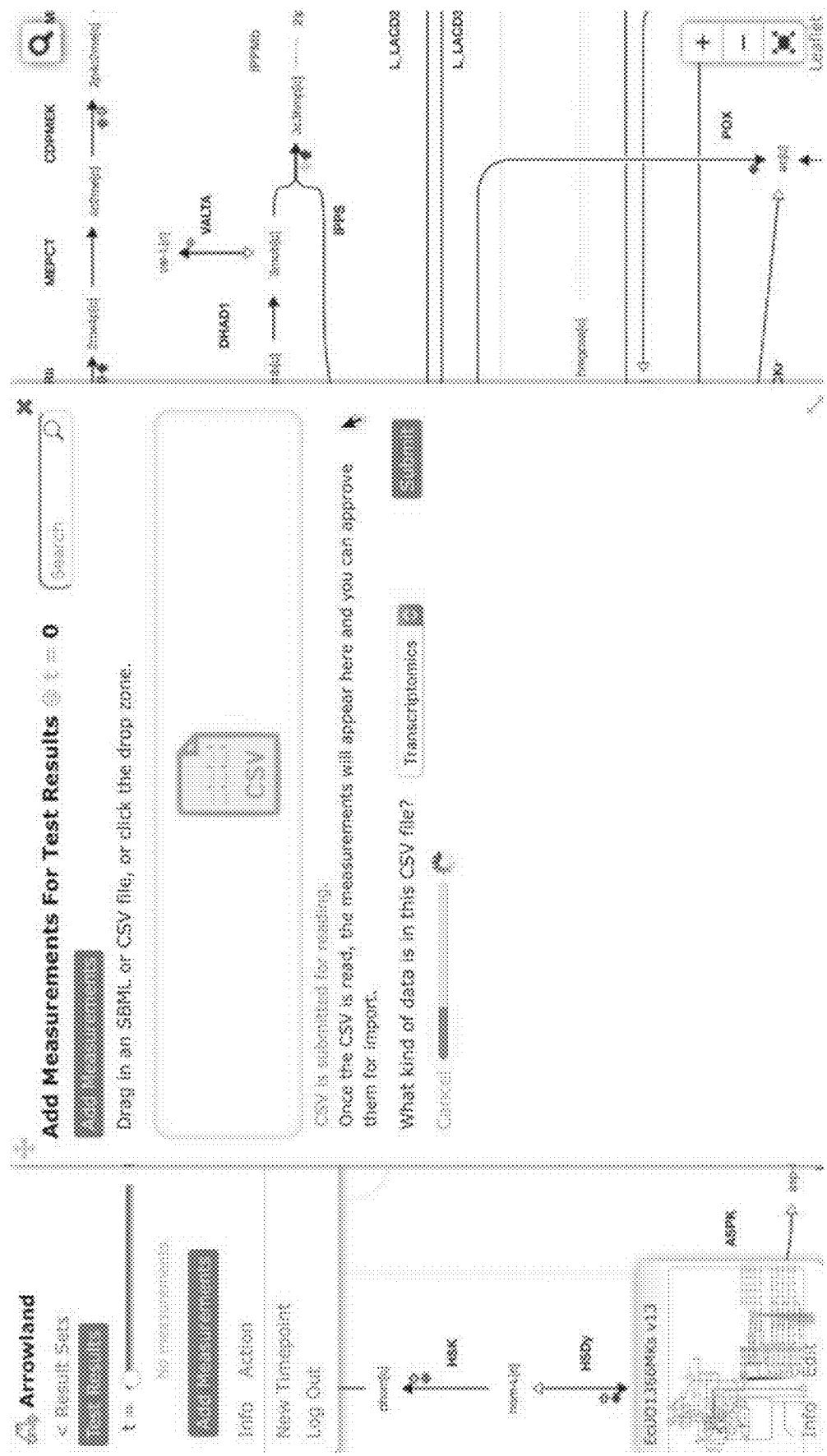
Figure 14Q:
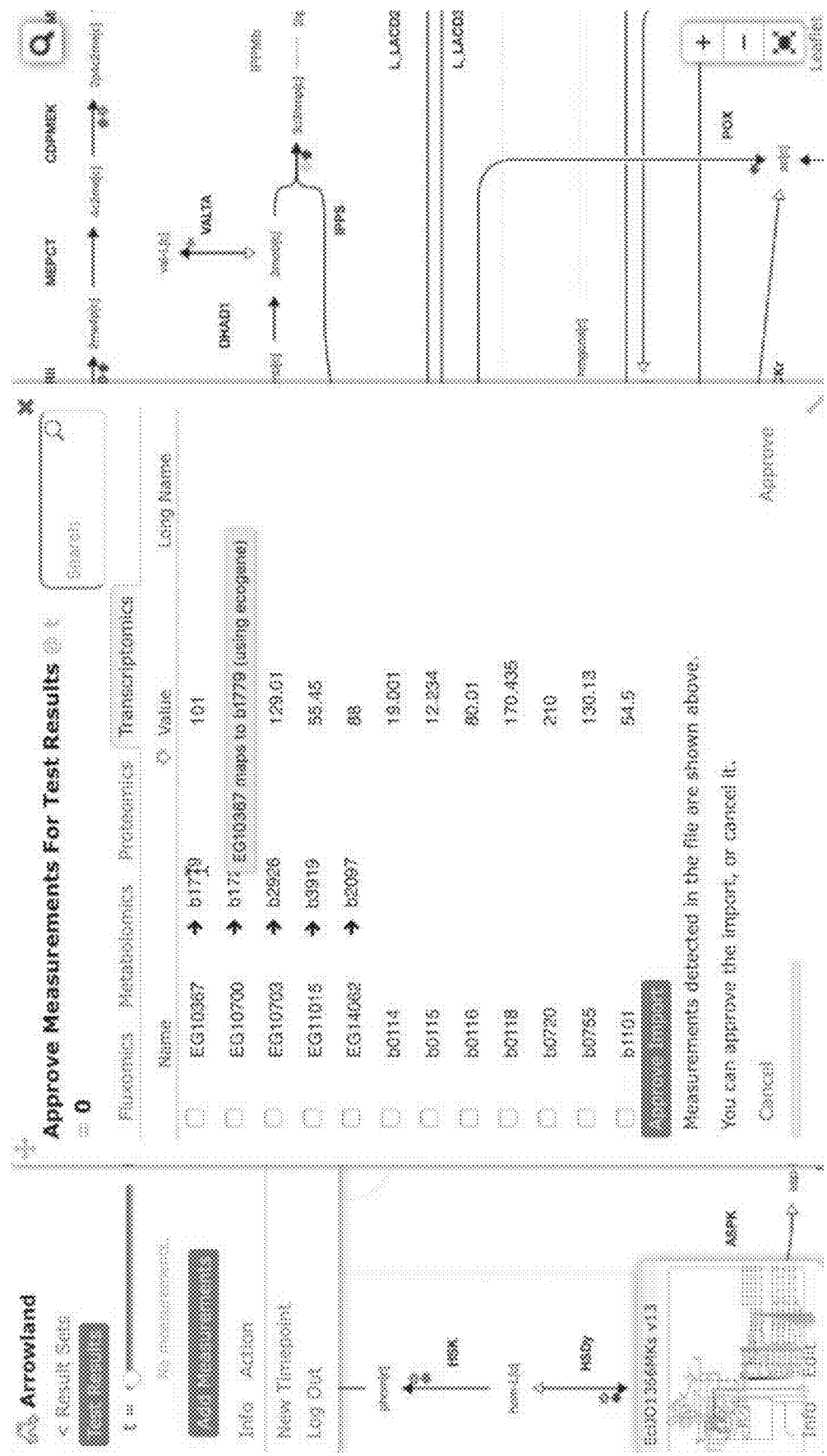
Figure 14R:
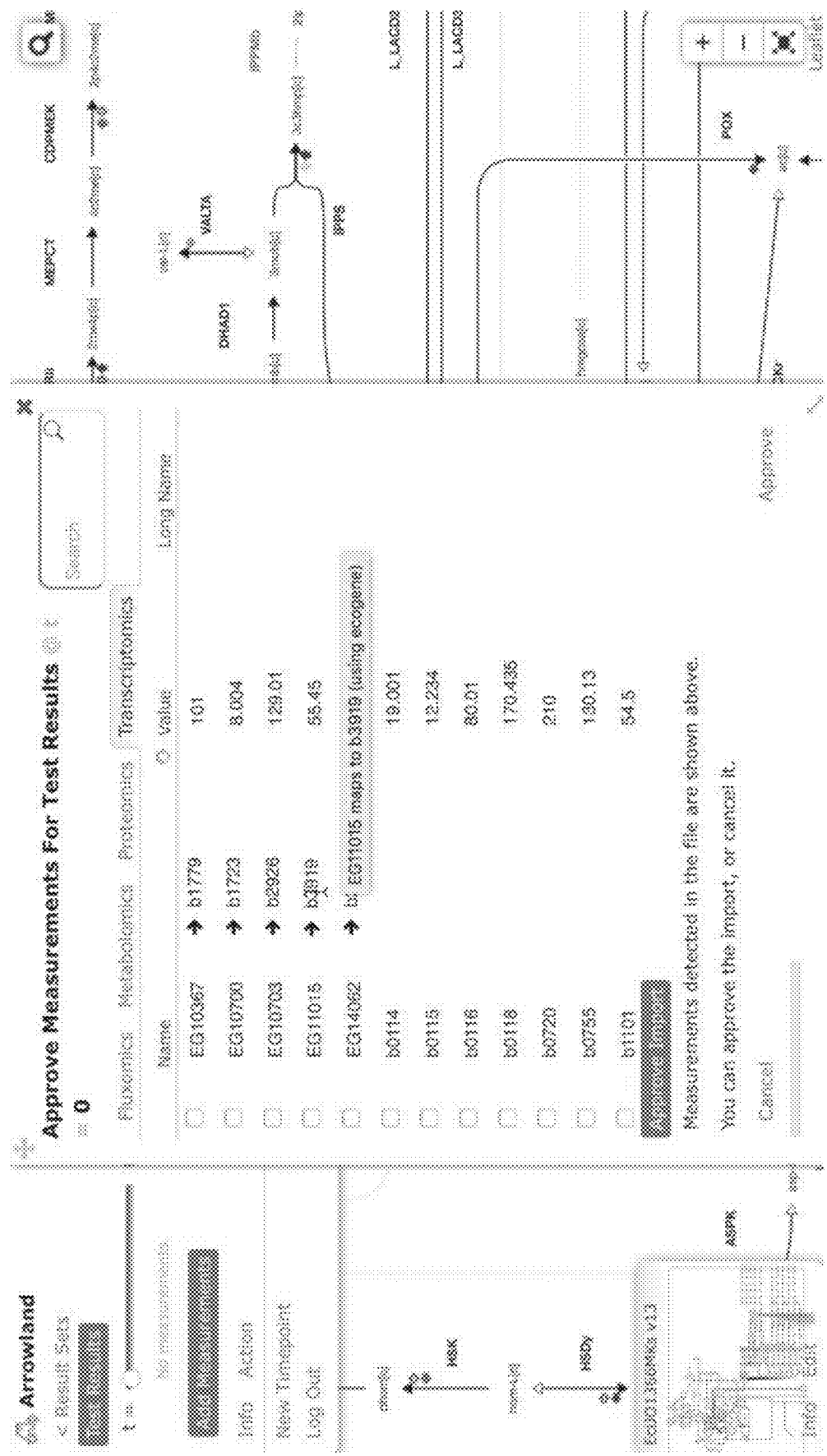
Figure 14S:
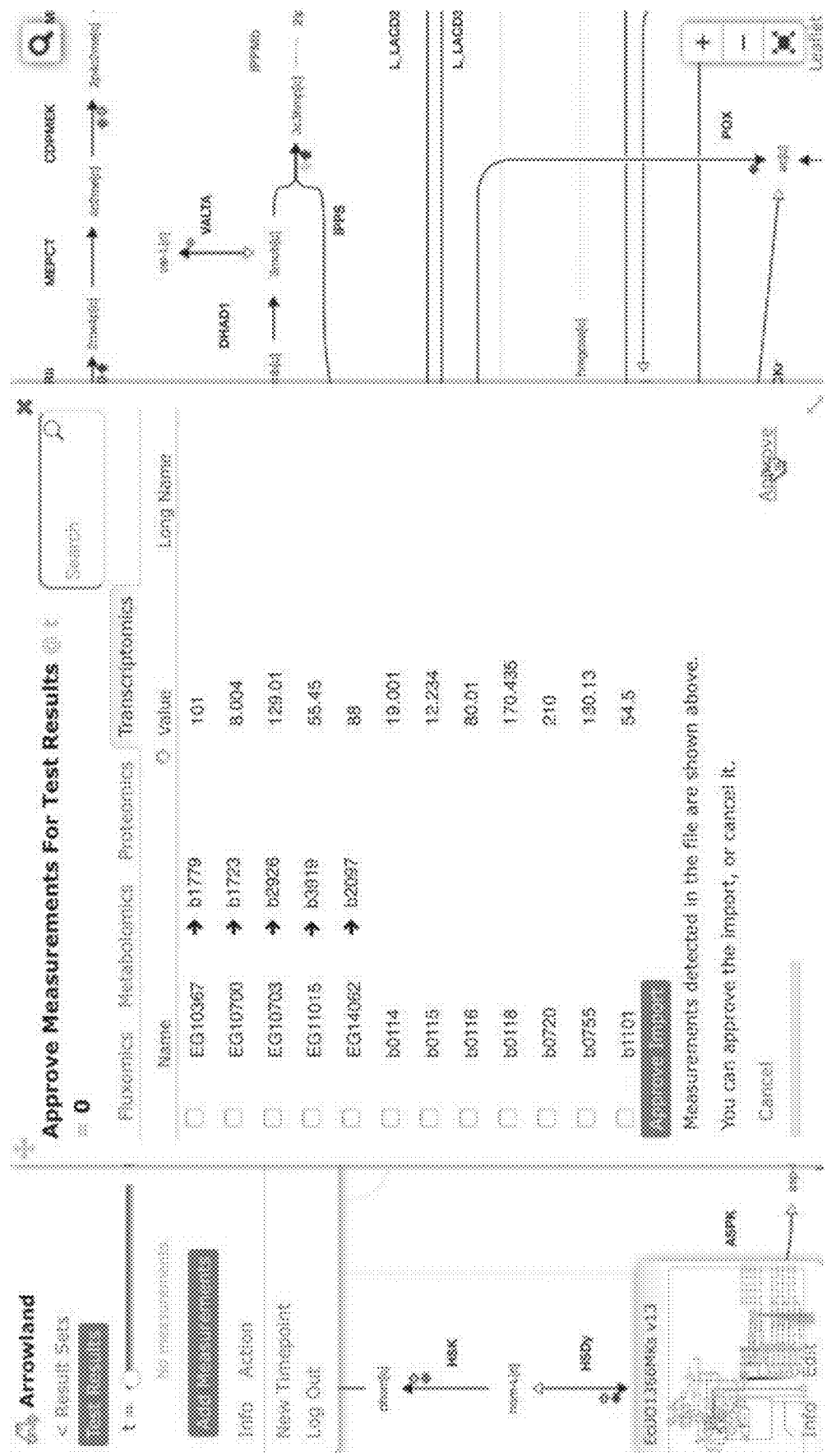
Figure 14U:
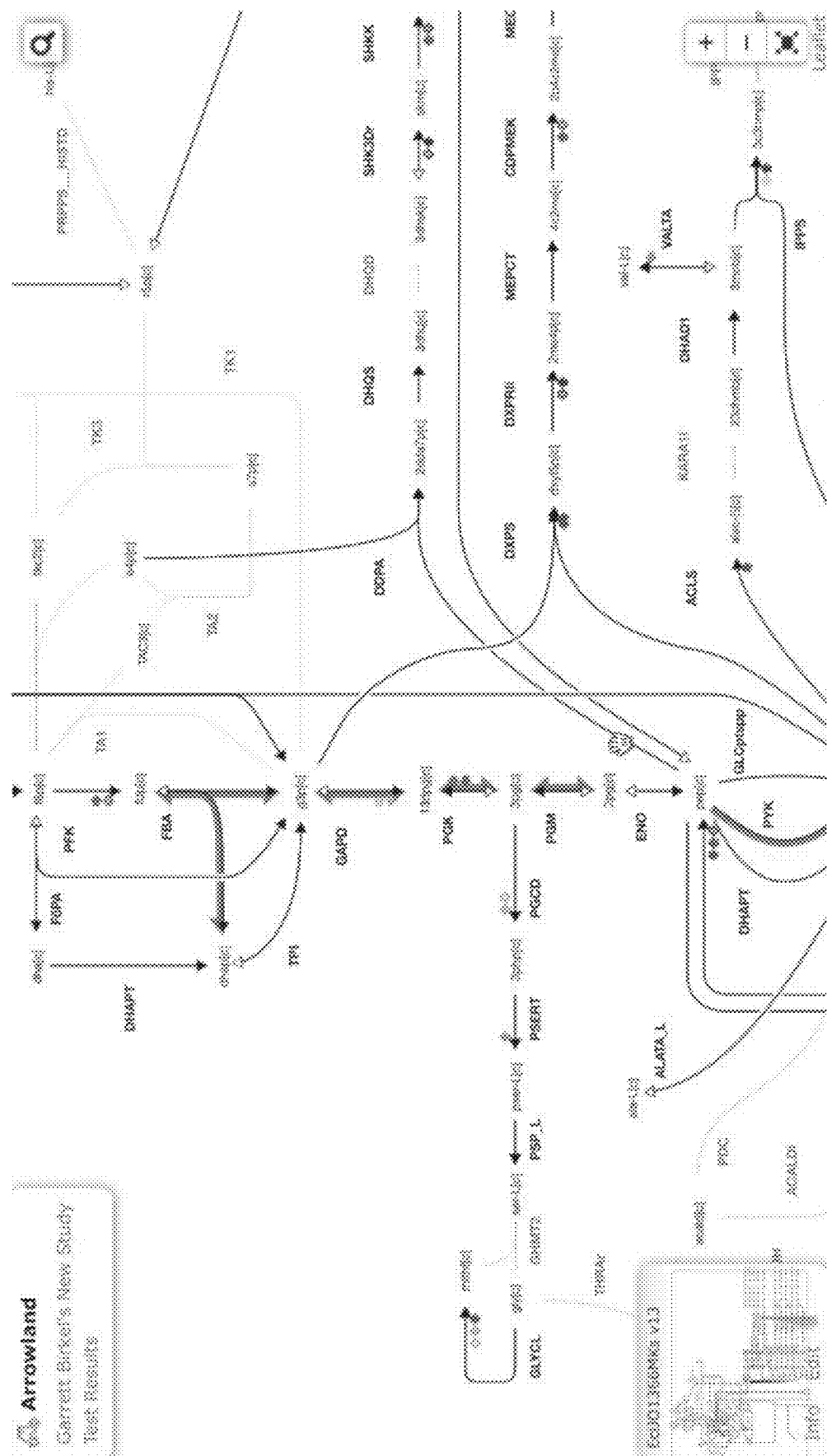
Figure 14V:
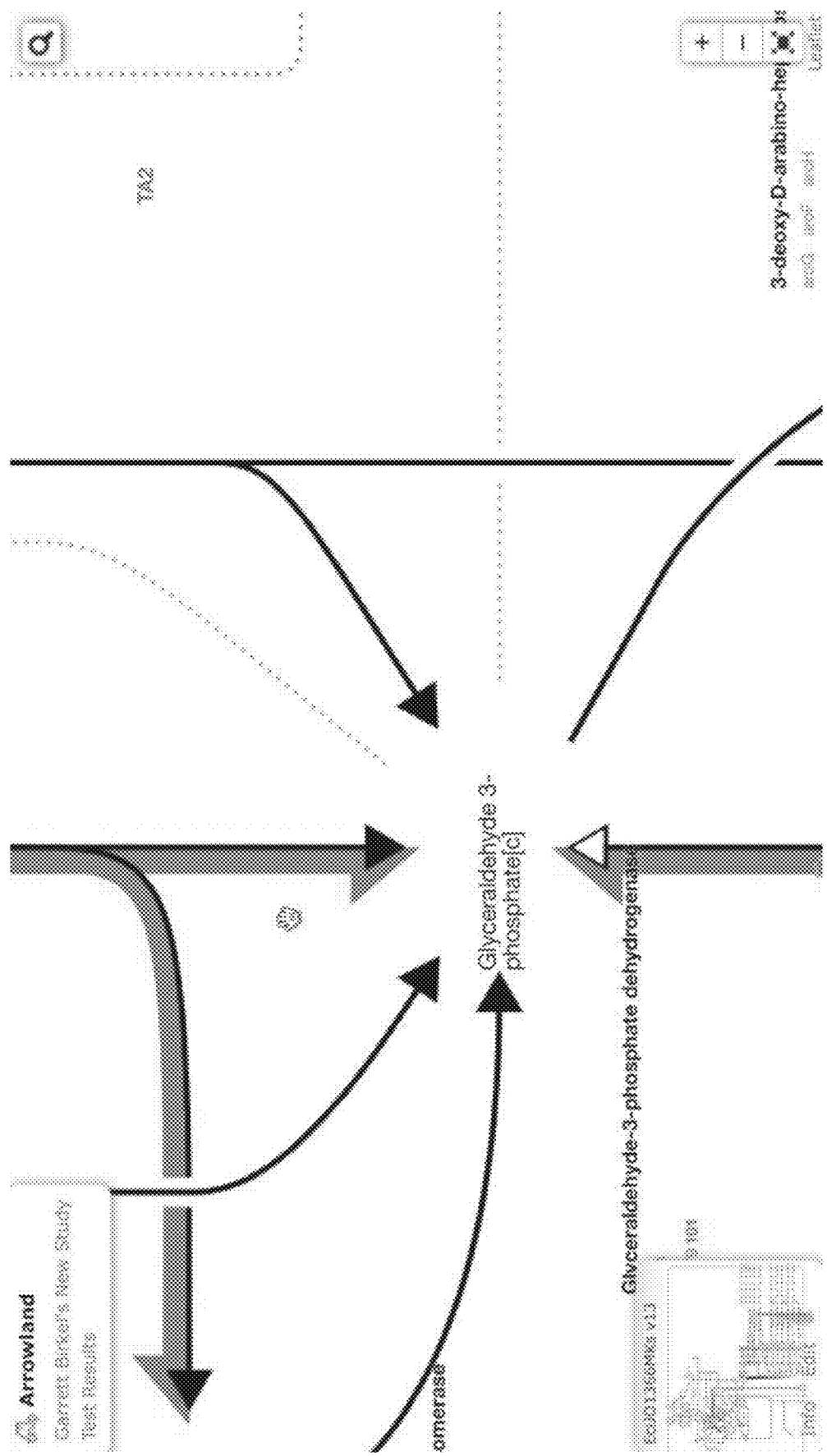
Figure 14W:
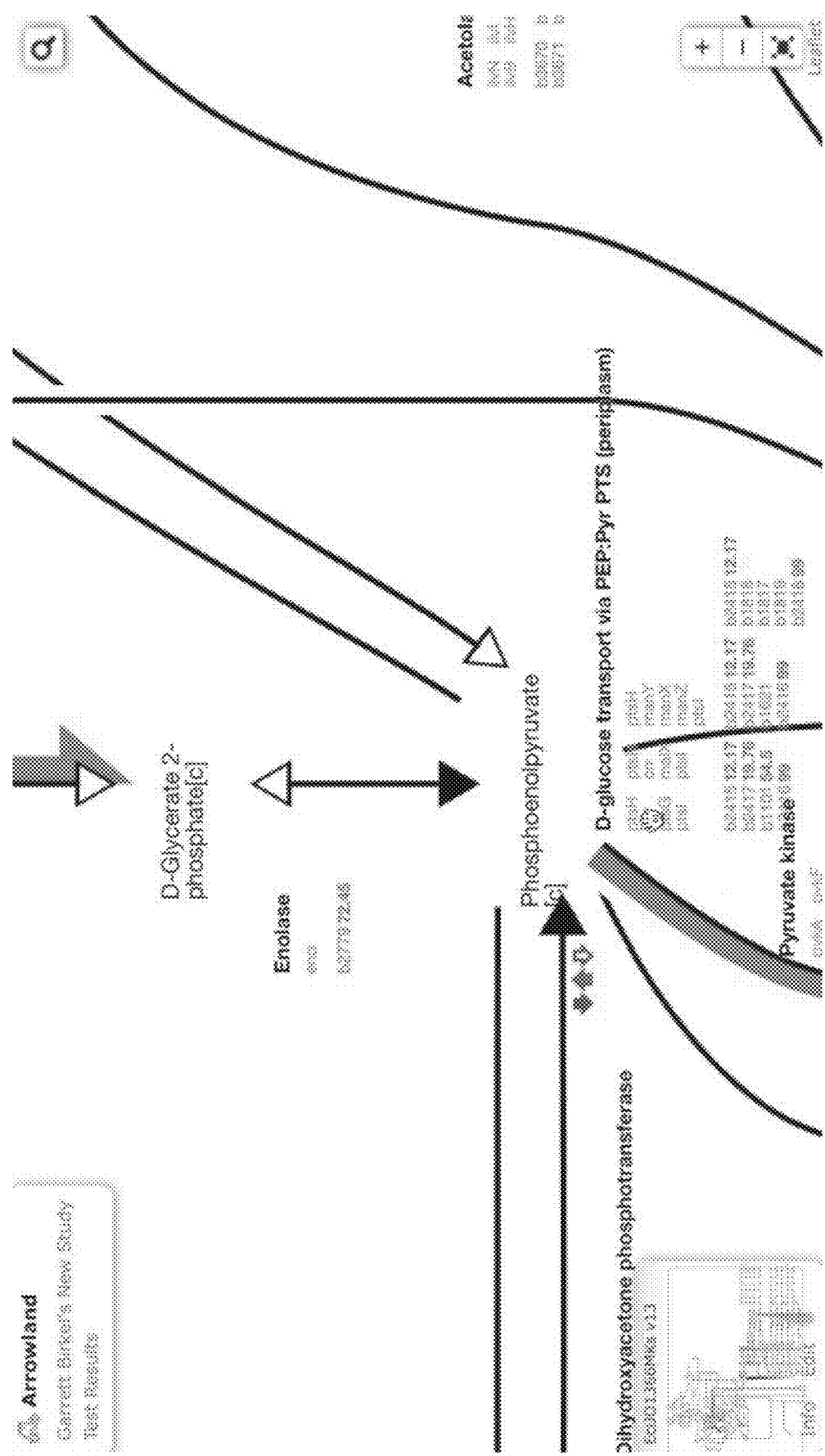
Figure 14X:
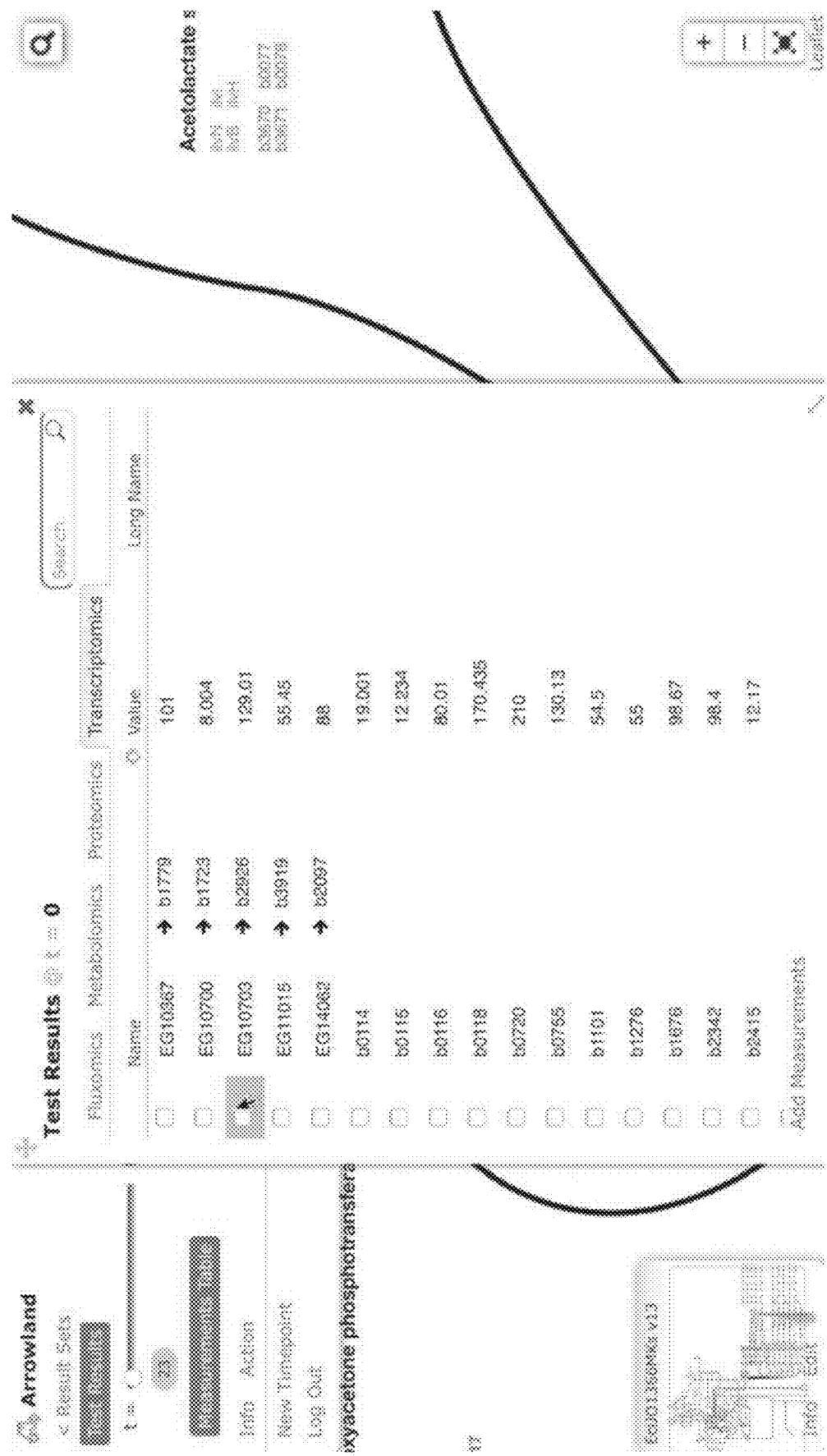
Figure 14Y:
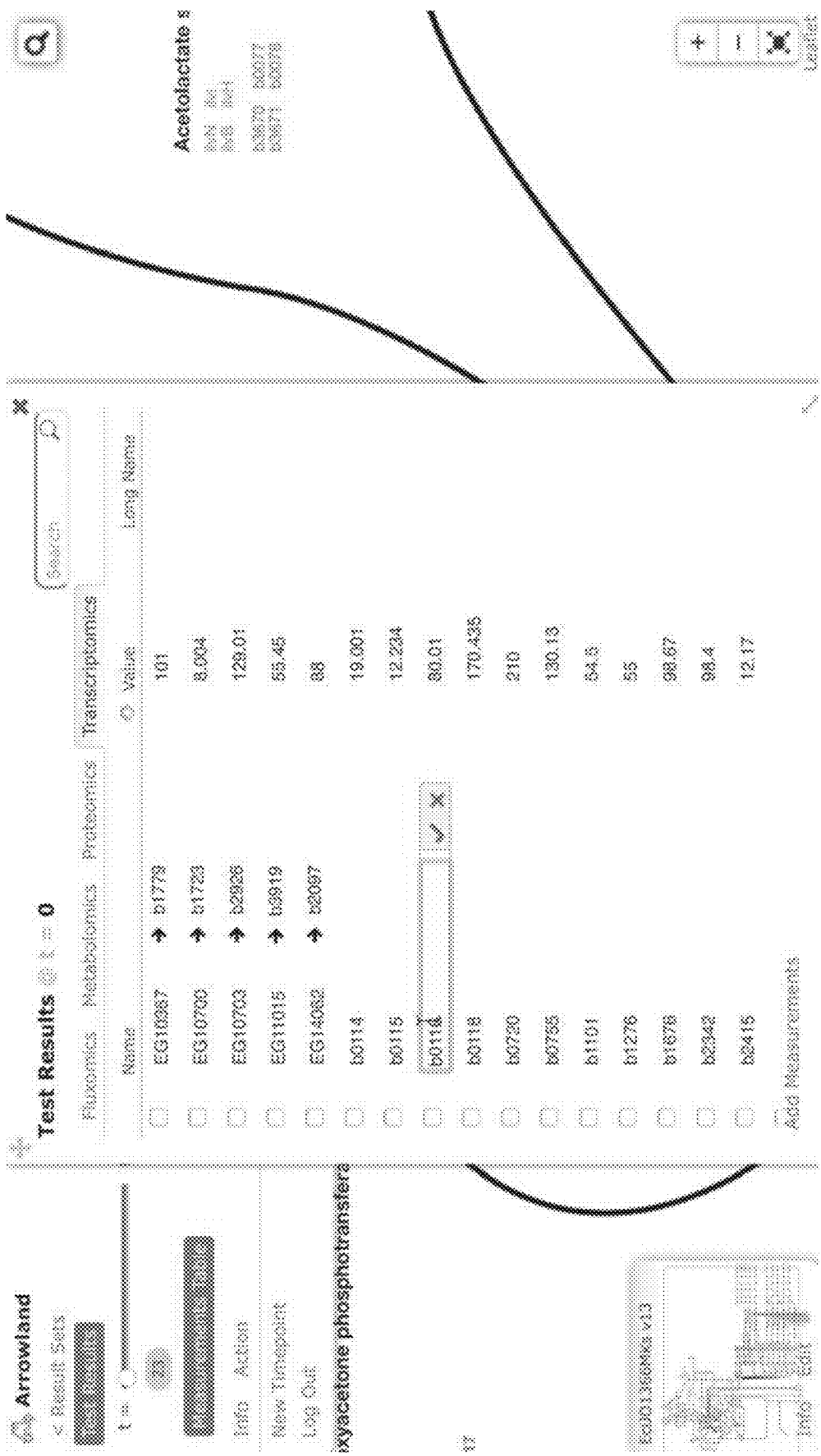

FIGS. 14A-14Y are screenshots showing examples of importing transcriptomics data from a CSV file into Arrowland (public-arrowland.jbei.org/static/main/help/transcriptomics_csv_import.mp4, the content of which is incorporated herein by reference in its entirety). To show transcriptomics in Arrowland, a user may first create a study and a result set inside the study. The user may ensure the study has a default map and a default model assigned to it. The result set is selected and the data is then ready to be imported. The add measurements selection may be made to show the import window and the Drop Zone. The user can drop a CSV file containing transcriptomics, including gene names followed by rpkm values. The gene names may the in the format specified by the model, such as the b number format, or Arrowland may convert the gene names in a different format, such as the ecogene format, into the format specified by the model. The user may input to Arrowland that it should look for transcriptomics measurements. The user can approve the instructions by selecting the "approve" button. If the user wants to see the measurements in tabular format, the user may press the "measurements table". The user can edit the measurement values here or change which Gene the value belongs to.

Figure 15A:
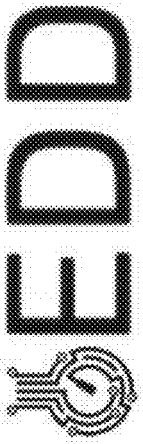
Figure 15B:
Figure 15C:
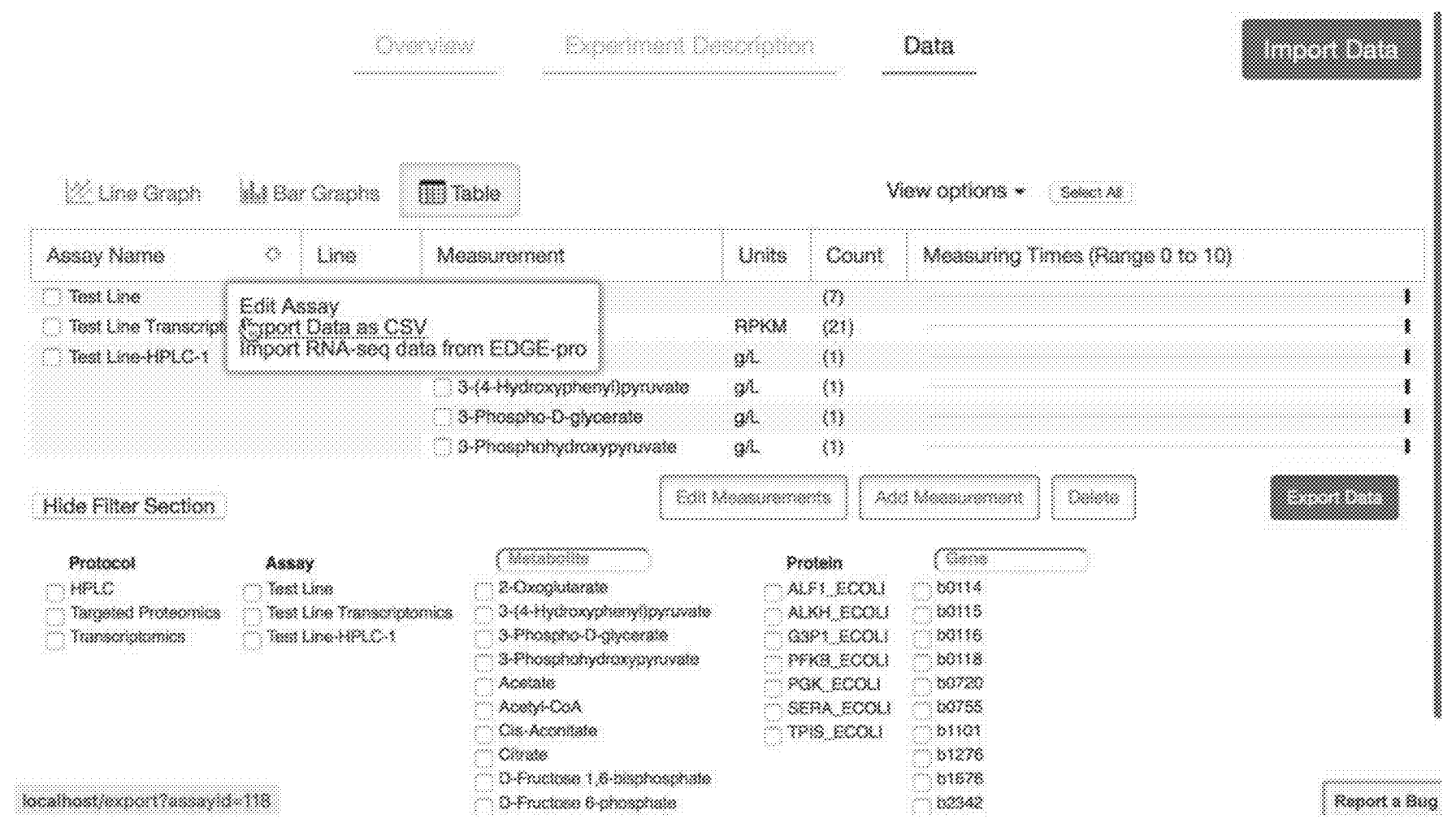
Figure 15D:
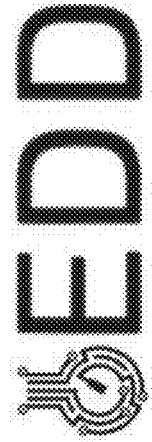
Figure 15E:
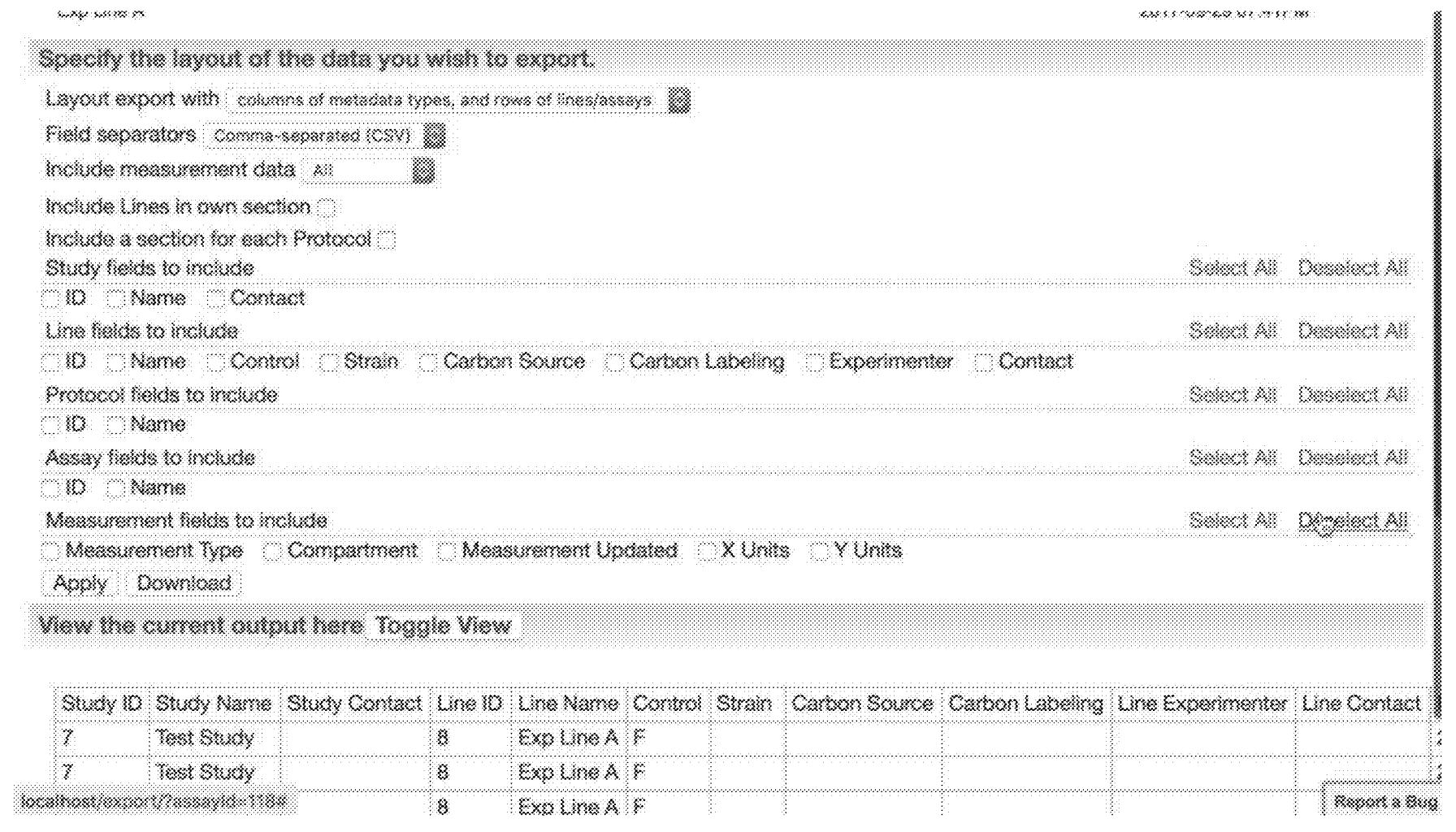
Figure 15F:
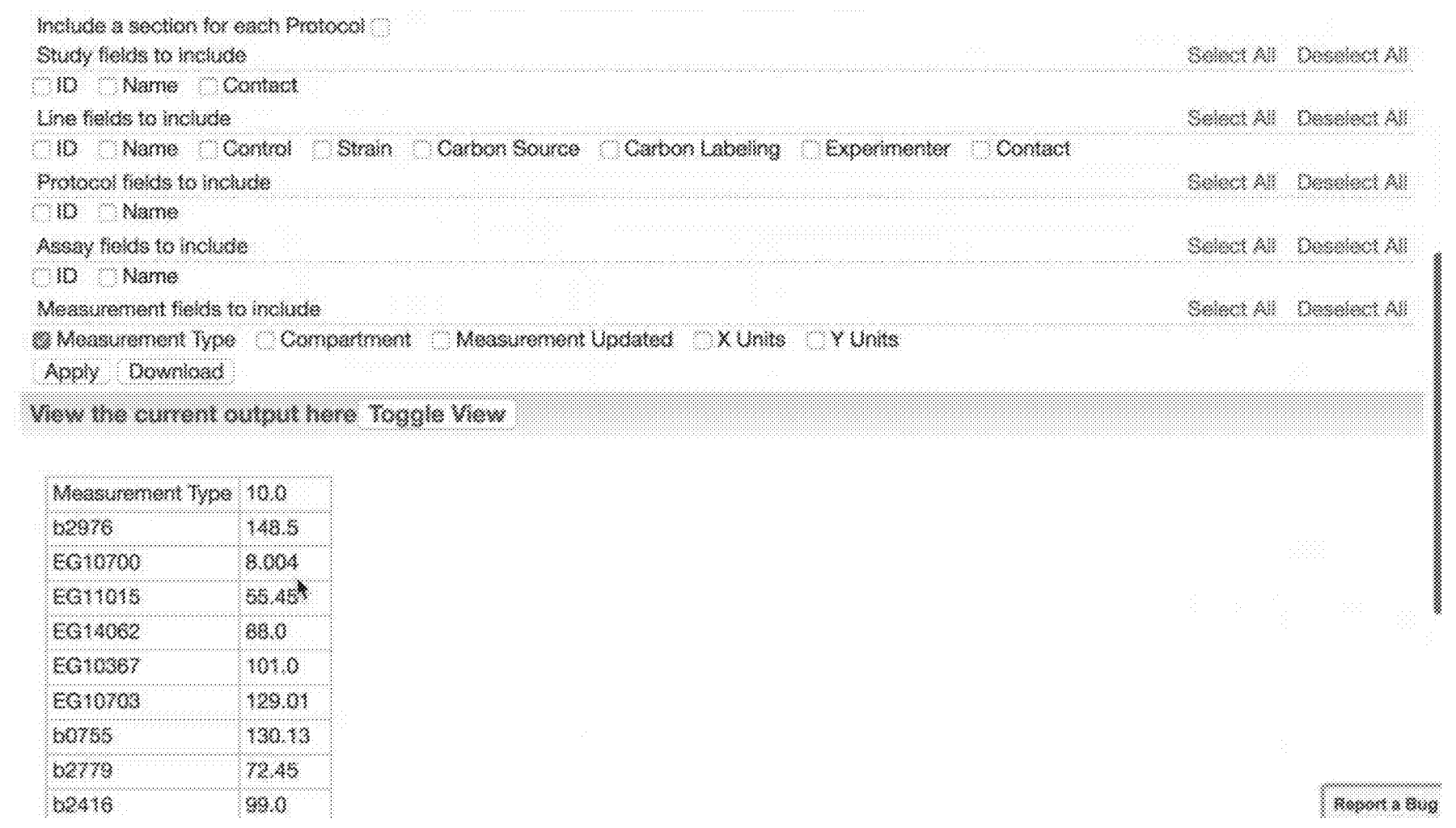
Figure 15G:
Figure 15J:
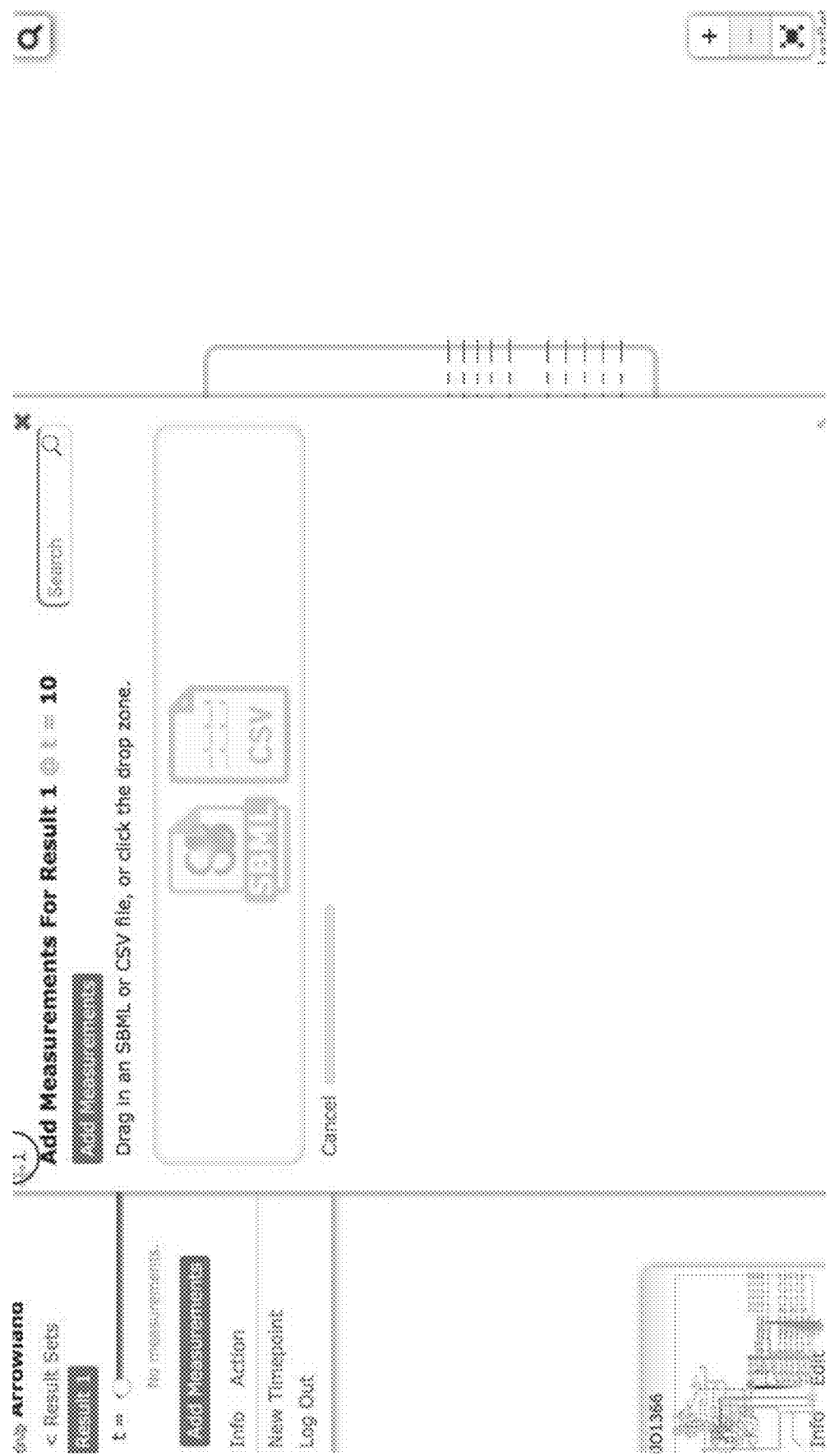
Figure 15K:
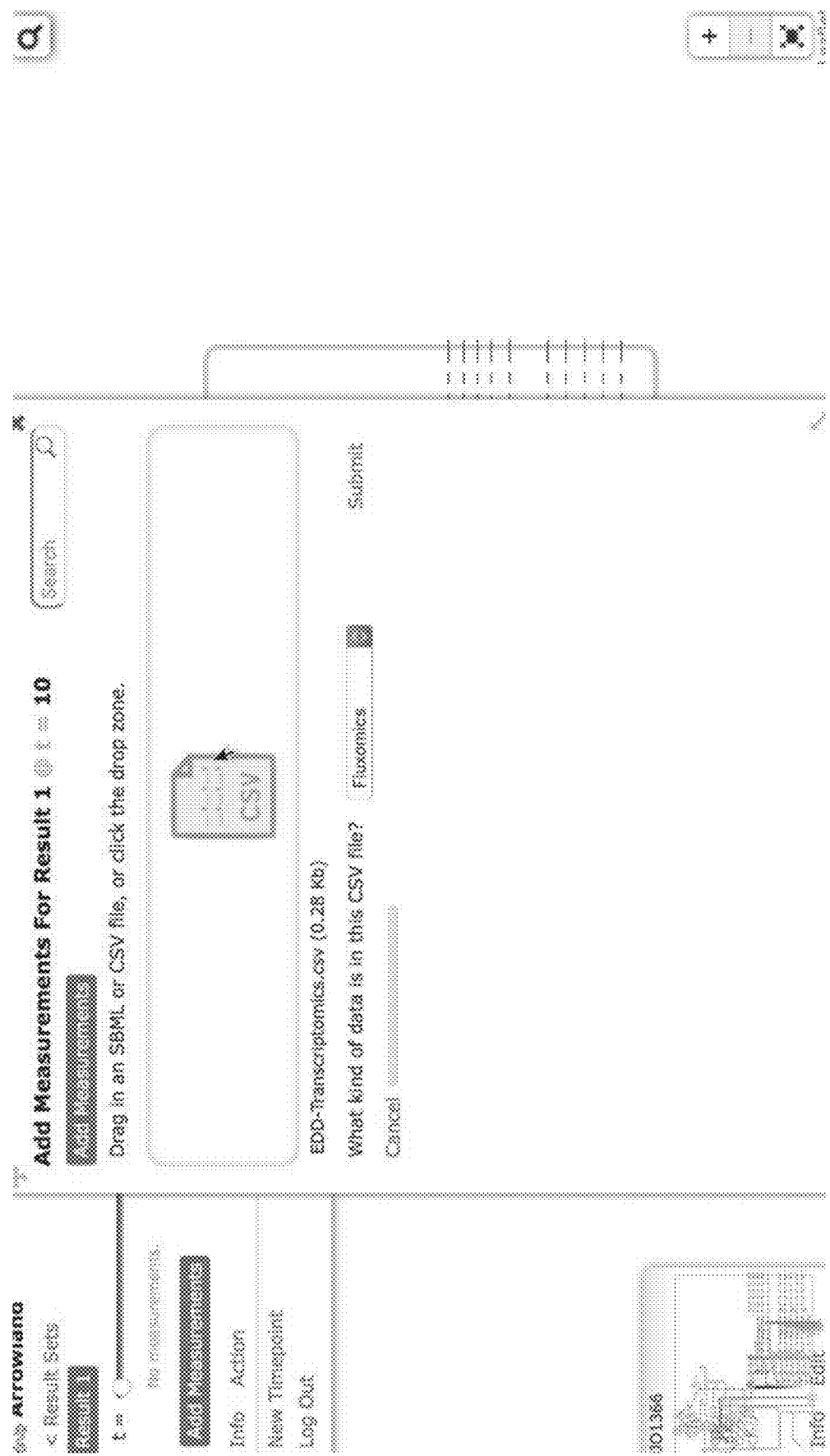
Figure 15M:
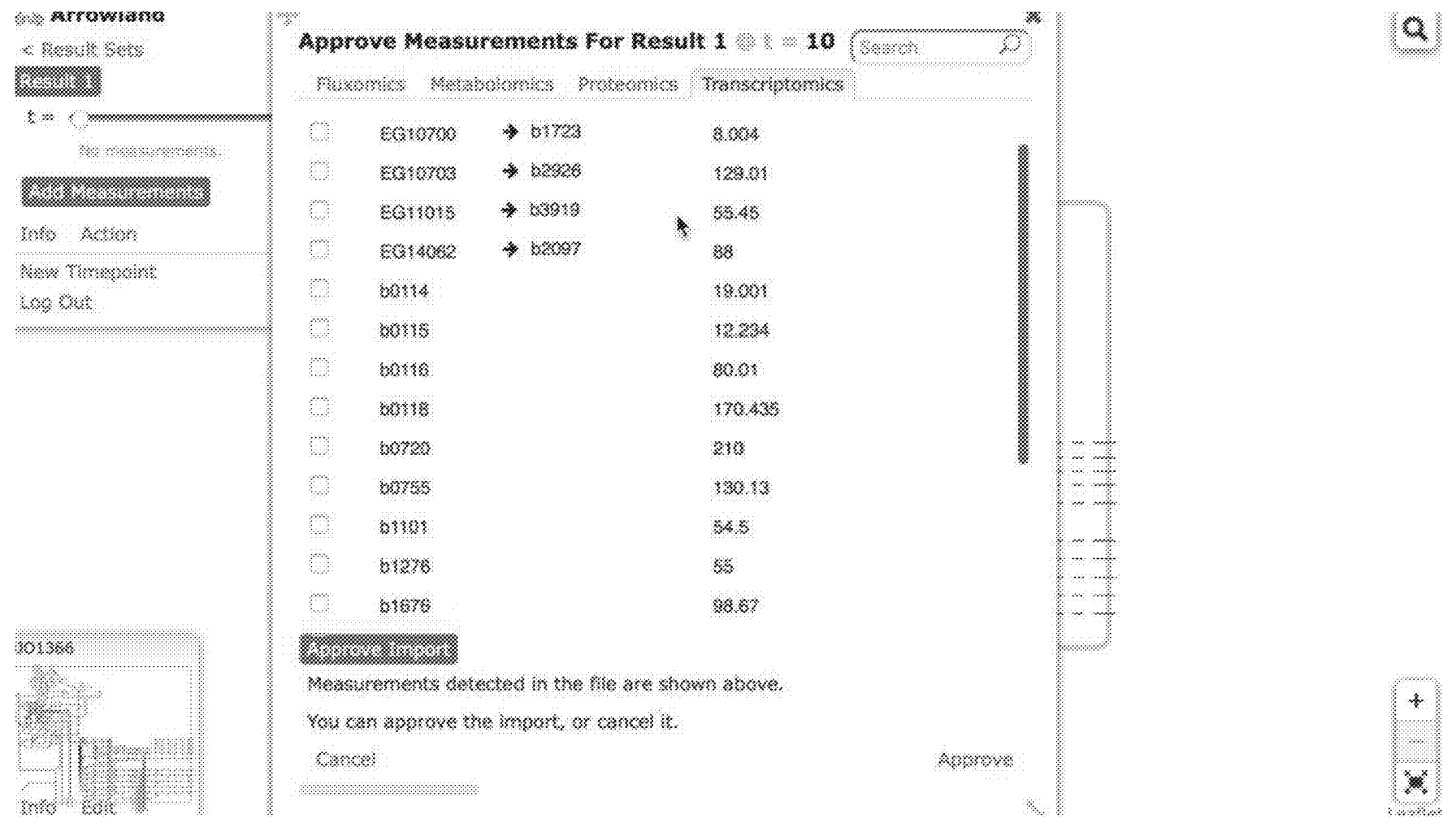
Figure 15L:
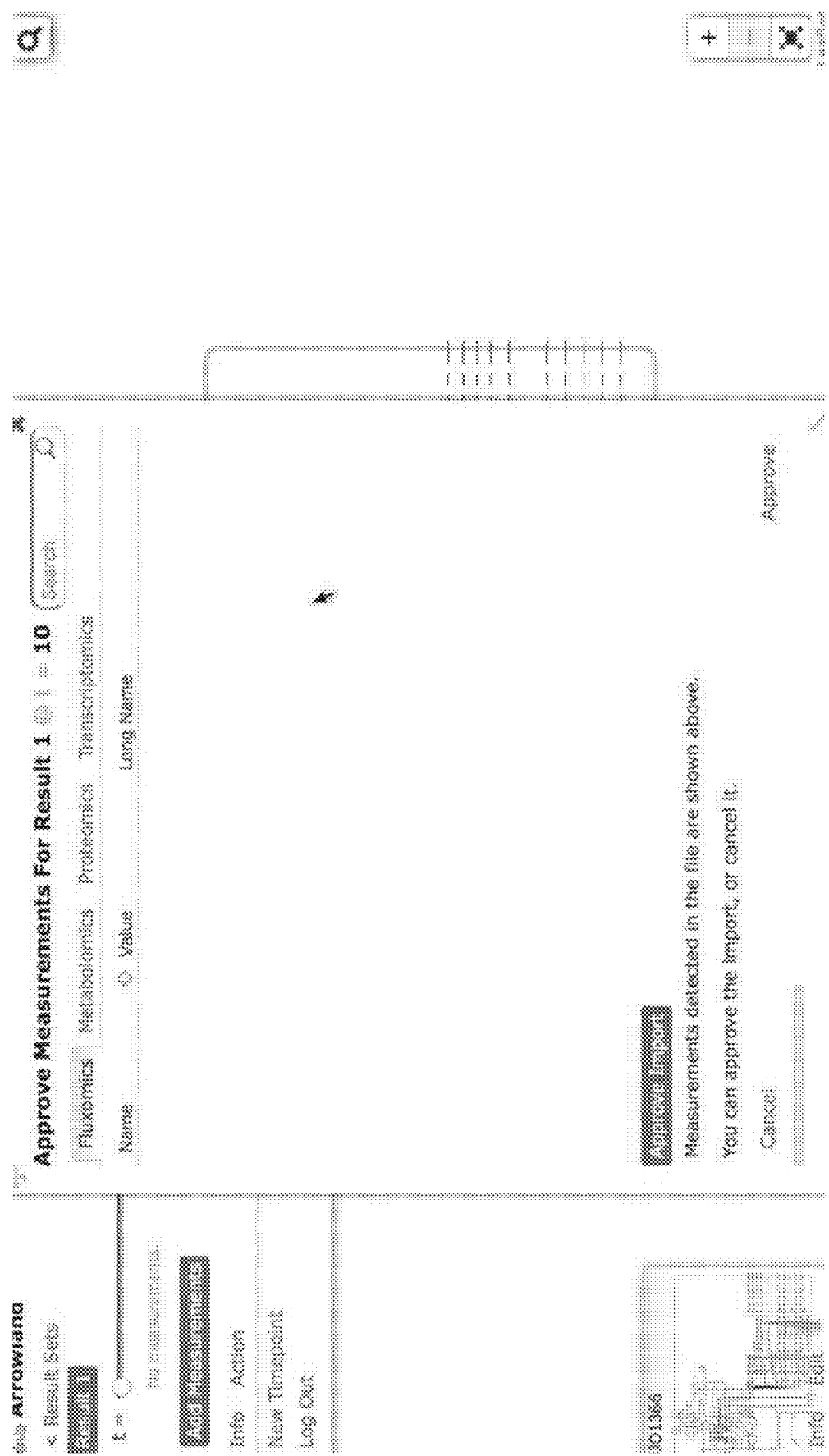
Figure 15N:
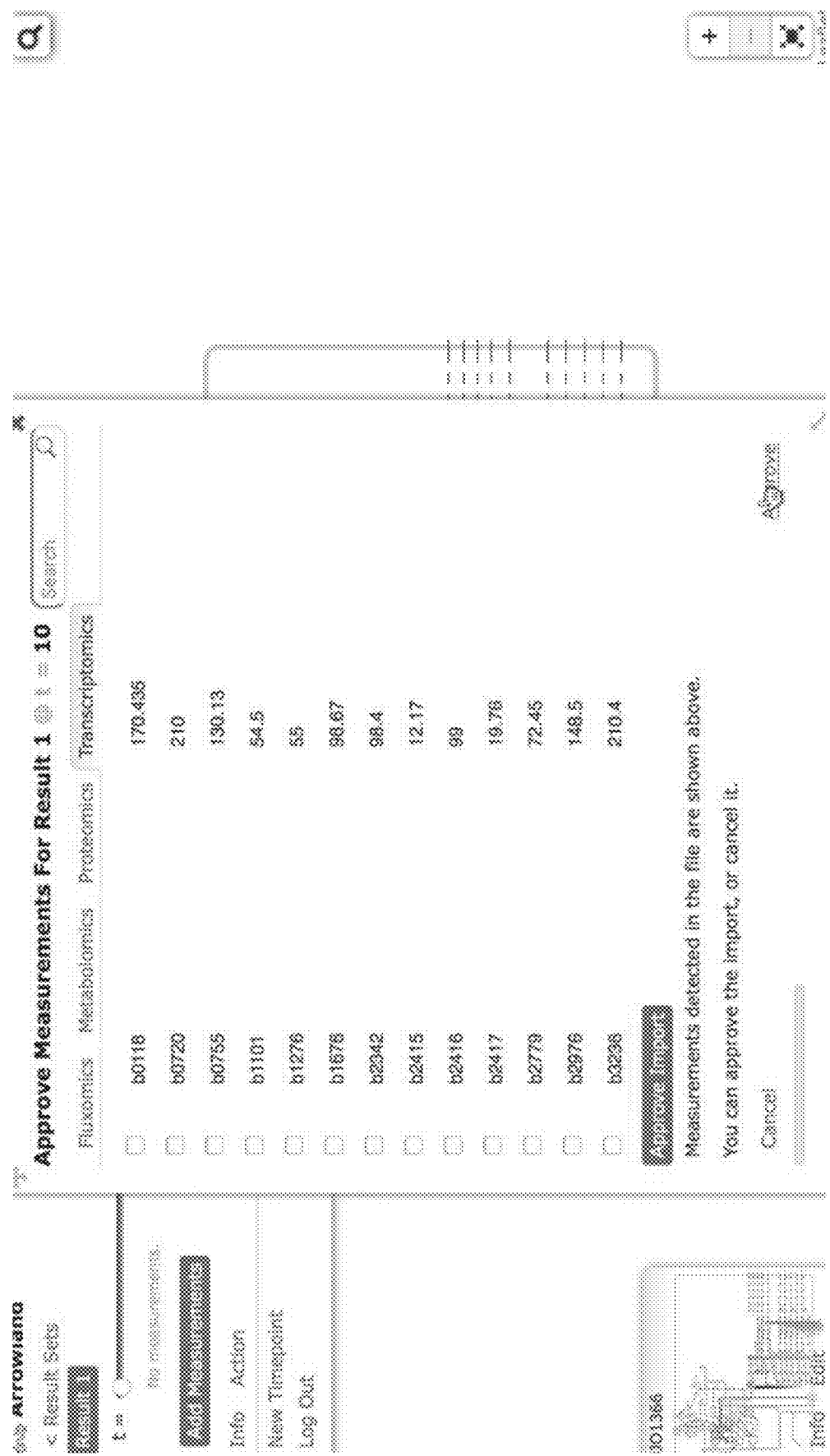
Figure 150:
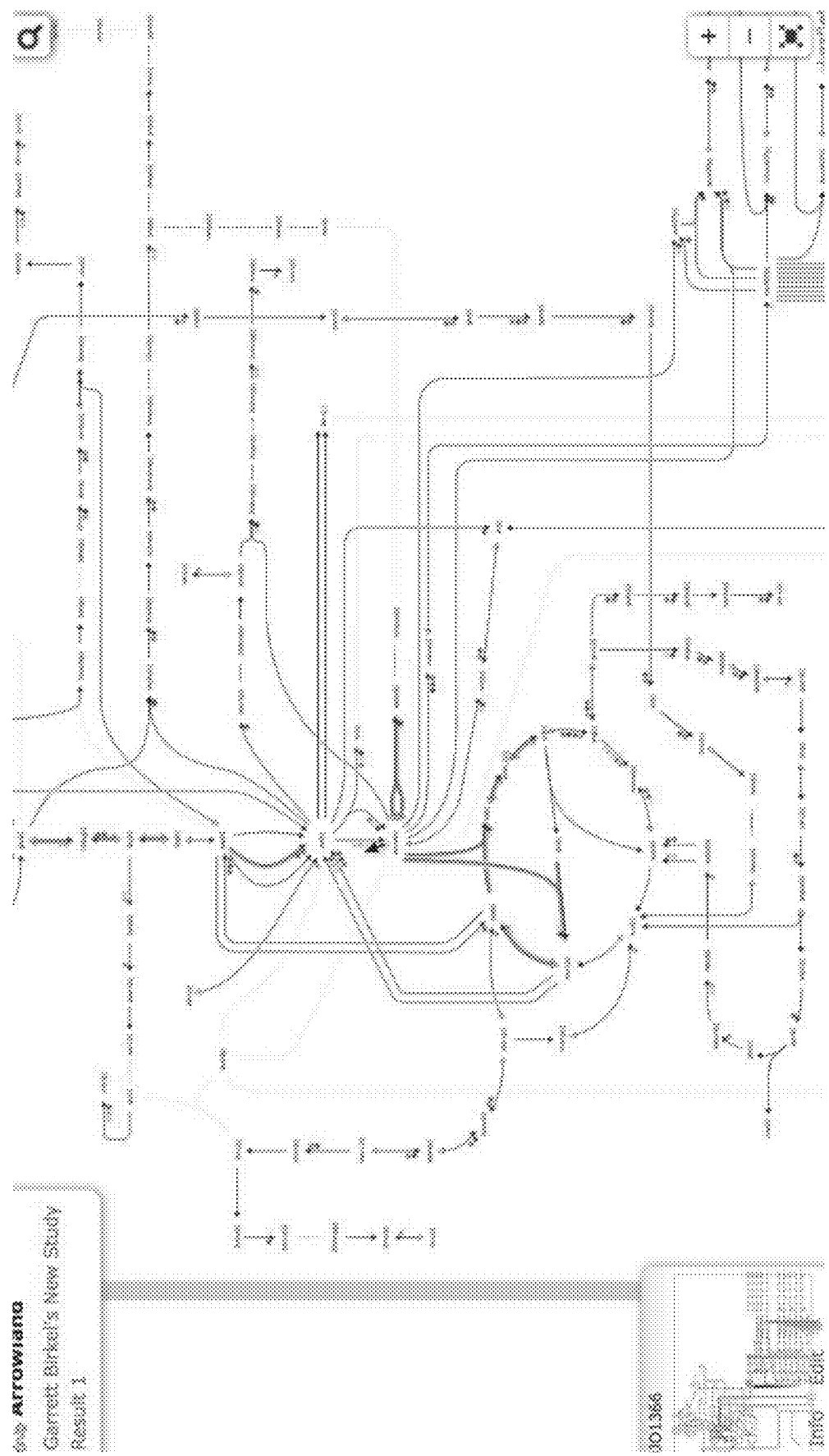
Figure 15P:
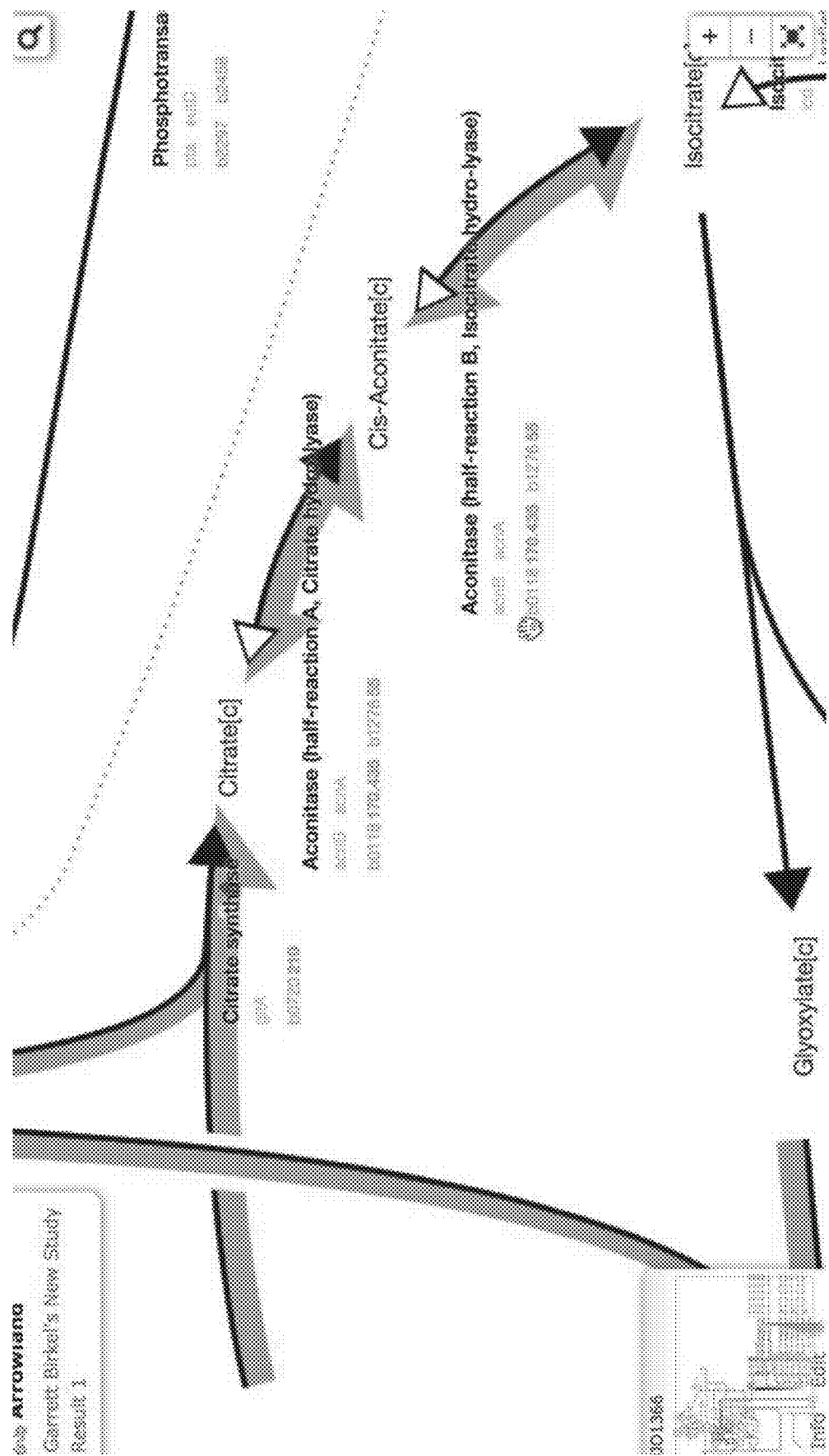

FIGS. 15A-15P are screenshots showing exemplary importing transcriptomics data from the Experiment Data Depot into Arrowland (public-arrowland.jbei.org/static/main/help/transcriptomics_edd_import.mp4, the content of which is incorporated herein by reference in its entirety). To get transcriptomics data from EDD into Arrowland, a user can first go to his or her study in EDD, view the data in table mode, and find the essay containing the transcriptomics data to export. The user can choose to export data as CSV. On the export page, deselect all the fields, leaving only the measurement type field selected. The user can apply the settings to confirm that the export will contain only gene names and values. Then the user can download the data. The user can then go to the study of interest in Arrowland which may have a default map and model selected. The user can choose the results that the data from EDD will be imported into and the time point in the results set. The user can add data from experiment data depot into Arrowland by dragging the CSV file into the drop zone. Any reaction that has transcriptomics data may gain a halo on one side. The user can zoom in to see specific proteomics values of interest.

Figure 16B:
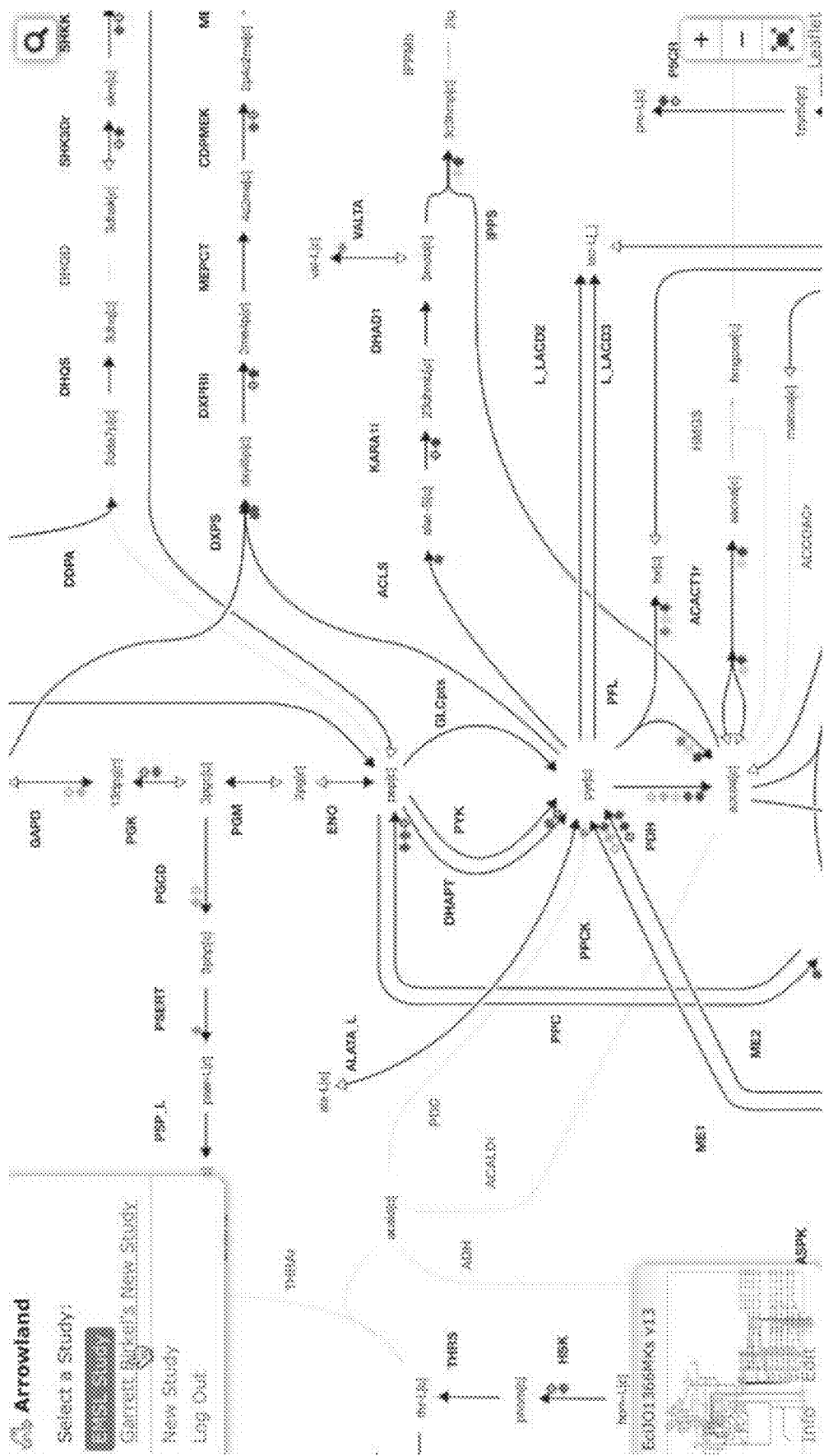
Figure 16C:
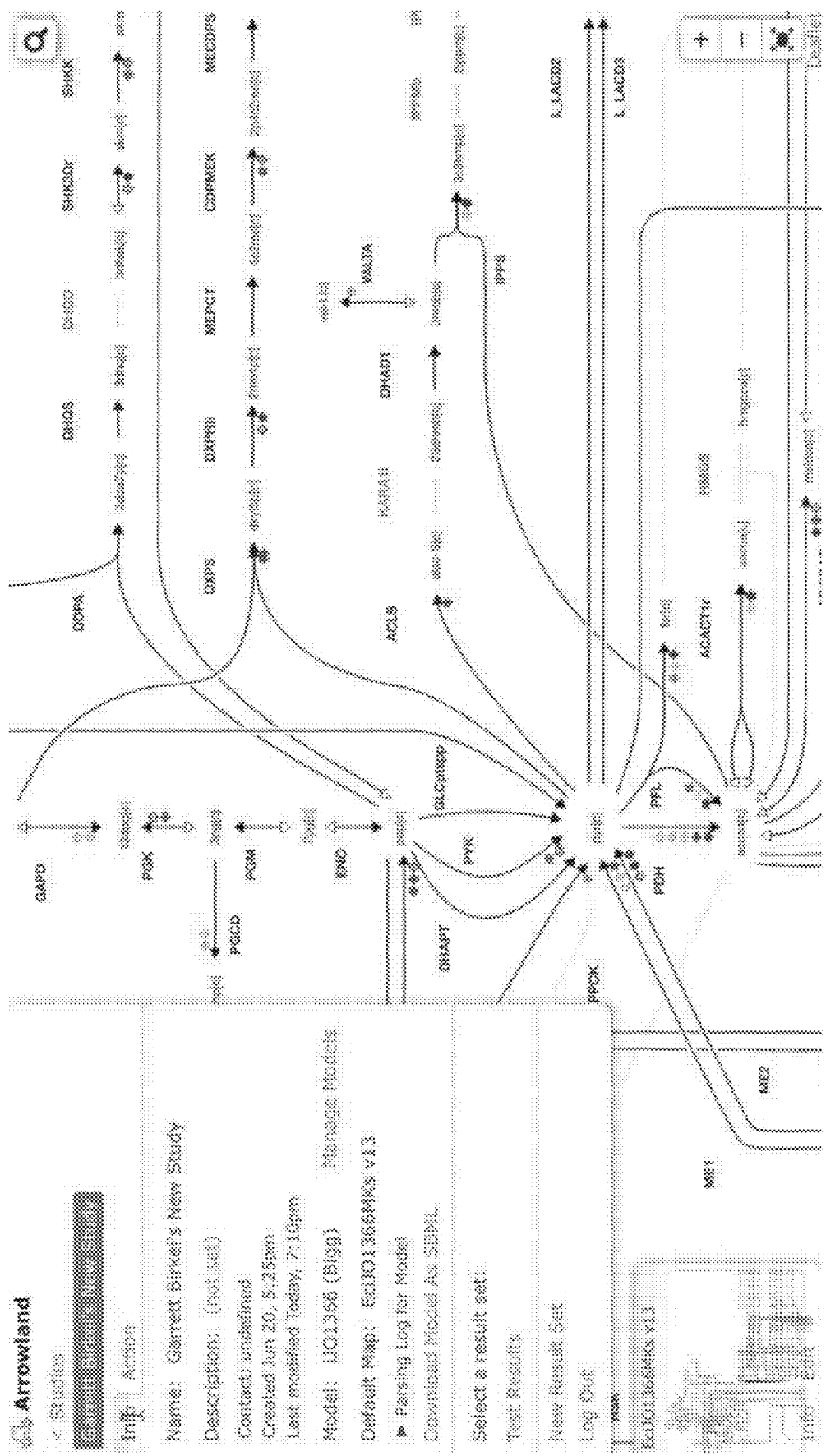
Figure 16D:
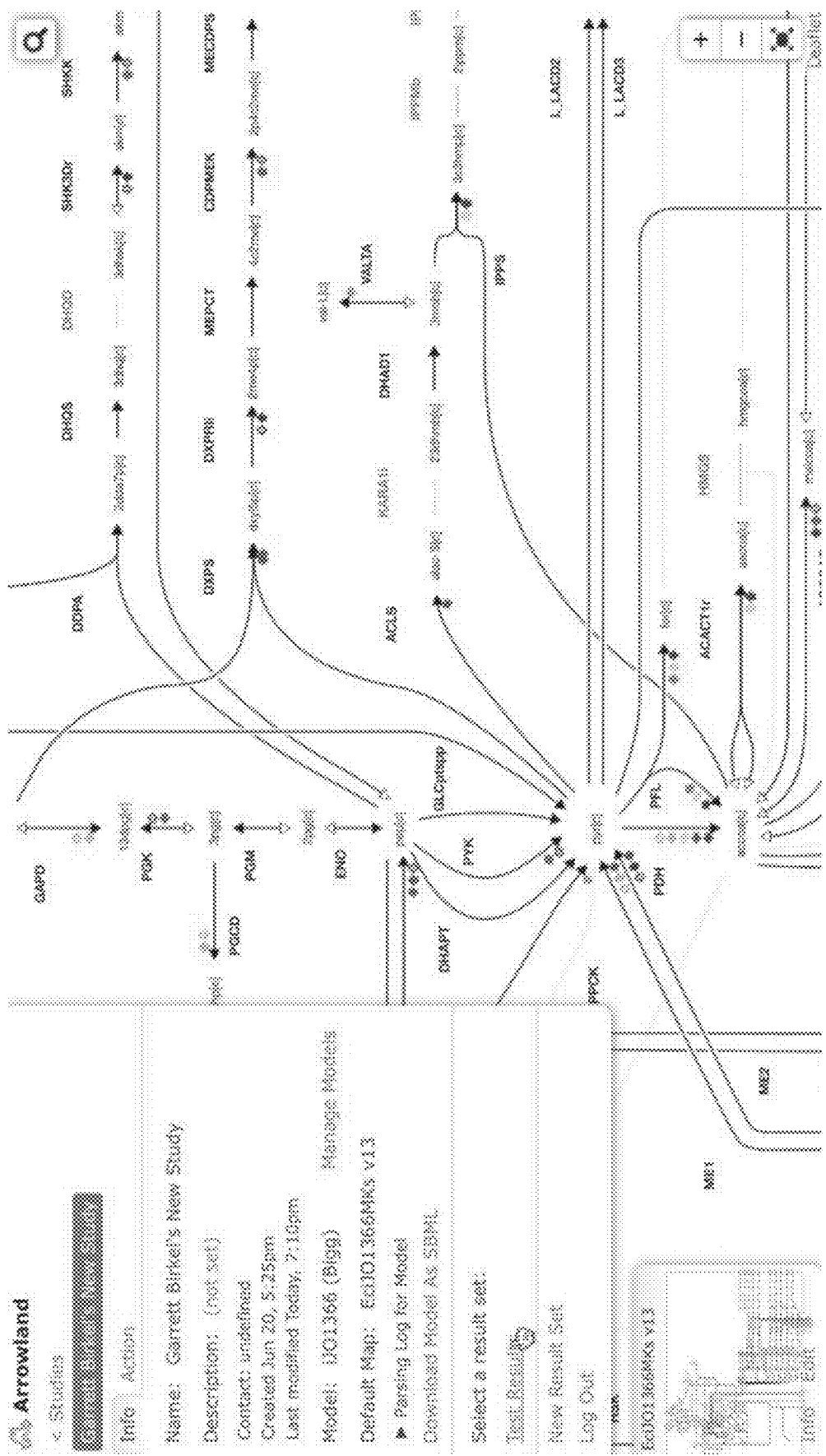
Figure 16E:
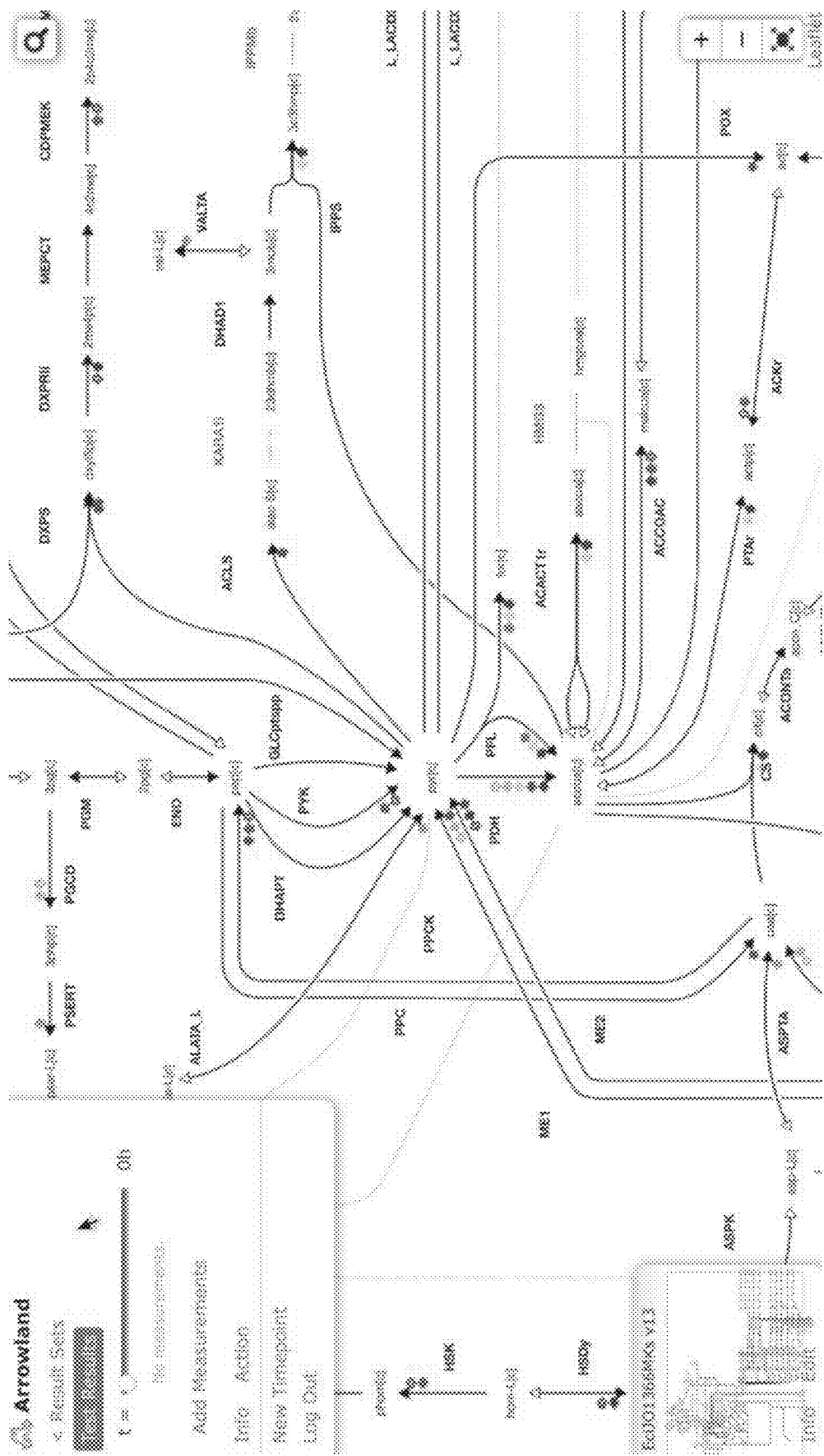
Figure 16F:
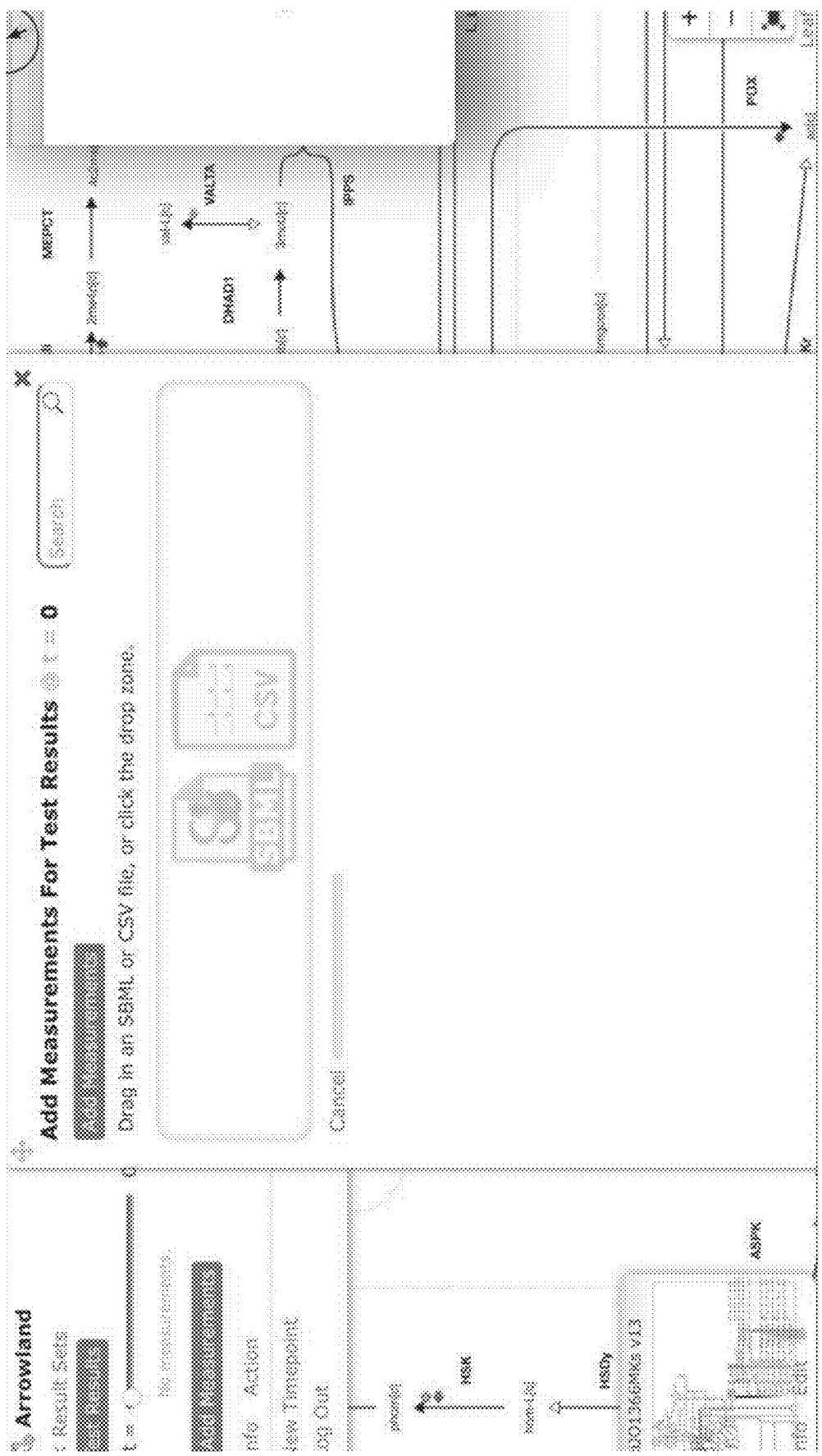
Figure 16G:
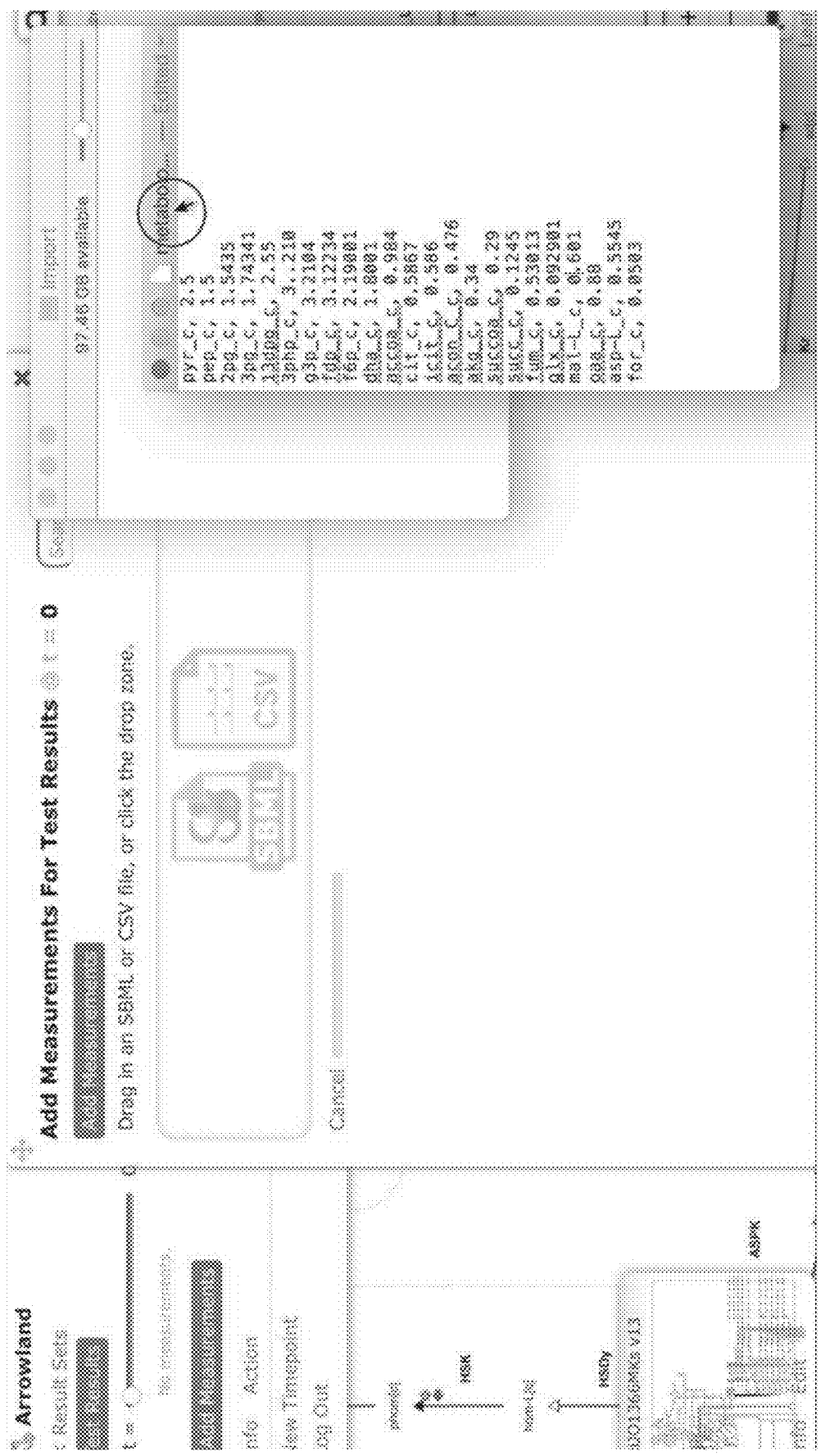
Figure 16H:
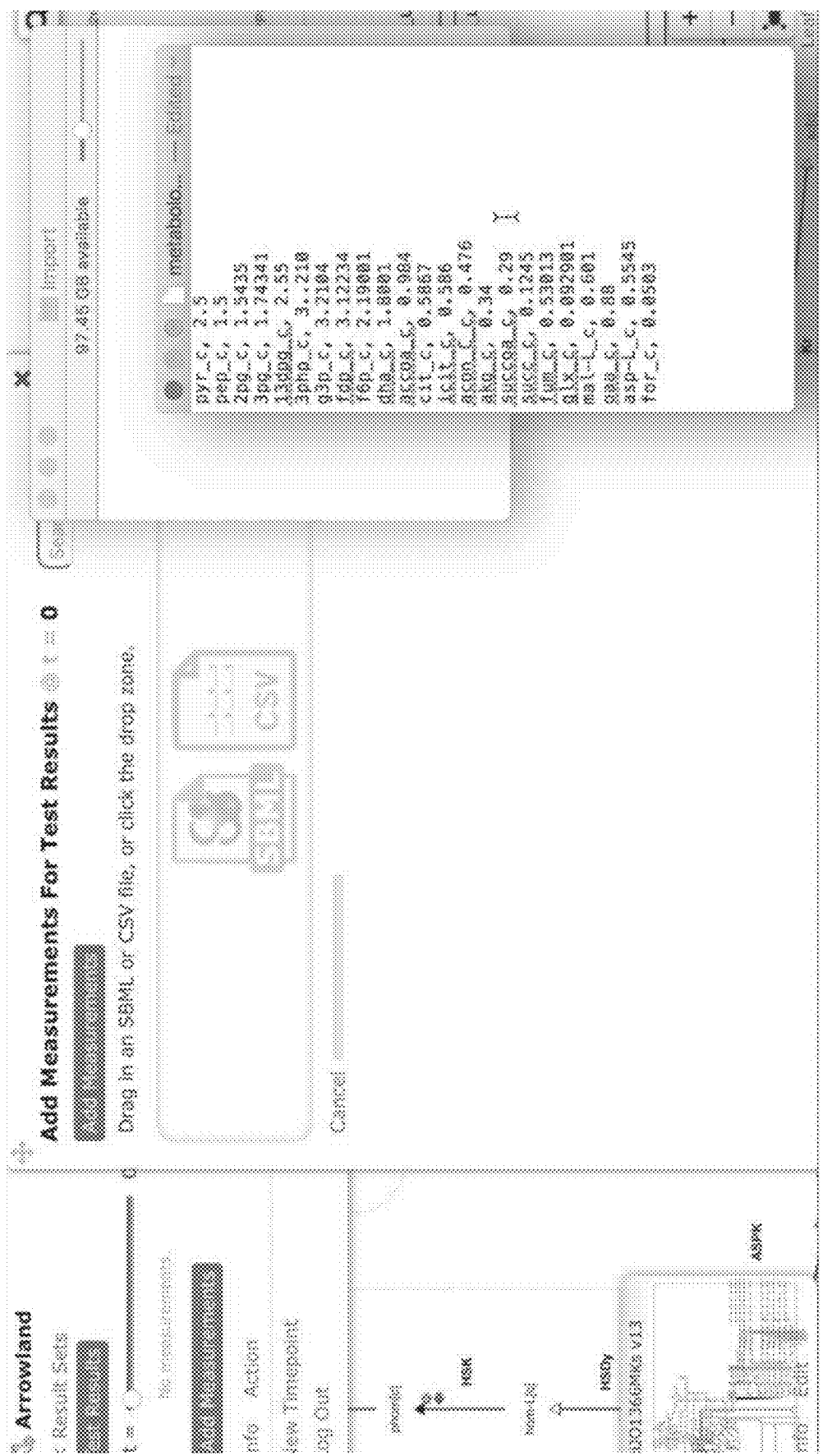
Figure 16I:
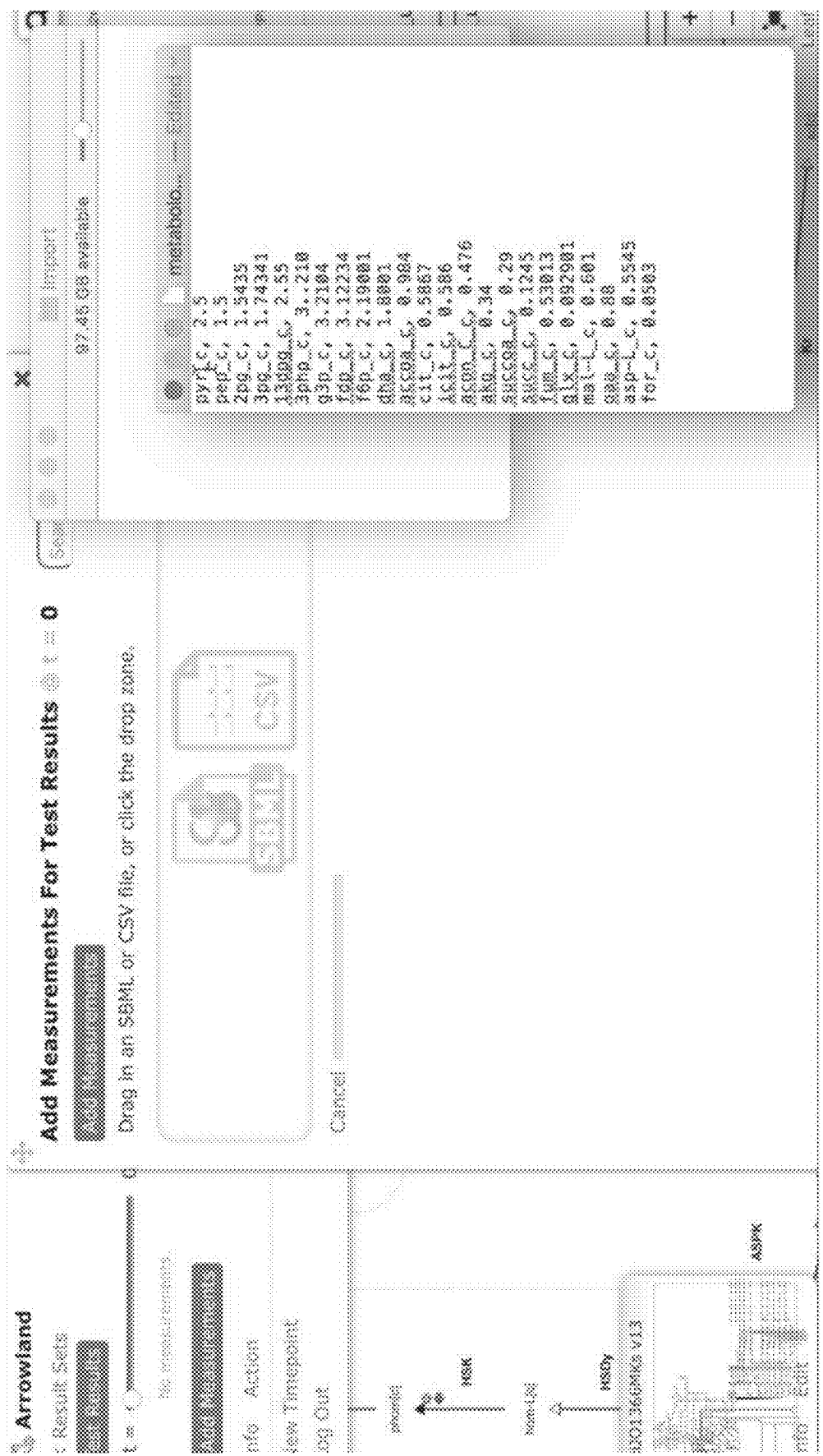
Figure 16J:
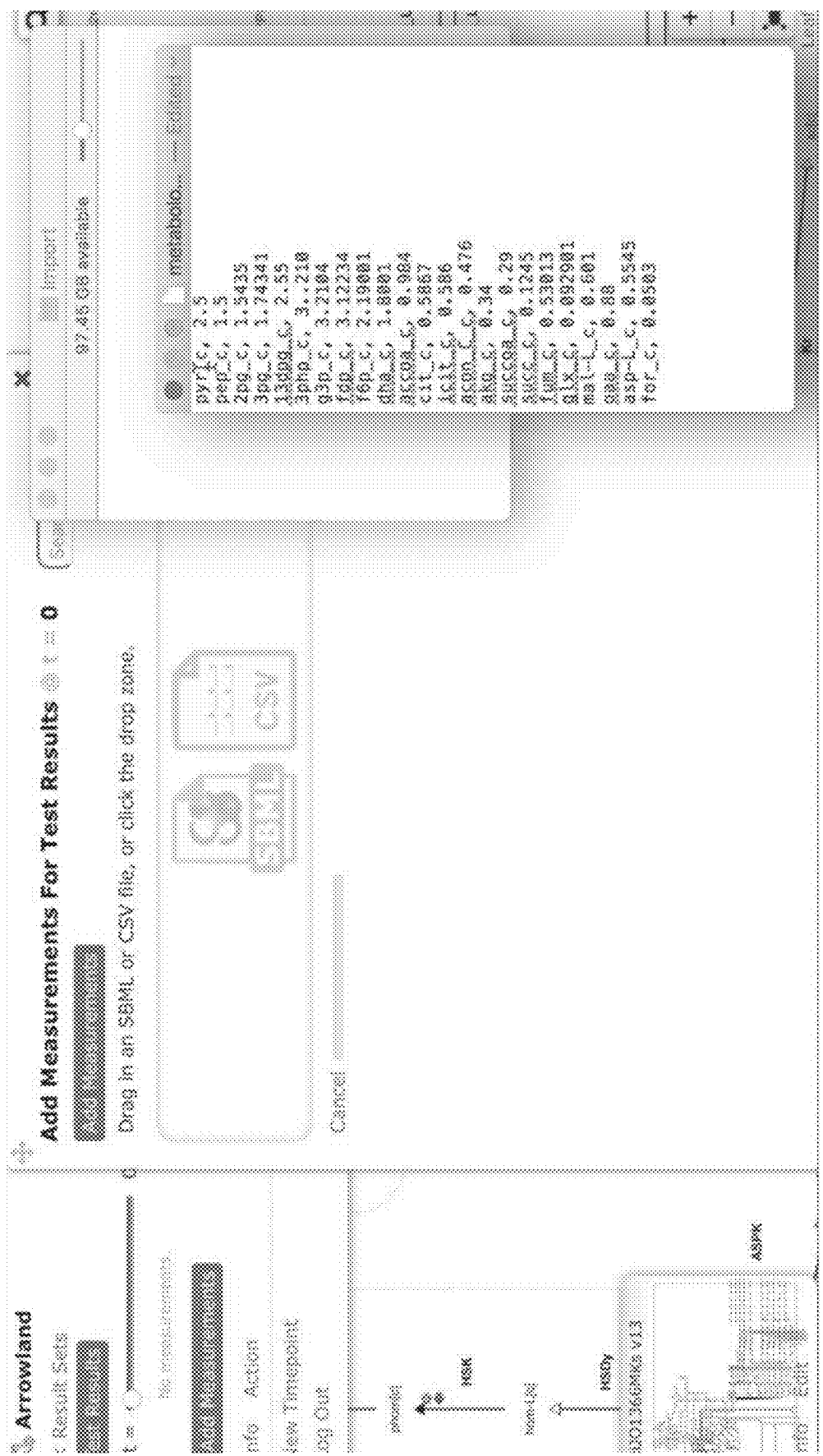
Figure 16K:
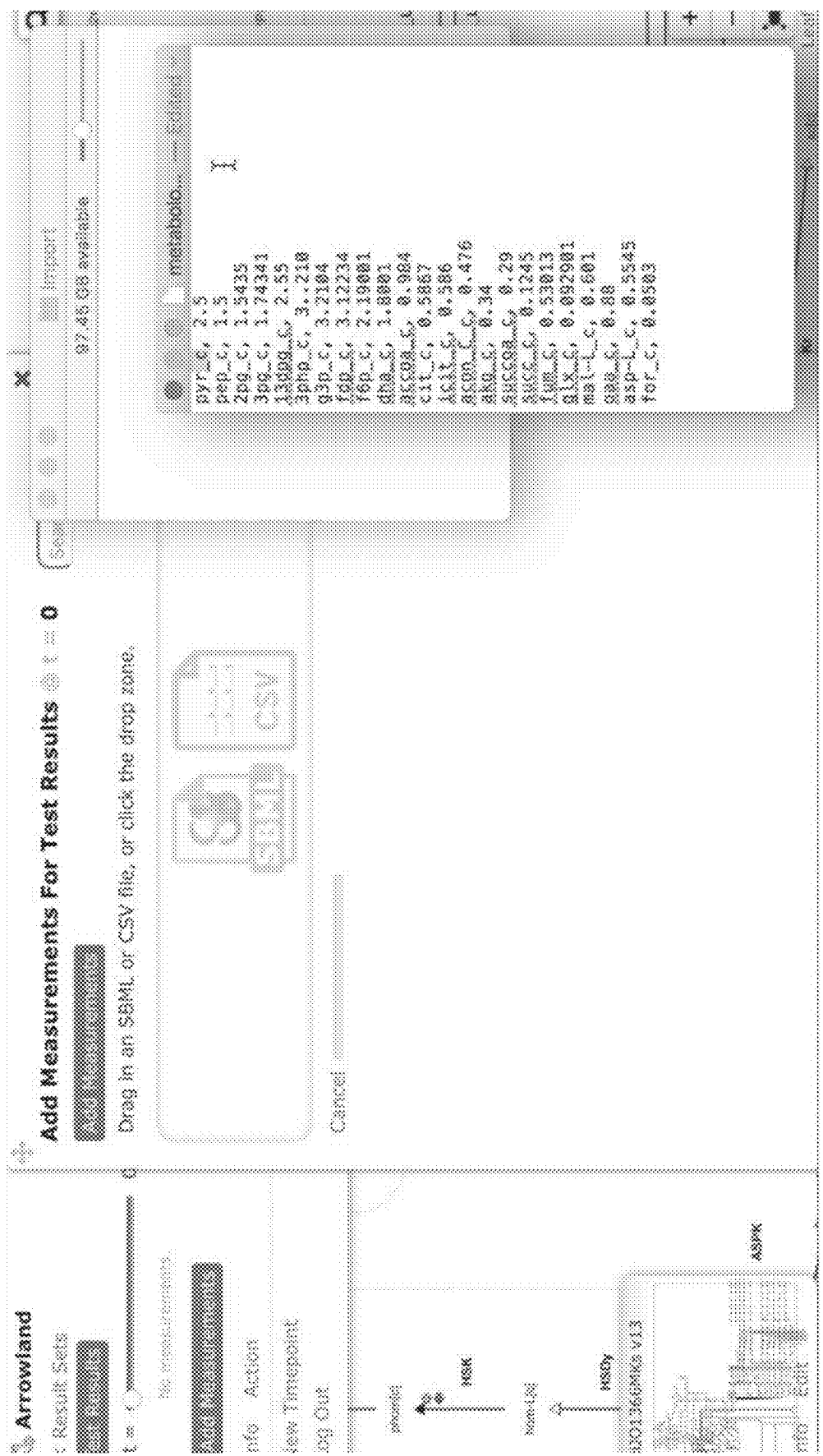
Figure 16L:
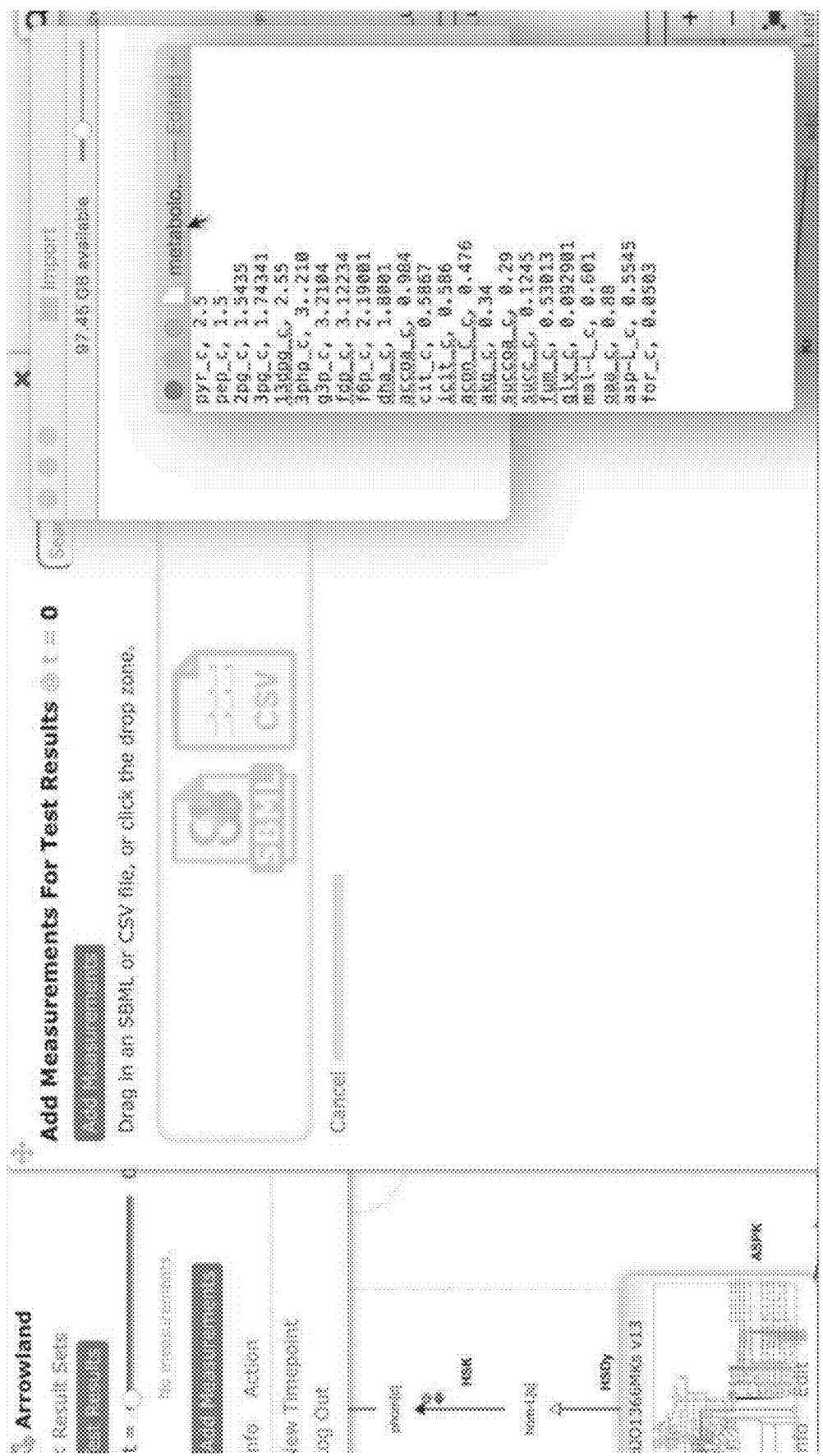
Figure 16M:
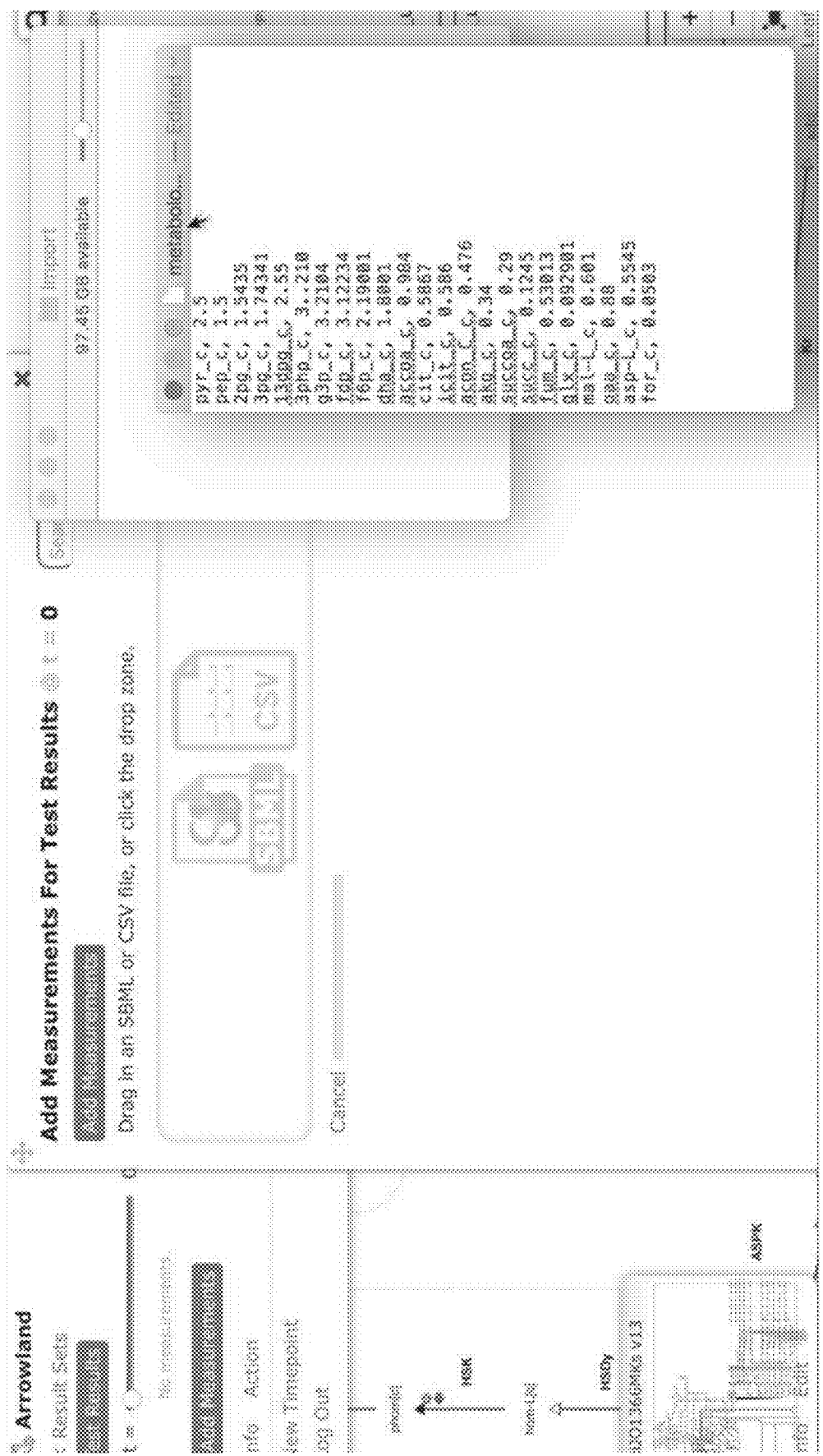
Figure 16N:
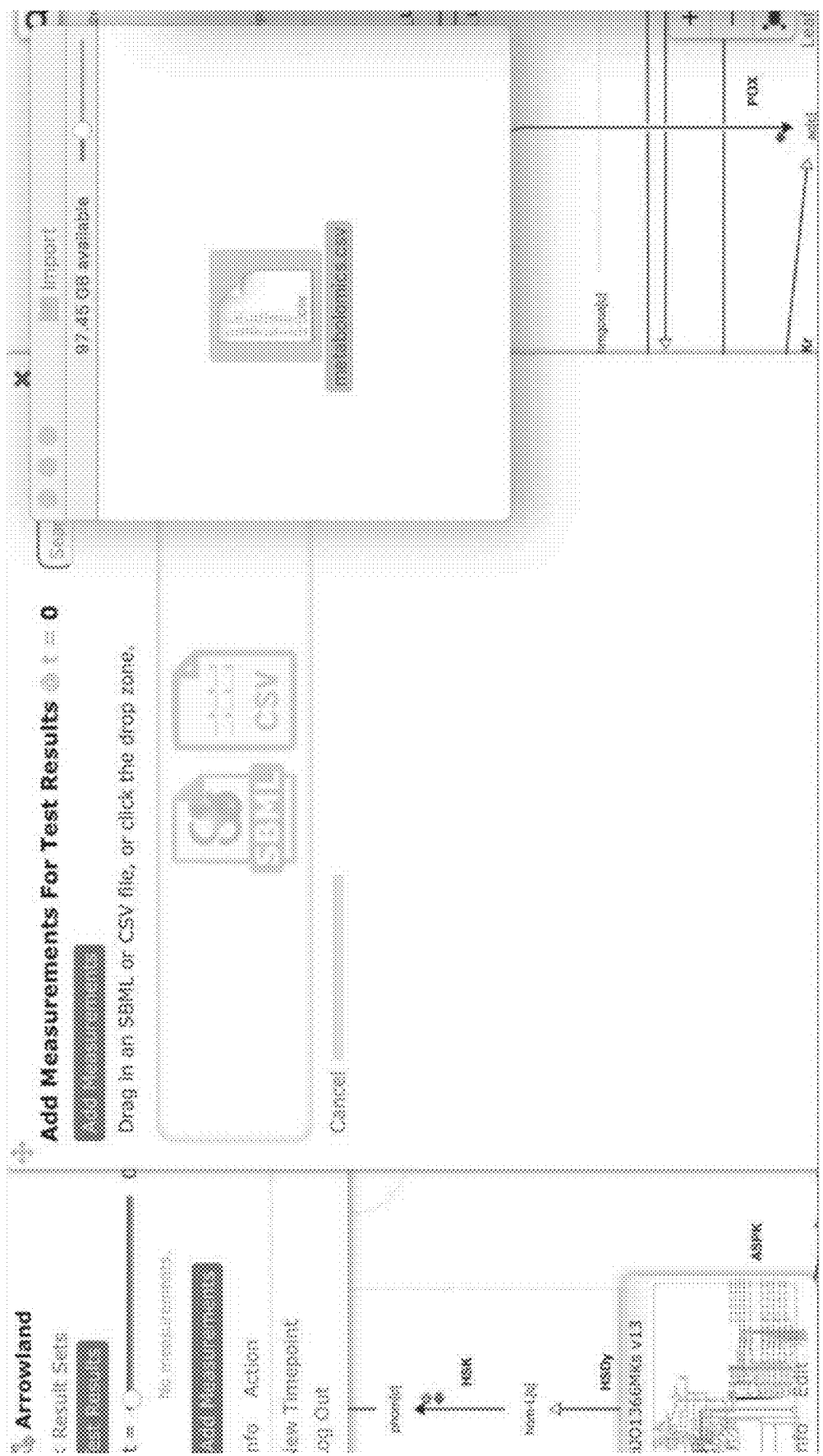
Figure 16O:
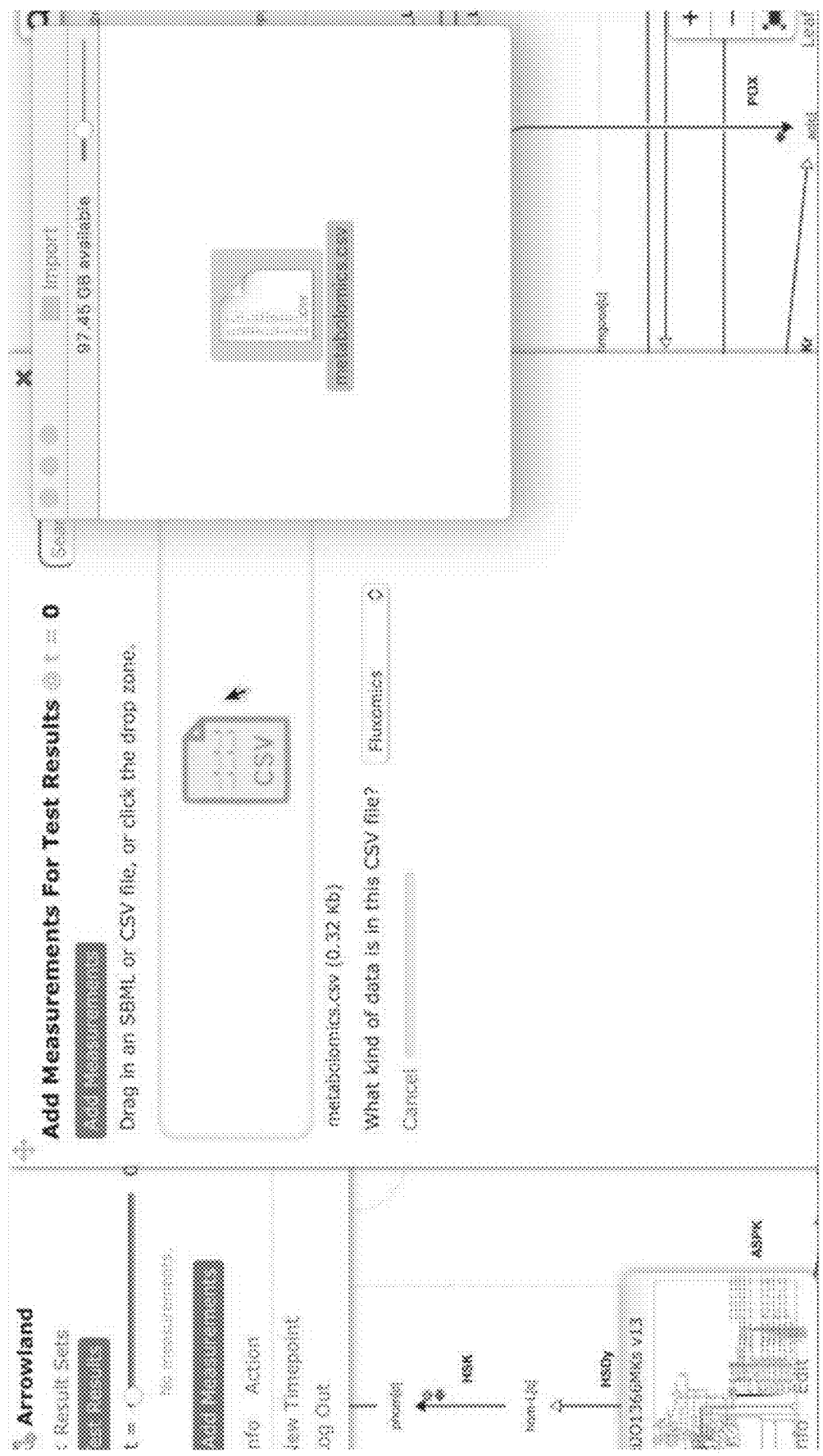
Figure 16P:
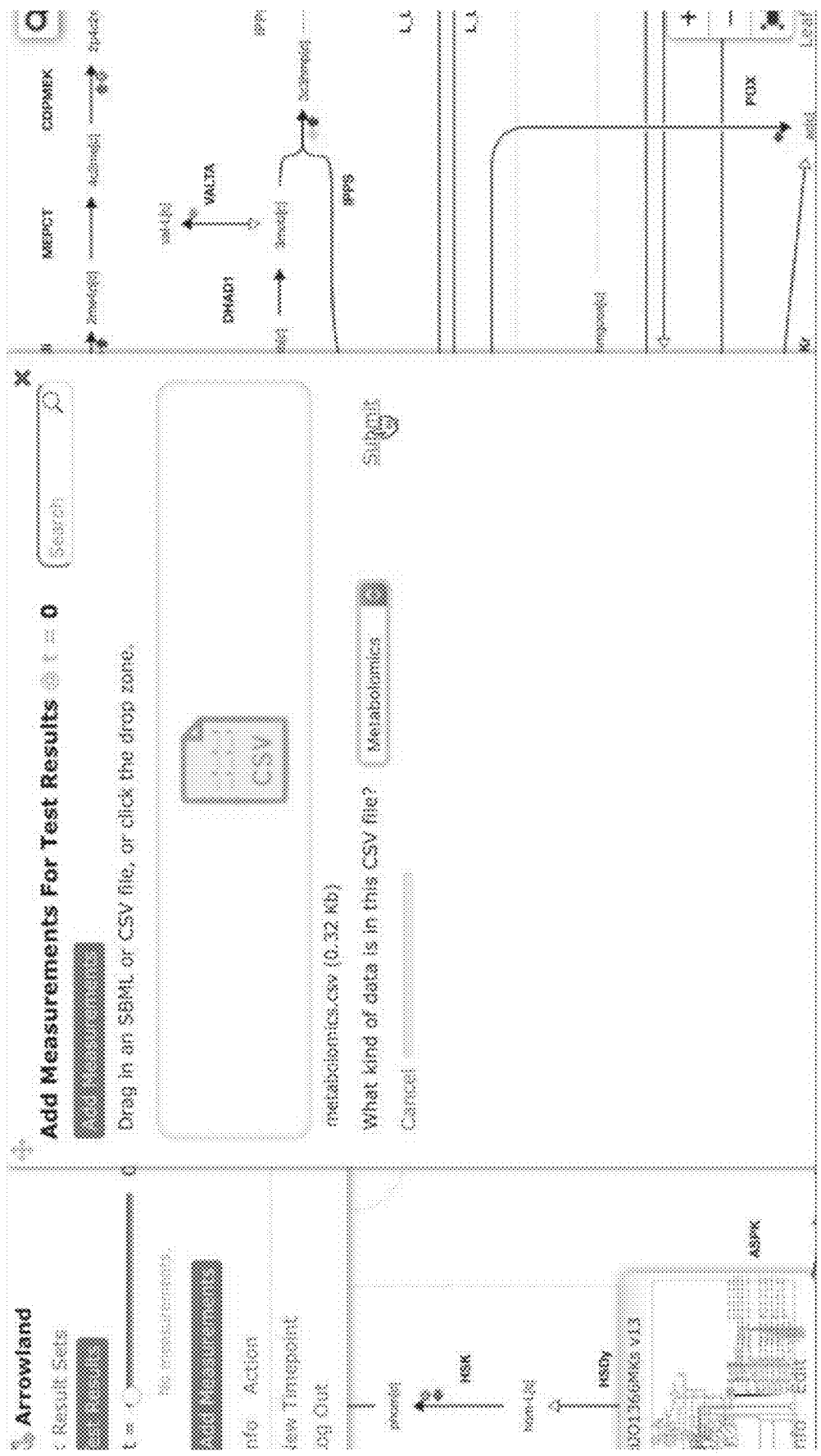
Figure 16Q:
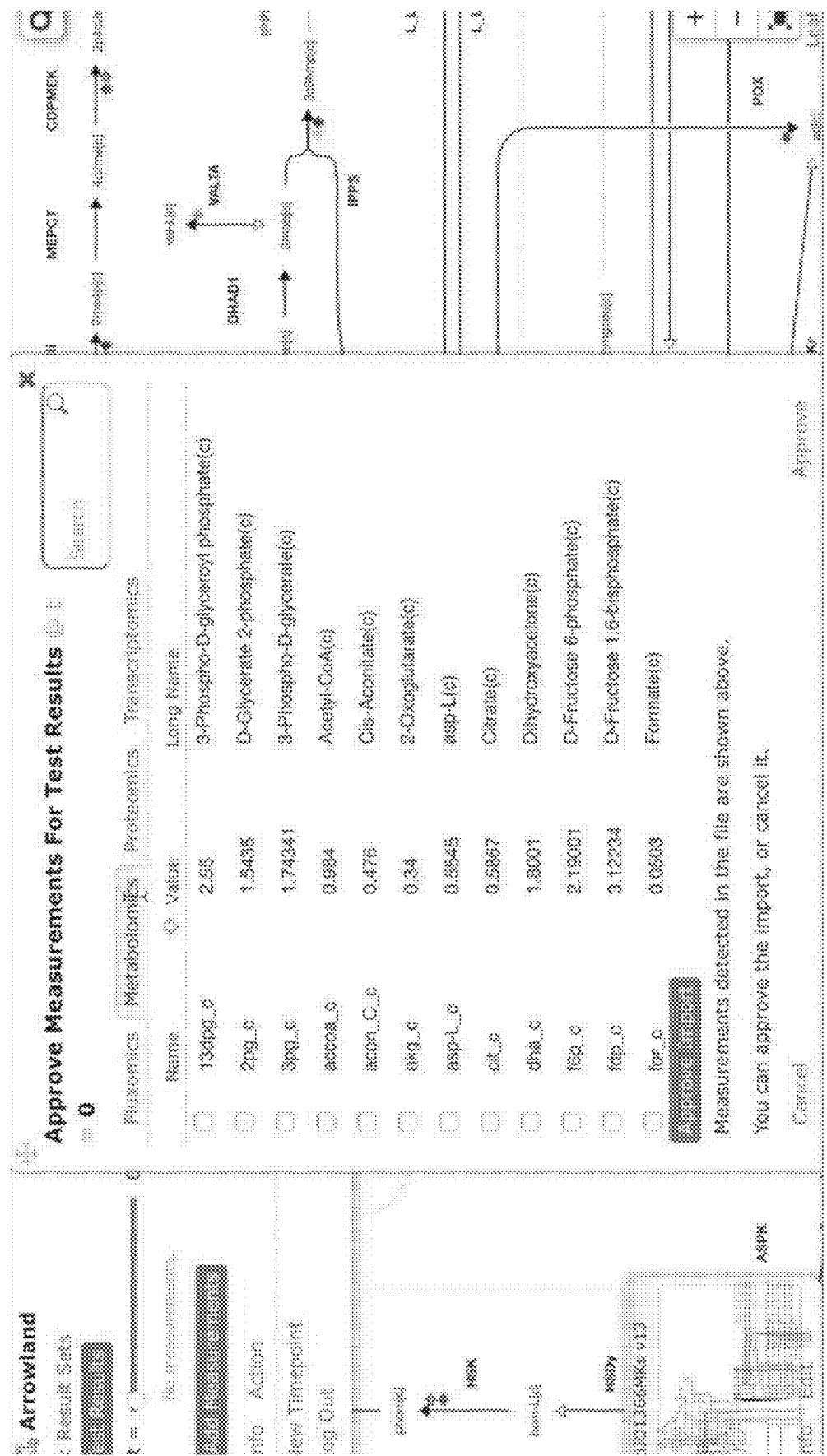
Figure 16R:
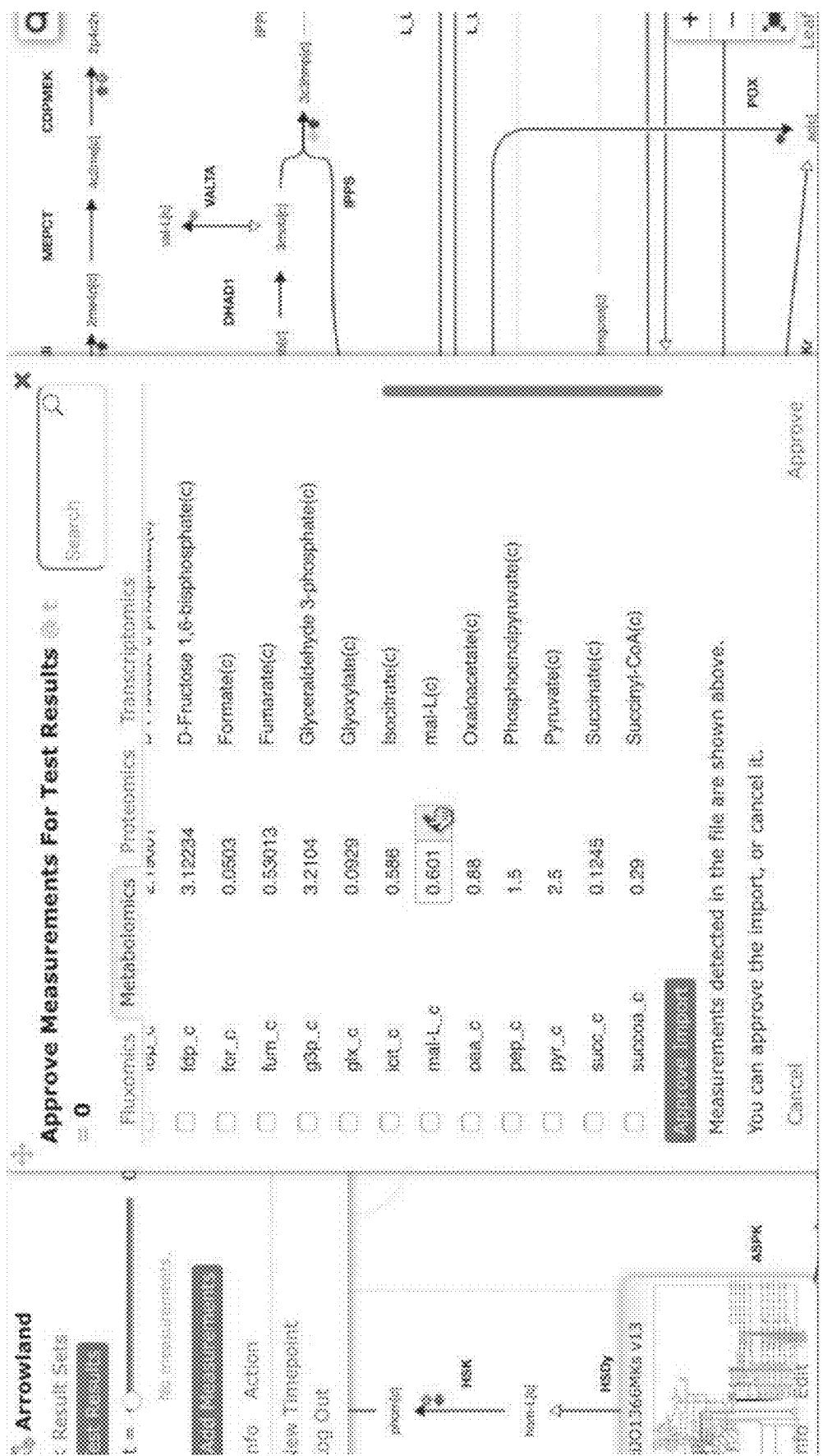
Figure 16S:
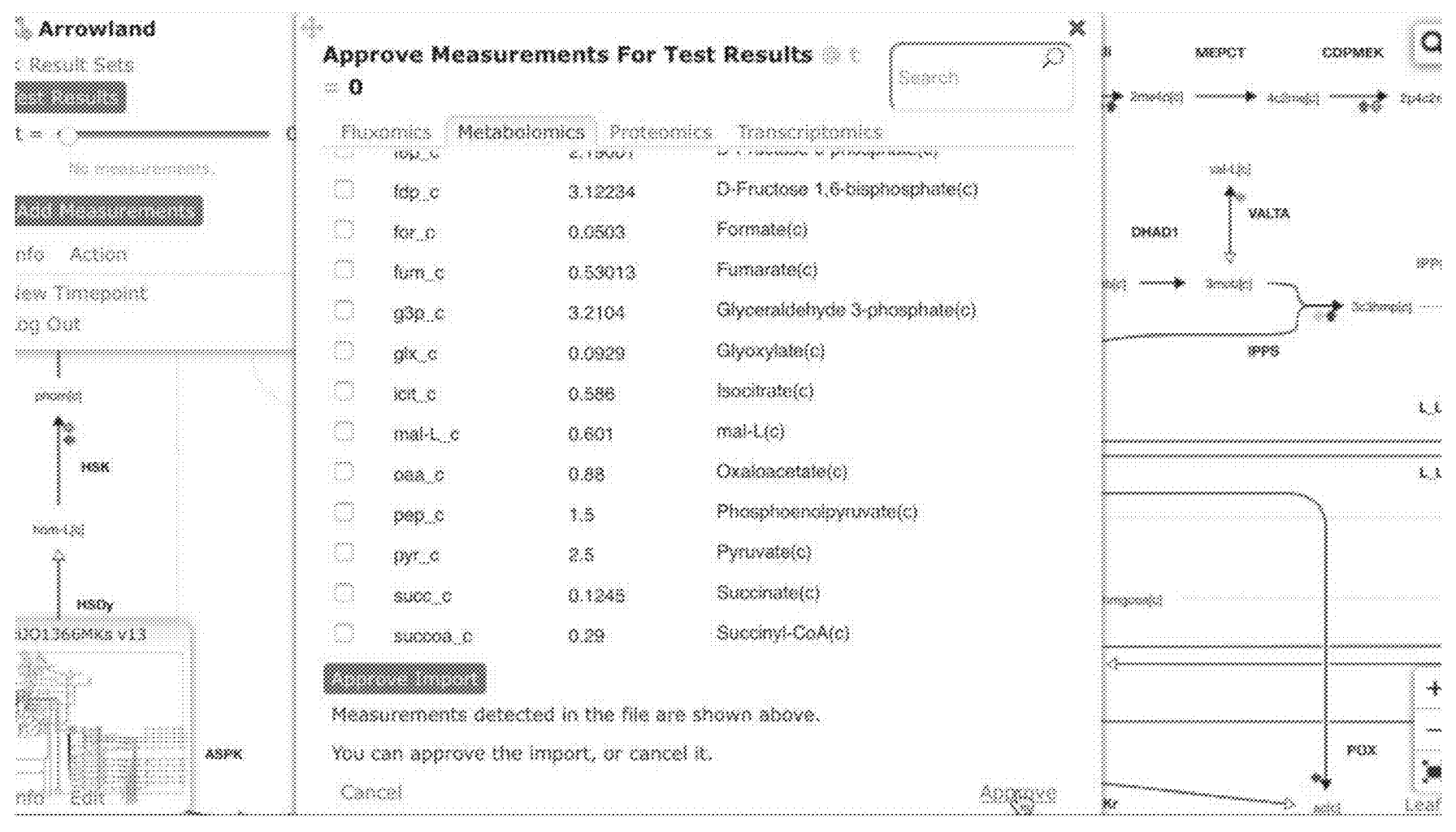
Figure 16T:
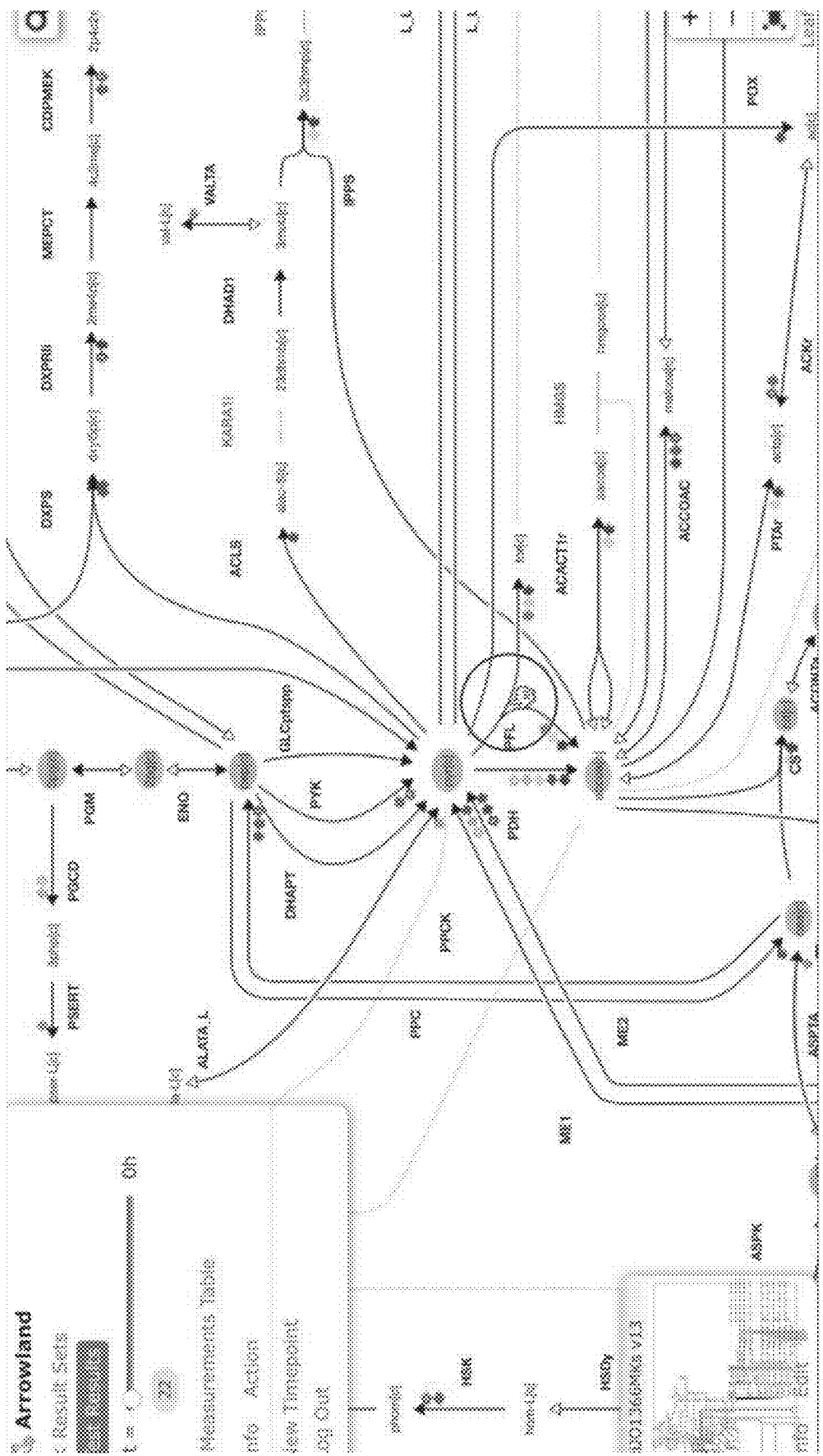
Figure 16U:
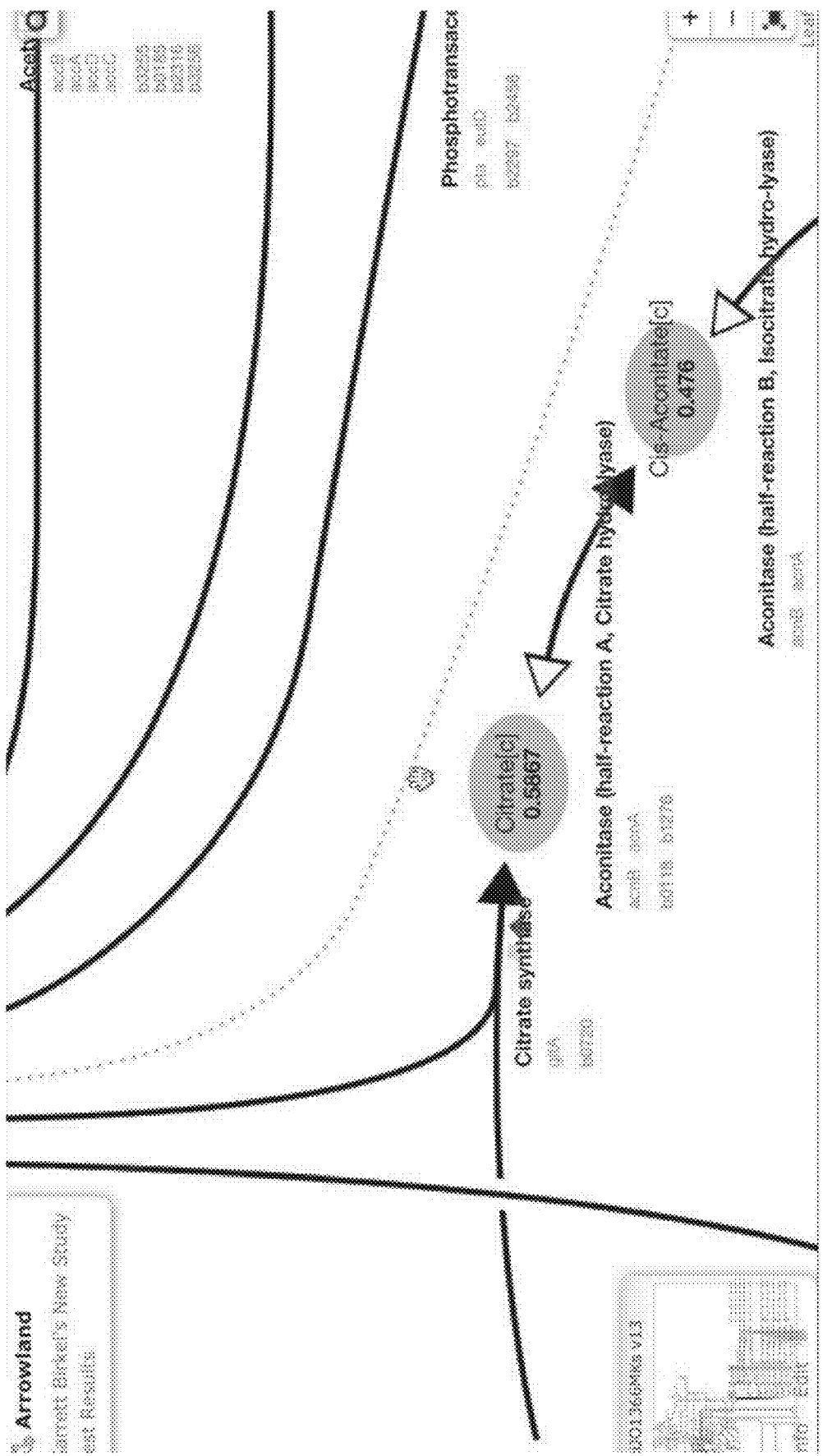
Figure 16V:
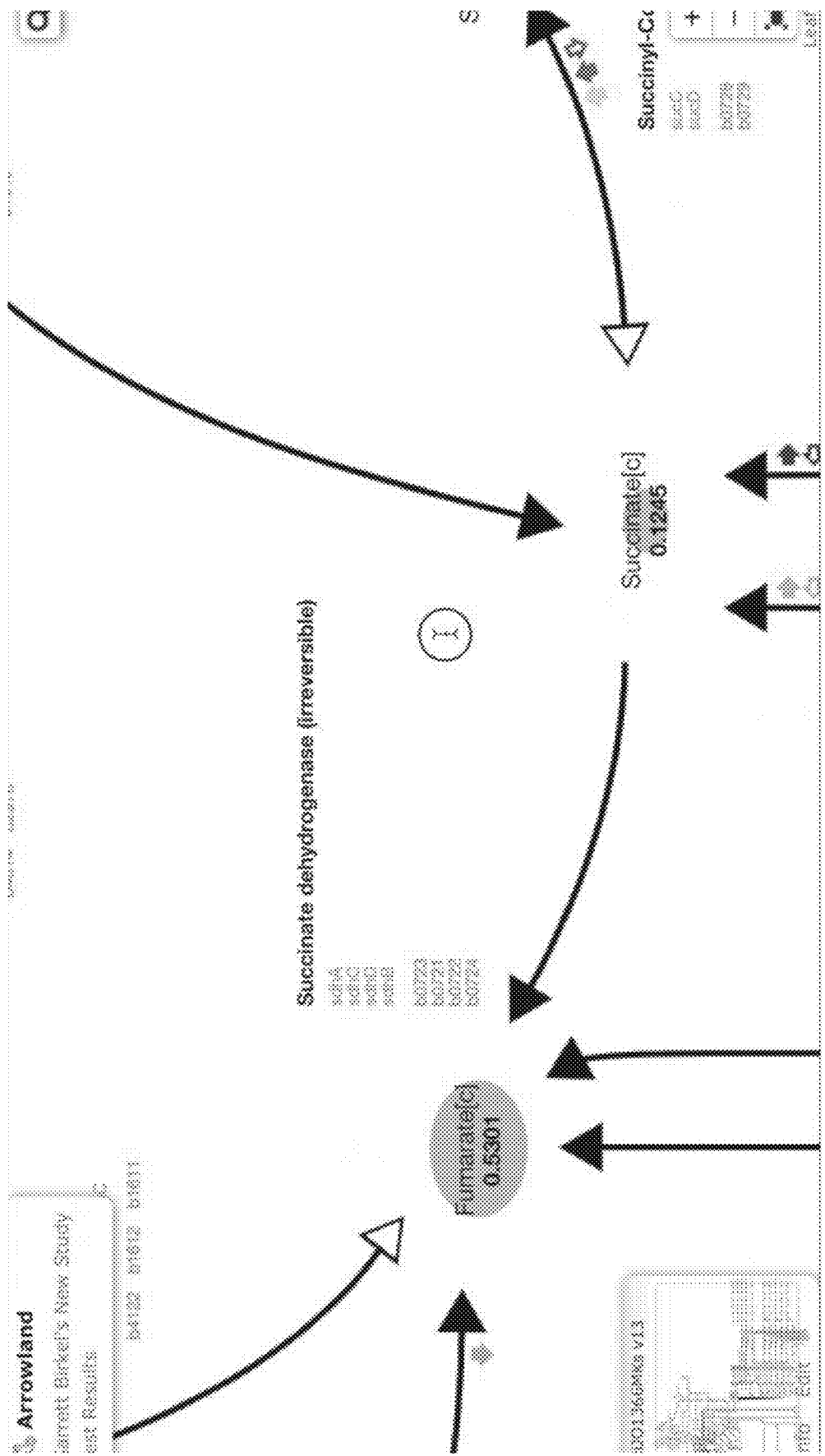
Figure 16W:
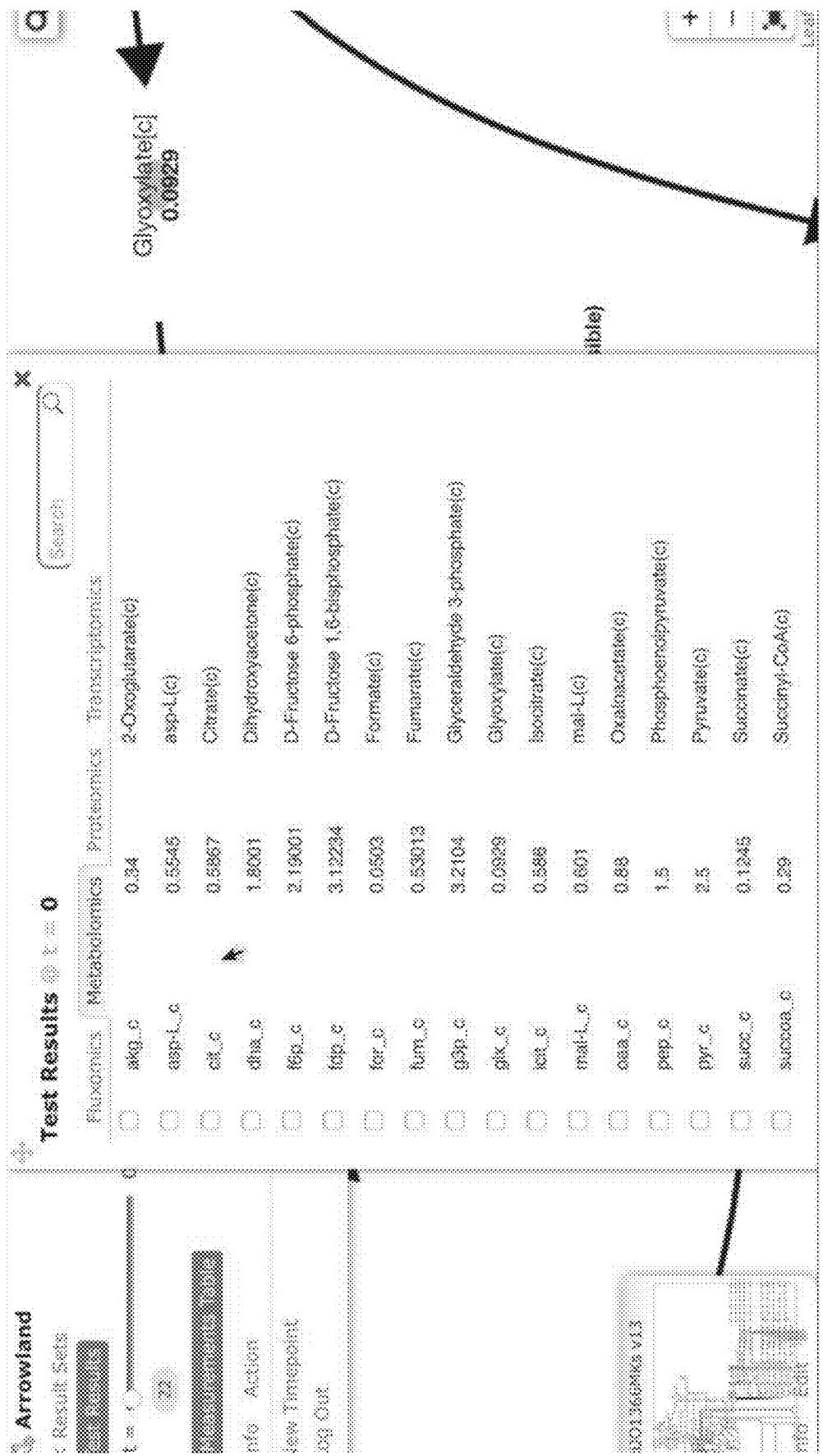
Figure 16X:
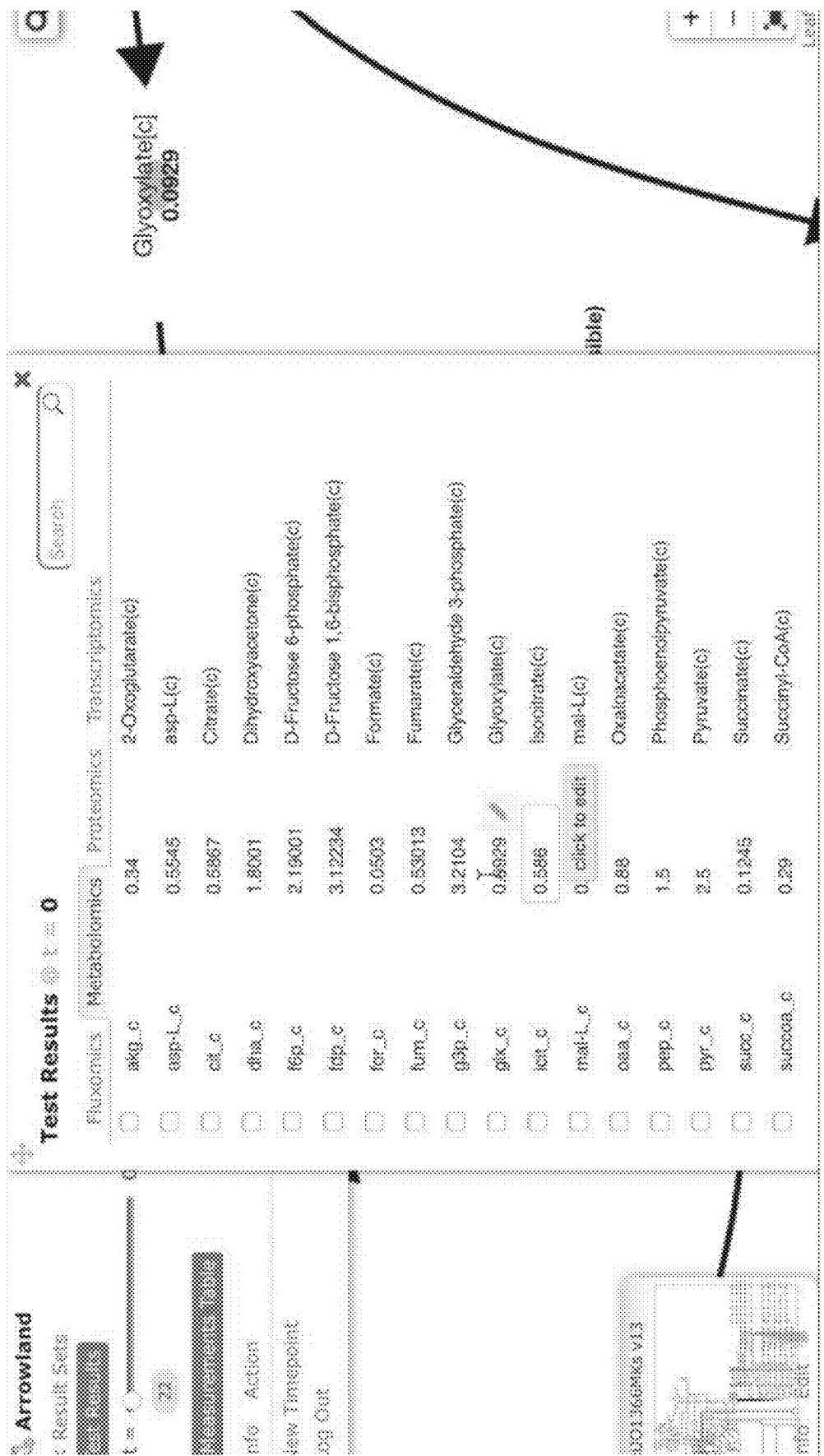
Figure 17A:
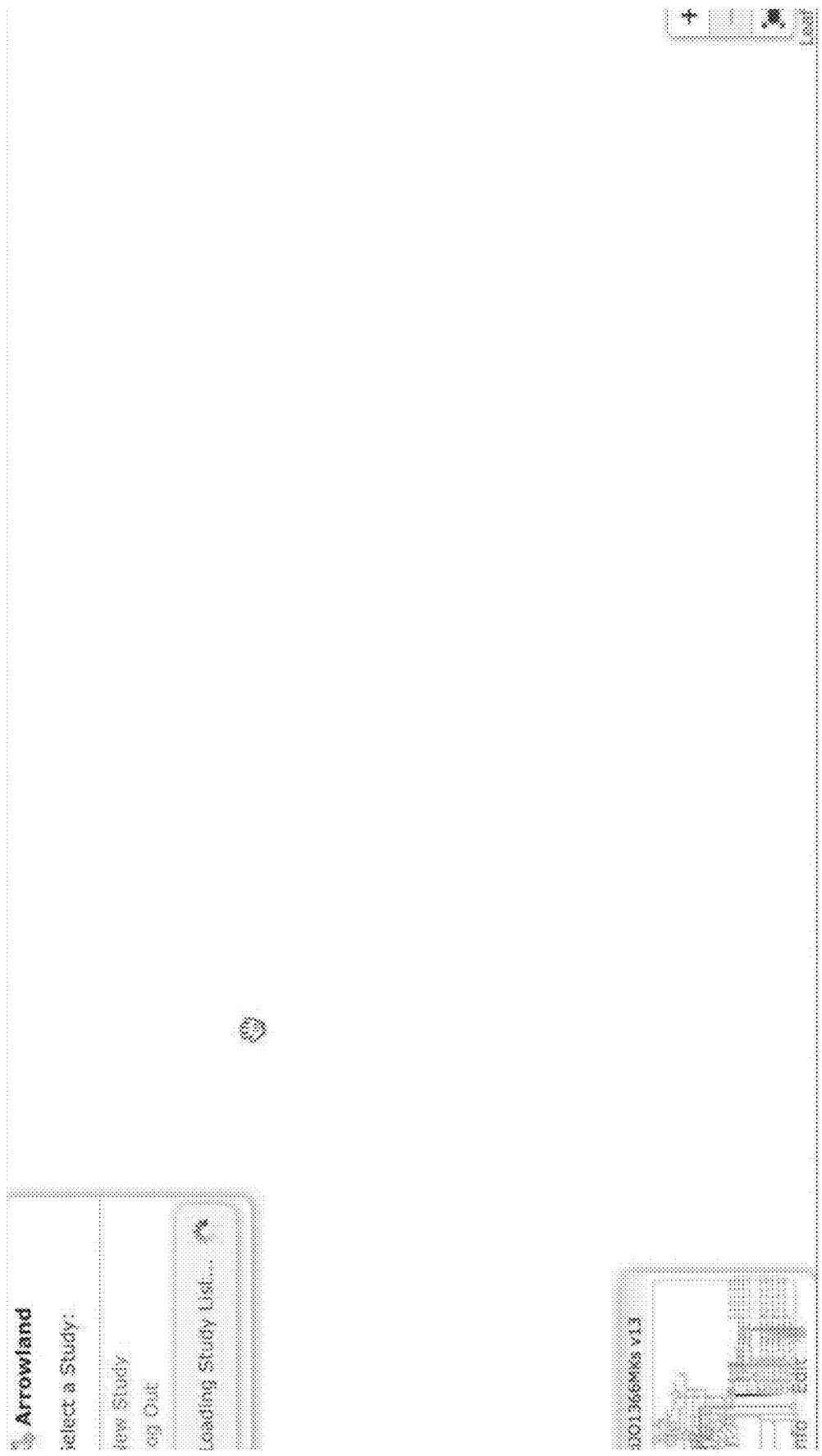
Figure 17B:
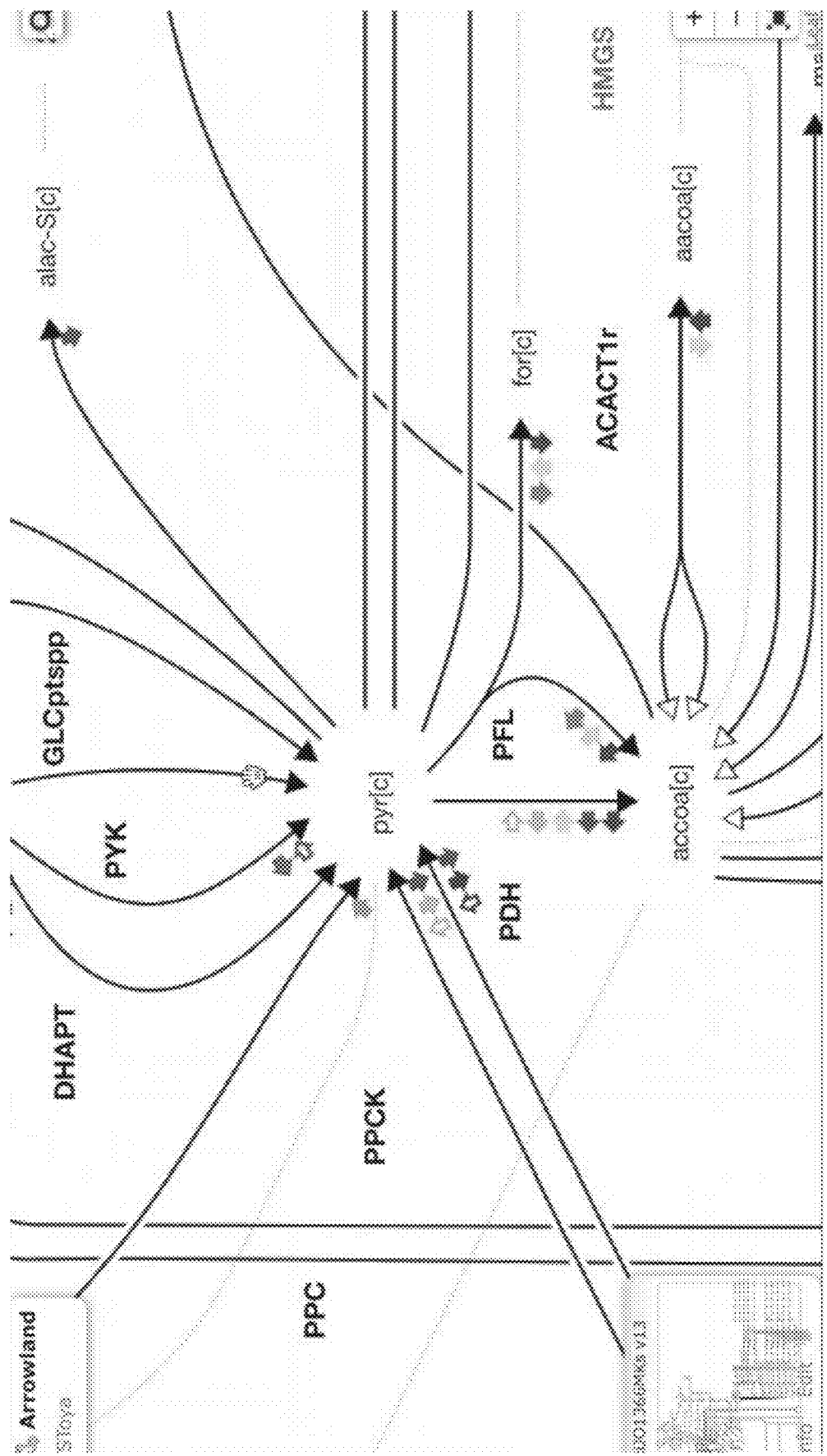
Figure 17C:
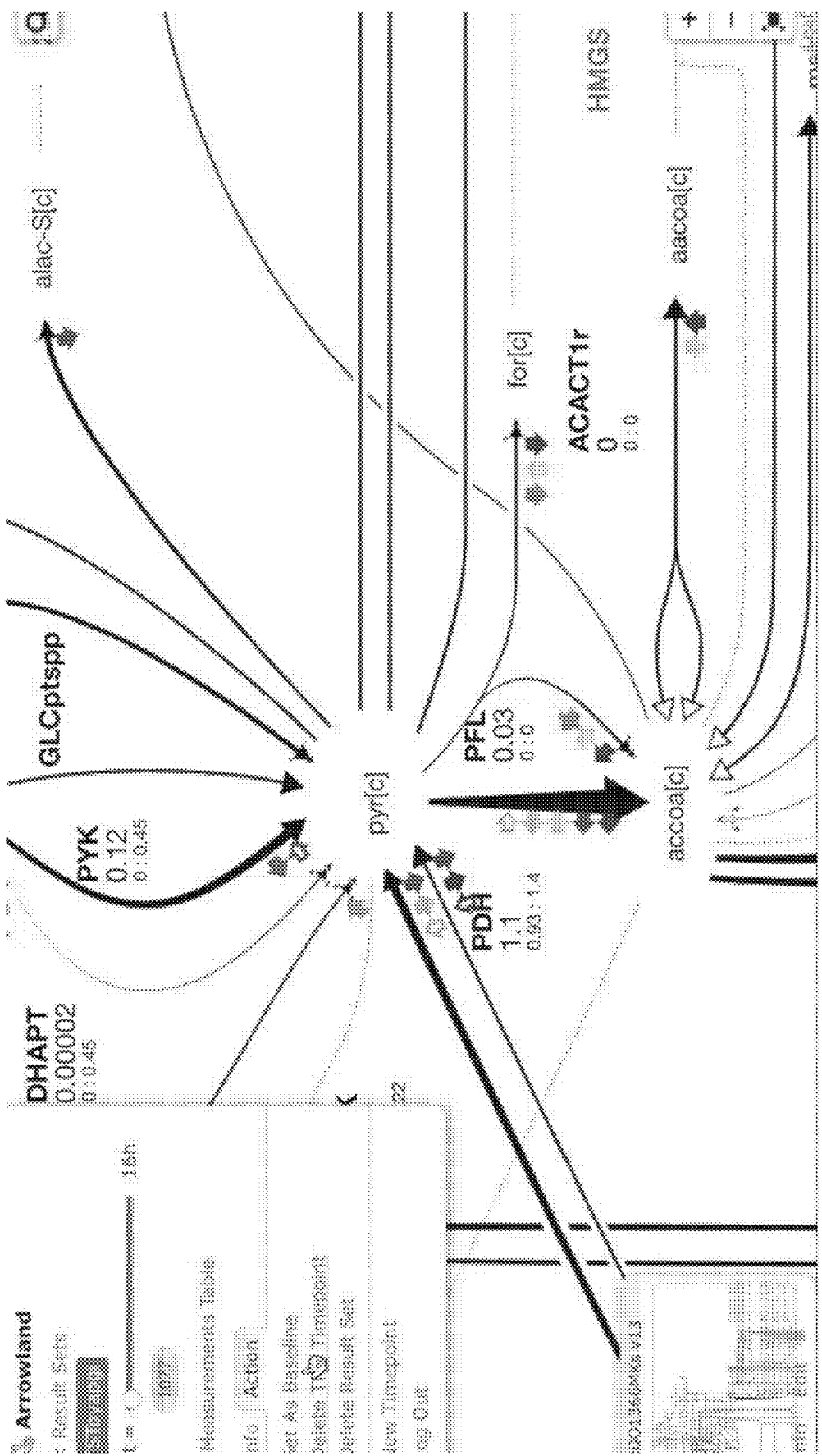
Figure 17D:
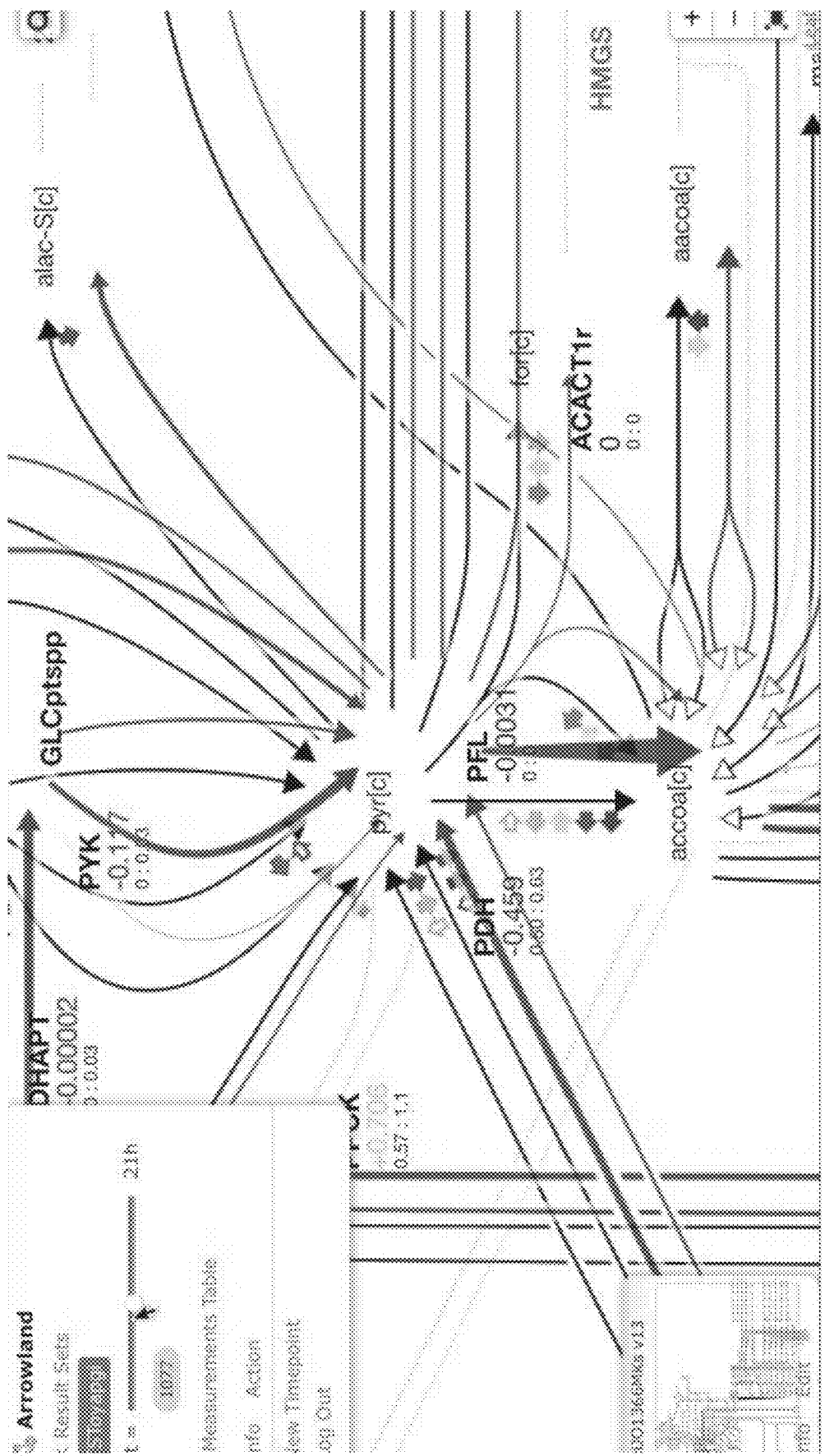
Figure 17E:
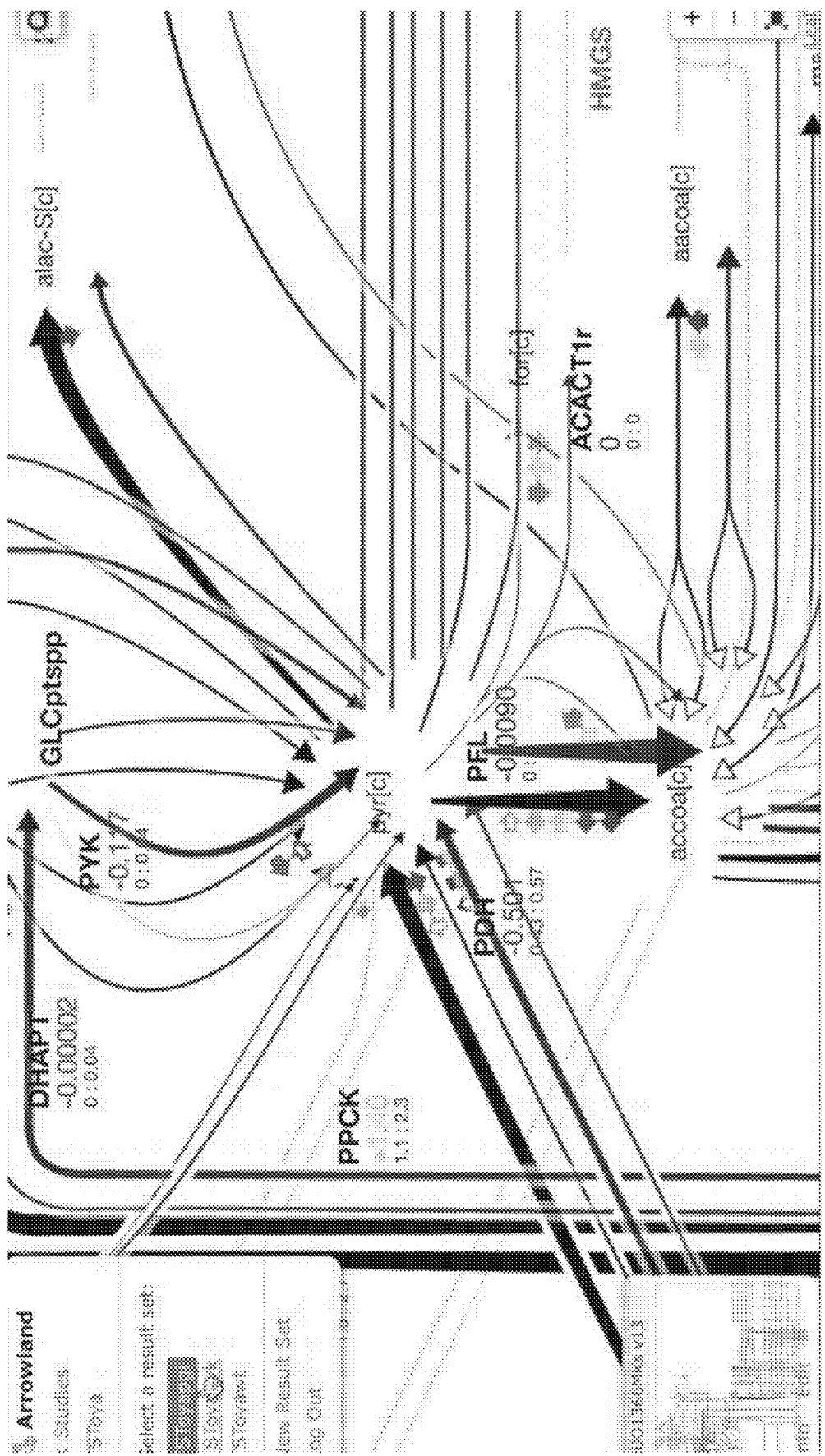
Figure 17F:
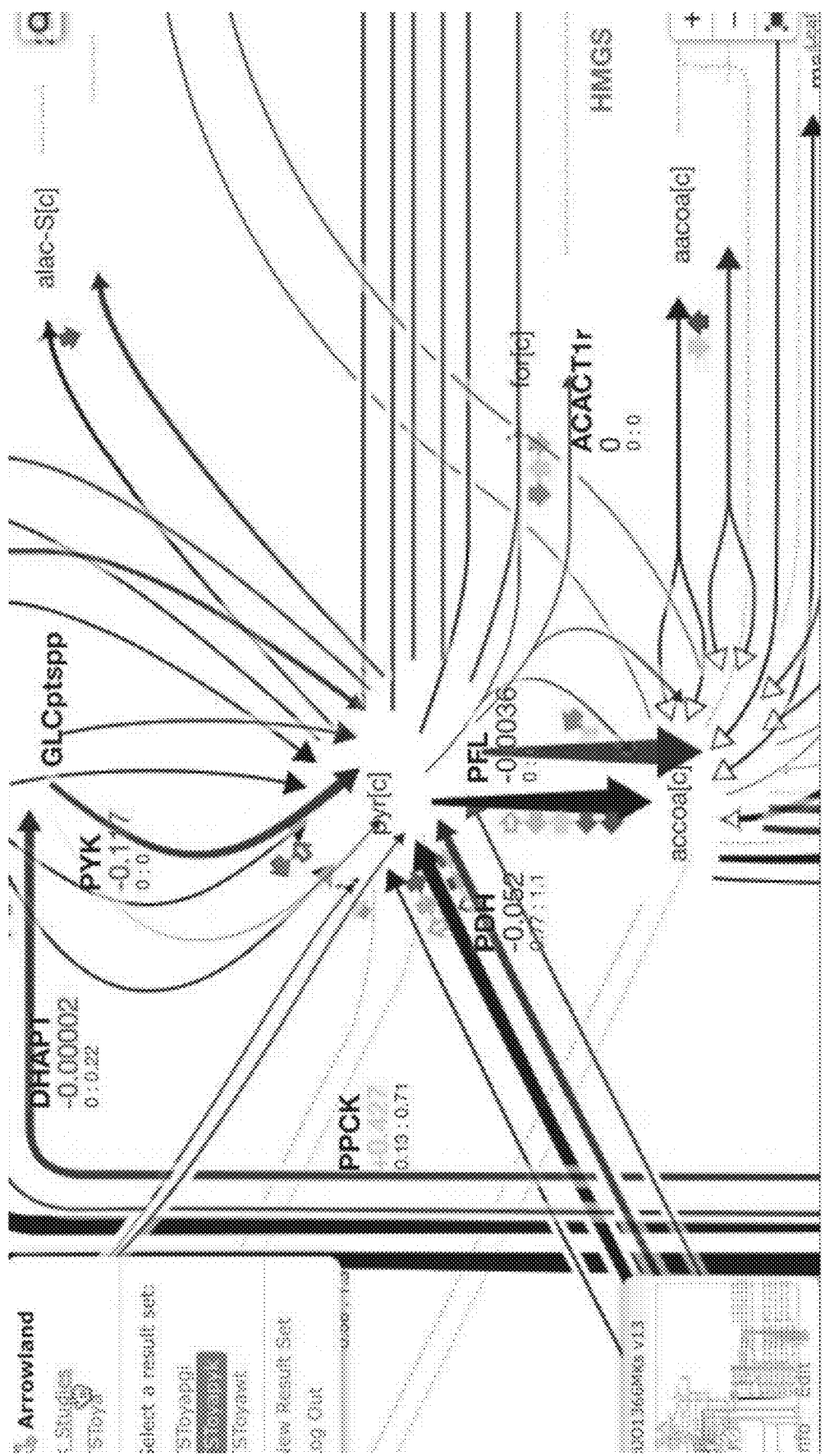
Figure 17G:
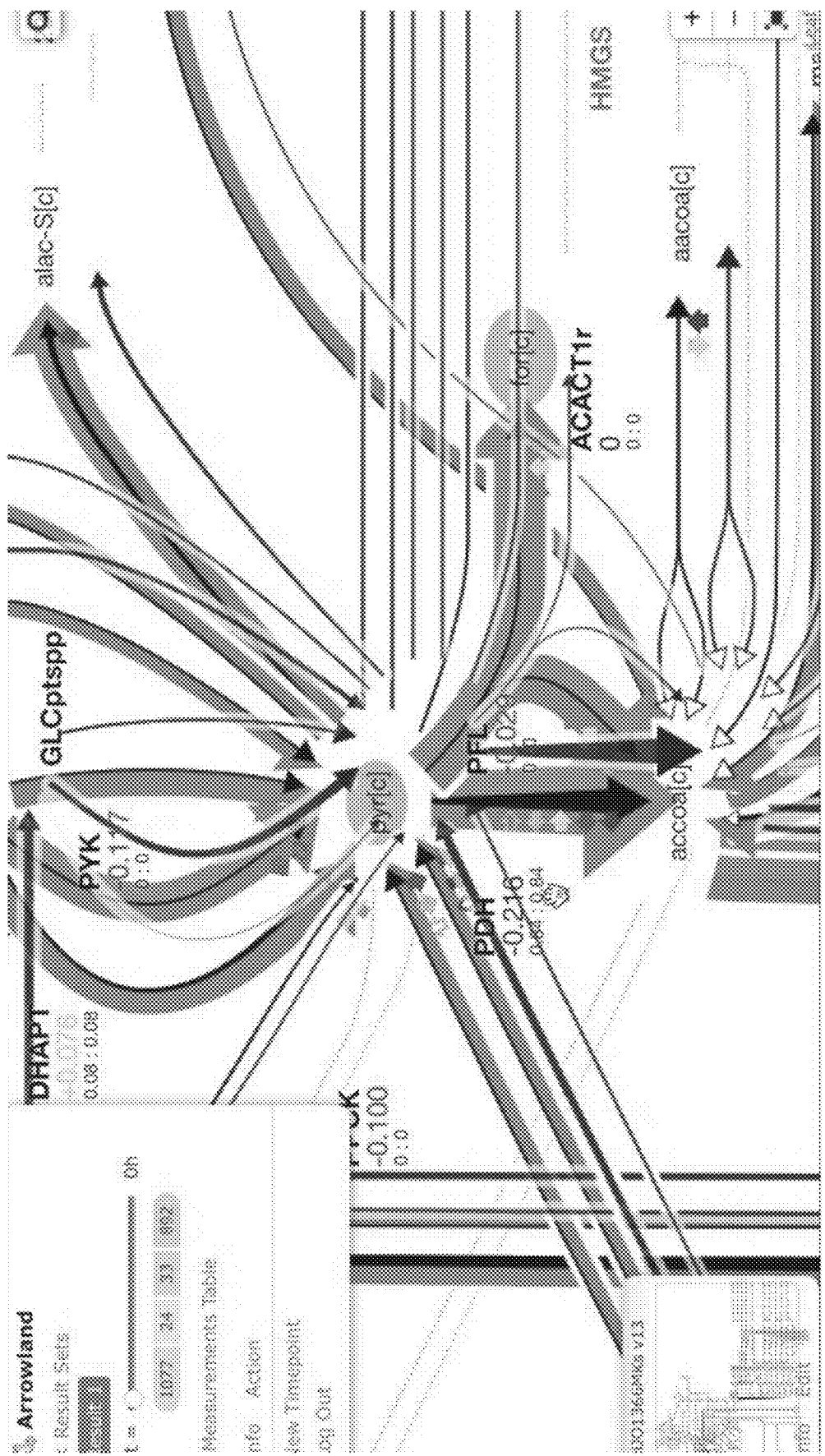
Figure 17H:
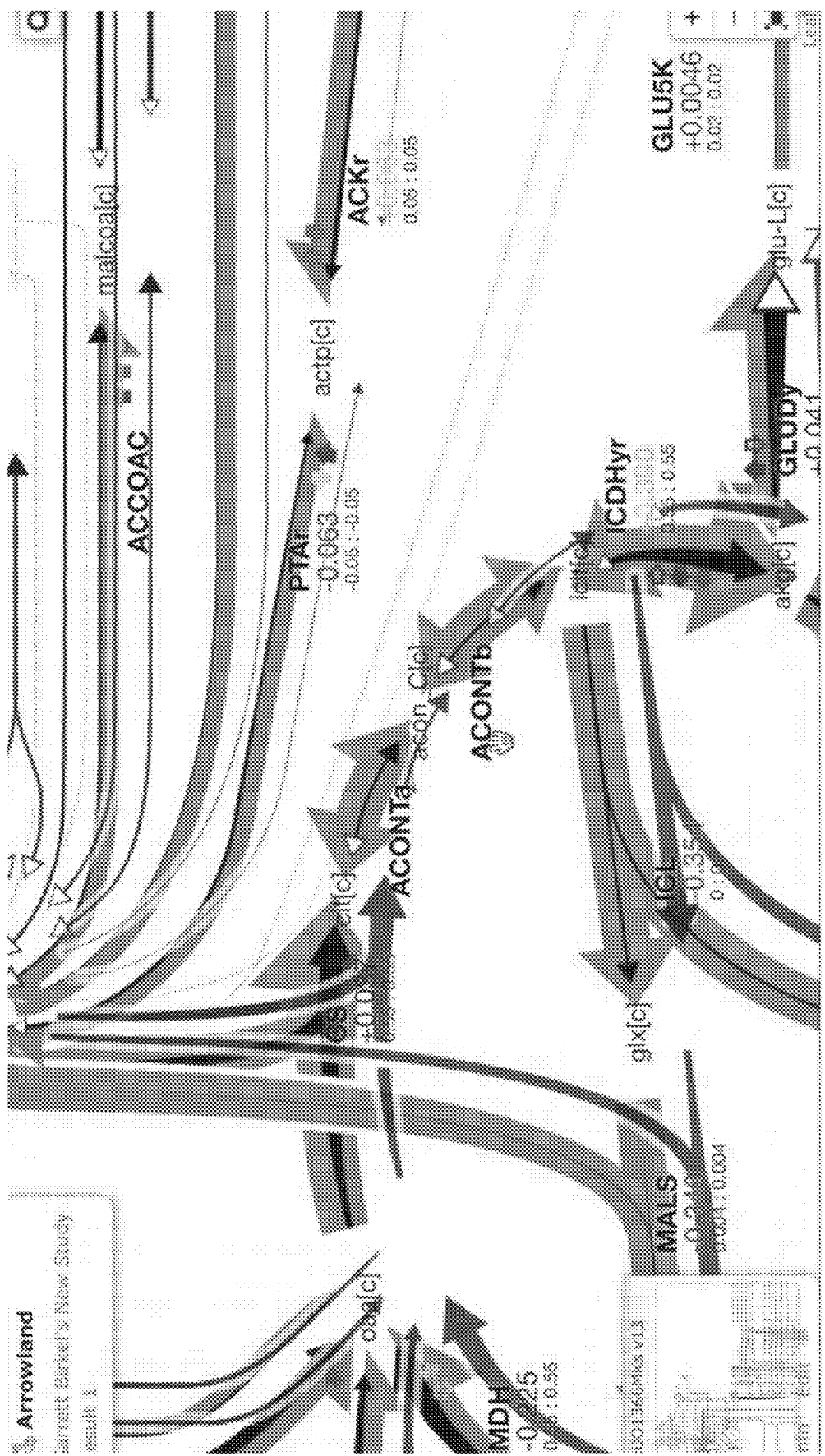
Figure 17I:
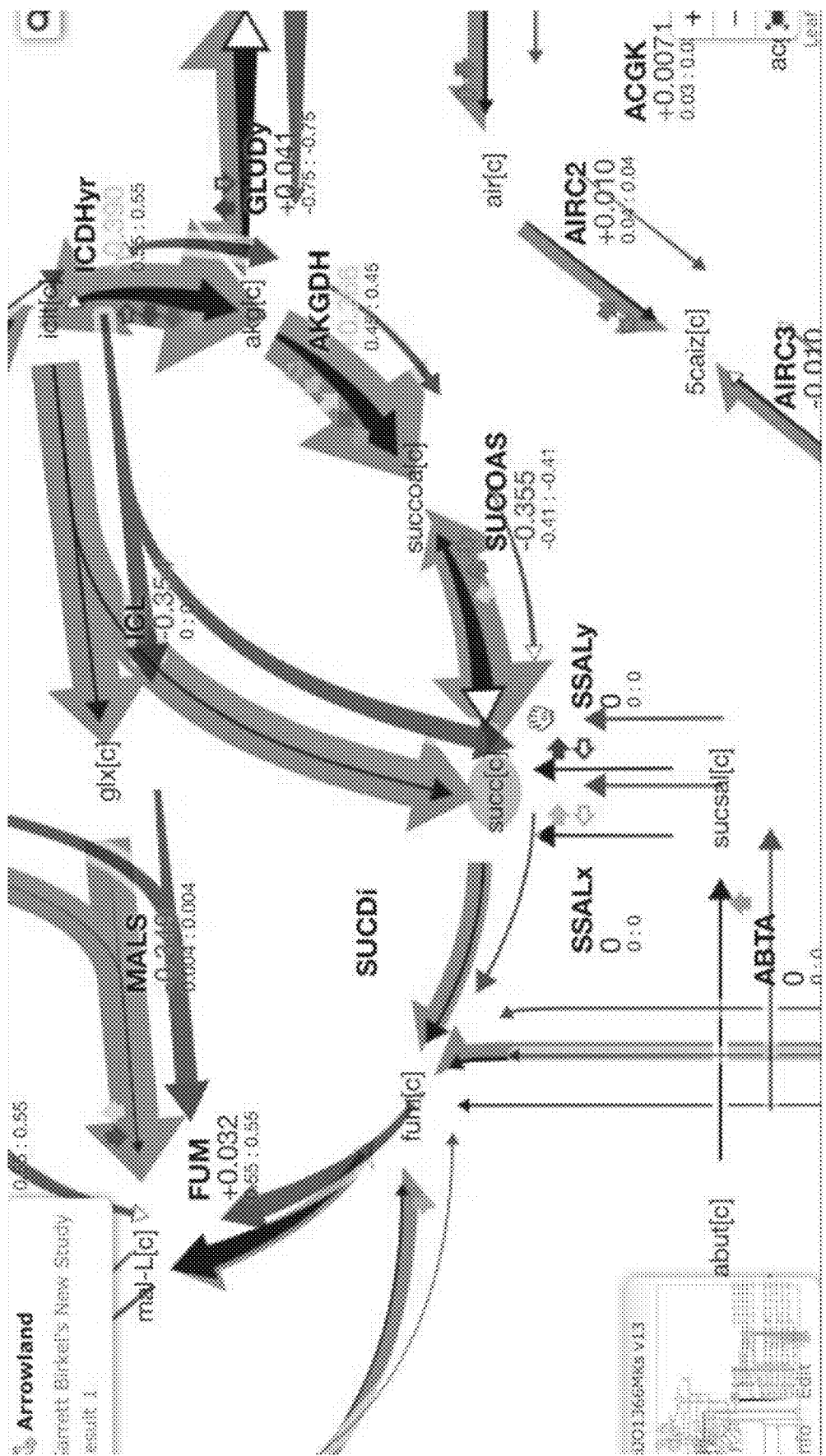
Figure 17J:
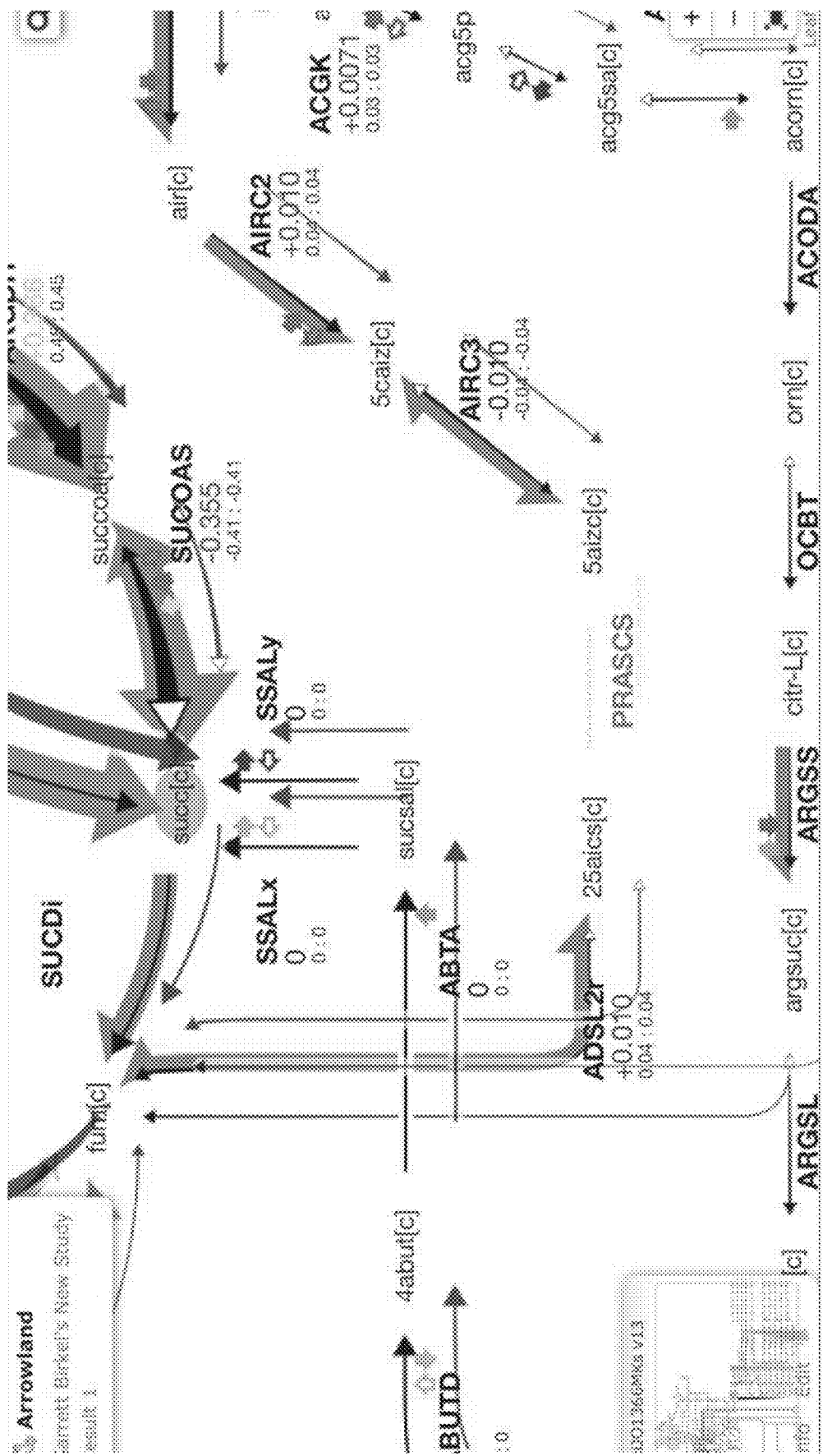
Figure 18A:
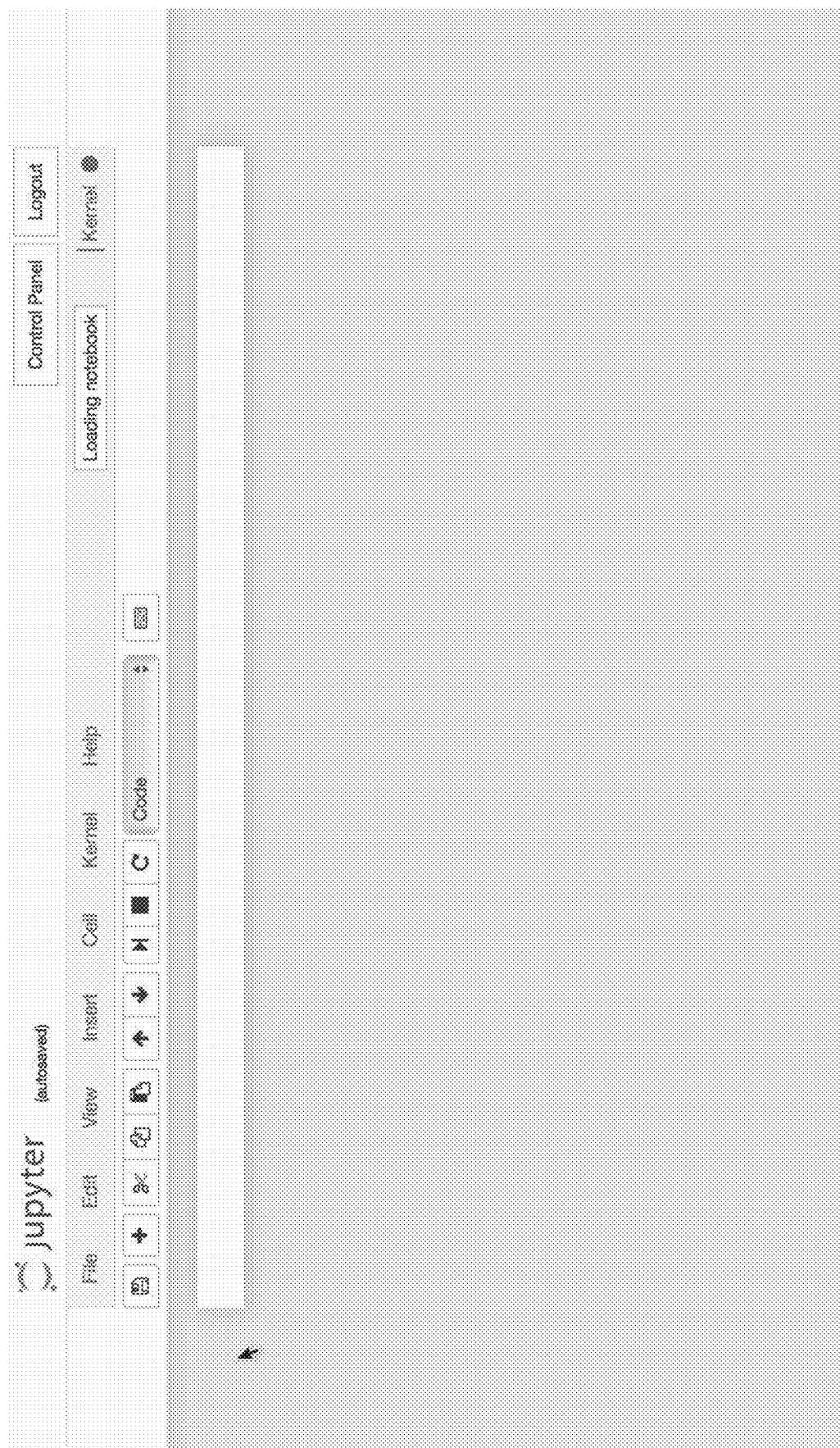
Figure 18B:
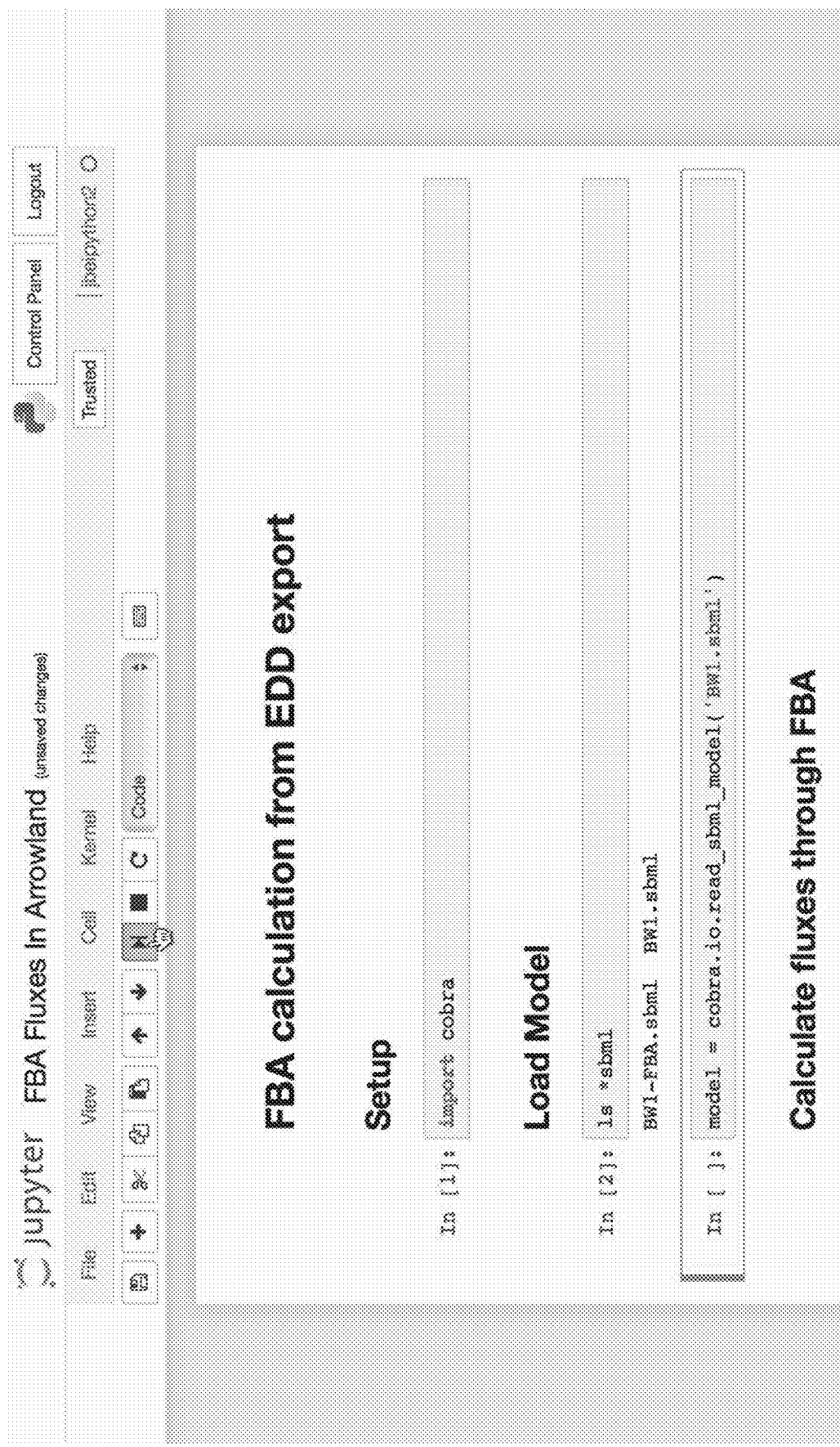
Figure 18F:
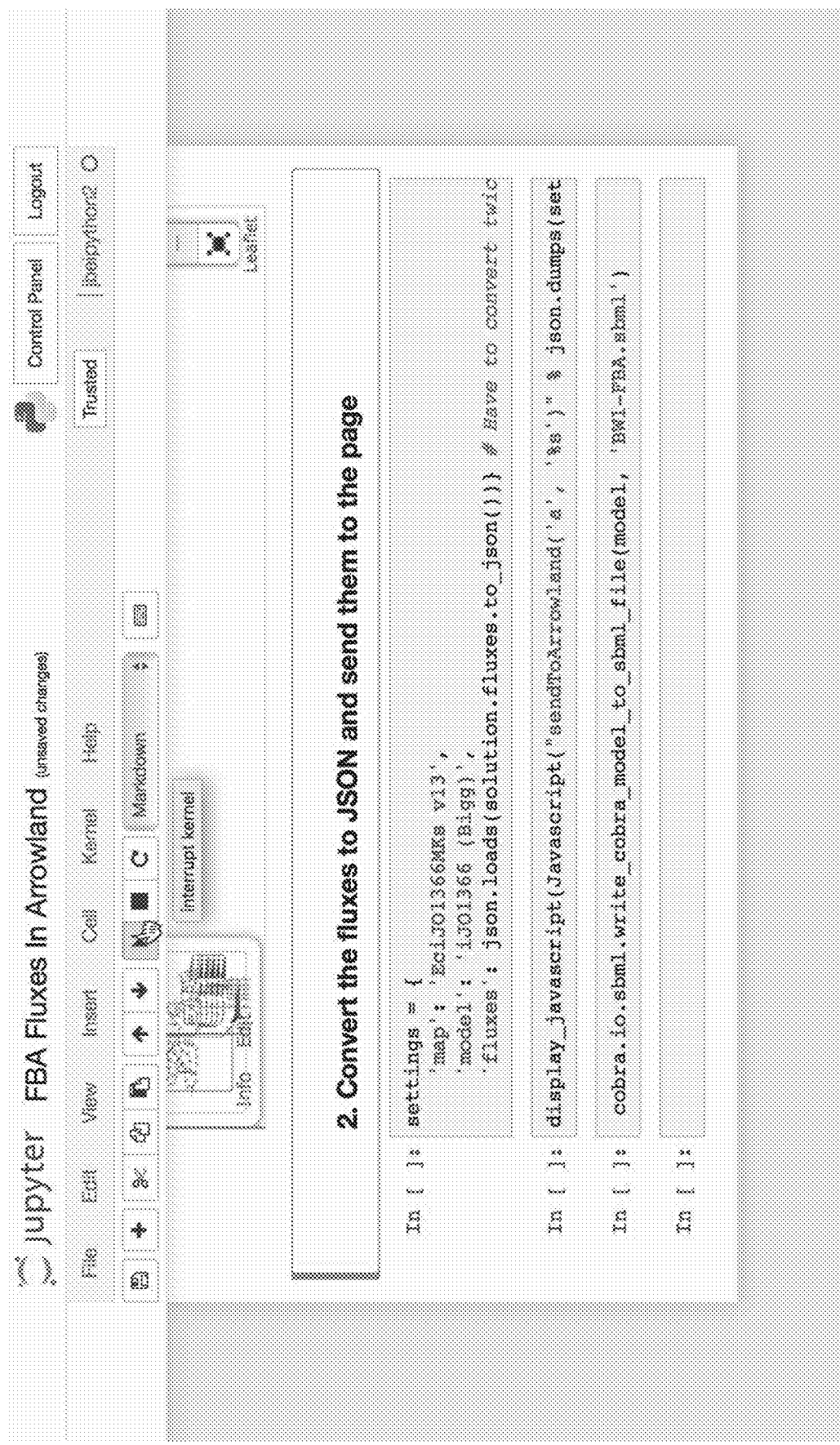
Figure 18G:
Figure 18H:
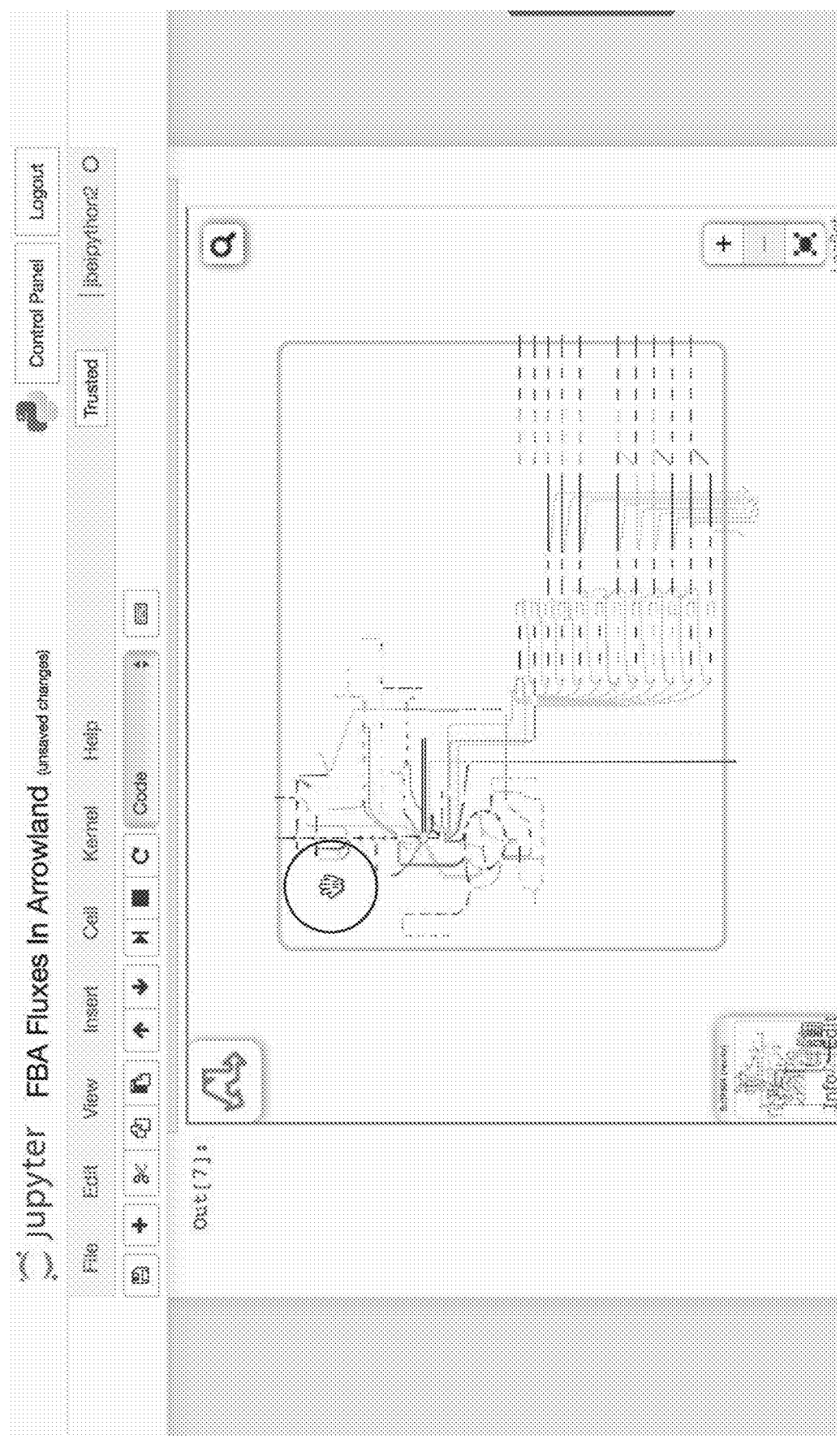
Figure 18I:
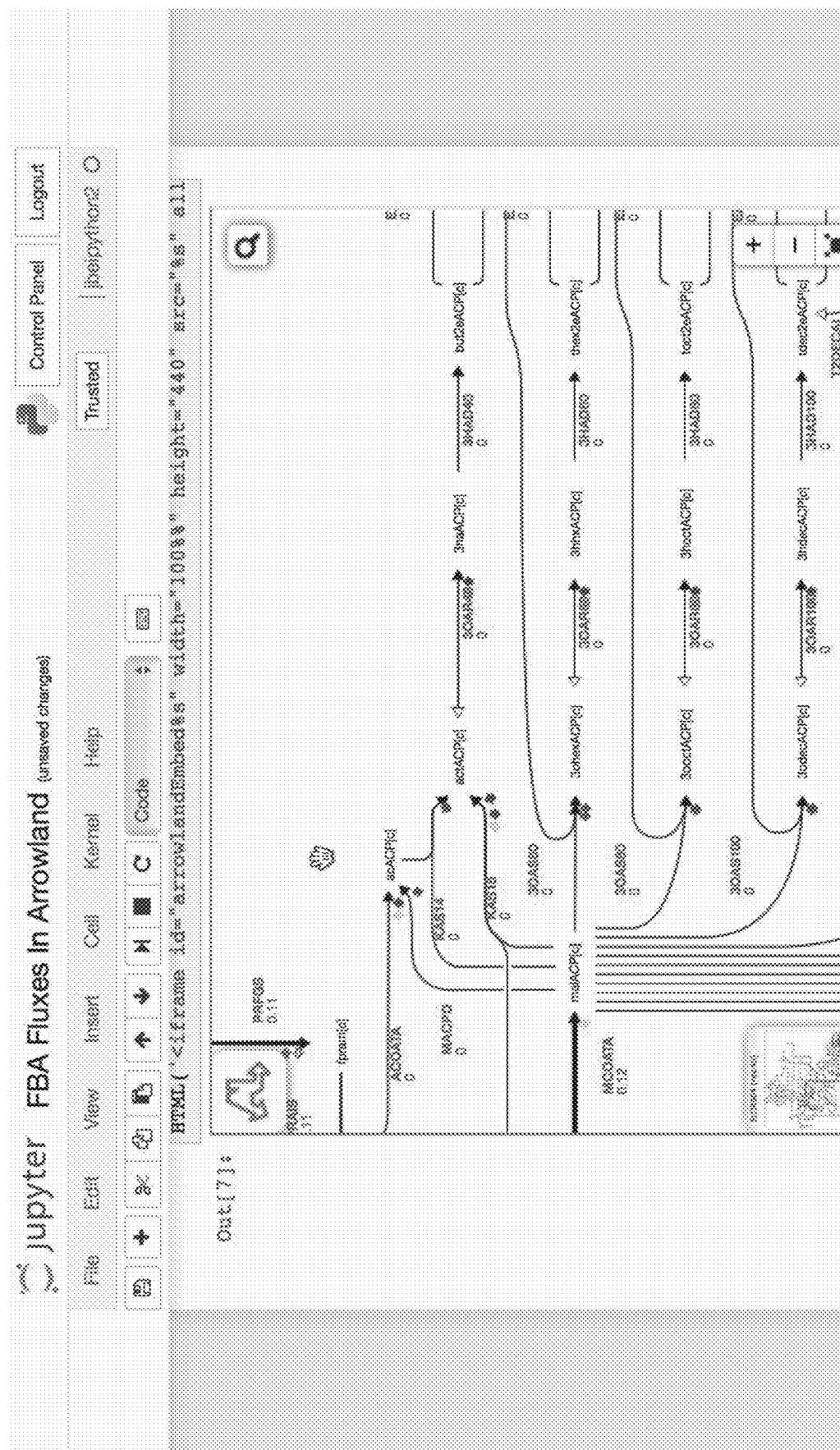
Figure 18J:
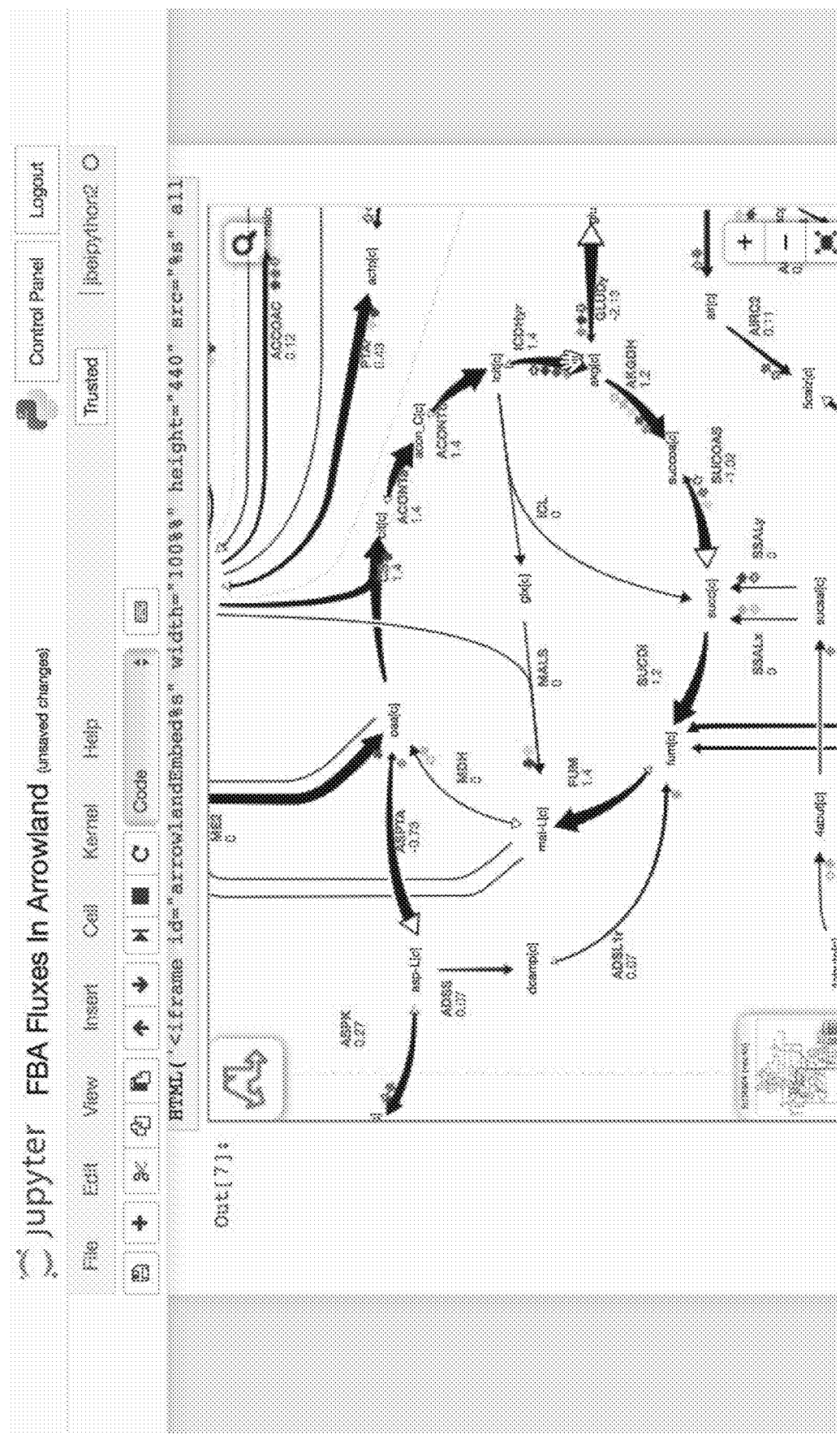
Figure 18K:
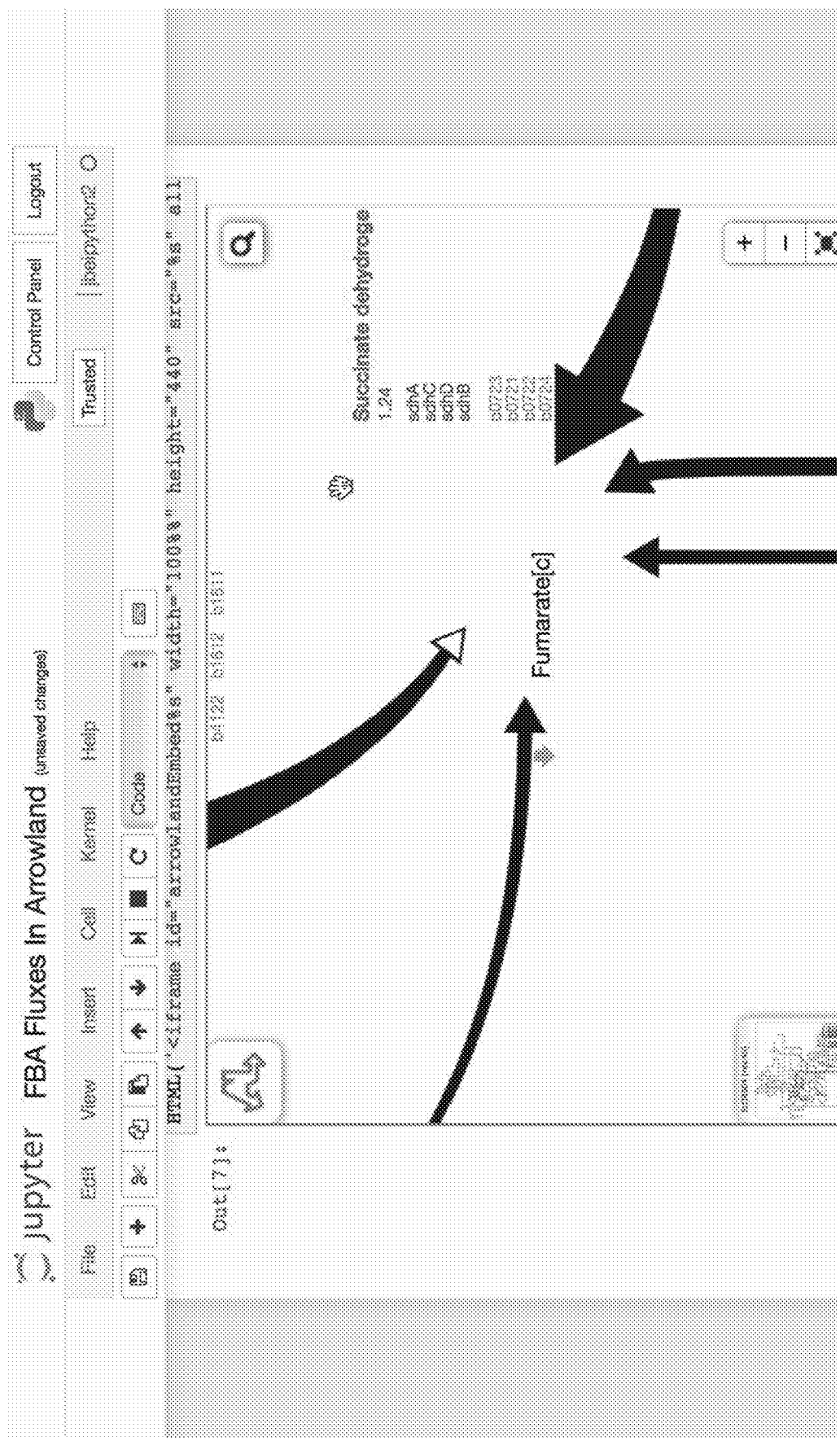

FIGS. 16A-16X are screenshots showing exemplary importing metabolomics data from a CSV file (public-arrowland.jbei.org/static/main/help/metabolomics_csv_import.mp4, the content of which is incorporated herein by reference in its entirety). To show metabolomics data in Arrowland, a user first creates a study and the result set inside the study. The study may have a default map and a default model. A result set is selected and a user is ready to import the data. The user may select "add measurements" to bring up the import window and the drop zone. The user can drop in a CSV file containing metabolomics, which may include names followed by values. In one embodiment, Arrowland expects metabolites to be specified using the short names in the UCSD big models database. For example, pyruvate on the first line is specified by pyr underscore c (pyr_c). The underscore part of the name specifies the compartment is intracellular. If the user does not specify a compartment, Arrowland will assume the measurement applies to all instances of that metabolites in the model regardless of compartment. The user may then drag the file to the program to tell Arrowland that it should look for metabolomics measurements. The window changes to show all the measurement Arrowland could find in the file. If the import is correct the user may to approve it. Every metabolite on the map that has metabolomic data is shown as a colored dot, the size of which reflects the quantity. The user may zoom in for exact values on the image. If the user wants to see measurements in tabular format, the "measurements table" button may be selected. The user can edit the measurement values here or change which metabolite of value belongs to.

FIGS. 17A-17J are screenshots showing an example of comparing two result sets together in Arrowland (public-arrowland.jbei.org/static/main/help/baseline_comparison_video.mp4, the content of which is incorporated herein by reference in its entirety). To compare two sets of results in Arrowland, the user may navigate to the first result to compare, including the specific time point. The user may then select the action Tab and select "set as baseline". The user may then navigate to the second result by dragging the time slider to another time point, or by navigating to a different result set, or by going to an entirely different study. A map of the first set of result appears with a light off set from the second set, allowing a user to browse both sets at once.

Figure 18E:
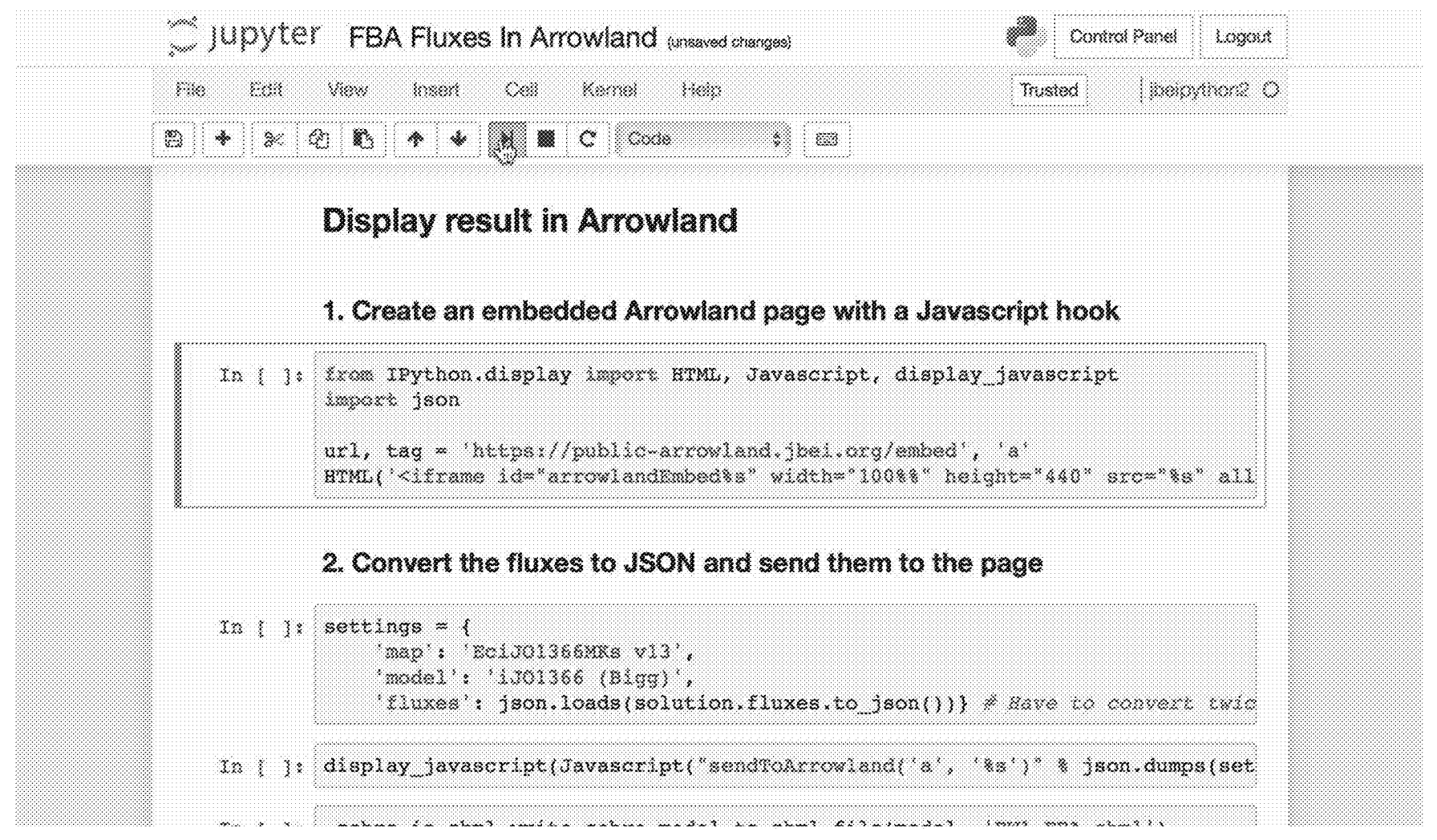

FIGS. 18A-18K are screenshot showing exemplary views of Arrowland displaying inline in a Jupyter Notebook.

Figure 19:
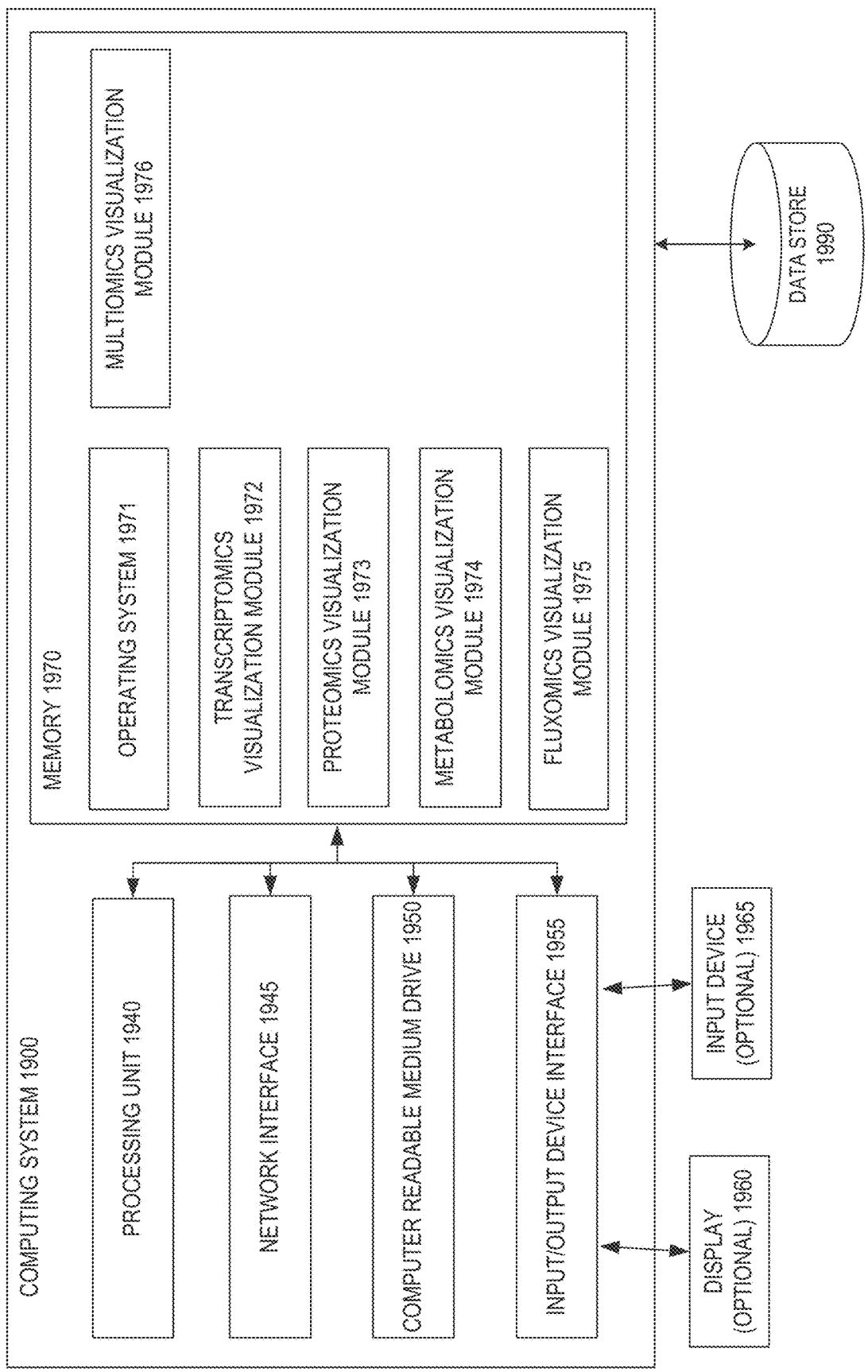

FIG. 19 depicts a general architecture of an example computing device configured to generate -omics and multiomics data visualization.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein and made part of the disclosure herein.

Overview

Whereas an organism's genome provides a blueprint to its capabilities, functional genomics information describes how those capabilities are actually being used within the organism. Disclosed herein is a system and methods for multiomics data visualization, referred to herein as "Arrowland." In one embodiment, the Arrowland system enables productive use of genomics and functional genomics data. In one embodiment, the system utilizes visualization software technologies. In one embodiment, the system enables simultaneous visualization of functional genomics data, such as transcriptomics, proteomics, metabolomics and fluxomics. In one embodiment, the system uses the latest web technology to produce a web based, browsable, online, multiscale, interactive depictions of an organism's metabolism.

In one implementation, "Arrowland" is a web-based software application primarily for mapping, integrating and visualizing a variety metabolism data of living organisms, including but not limited to metabolomics, proteomics, transcriptomics and fluxomics. This software application makes multiomics data analysis intuitive and interactive. It improves data sharing and communication by enabling users to visualize their -omics data using a web browser (on a PC or mobile device). It increases user productivity by simplifying multiomics data analysis using well developed maps as a guide. Users using this tool can gain insights into their data sets that would be difficult or even impossible to tease out by looking at raw number, or using their currently existing tools to generate static single-use maps. Arrowland can help users save time by visualizing relative changes in different conditions or over time, and helps users to produce more significant insights faster. Preexisting maps decrease the learning curve for beginners in the -omics field.

In one embodiment, state of multiomics data are presented in the browser as a two-dimensional flowchart resembling a map, with varying levels of detail information, based on the scaling of the map. Users can pan and zoom to explore different maps, compare maps, upload their own research data sets onto desired maps, alter map appearance in ways that facilitate interpretation, visualization and analysis of the given data, and export data, reports and actionable items to help the user initiative.

More specifically, the "intersections" of the maps represent metabolites (metabolomics). On a given map, a given metabolite can usually be represented only once, though there are sometimes exceptions made to simplify the visual layout. The "streets" of the maps represent chemical reactions that turn one metabolite into another, and are associated with the proteins catalyzing the reactions (proteomics). Also, each protein (represented as a street) in turn can be associated with one or more genes in a cell. When transcribed, those genes are translated into more of the proteins (transcriptomics). An Arrowland map or any subsection represents a sequence of possible chemical transitions, some irreversible, some reversible, by which one metabolite can be converted to another metabolite (fluxomics).

By modifying the maps with varying colors, line styles, patterns, directional indicators, decorative shapes and paths, users can create a unified presentation of multiomics data in Arrowland. By hiding and showing parts or layers of the map, in different viewing states, users can set their preference for browsing -omics data integration flexibly and intuitively.

Arrowland

Disclosed herein is Arrowland, a web-based software tool for viewing multiomics data (transcriptomics, proteomics, metabolomics, fluxomics) in an interactive, intuitive and multiscale fashion. Arrowland can facilitate multiomics data comparison and analysis, and this will promote the gathering of larger -omics data profiles.

Particularly challenging is visualizing all four -omics data types (transcriptomics, proteomics, metabolomics, fluxomics) simultaneously in an interactive manner. These types of visualization of several data types are particularly useful because they provide independent lines of inference for the researcher: e.g. if a pathway proteins are upregulated, seeing transcripts increase and metabolites change accordingly provide extra assurance of increased pathway activity. Here, we present a new tool, Arrowland, for simultaneous visualization of functional genomics data (i.e. transcriptomics, proteomics, metabolomics and fluxomics, FIG. 1). Arrowland uses the latest web technology to produce a web-based, browsable, online, multiscale depiction of metabolism, reminiscent of e.g. Google maps or Bing maps. In some embodiments, Arrowland is able to display multiple -omics data type in a single map, and compare different conditions in an intuitive and interactive manner.

Arrowland provides convenient data input in two different ways. The first one is a "direct" method, in which the single -omics data is input in a CSV file which details the labels and values for each label. However, one must be careful so that these labels and values conform to the data standards expected by Arrowland. These requirements can be automatically taken care of by the second input alternative, where data is obtained in a standardized fashion from the Experiment Data Depot (EDD), an interactive online open-source tool that serves as repository of experimental data.

Visualization of -omics data is provided in an interactive web map similar to those used in geographical maps such as Google Maps or Bing Maps. The user can interactively explore metabolism by dragging the map and zooming in where desired to as to obtain more details. Maps display different levels of detail on different zooming levels: at the lowest level of resolution the user can view the general structure of metabolism and at the highest level of resolution the user can view gene, protein, metabolite and reaction names as well as transcript levels, protein numbers, metabolite concentrations and estimated fluxes. Links to databases such as BIGG are provided as part of the map.

The metabolic map configuration allows for simultaneous viewing of transcriptomics, proteomics, metabolomics and fluxomics data. Furthermore, this compact disposition also allows for the comparison of all these four types of data in a single image. Hence, trends in different -omics data types can be compared and used as orthogonal lines of evidence.

In one implementation, the availability of Arrowland as an add-on for Jupyter notebooks provides metabolic engineers and computational biologists with a tool that can be used simultaneously with prediction enabled by packages such as COBRApy or the jQMM library.

Arrowland Implementation
Metabolic Models and Maps

Models can be obtained from a BIGG database and input in SBML, which contains all reactions and metabolites. Maps in svg format contain a position for each reaction and metabolite. Metabolites and reactions can be repeated in maps. Maps in svg format are easily modifiable.

In some embodiments, metabolic maps in Arrowland depict reactions, metabolites and cofactors for a single organism (See FIGS. 2A-2C), as described in a corresponding genome-scale model (GEM). Reactions may be depicted with black curved or straight arrows connecting metabolites, which may be shown by their abbreviation or full name, depending on the resolution level. In one embodiment, metabolites are displayed as nodes connected by arrows, such as black arrows or arrows of another color, which denote reactions. Cofactors may be shown as smaller thicker colored arrows, perpendicular to the corresponding reaction (See FIGS. 2A-2C). In one embodiment, cofactors are shown as smaller arrows, such as colored arrows, that are not parallel to the corresponding reaction. These arrows may be automatically placed next to the reaction. Information on each cofactor arrow and its legend may be obtained or displayed by clicking on the associated reaction and the "Stoichiometry" tab. Clicking on a metabolite or reaction may open a dialog providing links to the metabolite or reaction entry in several databases, such as BIGG, KEGG, BioCyc, ChEBI, EAWG-BBD, ModelSEED, MetaNetX, and HMDB.

Figure 1:
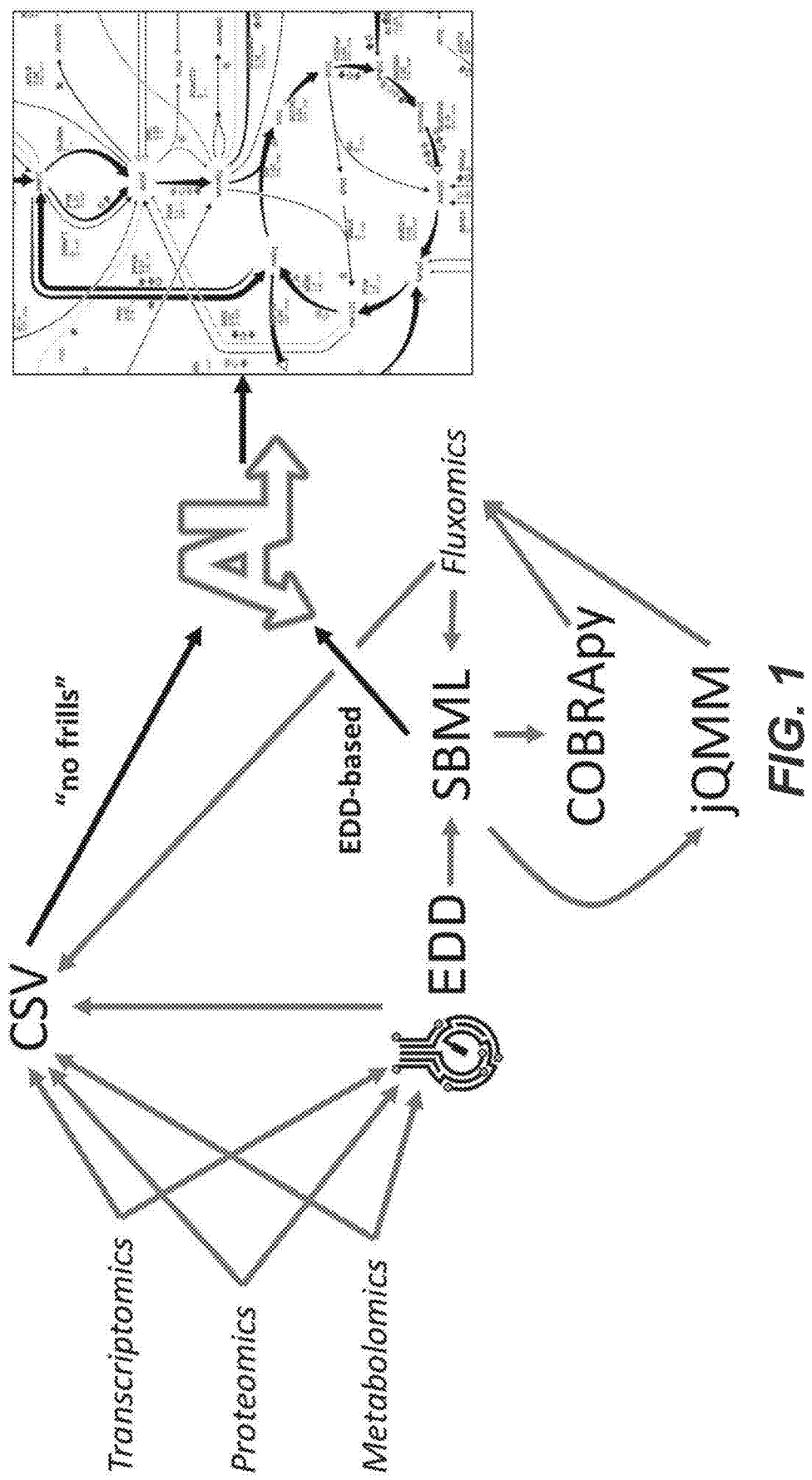
FIG. 1 shows data input in a multiomics data visualization system, referred to herein as Arrowland. Arrowland provides two alternatives for data input. The "no frills" alternative uses a CSV file type containing labels and values or -omics data. The EDD-based alternative uses an SBML file obtained from the Experiment Data Depot, an online repository for experimental information. Flux is typically calculated from the EDD SBML output using existing libraries (COBRApy or jQMM) and then added to the SBML file.
Figure 6:
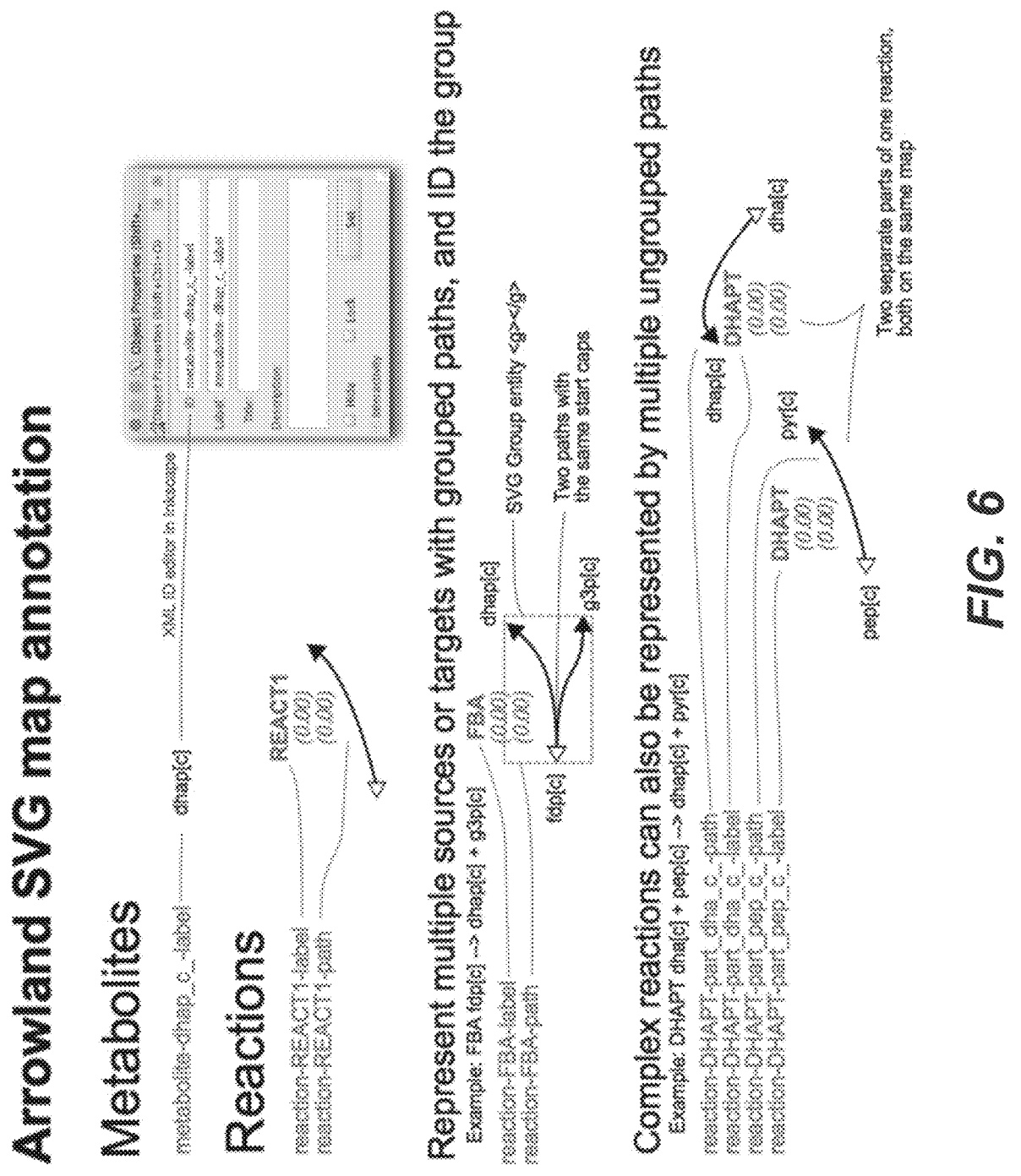

These types of metabolic maps may provide a more intuitive visualization of flux at low resolution levels, emphasizing flux continuity to the user. In one implementation, this type of metabolic mays be compact, such that it allows a depiction of several types of -omics simultaneously (FIGS. 3A-3C). In one embodiment, the type of metabolic map highlights continuity of flux, so that fluxes coming in and out of every node representing a metabolite can be viewed. This allows metabolites and reactions to appear in multiple places on a single map. Metabolic maps may be provided in SVG (Scalable Vector Graphics) format. An annotation standard that links metabolic maps to the corresponding GEM(s) may be implemented (FIGS. 1 and 6). The metabolic maps may be created for each GEM. In one implementation, Arrowland provides a map for the *E. coli* iJR904 GEM. Other maps for different organisms may be created with a SVG editor. Metabolic maps may require a consistent ontology to be complete and rigorous, so they may be based on GEMs. GEMs may provide comprehensive descriptions of metabolism, providing information for all reactions in metabolism, including products, reactants, stoichiometry and gene/protein associations. Products and reactants may be displayed as nodes in an Arrowland display. Each map may be tied to a GEM, that is provided in SBML (Systems Biology Markup Language) format and obtained from the BIGG (Biochemical Genetic and Genomic) database, for example.

The data to be displayed in Arrowland may be organized according to a hierarchy: the highest level object is a study, and different result sets are associated with a study.

Software Engineering

Front End

The front end of Arrowland can be based on the Leaflet mapping package using a combination of JavaScript and typescript. Typescript (typescriptlang.org) is a superset of the JavaScript language that allows type-checking and compiles to plain JavaScript. Leaflet is designed to draw grids of rasterized tiles prepared in advance on a server, or relatively simple vector graphics drawn in browser.

To display complicated networks on current hardware, a hybrid method has been developed that constructs portions of a network as vector graphics in small SVG documents (w3.org/TR/SVG11/), then rasterizes them into tiles within the web browser, using a rendering queue and an aggressively pruned cache to keep the memory footprint low. This hybrid tile layer may be combined with a collection of HTML layers to provide text information at different zoom levels, and an additional SVG layer that is not rasterized and is used to draw selection indicators and give other interactive feedback.

Leaflet may be used for mapping geographic data which may take the form of large rasterized planes of images representing a physical space, possibly overlaid with interactive labels attached to points or shapes. For this purpose Leaflet offers a handful of APIs to connect to servers that provide geographic data prepared in this way, for example, the OpenGIS specification. However, these APIs are not suitable for displaying multiomic data because nodes and connections in metabolic maps do not correspond to any real 2D or 3D space.

Figure 8:
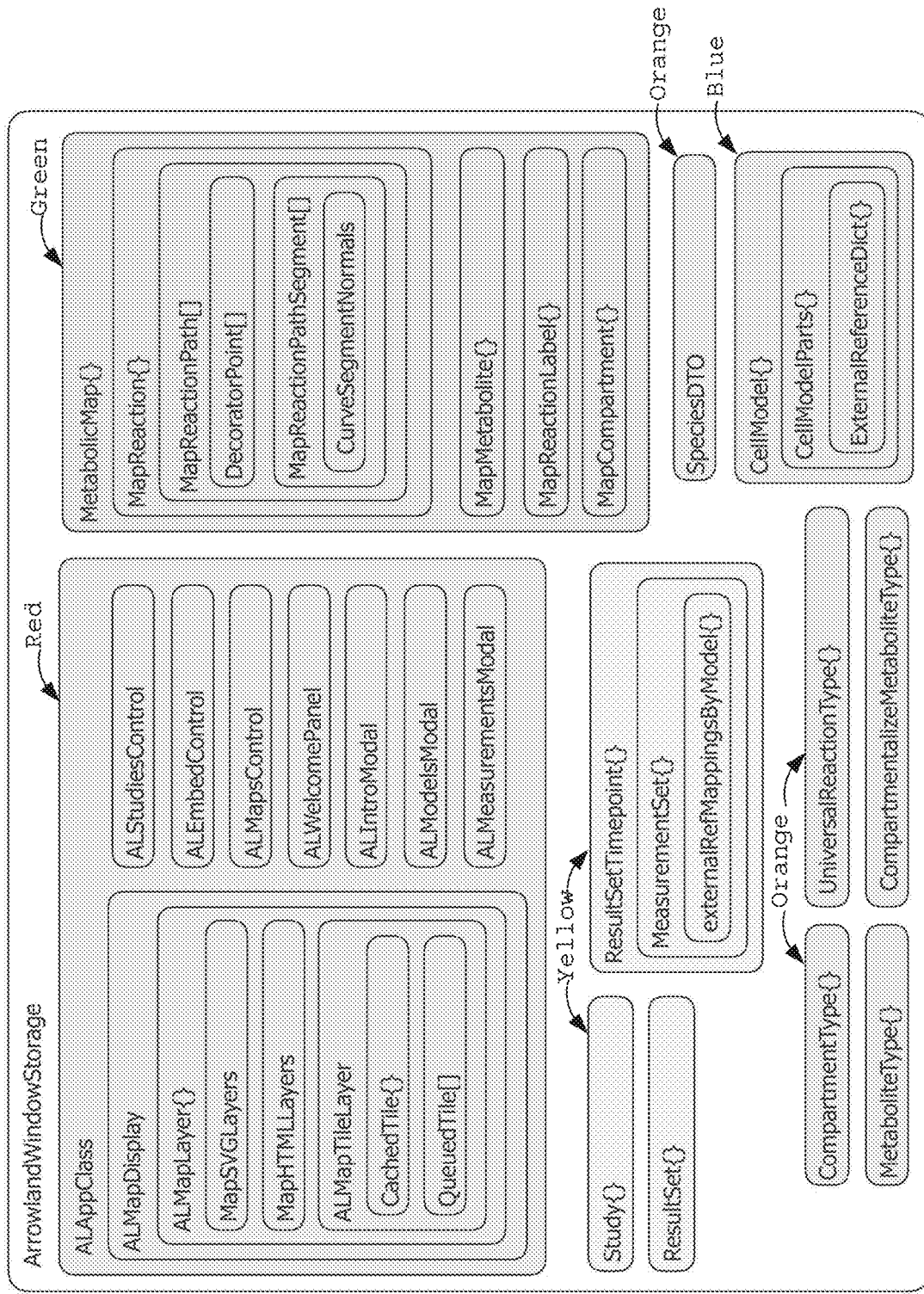
FIG. 8 is a schematic illustration of object allocation hierarchy in Javascript namespace on the client browser. The coloring indicates a correspondence to the Django-level data classes in FIG. 9. A curly braces suffix indicates a dictionary of the given object, and a square brackets suffix indicates an array of the given object. Objects without a suffix are allocated exactly once inside their enclosing object. Some objects have been removed for clarity.

In one embodiment, the Arrowland front end defines a hierarchical data structure (colored "green" in FIG. 8) that connects basic geometric shapes, such as boxes, ellipses, and bezier curves, with one or more metabolic entities, such as compartments, metabolites, reactions, and constructs and caches HTML and SVG objects on-demand as they are needed for drawing map tiles or displaying labels. These objects may be built separately depending on the currently selected map, model, and measurements in the Arrowland interface.

Arrowland may also implement a collection of user interface elements for organizing and manipulating metabolic models, maps, and user data. These elements may be instantiated once by corresponding classes (colored "red" in FIG. 8) when the Arrowland site is loaded, and the objects may be housed in an Arrowland "application" object (ALandApp) which is in turn housed in an Arrowland "window" object (ALWindow). This implementation may keep the JavaScript namespace to a minimum. After the initial page load and login, all subsequent data fetched from the server may be stored in the ALWindow object. As information is fetched in JSON from the server, such as maps, measurements, models, it is instantiated and sorted into the appropriate dictionaries of objects (colored "orange," "yellow," "blue," and "green" in FIG. 8) inside the ALWindow object.

Redundant or duplicative information, such as the same metabolite definitions fetched twice, is folded over itself in these dictionaries to keep memory usage low. This is valuable when browsing Arrowland on a cellphone using, for instance, a map and model with 10,000 reactions and 15,000 genes and proteins to display 150,000 measurements across 10 time points.

Map tiles may be created in the browser by assembling intermediate SVG files. All the bounding boxes for all the reaction paths may be determined in advance, for example on the server, and provided to the front end. Each time a tile is requested, the front end compares the bounding box of the tile with that of each reaction path, and accumulates a list of any paths whose boxes intersect the tile. Then it composes a small SVG document consisting of only those paths, which may be post-processed to show flux amounts, plus some SVG commands to define the arrowheads that cap some paths. Once built, the SVG strings for each path may be cached for use in constructing nearby tiles.

Figure 5:
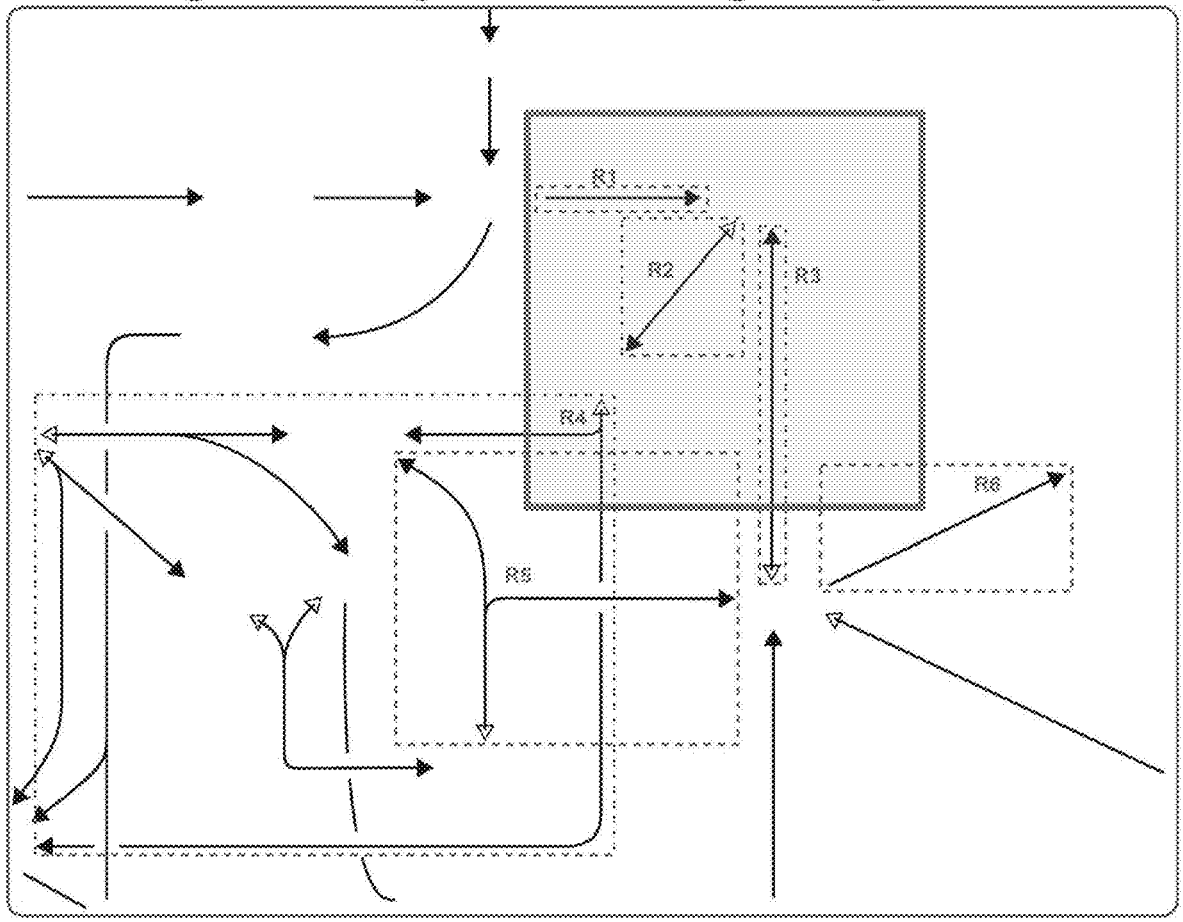
FIG. 5 is a schematic illustration of generating a single tile in Arrowland. Reactions R1-R6 have bounding boxes that fall within the target tile area, so their path data is expressed in a single short SVG document with a view box set equivalent to the tile's size and location. The resulting document renders a square tile. Once built, the SVG strings for each path are cached for use in constructing nearby tiles.
Figure 7:
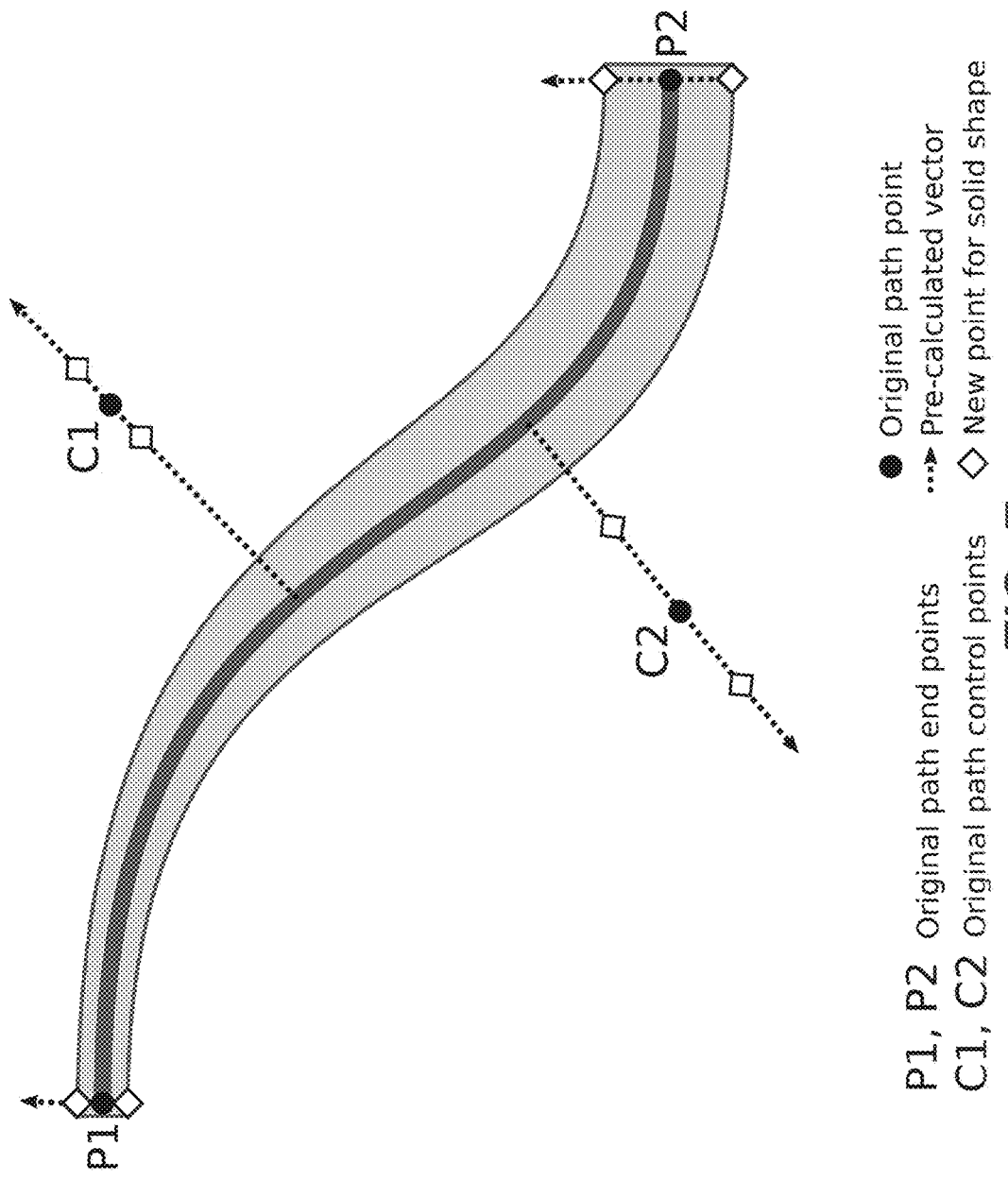
FIG. 7 is a schematic illustration of building tapered shapes from paths with pre-calculated vectors. The vectors are used to reposition the four points of the original bezier curve, and the intensity multipliers are used to more precisely reposition the two control points. Using these six values, the original Bezier curve can be offset by any amount in O(1) time.

In one implementation, the content of the resulting SVG document is copied onto an HTML canvas element, effectively rasterizing it into an image that can be drawn quickly on the screen. In this implementation, the SVG document itself was not passed to Leaflet for use as a tile and the browser would not render the SVG document as a vector graphics element, resulting in improved performance. An example of this implementation is outlined in FIG. 5. In the figure, reaction paths R1-R6 have bounding boxes (shown as dotted boxes) that fall within the target tile area (the solid box), so their path data is placed into an SVG document (shown under the illustration) with a view box set equivalent to the tile's size and location.

Using small intermediate SVG files as a source for tiles, rather than one large SVG file of the entire network may result in significant memory savings as well as faster rendering. Each intermediate SVG file may be discarded directly after use, and only the resulting rasterized image (on the canvas element) is cached. The strings that draw each reaction path may be cached as they are built, eventually adding up to a collection of strings as large as the entire network, but they can be used to assemble different versions of tiles at multiple zoom levels, for example, without cofactors when zoomed all the way out, in a way that a monolithic SVG document cannot.

Back End

The back end may be written in python using the Django framework (djangoproject.com), and a number of extensions to the Django framework, including the authentication library, environment library, and redistribution library, such as django-allauth, django-environ, and django-redis, respectively. The backend system may use the Celery task runner and theRabbitMQtask queue for asynchronous execution of long-running tasks such as SBML model and SVGmap imports.

Figure 9:
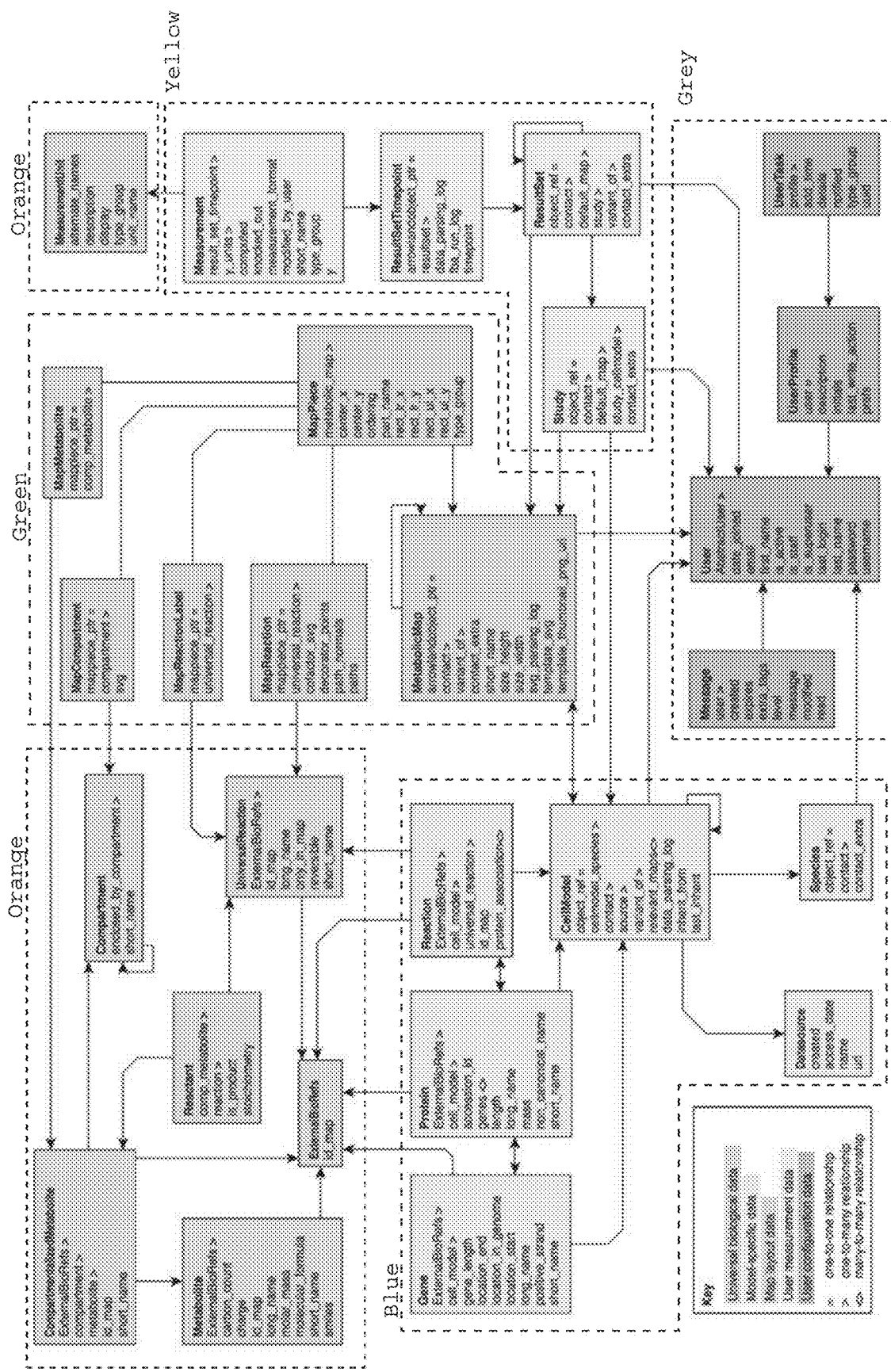
FIG. 9 is an exemplary block diagram of a Django-level data model. Tables are grouped by color shown as outlined boxes. Orange tables describe universal components across all metabolic models. Teal tables describe metabolic models and their components. Green tables describe maps and map component layouts. Gray tables describe users, and yellow tables describe user data including measurements. Some tables used by Django extensions have been removed for clarity. The caret suffix on a field indicates it forms a one-to-many relationship. The equals suffix indicates a one-to-one relationship.

The data models used in Django are described in FIG. 9. The models may be divided into five categories based on their use. One category is user configuration data (colored "grey" in FIG. 9) which integrates with the django-allauth module and Celery task runner, and stores permission information for making measurement data viewable to other users. Along with the "User" model in this category, the user measurement data models (colored "yellow" in FIG. 9) create a hierarchy of Users, Studies, Result Sets, Result Set Time points, and individual Measurements, to organize each user's experiment data.

Figure 4:
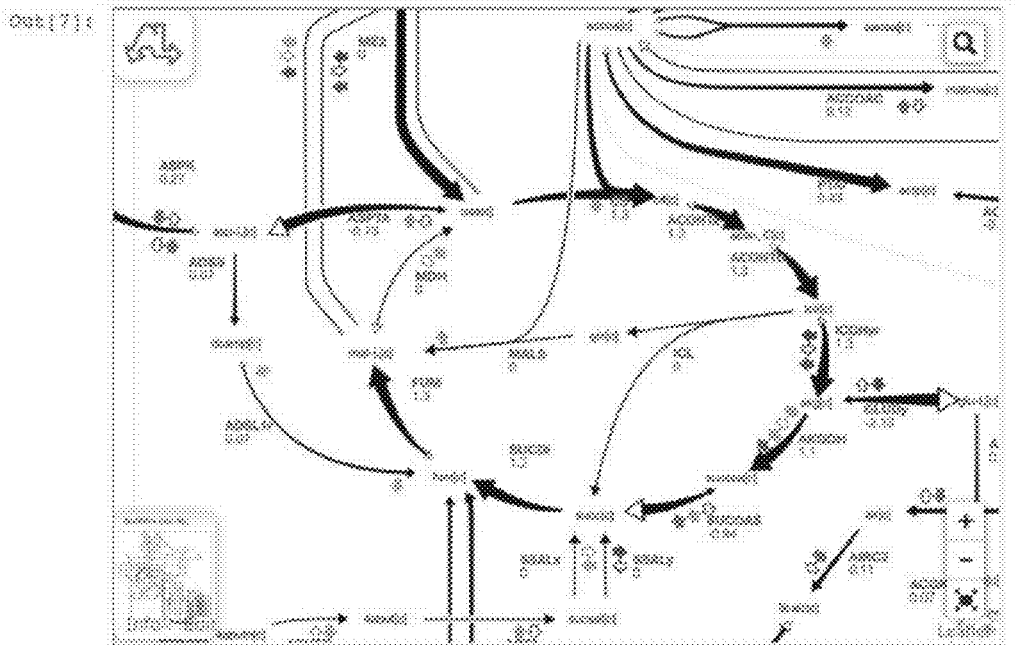
FIG. 4 illustrates interactive map customization. Integration with Jupyter Notebook allows for interactive sessions of predictions followed by the corresponding visualization.

Models that describe the structure of metabolic networks may span two categories—one containing per-network information ("model specific data" in FIG. 9), and one containing information that applies (or potentially applies) to all networks ("universal biological data" in FIG. 9). This division is based on the metabolic network description. For example, most networks reference a universally accepted definition of a formate molecule even if they use a different name to identify it ("283" in PubChem, "for" in BIGG,) but only some networks share definitions for genes and proteins, meaning that identifiers which may have identical names should be kept distinct based on their originating network. When Arrowland imports a metabolic network in an SBML document, it considers the metabolites ("species" in the SBML nomenclature) and reactions to be universal, and creates new universal records, such as "UniversalReaction" and "Metabolite" in FIG. 8, for any that Arrowland, or the user's instance of Arrowland, has not encountered before. Arrowland may then create network-specific records for each gene, then each protein, then each reaction ("Gene", "Protein", "Reaction" in FIG. 4) to carry and link the network's protein and gene associations for each reaction, which are very likely to be unique for that network. Using two models for reactions ("UniversalReaction" and "Reaction") may reduce data redundancy, since the reactants and stoichiometry for a given reaction do not vary, while the protein associations and external references may. Arrowland may store external references for every network-related record, gathered from the relevant section of each SBML document and encoded in a simple JSON format. These may be used to provide reverse references on the front end when mapping measurements to networks, and to provide links to external databases.

The back end may use jQMM for dealing with models and SBML files.

The remaining category of back end models may concern map layout data (colored "green" in FIG. 9). In Django, these models are represented as one class for identifying maps ("MetabolicMap" with one record per map), and four classes that are subclassed from a parent ("MapPiece"). In the database these become six tables, with "MapPiece" a distinct entity.

Maps may be imported into Arrowland as SVG files. When the SVG is parsed, Arrowland may look for a group element with the id "map element group", and consider any path elements inside it to represent reactions, and any text elements to represent either reaction labels or metabolite labels. Arrowland may associate these elements with known metabolites/compartments and reactions by examining their XML ID strings. For example, a path element (or a group element containing path elements) with the ID "reaction-PSP L-path" would be associated with the reaction named "PSP L", and Arrowland would extract the drawing commands from the path(s) and create a new MapReaction record referencing that reaction. Arrowland may expect paths to be composed of any number of straight lines or cubic bezier curves, and if any other SVG commands are present, Arrowland may attempt to convert them.

Arrowland maps enables a web browser to smoothly render thousands of curved, tapered arrows with clean overlaps (arrows below render with gaps to admit arrows above). In part this is accomplished by the tiling system described herein.

Calculating the parameters to draw a series of curved arrows with some arbitrary taper relative to a template curve is computationally expensive. The bezier paths may need to be rebuilt as solid shapes, composed of two halves that follow either side of the original paths with a slowly varying offset. If Arrowland had to recompute each shape for every flux magnitude of every reaction path from scratch, the interface would slow down very significantly.

Instead, Arrowland may compute "path normals" (visible in the MapReaction model in FIG. 9). When the paths of a template SVG map are first imported, each bezier curve may be run through a function that uses a geometric approximation method to compute four vectors and two intensity multipliers. The vectors may be used to reposition the four points of the original bezier curve, and the intensity multipliers may be used to more precisely reposition the two control points. Using these six values, the original bezier curve may be offset by any amount in O(1) time. When the Arrowland front end constructs the solid shapes used to represent flux values, it may construct each half of the shape using the same "path normals" to offset each bezier curve by positive and negative amounts.

All back end Arrowland services may run inside docker containers. The configuration can be customized to suit various production environments. These containers may be distributed across two virtual Docker networks: a proxy network and a back-end network. Only the proxy network may be visible to the host network that Docker runs on, while the back-end network may only be visible to the proxy network, insulating most of the containers comprising Arrowland, for added security. The containers expose only the network ports necessary to operate the services they run, and are interconnected via the back-end network.

Flux Scaling

The following function relates the arrow width represented in Arrowland with the reaction flux:

function
def fluxToArrowScaler(v):
if not v:
  return 0

$v = abs(v)$

Above x=9.1 we scale logarithmic past about 14 if v>9.1:

$v = 13.4 + math \cdot log(v - 6.05)$

Between about x=⅔ and x=9.1 we scale logarithmic on a range from approximately 8 to 14 elif v>=0.66:

$v = (8 * math \cdot log((v * 0.33) + 2)) + 1.63$

Below x=⅔, we approach 8 on a sharp curve that inflects at around x=⅓
else:

$j = 1 - math \cdot sin((math \cdot pi / 2.1) * v)$ $v = 8 - (8 * (j * j * j))$ return v The same function is used to produce the width of the transcriptomic and proteomics side halos and the metabolomics circle radius.

Altogether, these data show one example Arrowland implementation.

Capabilities

Convenient Data Input

Figure 2C:
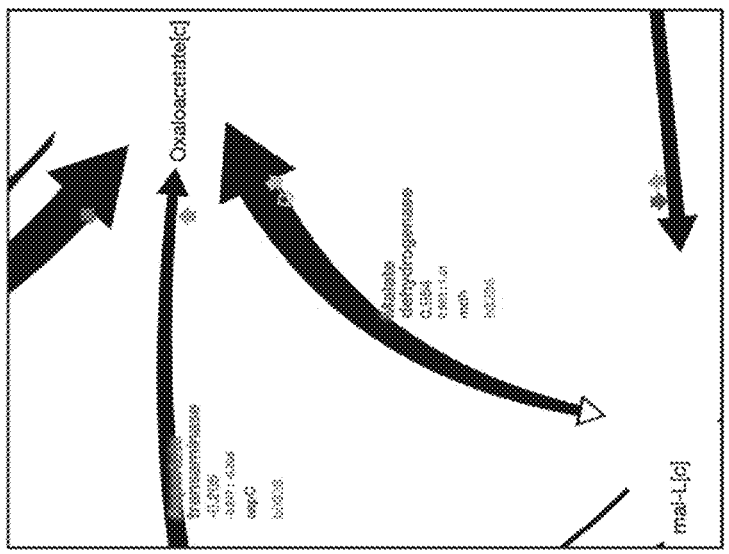
FIGS. 2A-2C show exemplary flux visualizations at different resolution levels. Metabolic flux for each reaction is shown as the thickness of each arrow. More details are revealed as the user zooms into the map: at the lowest resolution (FIG. 2A) a general view is available that offers an intuitive understanding of flux flow throughout cell metabolism. Zooming in (FIG. 2B) offers a more limited view of metabolism, but more details are revealed: in this case, reaction names, as well as fluxes and confidence intervals are presented in red. At the highest resolution level (FIG. 2C), only a few reactions are presented but information on protein and gene names is available, as well as full names for reactions and metabolites (instead of abbreviations). Transition between all resolution levels is seamless and interactive through the mouse scroll button, as in geographical maps such as Google or Bing maps.
Figure 2B:
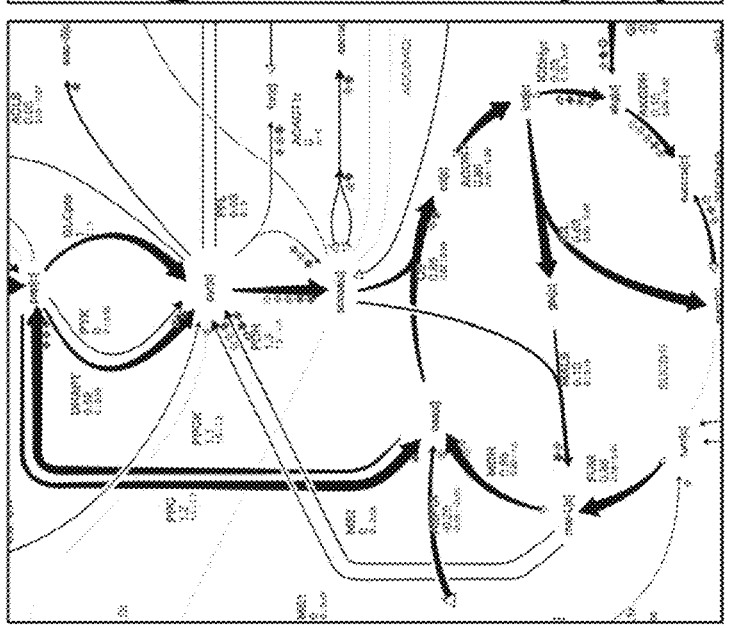
Figure 2A:
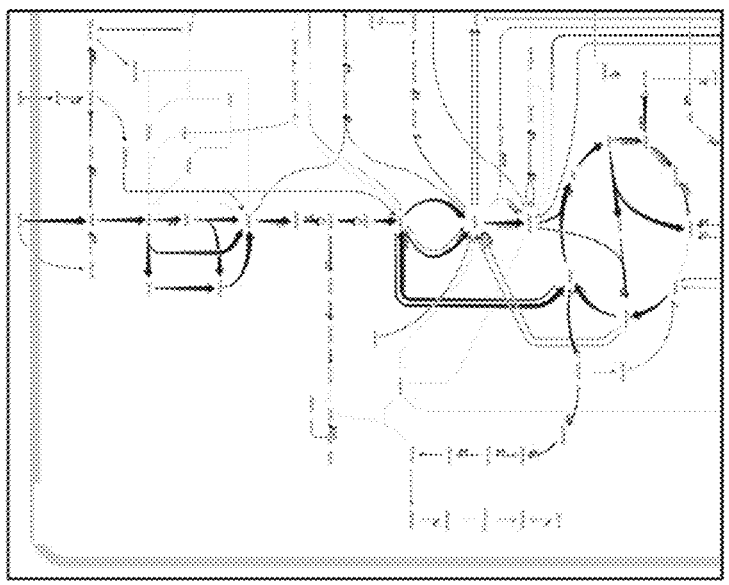

In some embodiment, Arrowland provides two different ways to conveniently load -omics data for visualization. The first one involves a CSV (Comma-Separated Values) file as input, containing two columns: the key (gene, protein, metabolite or flux name) and the corresponding value. The key name for the gene, protein, metabolite or reaction must conform to the standard in the corresponding SBML model file. Currently, all SBML model files in Arrowland are obtained from the BIGG database (King et al., A platform for integrating, standardizing and sharing genome-scale models. *Nucleic Acids Res*, January 2016, 44:D515-22; the content of which is incorporated by reference in its entirety). Data input can be done by dragging and dropping the file on the landing pad (See FIGS. 11A-11T) and the -omics data can be immediately viewed on the metabolic map (FIGS. 2A-2C). In order for Arrowland to properly parse this data, a model and map can be selected in the study (see "Metabolic models and maps" section).

The second way to load -omics data into Arrowland involves the Experiment Data Depot (EDD). EDD is an online tool designed as repository of experimental data and metadata (https://public-edd.jbei.org/), which provides data in standardized formats to be use by analysis tools such as Arrowland. EDD provides two types of outputs. The first one is a CSV file where the keys and values are automatically formatted for input into Arrowland. The second one is an SBML file which is properly formatted as input into Arrowland. The use of EDD in combination with Arrowland provides a quick, automatic and efficient way to visualize -omics data once it is loaded into EDD, eliminating the consuming task of translating between different -omics data standards.

Flux Data Visualization

Once data is loaded into the system, Arrowland provides an interactive, intuitive, multiscale interface for exploring metabolic maps (FIGS. 12A-12AA), similar to those developed for geographical maps (e.g. Google Maps™, or Bing Maps™). The user can interactively drag and move the map to focus on different part of metabolism and intuitively explore the metabolic map. Wherever more detail is desired, the mouse rollover provides zoom capabilities to zoom in, change the scale, and obtain more details or zoom out and get a general view of metabolic fluxes (See FIGS. 12A-12AA and FIGS. 2A-2C). Several description levels for different scales allow the displayed information to change at different zoom levels. At the closest zoom level, full metabolite and reaction names, as well as associated proteins and genes, and corresponding fluxes are shown. At the furthest away zoom level, all names are eliminated and only the general flux profile can be appreciated. The flux maps have been designed to facilitate this overall flux profile examination at the lowest resolution over other flux map types (King et al., A Web Application for Building, Sharing, and Embedding Data-Rich Visualizations of Biological Pathways. *PLoS Comput Biol*, August 2015, 11:e1004321; the content of which is incorporated by reference in its entirety). Links to the BIGG database are provided when clicking on reaction or metabolite names, so the user can obtain all the information on the reaction or metabolite under investigation. Reaction flux can be represented through black arrows of different thickness, according to the formula presented above.

Transcriptomics, Proteomics and Metabolomics Data Visualization

In one embodiment, Transcriptomics and proteomics data are represented in Arrowland as halos of different colors (blue for transcriptomics, red for proteomics) at each side of the black arrow representing the reaction (See FIGS. 3A-3C).

The width of each halo quantitatively represents the RPKM (Reads Per Kilobase of transcript per Million mapped reads, for transcriptomics) or the number of proteins per cell (for proteomics) for each reaction, according to the scaling formula presented above. These quantitative values of RPKM and proteins per cell can be directly observed by zooming all the way in the reaction (FIGS. 3A-3C). Metabolomic data is represented through circle of size depending on the metabolic concentration through the same scaling formula presented above.

The complementary and non-overlapping ways in which these -omics data are visualized allows Arrowland to display all these -omics data simultaneously. Furthermore, as shown below, this visualization scheme allows Arrowland to compare two different -omics data sets (e.g. for different time points or conditions) in a single image.

Comparison of Different Conditions and Time Points

Arrowland is able to compare two different -omics data sets by using the same visualization scheme detailed above, but have it slightly shifted, 10% transparent and its color slightly color shifted to green or indicate the non-baseline -omics profile. It is possible to compare different -omics data sets by setting a base line and then changed the compared data set. The compact visualization scheme described above allows for a comparison of the full -omics data set in a single image, unlike other tools.

Embedding in Jupyter Notebooks

Arrowland can be used in conjunction with Jupyter notebooks to provide interactive visualization. Jupyter notebooks are computable notebooks that contain live code, equations, visualizations and explanatory texts. As such, they have become the main analysis exchange tools for data scientists and modelers. Arrowland provides a python function that can take a json file containing -omics data and display it as a cell in the jupyter notebook (See FIG. 4). The cell provides all the interactive data visualization capabilities described herein (FIGS. 16A-16X). Data can be updated. In this way, modelers can interactively test their results (i.e. different flux prediction methods such as MoMA or ROOM) and share their results in a single notebook.

Additional Capabilities

In one embodiment, Arrowland includes the capability of interactive metabolic engineering, where a metabolic engineer can interactively knock out a reaction and see the predicted response for the cell's metabolism in terms of byproduct or other metabolic fluxes. Arrowland may be implemented to make map changes and additions more convenient. For example, map changes and additions may not be directed performed on a SVG. Arrowland may describe microbes or multicellular organisms.

For example, Arrowland may describe how fluxes are exchanged between different species at the lowest resolution level and metabolism for each species at the highest resolution level.

Arrowland Usage

In one implementation, examples of Arrowland usages are shown in Table 1, which include: visualizing transcriptomics, proteomics, metabolomics, and fluxomics data, visualizing all these four types of -omics data simultaneously, and comparing -omics data sets (e.g., -omics data sets of two or more different samples or of a sample at two or more time points).

TABLE 1

Example Arrowland usage

Figure 10B:
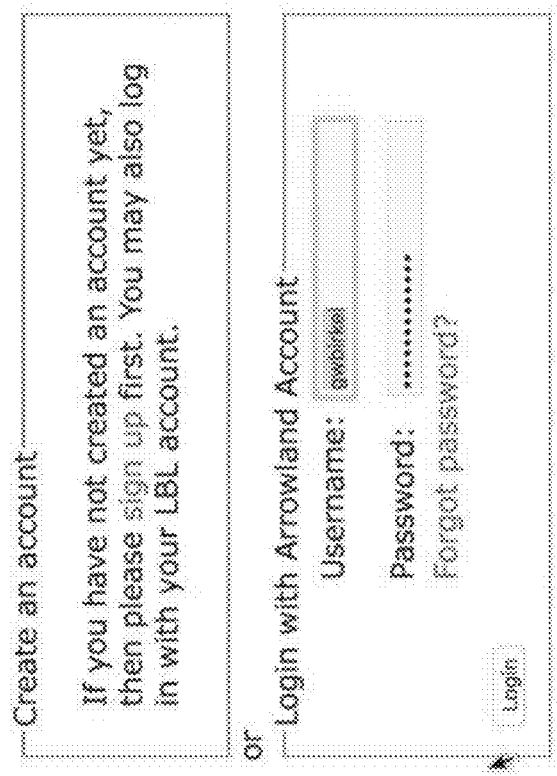
FIGS. 10A-10AP are screenshots of an exemplary overview of the data import process, with SBML and CSV files into Arrowland (public-arrowland.jbei.org/static/main/help/multi_omics_import.mp4; public-arrowland.jbei.org/static/main/help/import_tutorials.html; the content of each of which is incorporated herein by reference in its entirety). To get the data into Arrowland, a user first needs to login in. Once that is done, the user may create a new study if the user does not have one already. A study is the top-level container for data in Arrowland. A study is created with a default map and model selected and may be changed. Within the study, the user may want to create one new result set. Generally speaking, data from one experiment goes into one result set. All the measurements in a result may have time points associated with them. For example, T equals zero for measurements taken at the beginning of an experiment, and T equals 2.5 for measurements 2 and ½ hours later. Arrowland, by default, assumes the user is importing data for T equals 0. The user can change that default and add more time points if desired. Arrowland may accept data in two formats: CSV and spml. A CSV file includes a long list of labels and values so when the user drops it in, the user gives Arrowland additional context by specifying this CSV file has fluxomics values and therefore the labels in the file refer to reaction names. A file may contain reaction names not found in the model currently assigned of the study. Arrowland can still import and store those labels and values. The warning indicates that these labels and values currently have no effect. After approval, flux appears. The user can review the data in tabular form at any time by bringing up the measurements table. From the measurements table, the user can also add more data to this result set, for example, from a spml file that contains fluxomics, transcriptomics, metabolomics and proteomics all together. Some values, for example the fluxomics values, found in the spml may collide with values already in the result set. These may be edited, or the entire import may be rejected. Once approved, the map with all data is reloaded.
Figure 10M:
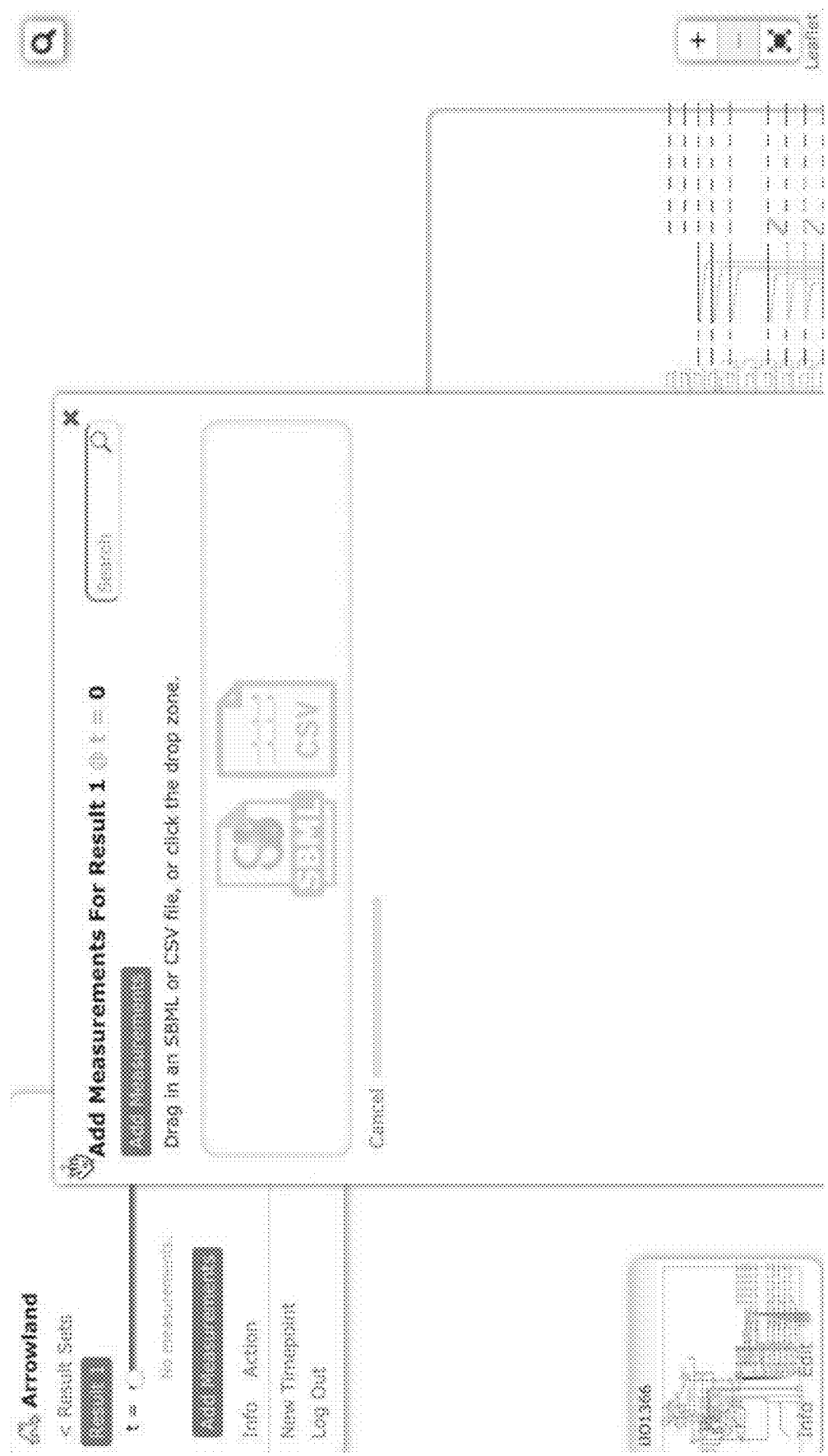
Figure 10N:
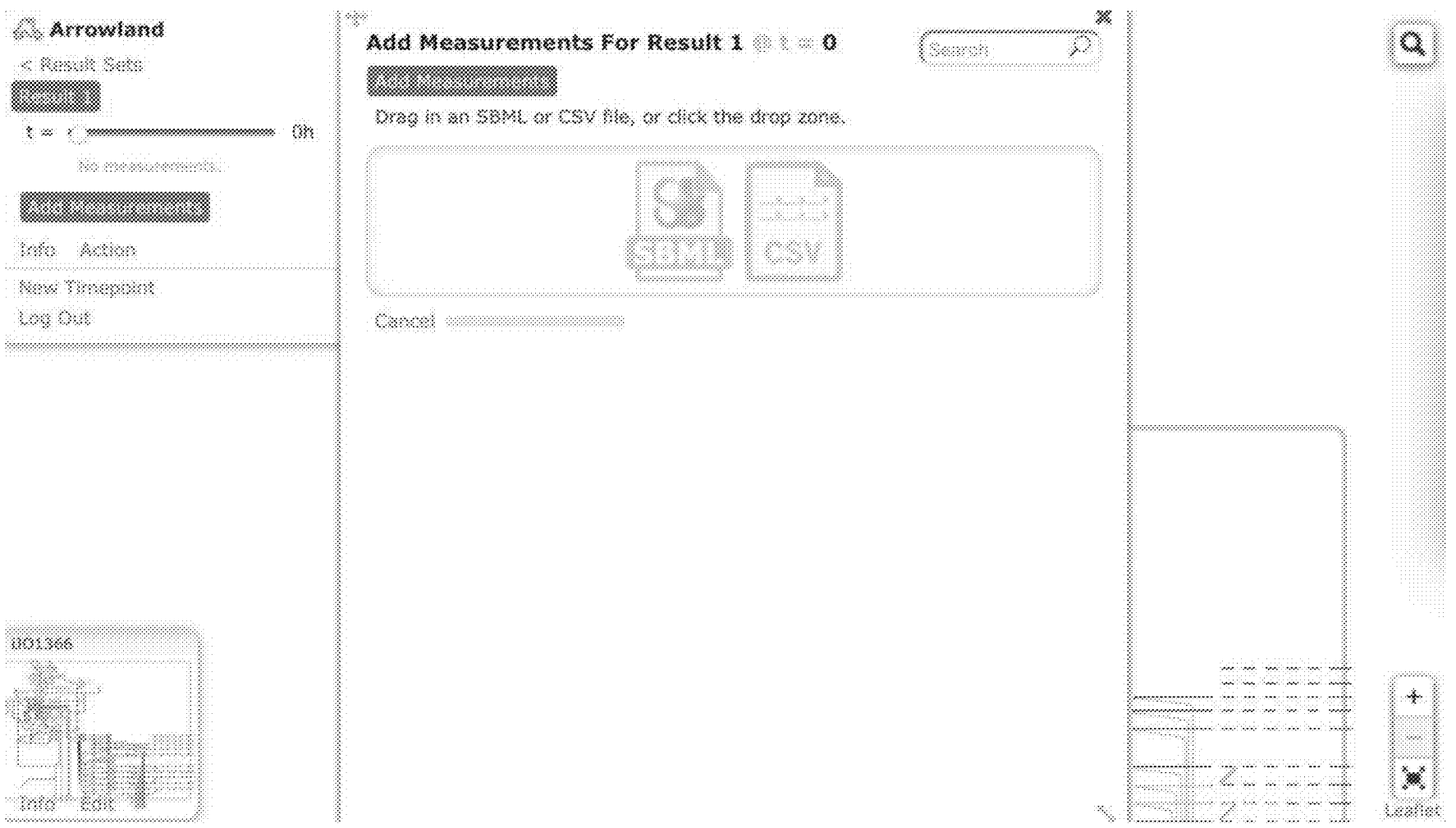
Figure 10O:
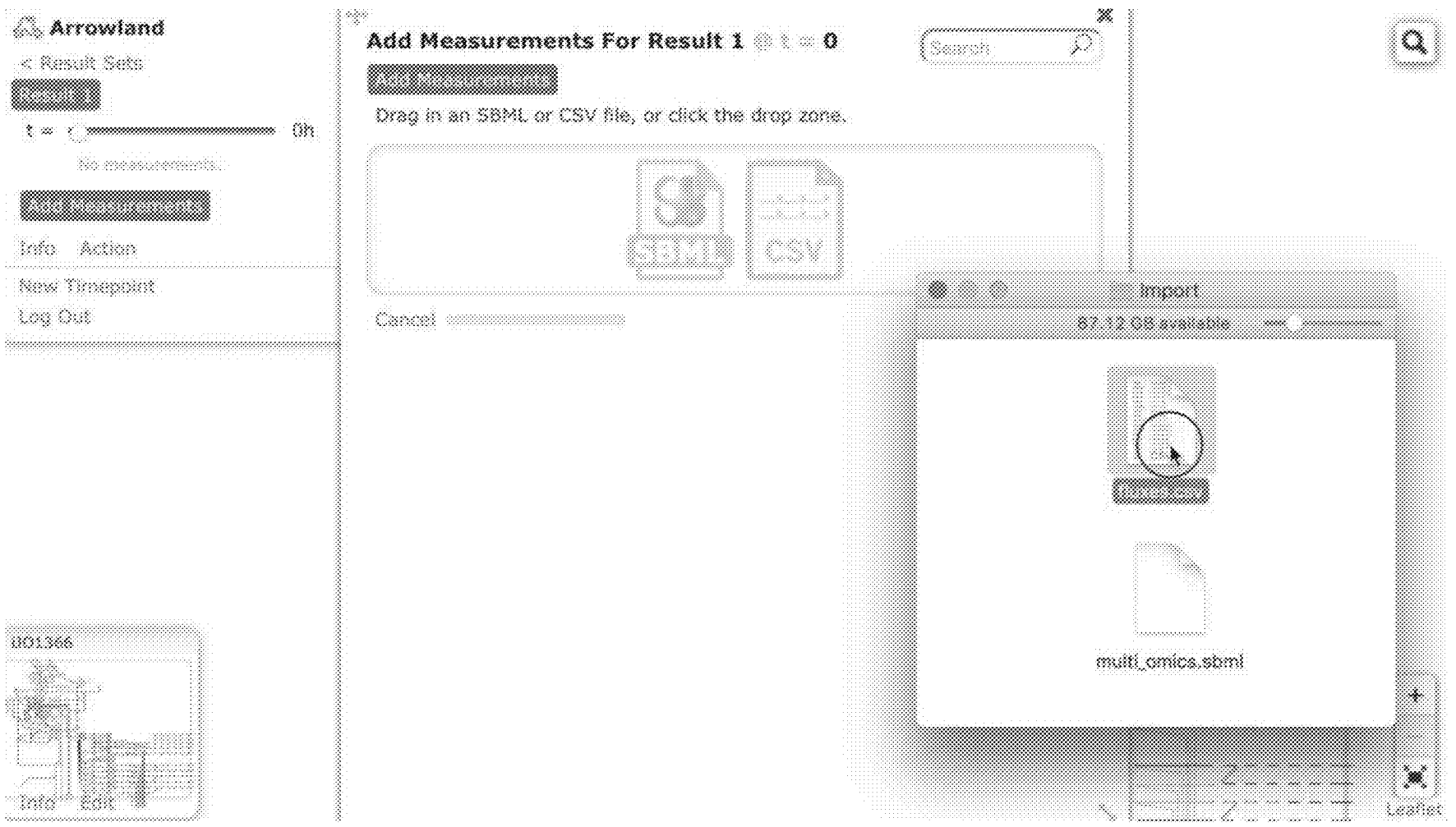
Figure 10P:
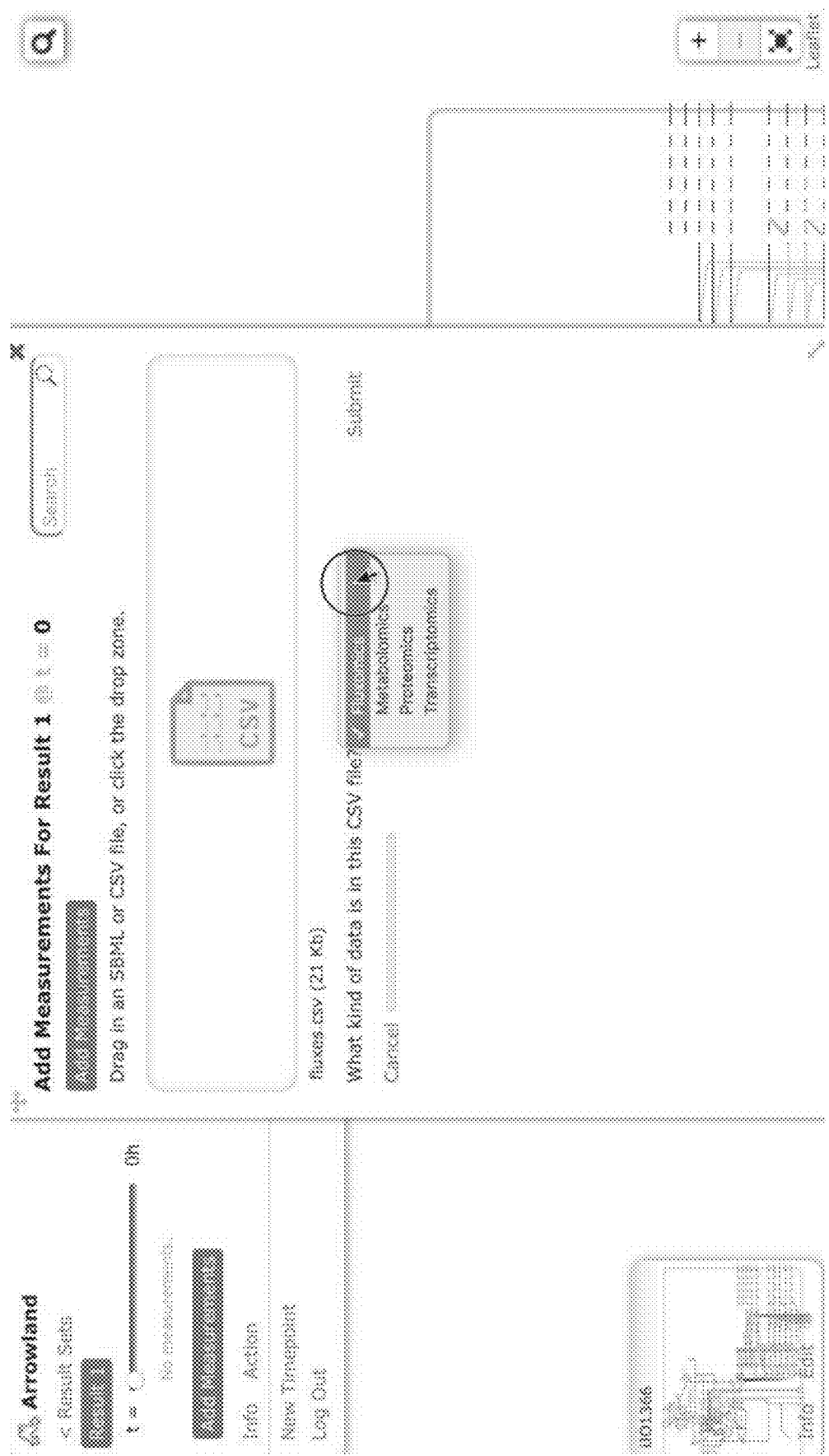
Figure 10Q:
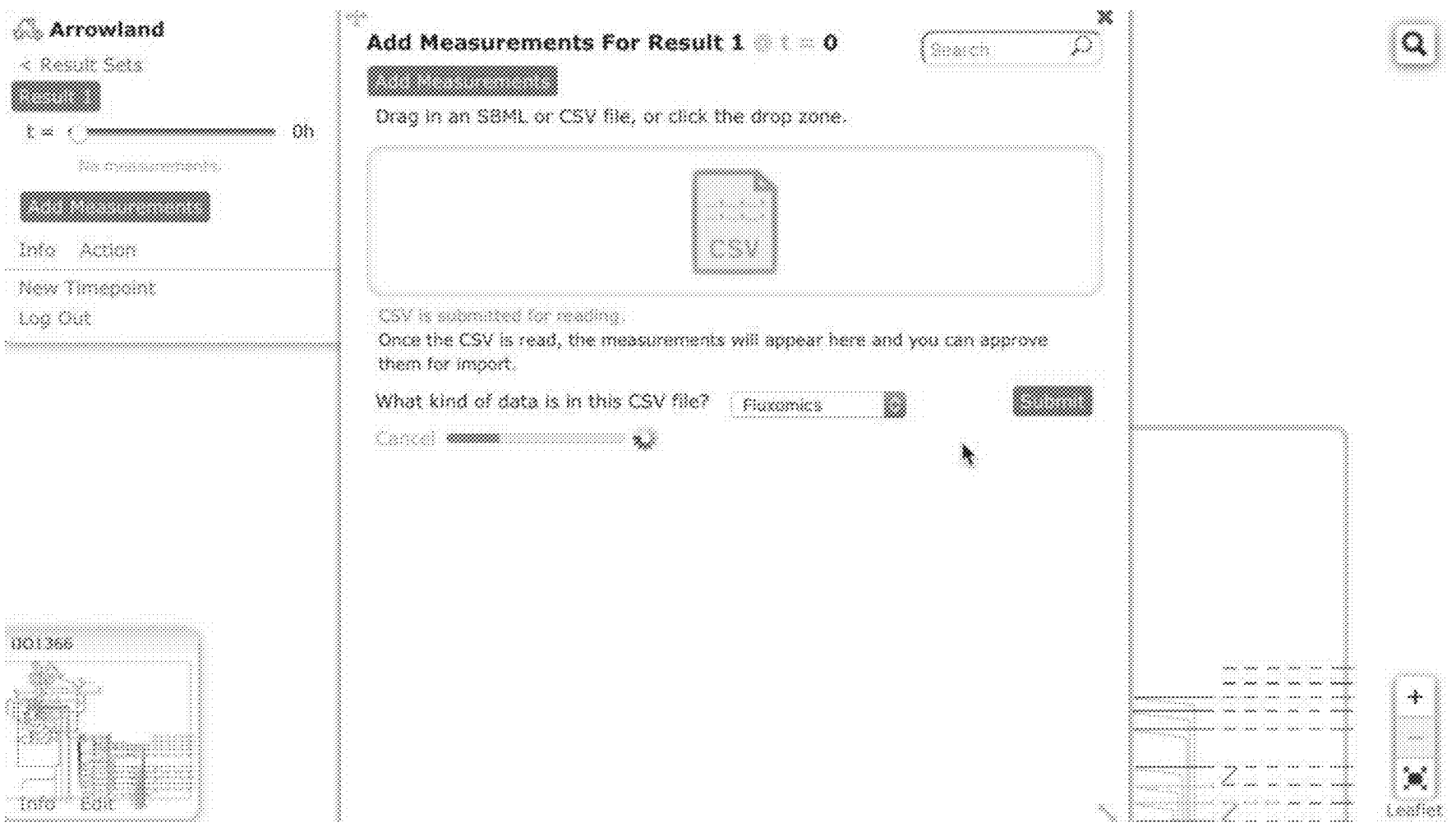
Figure 10T:
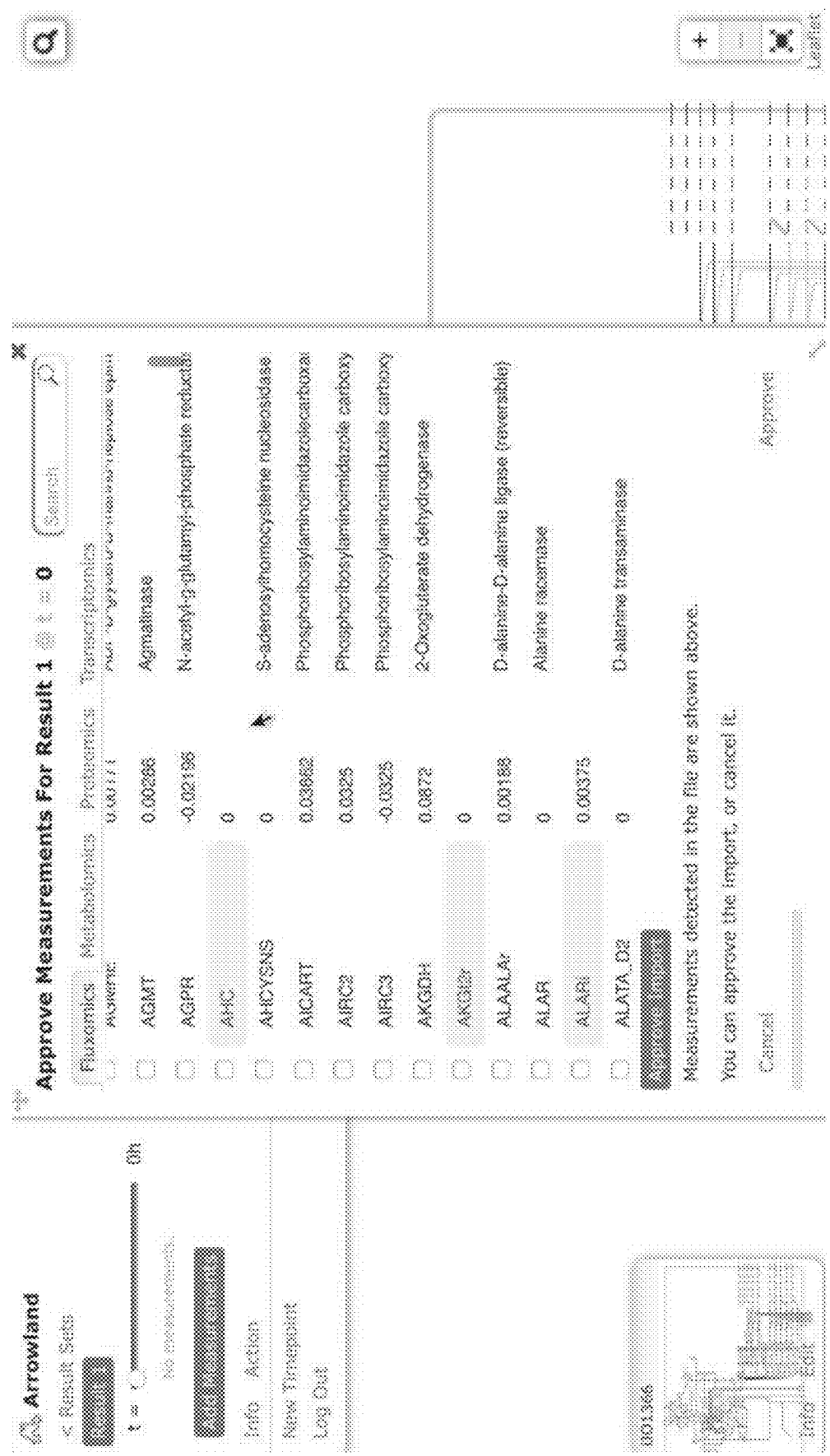
Figure 10U:
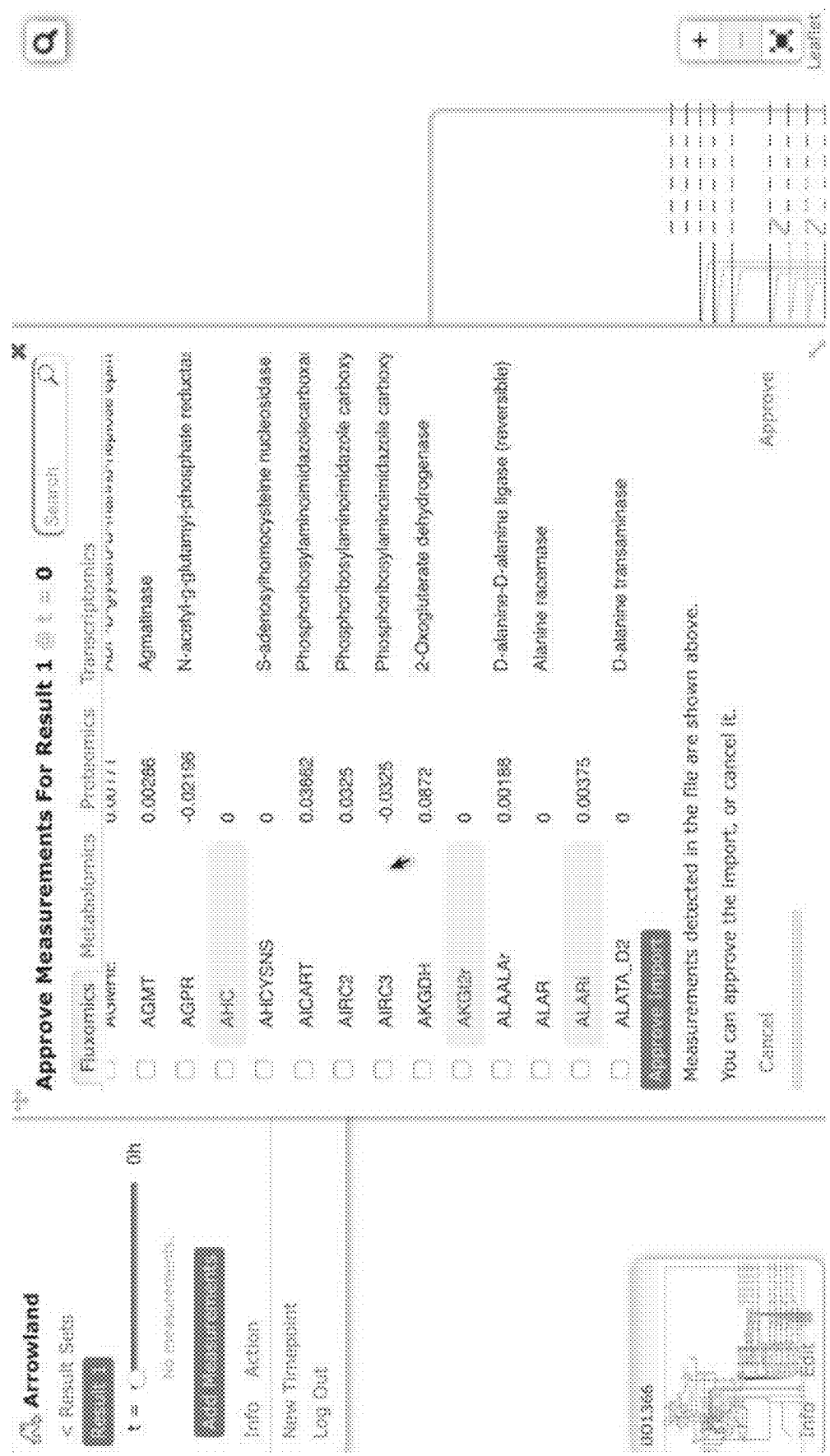
Figure 10X:
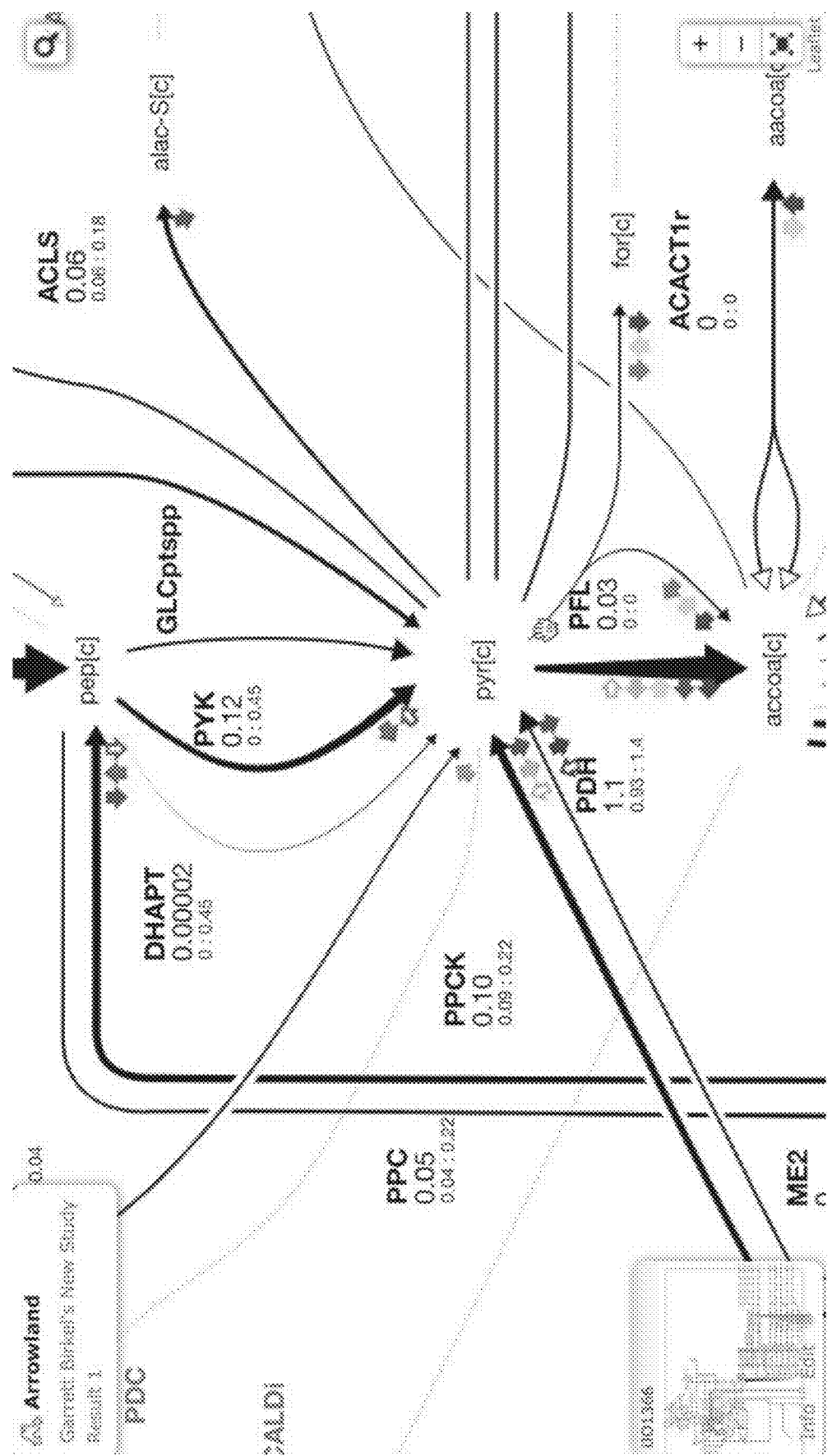
Figure 10Y:
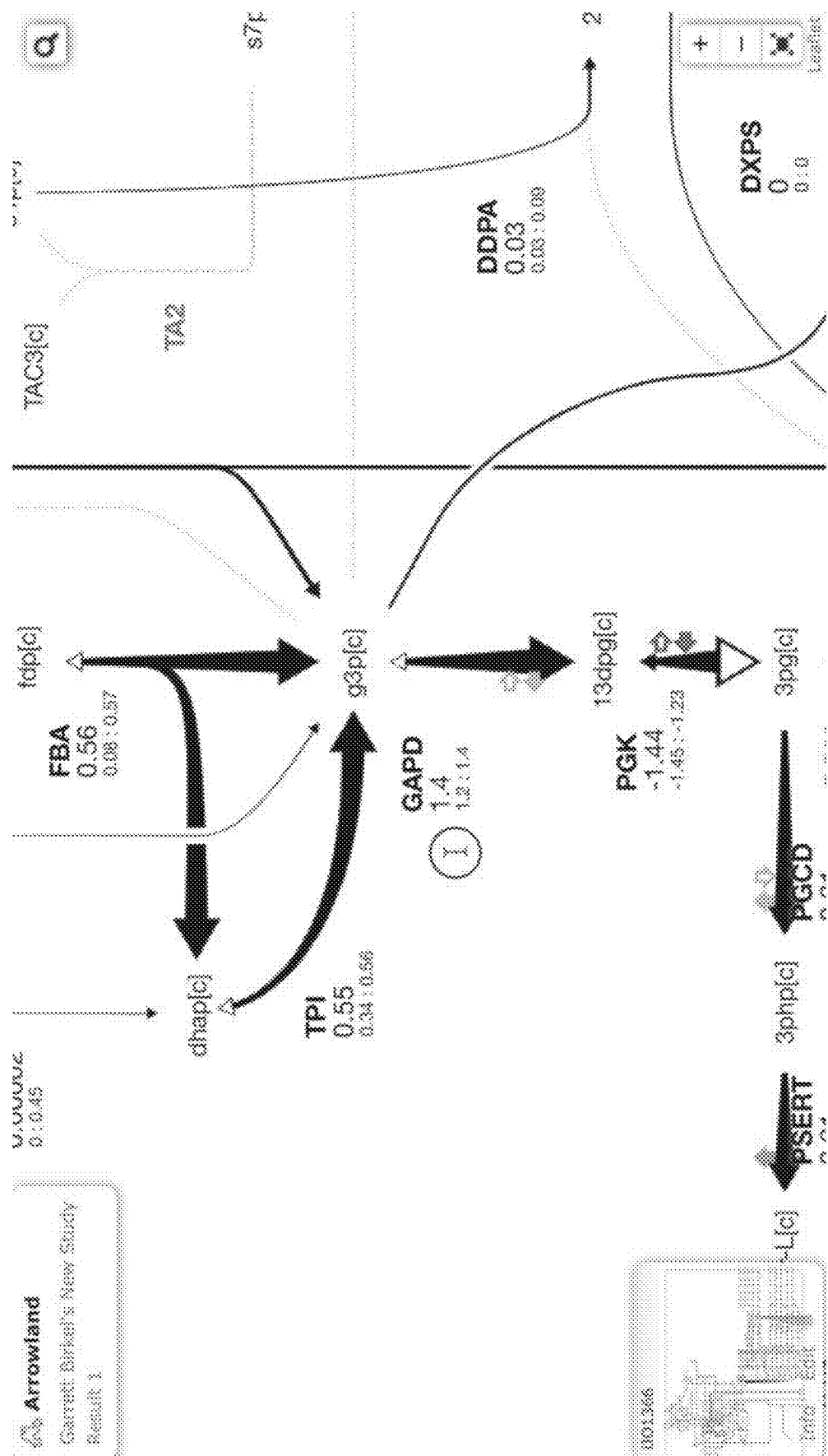
Figure 10Z:
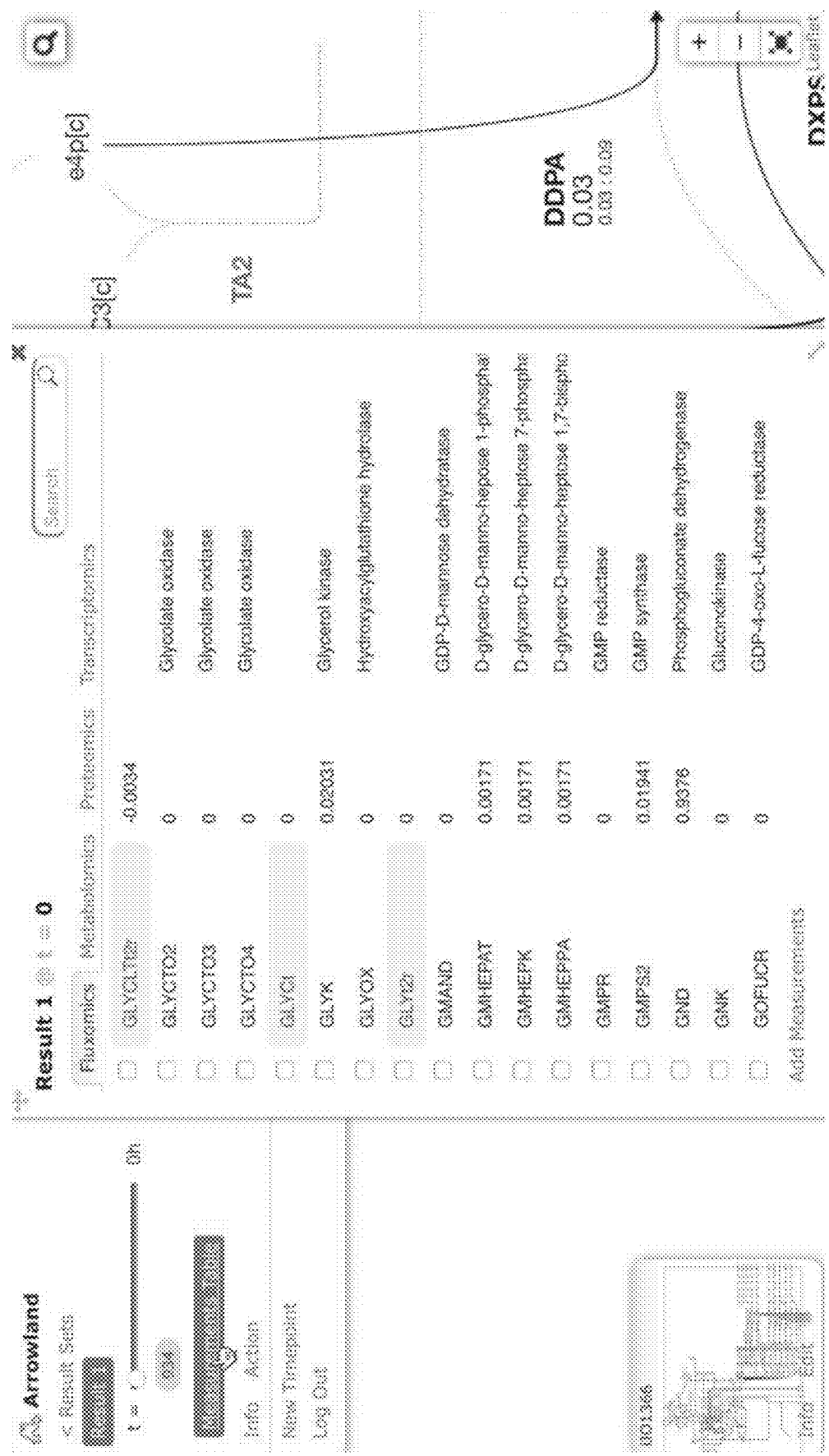
Figure 10A:
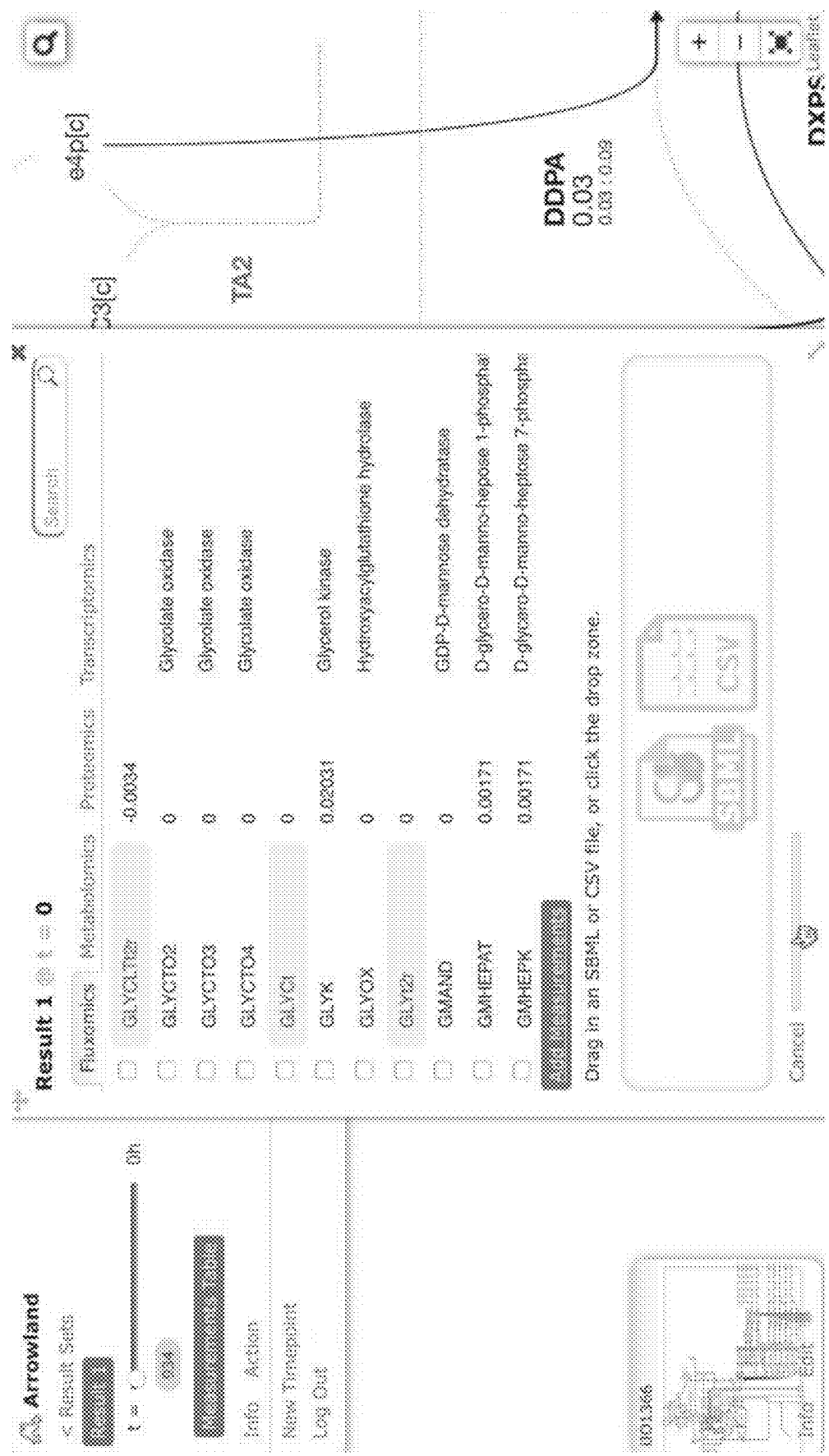
Figure 10A:
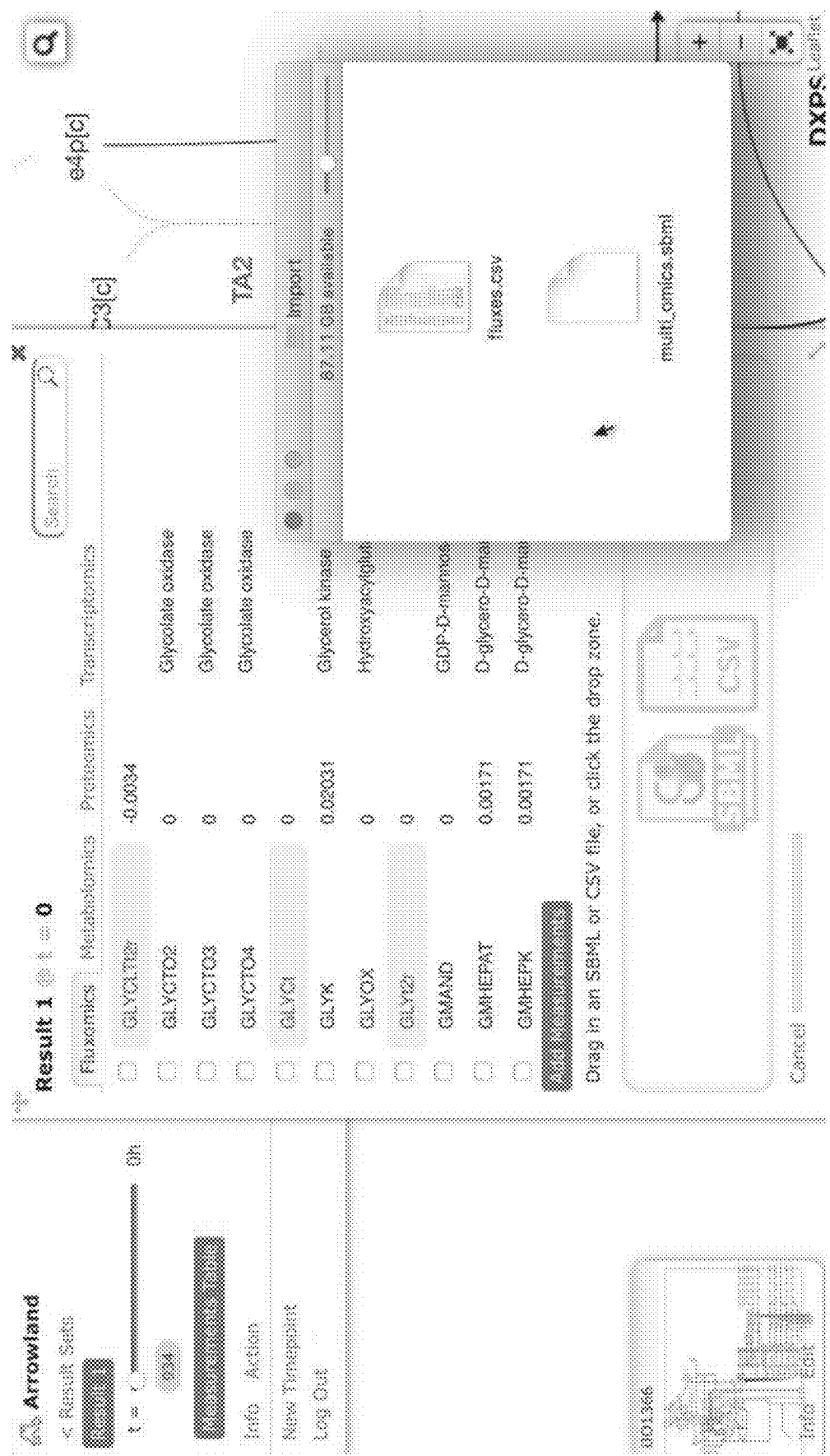
Figure 10A:
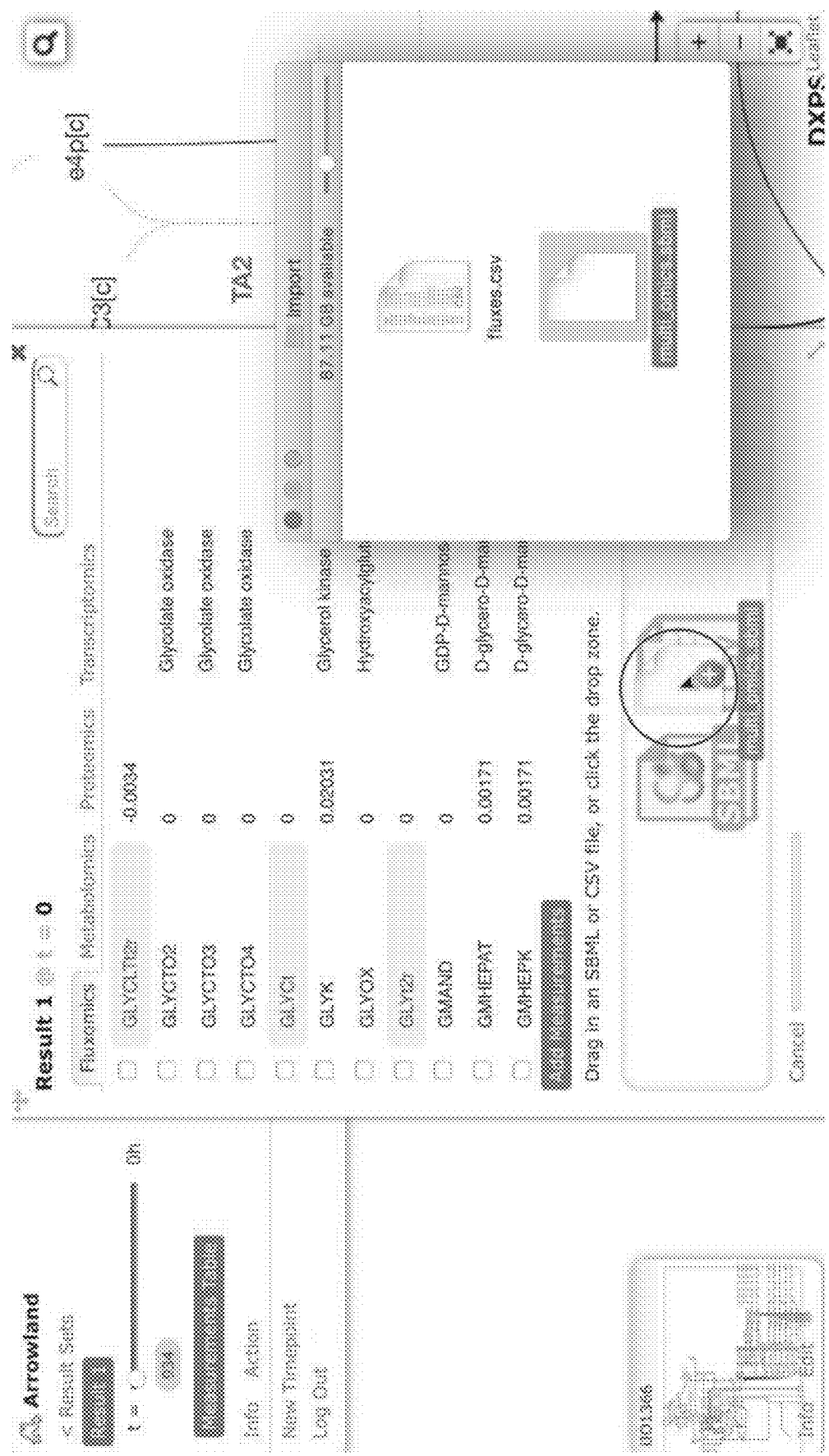
Figure 10A:
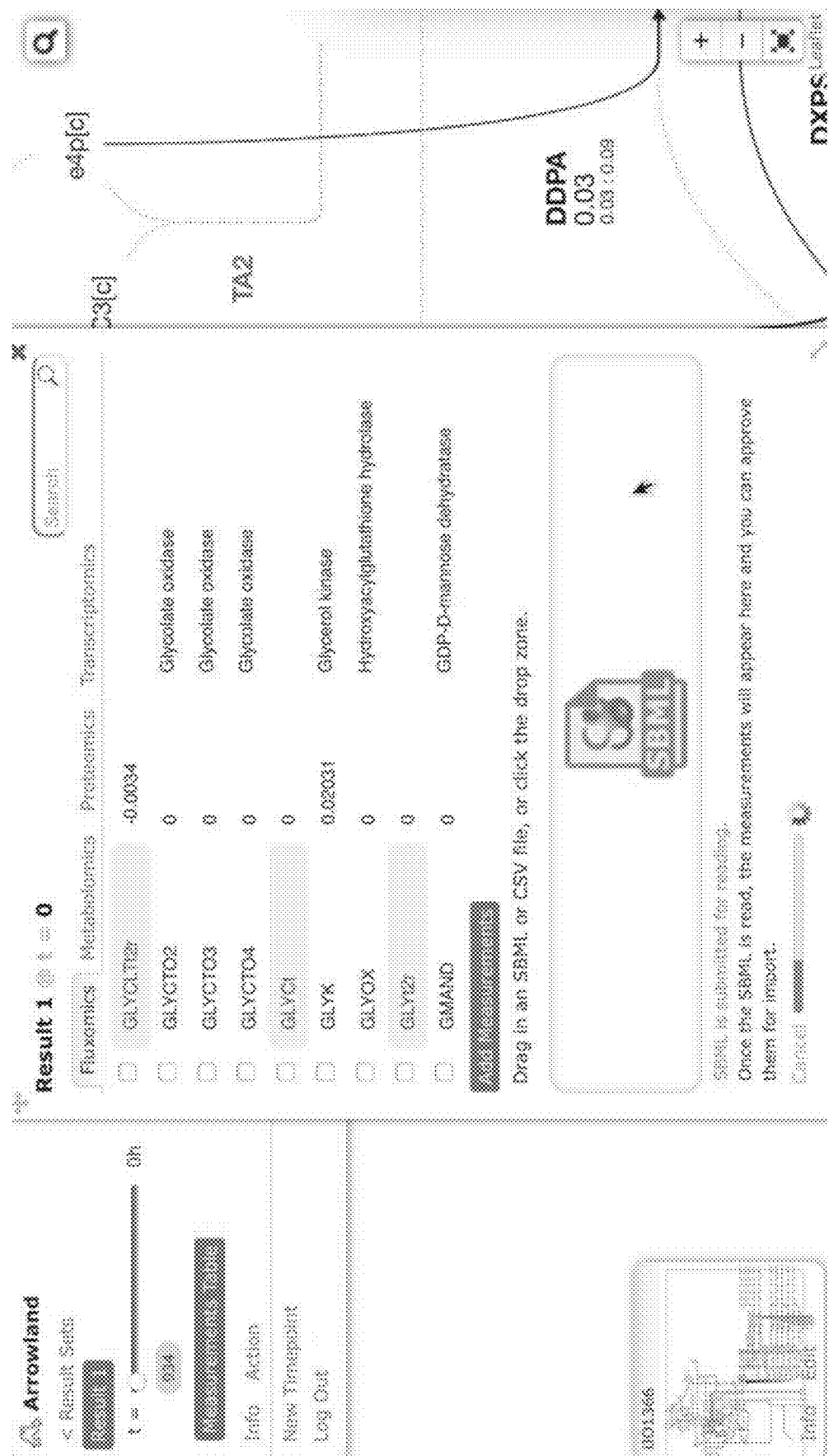
Figure 10A:
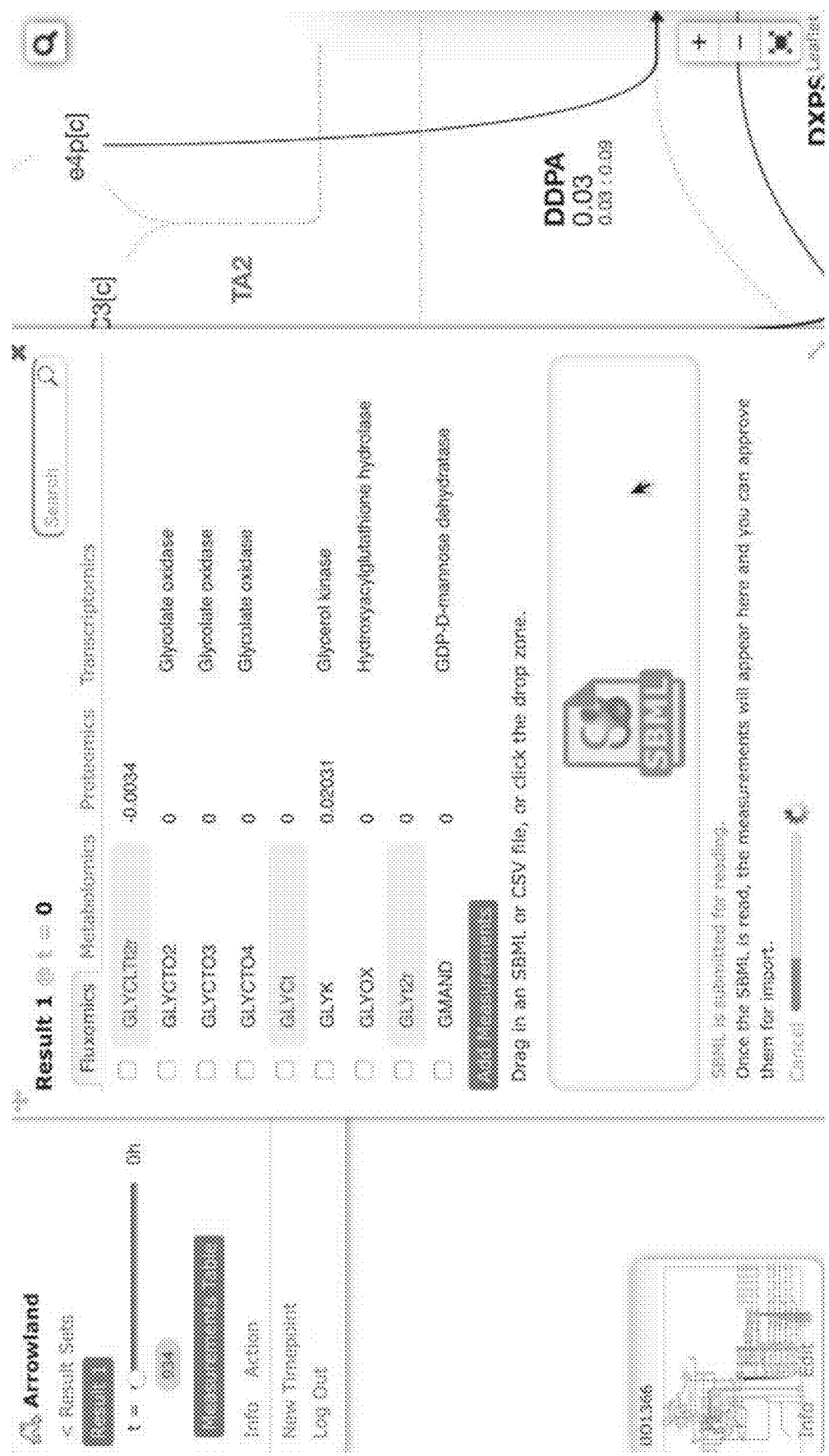
Figure 10A:
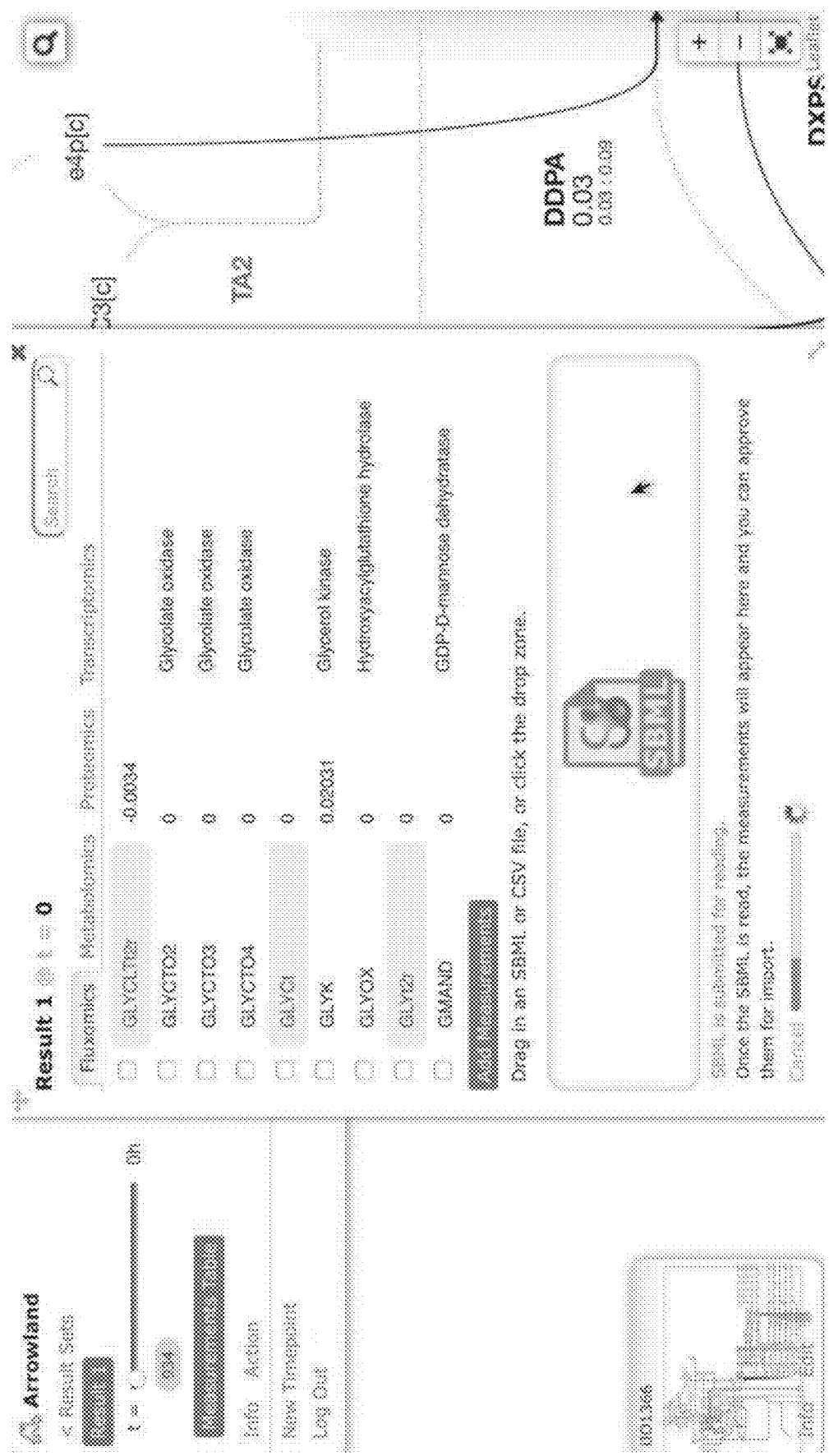
Figure 10A:
Figure 10A:
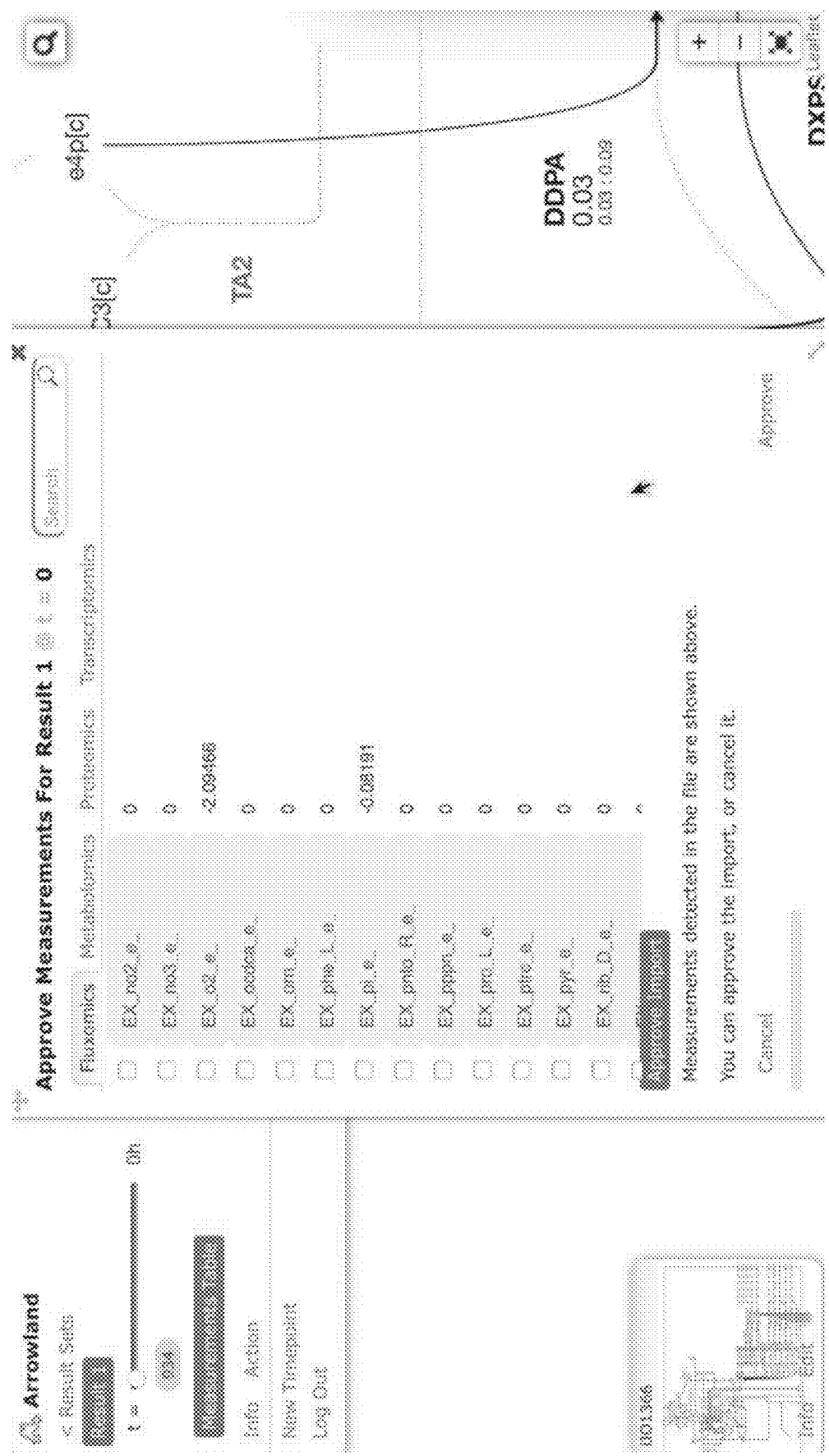
Figure 10A:
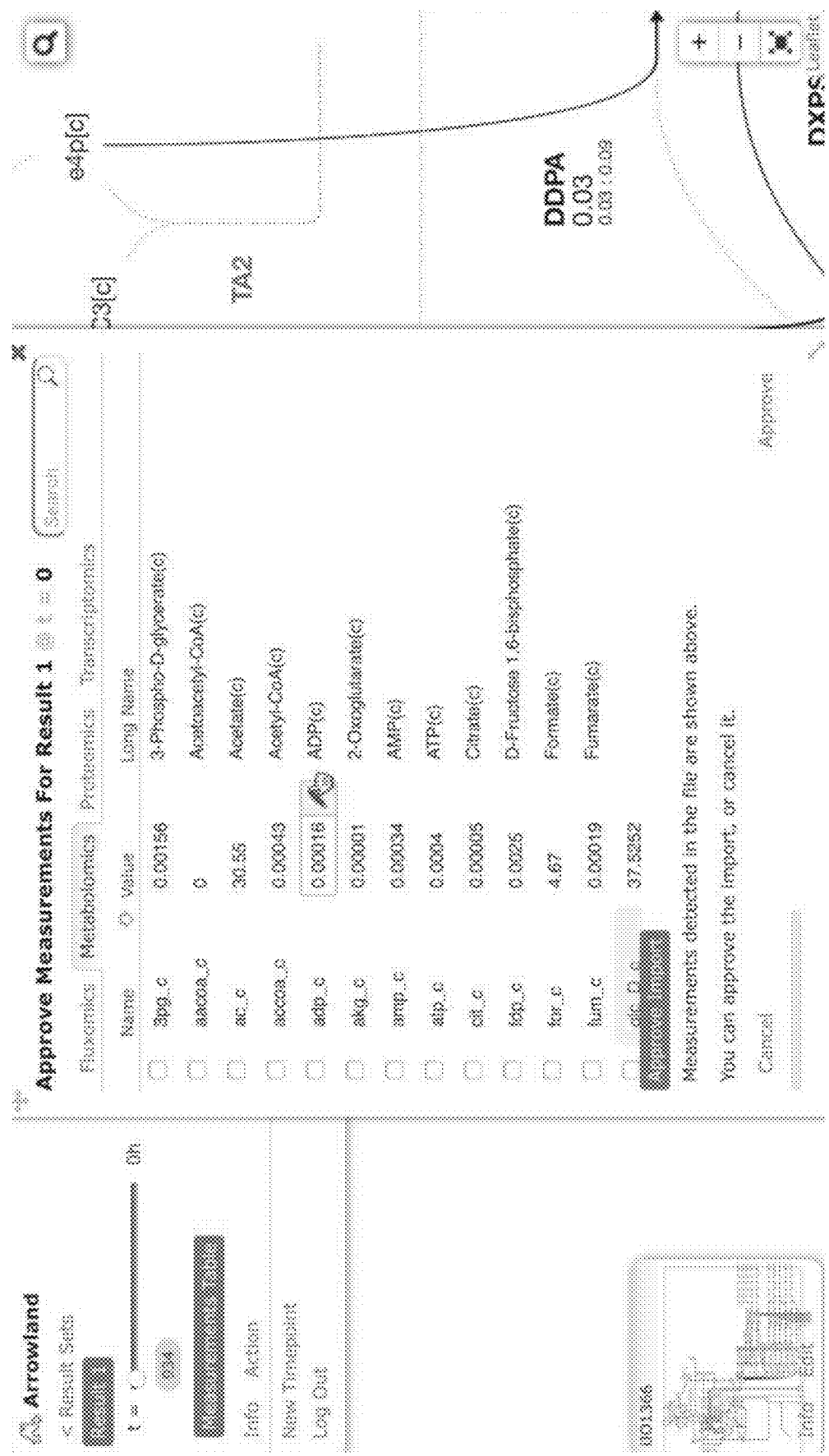
Figure 10A:
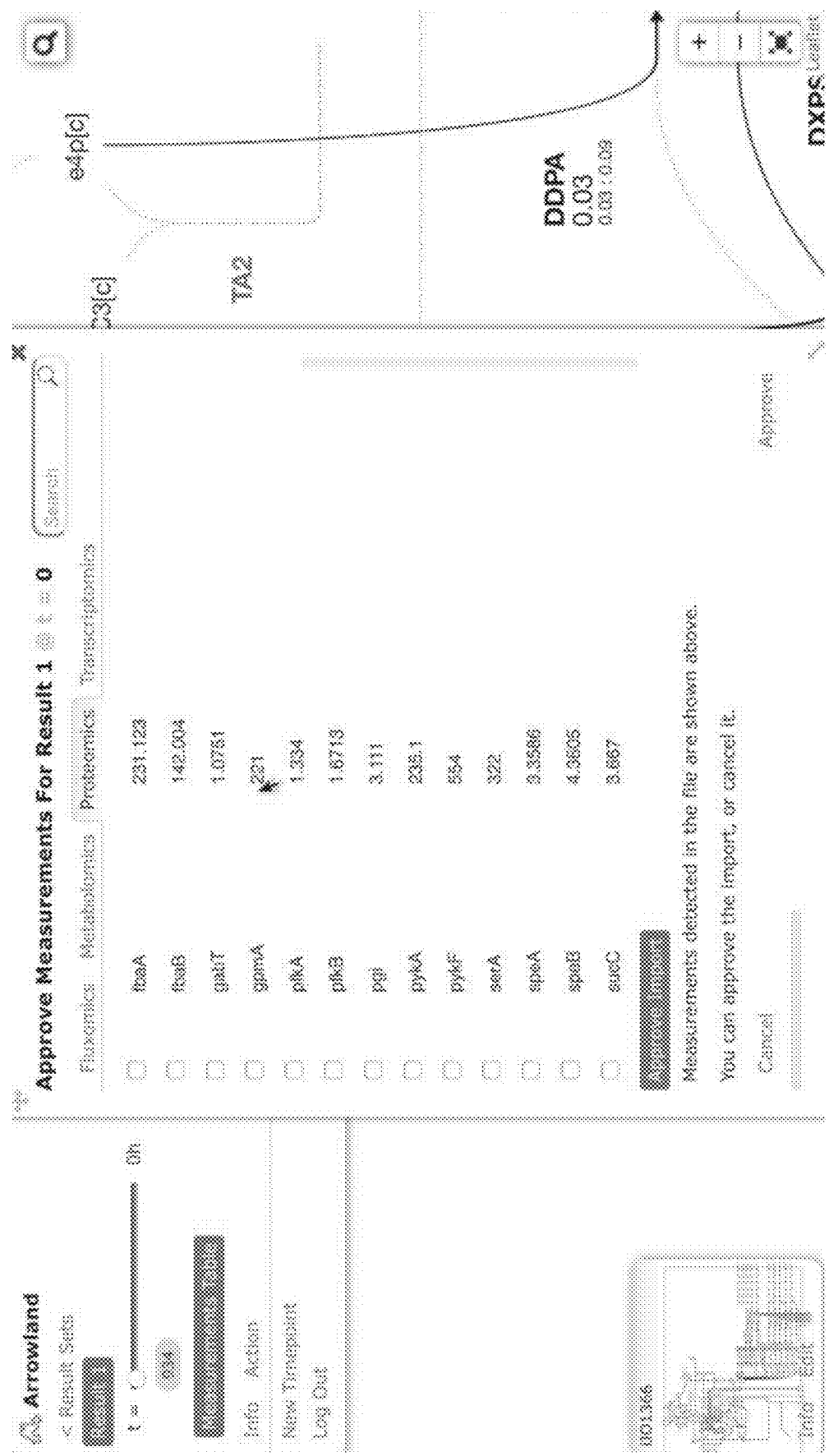
Figure 10A:
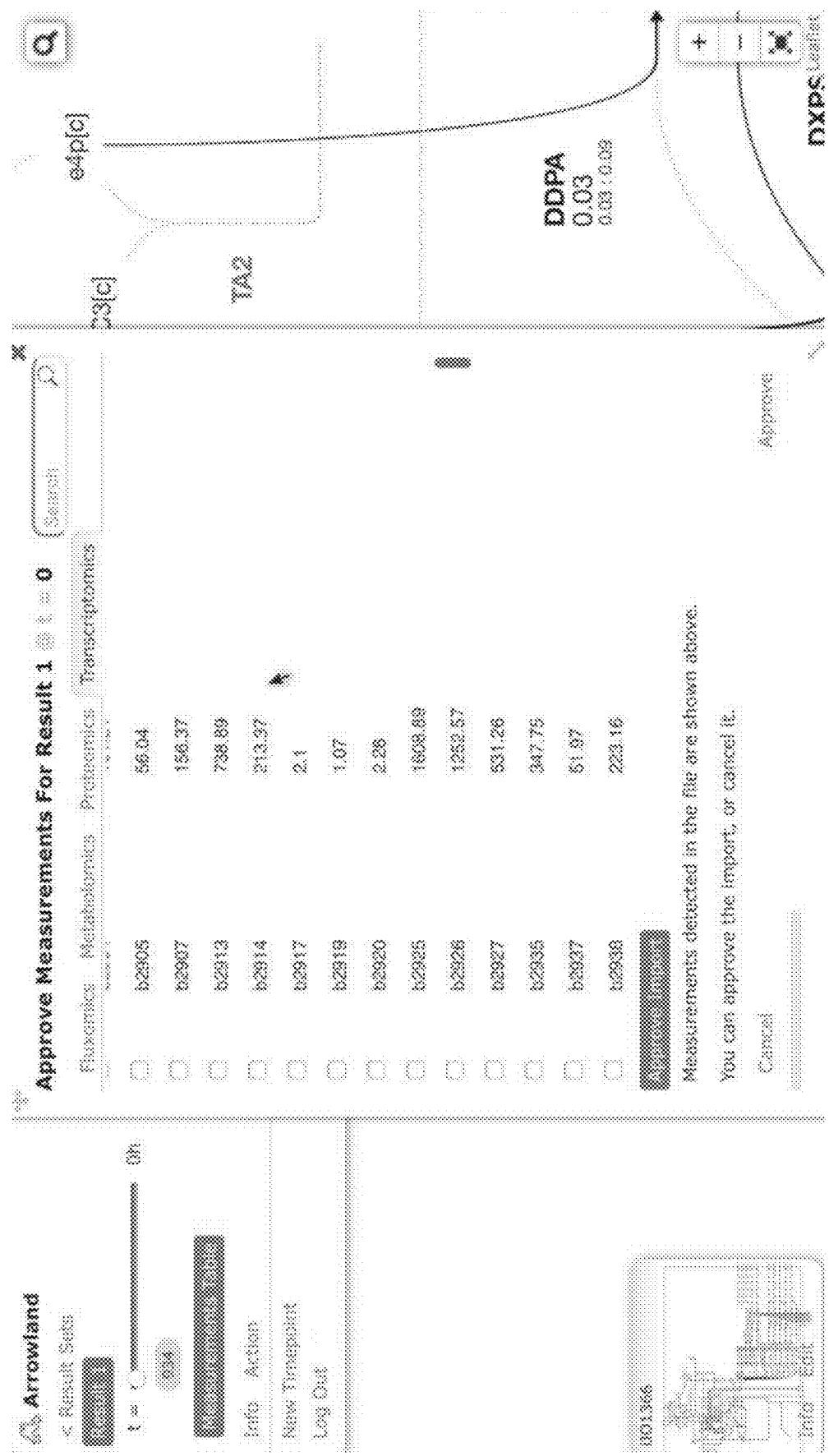
Figure 10A:
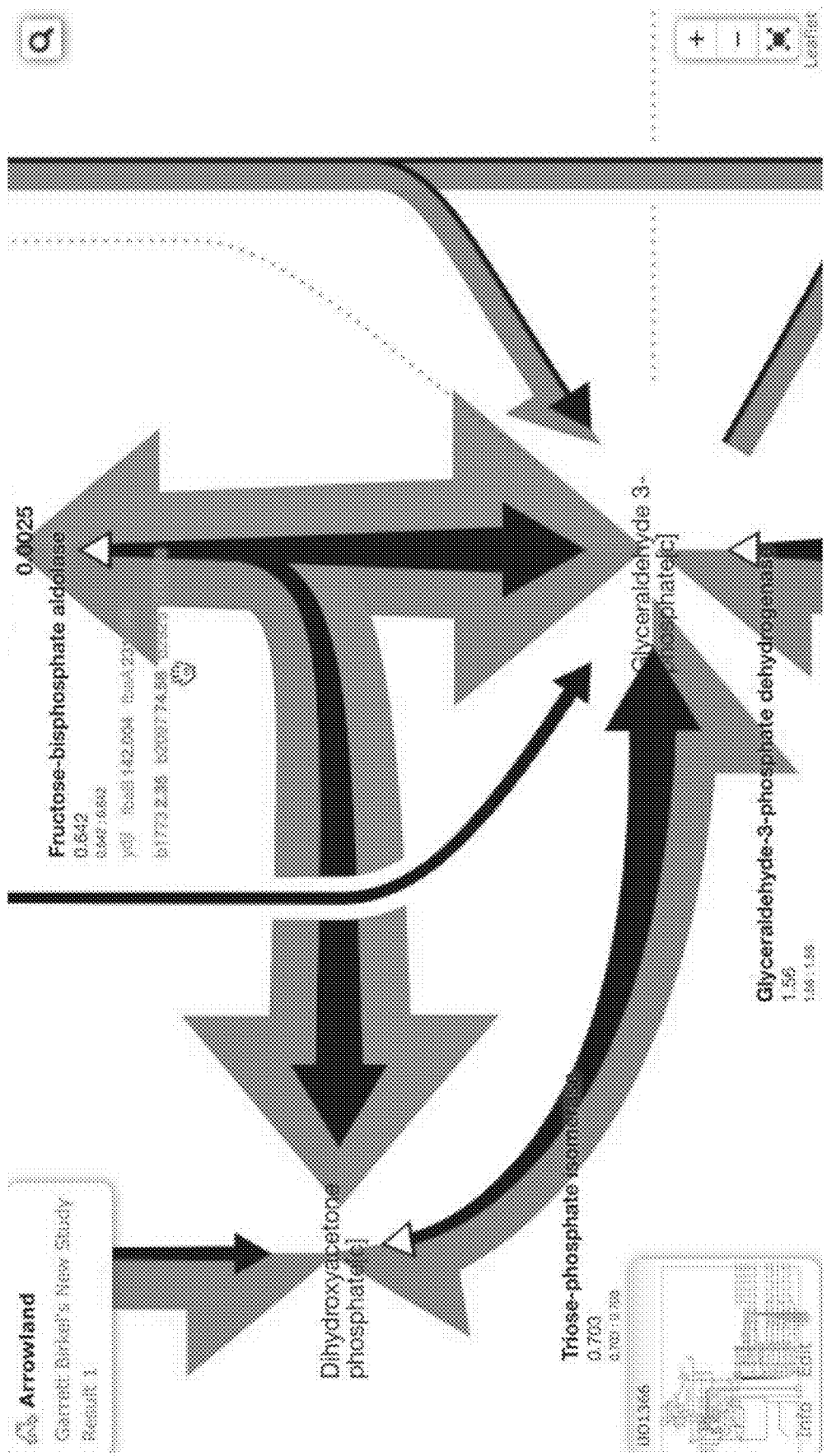
Figure 10A:
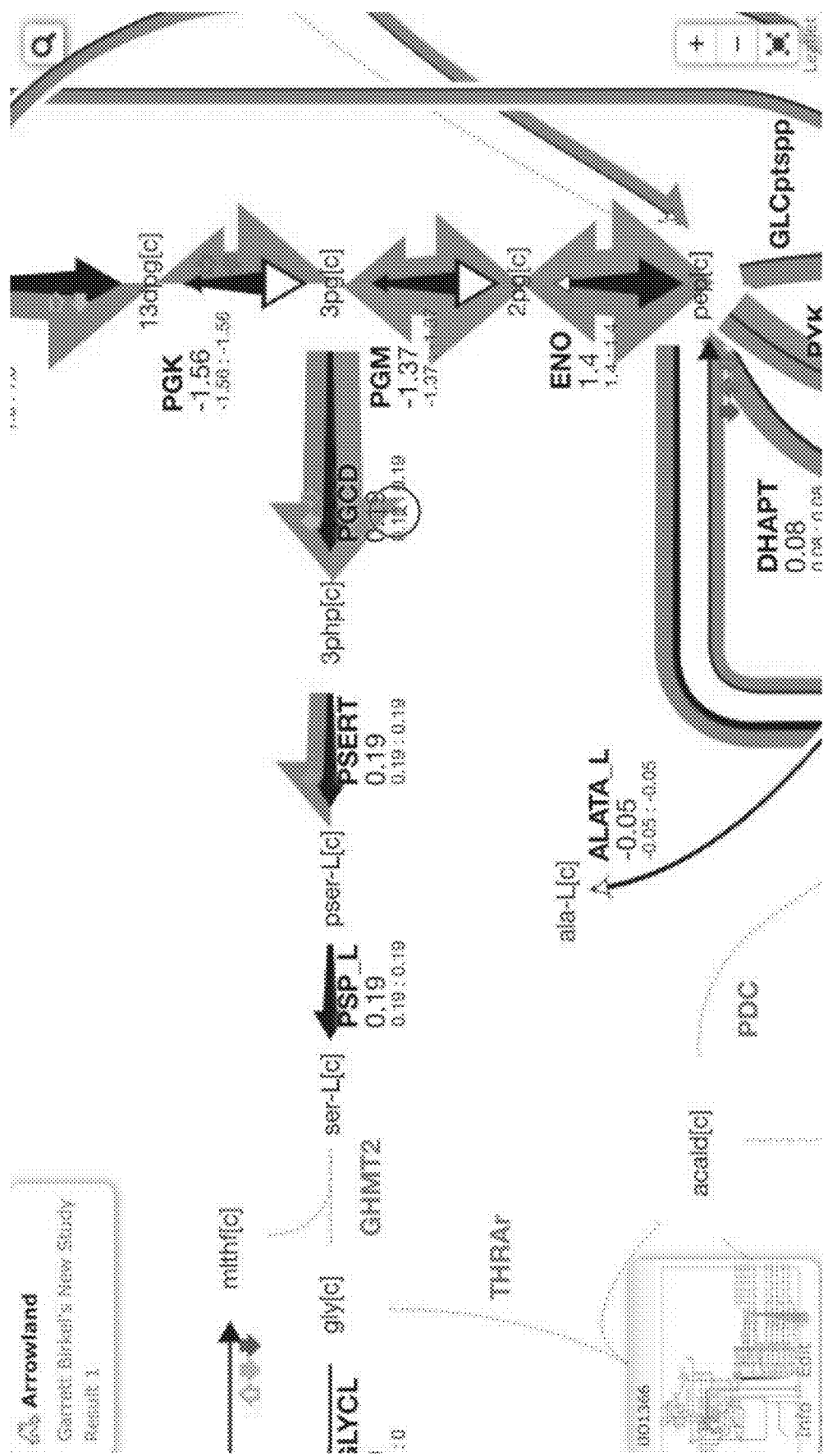
Figure 10A:
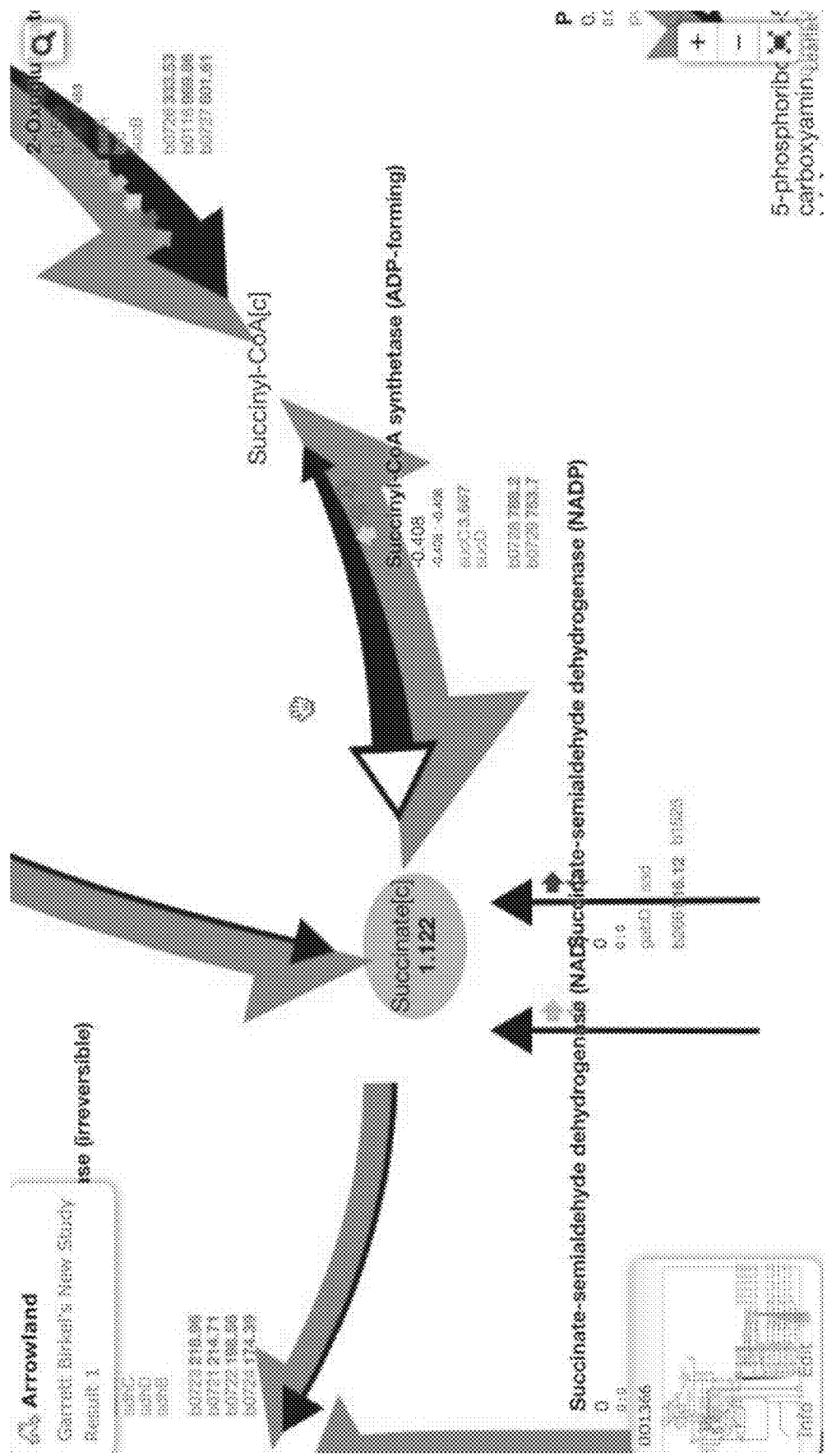
Figure 10A:
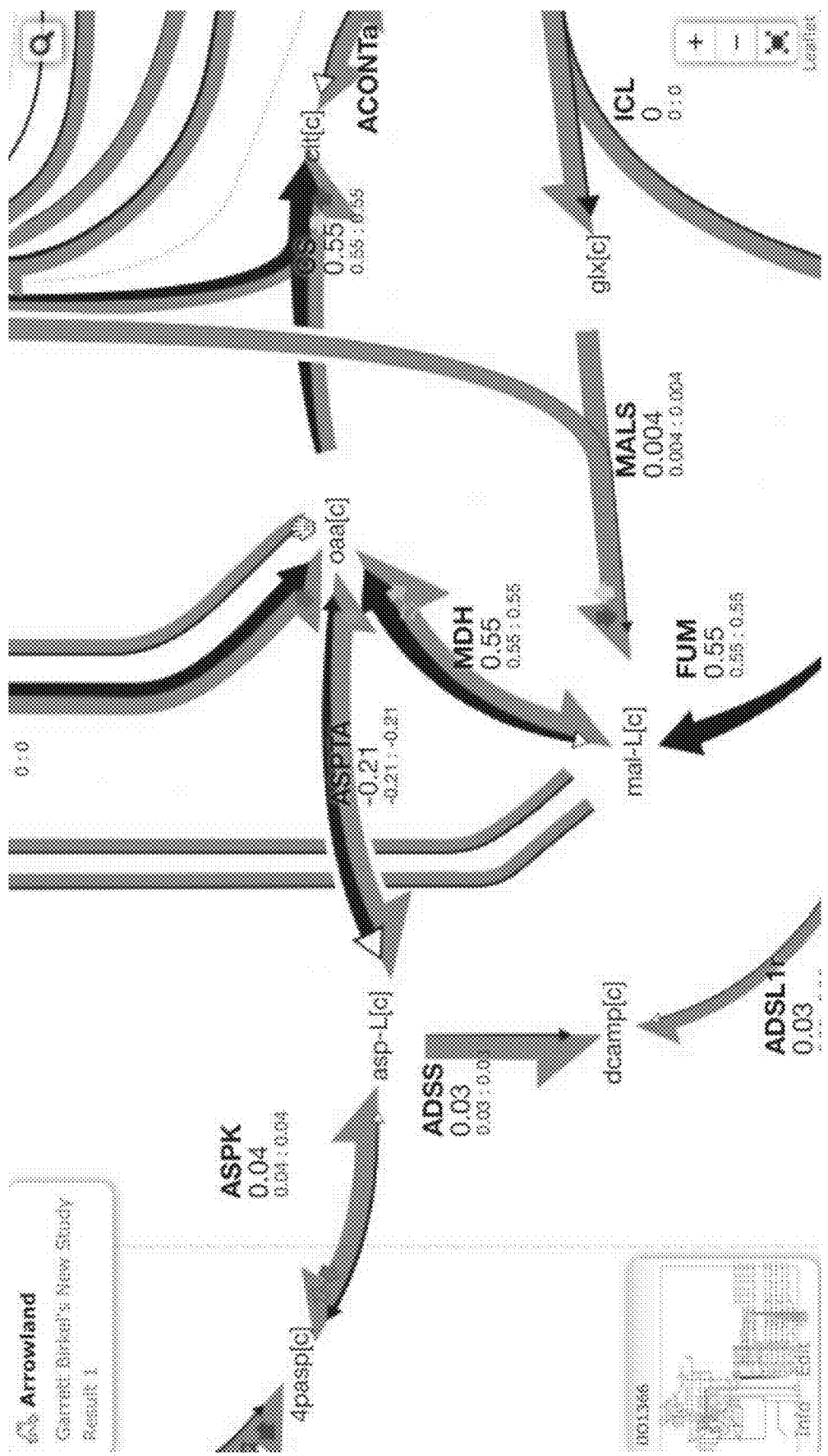
Figure 10A:
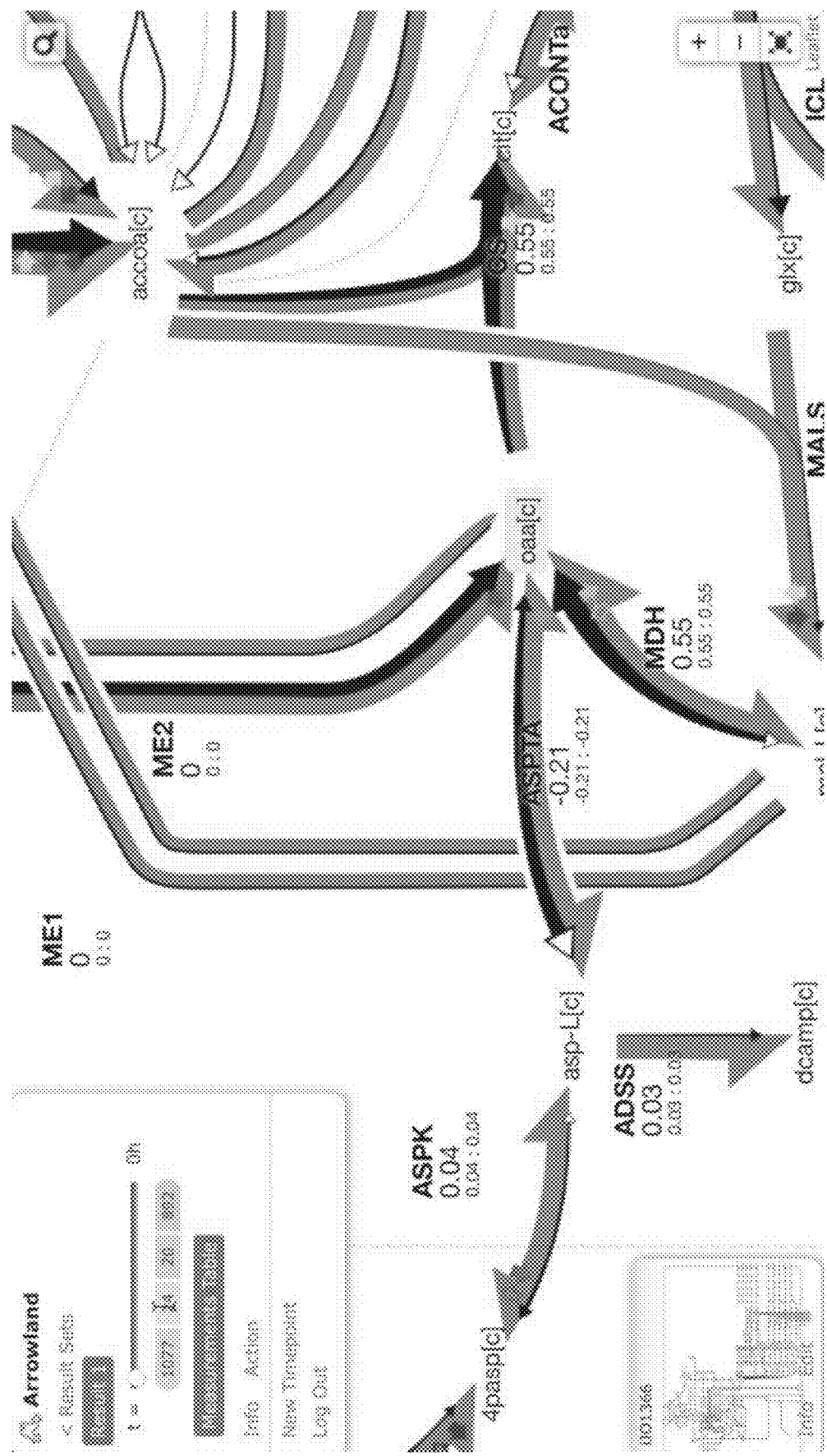
Figure 11A:
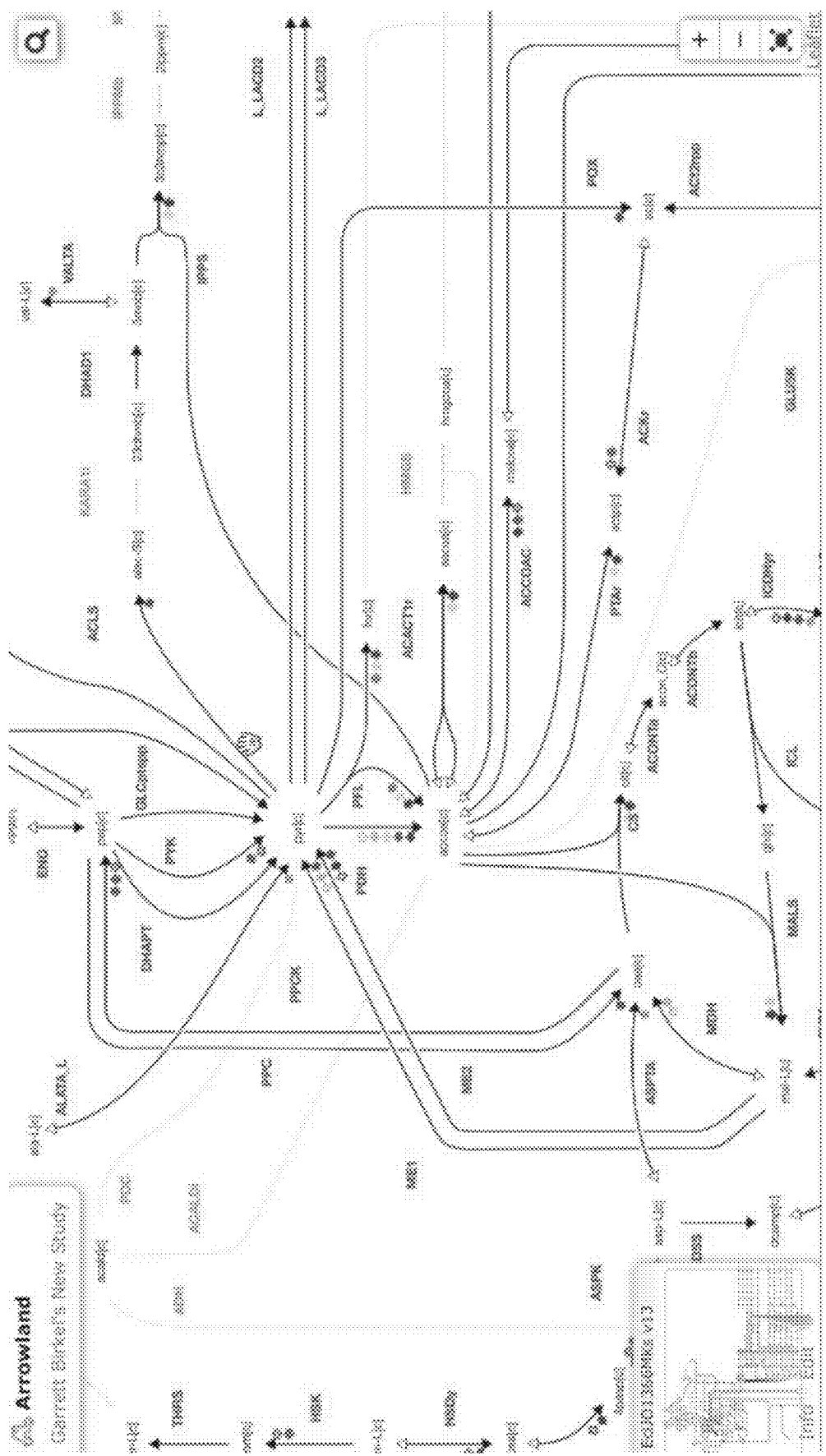
Figure 11B:
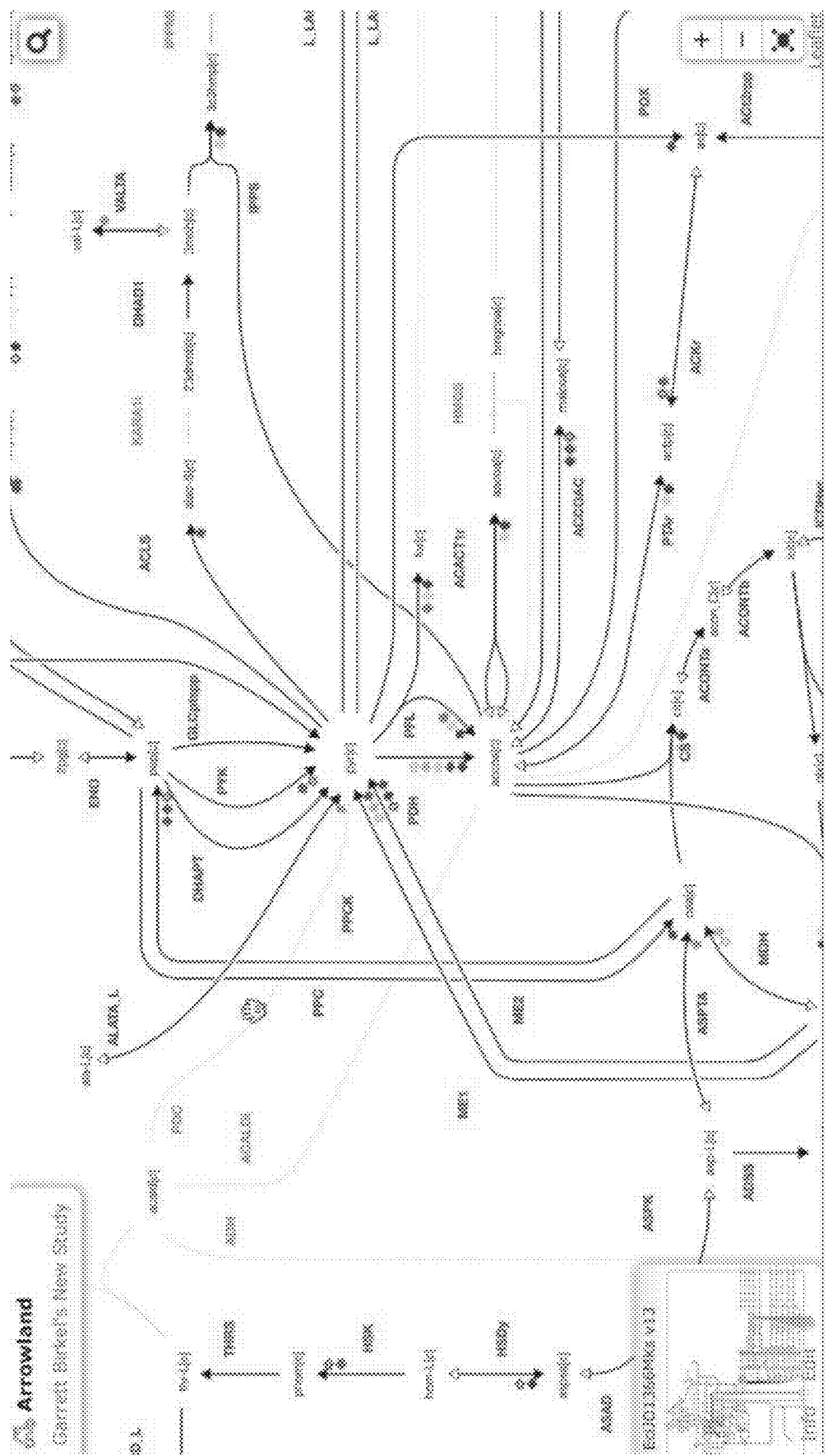
Figure 11C:
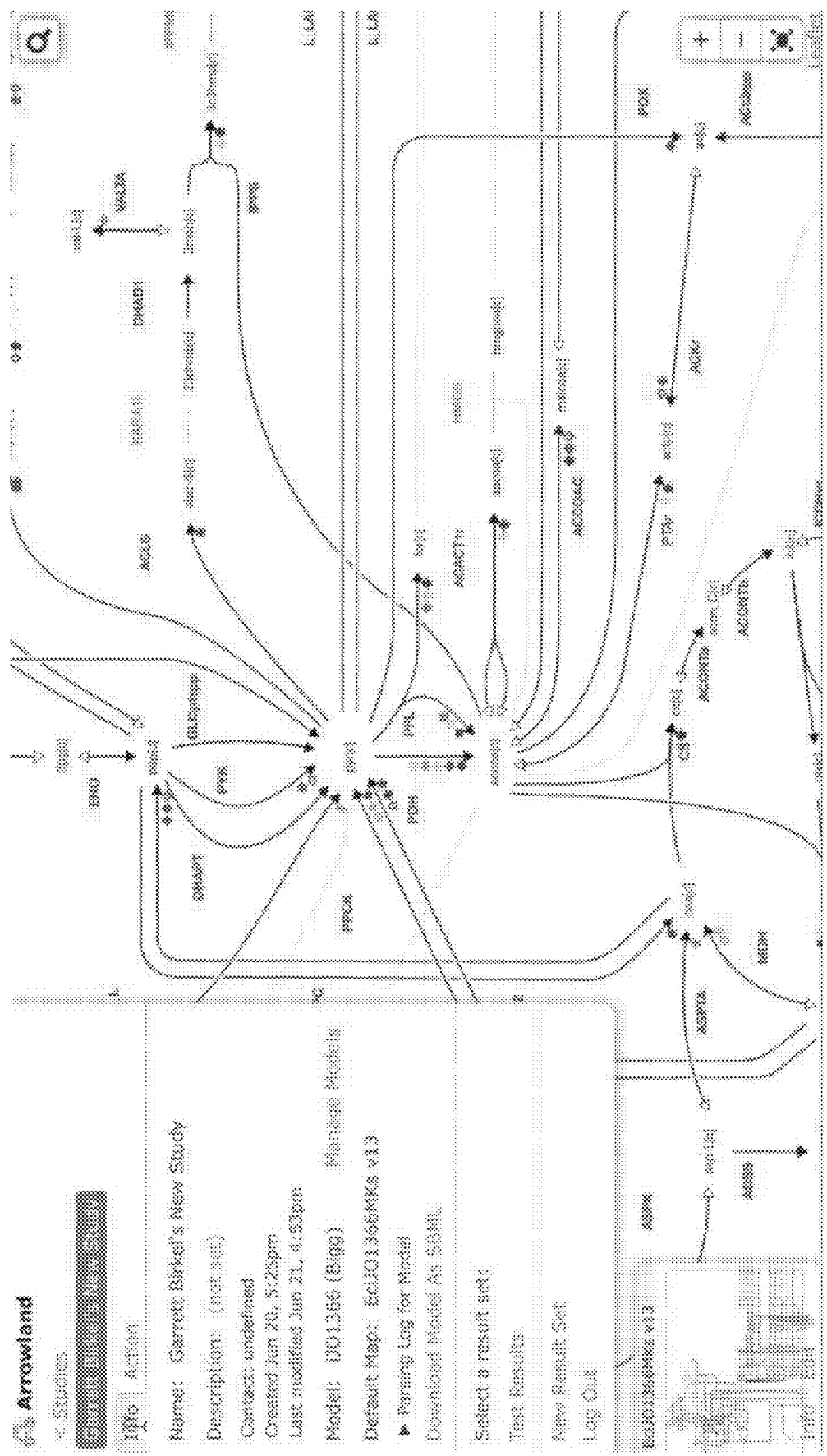
Figure 11D:
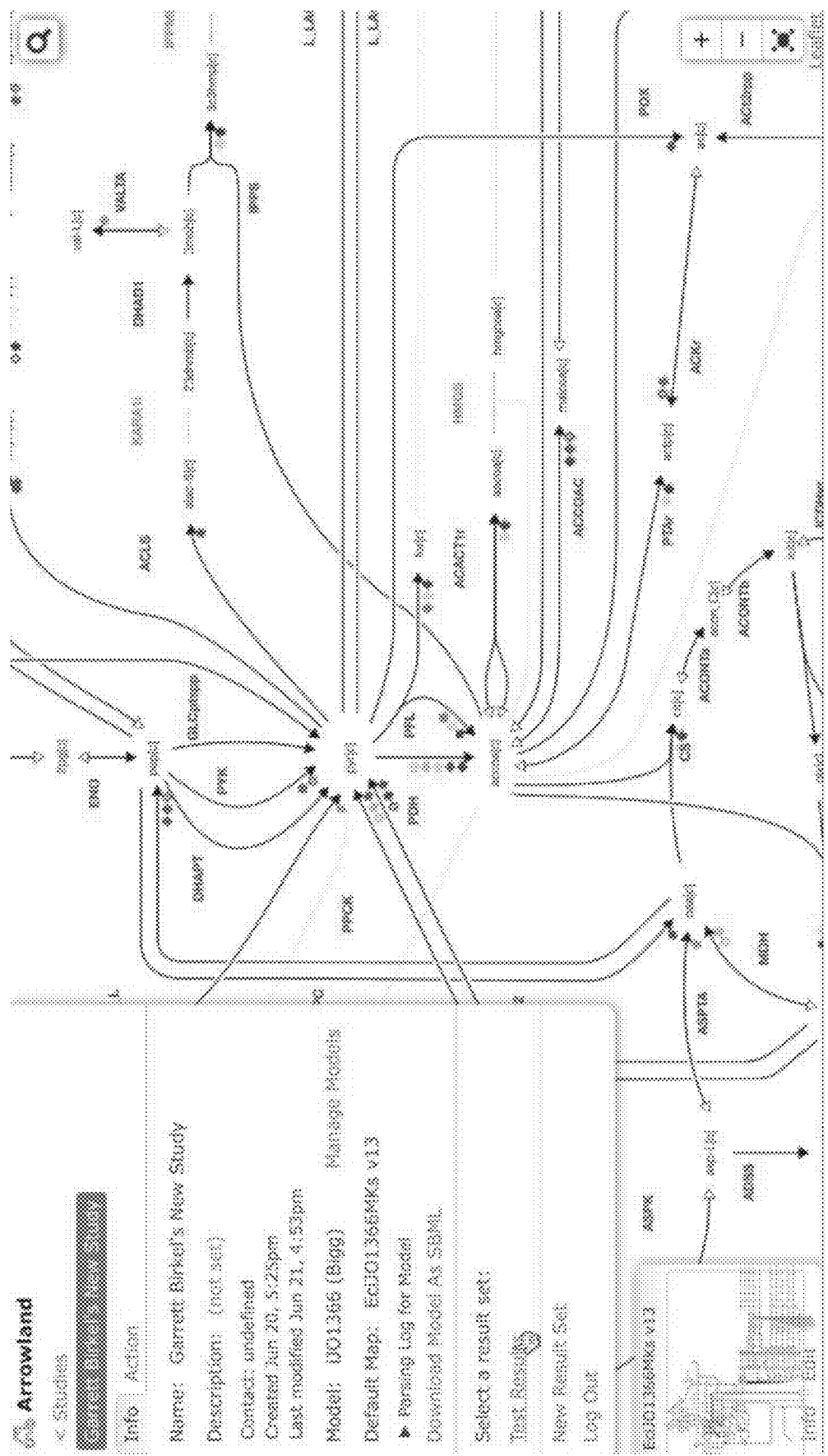
Figure 11E:
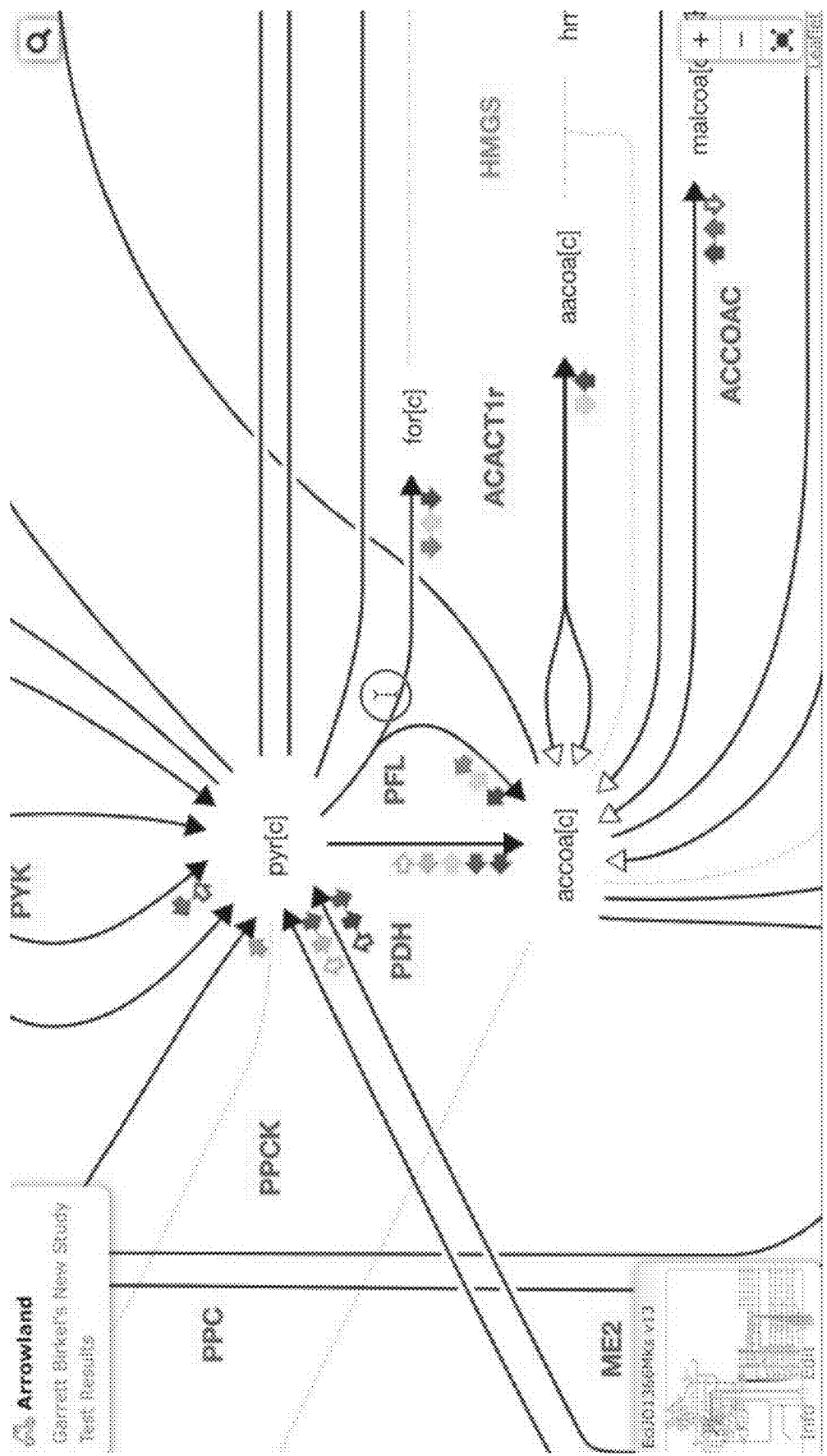
Figure 11F:
Figure 11G:
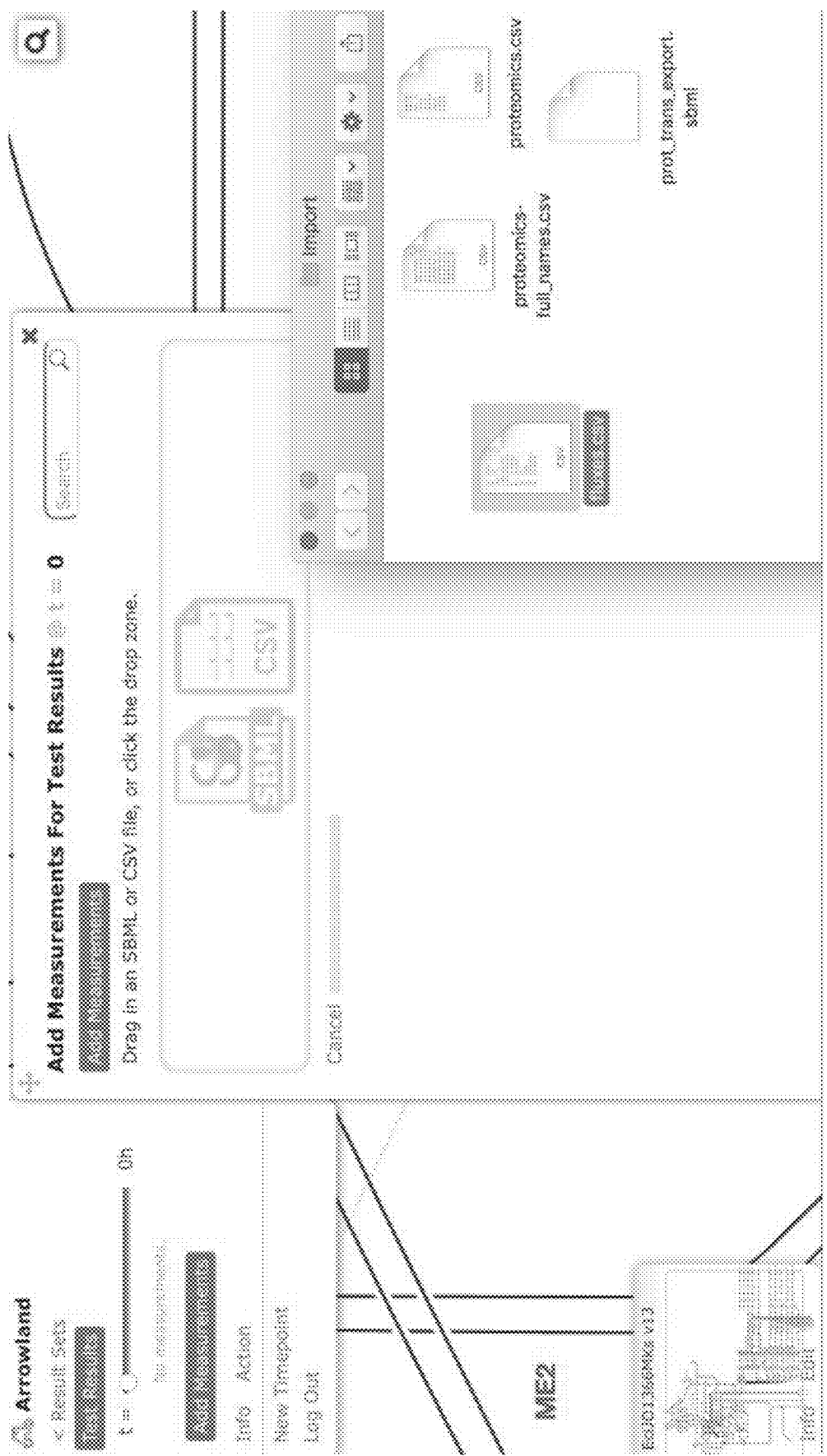
Figure 11H:
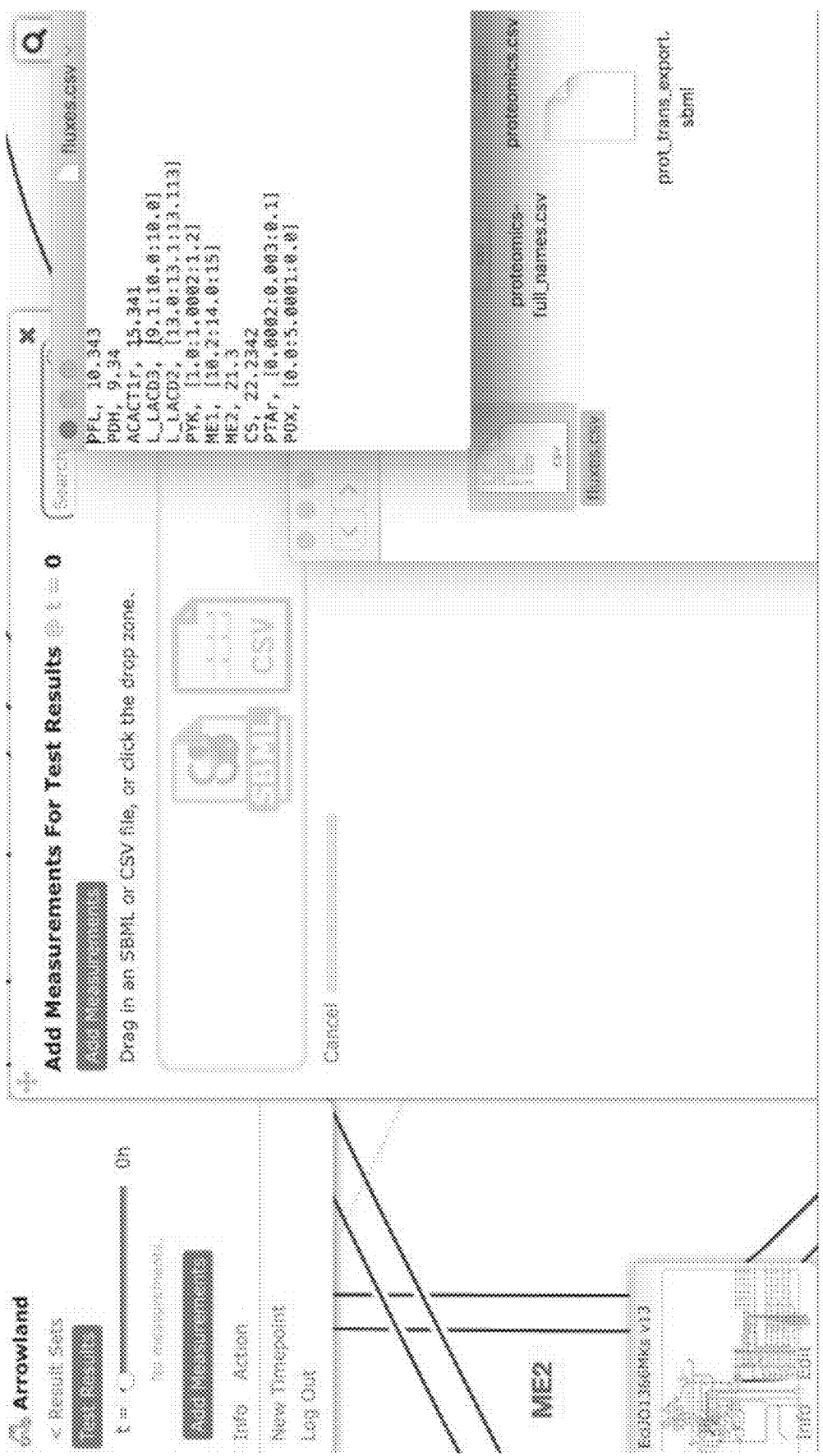
Figure 11I:
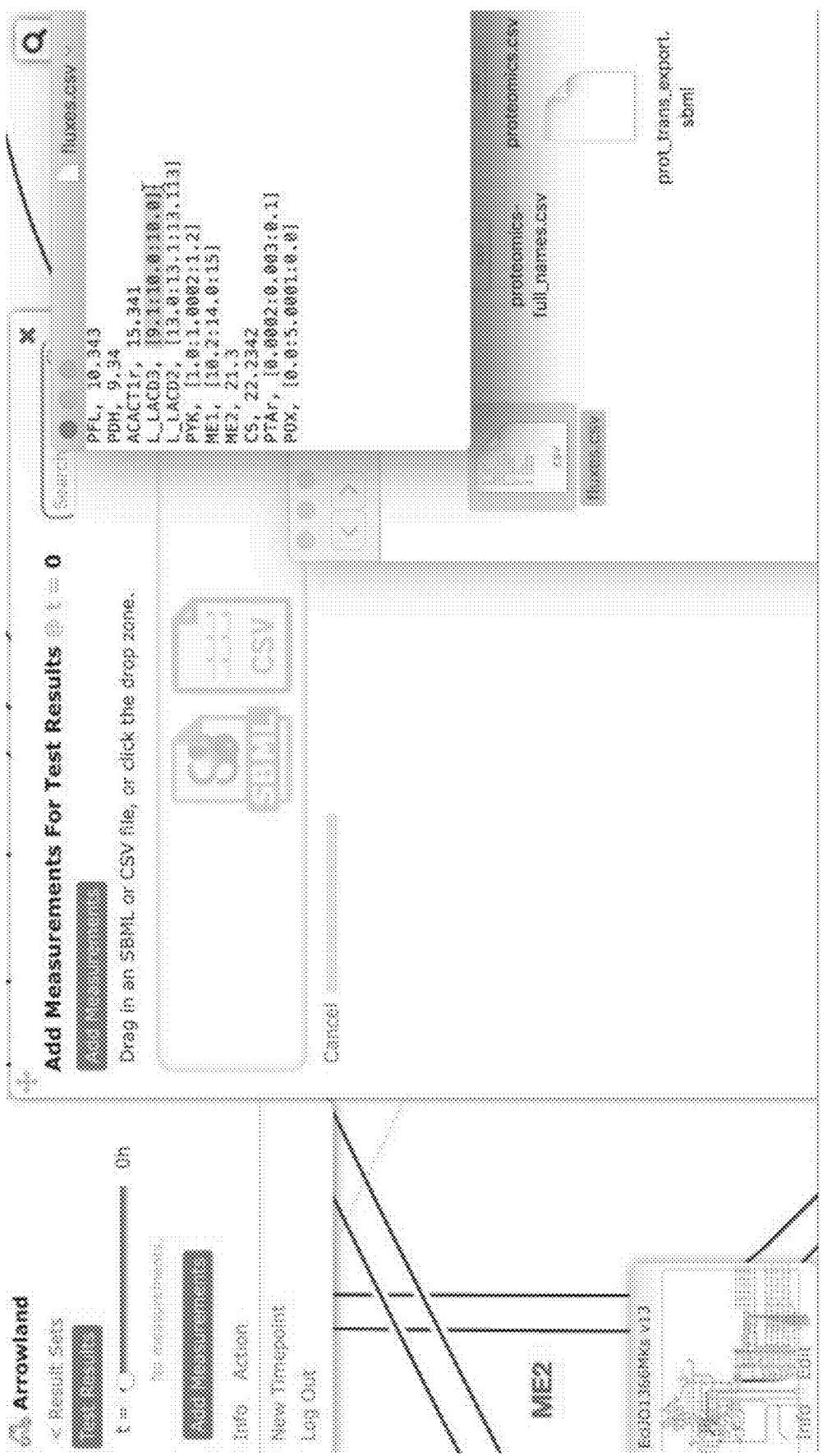
Figure 11J:
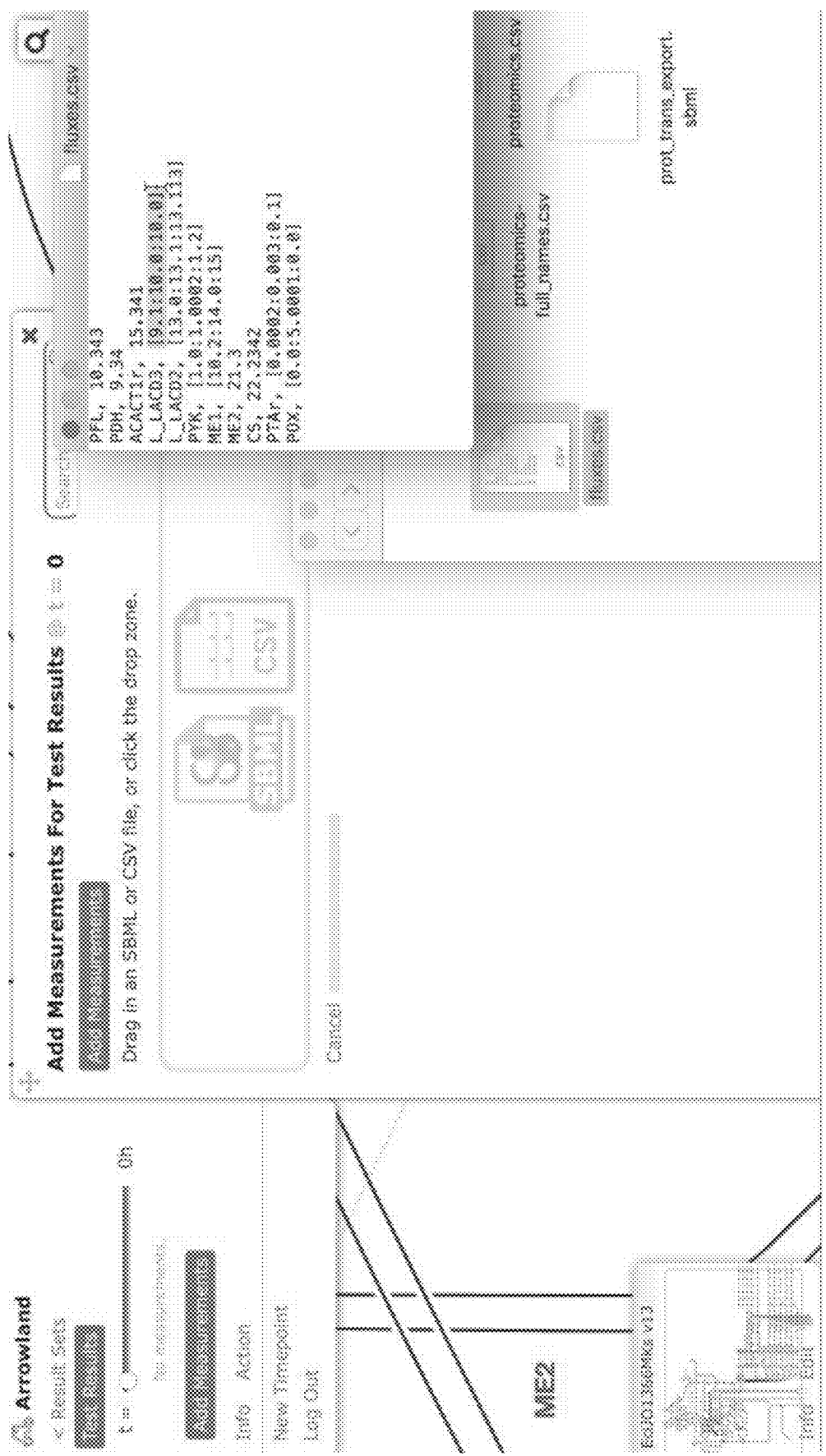
Figure 11K:
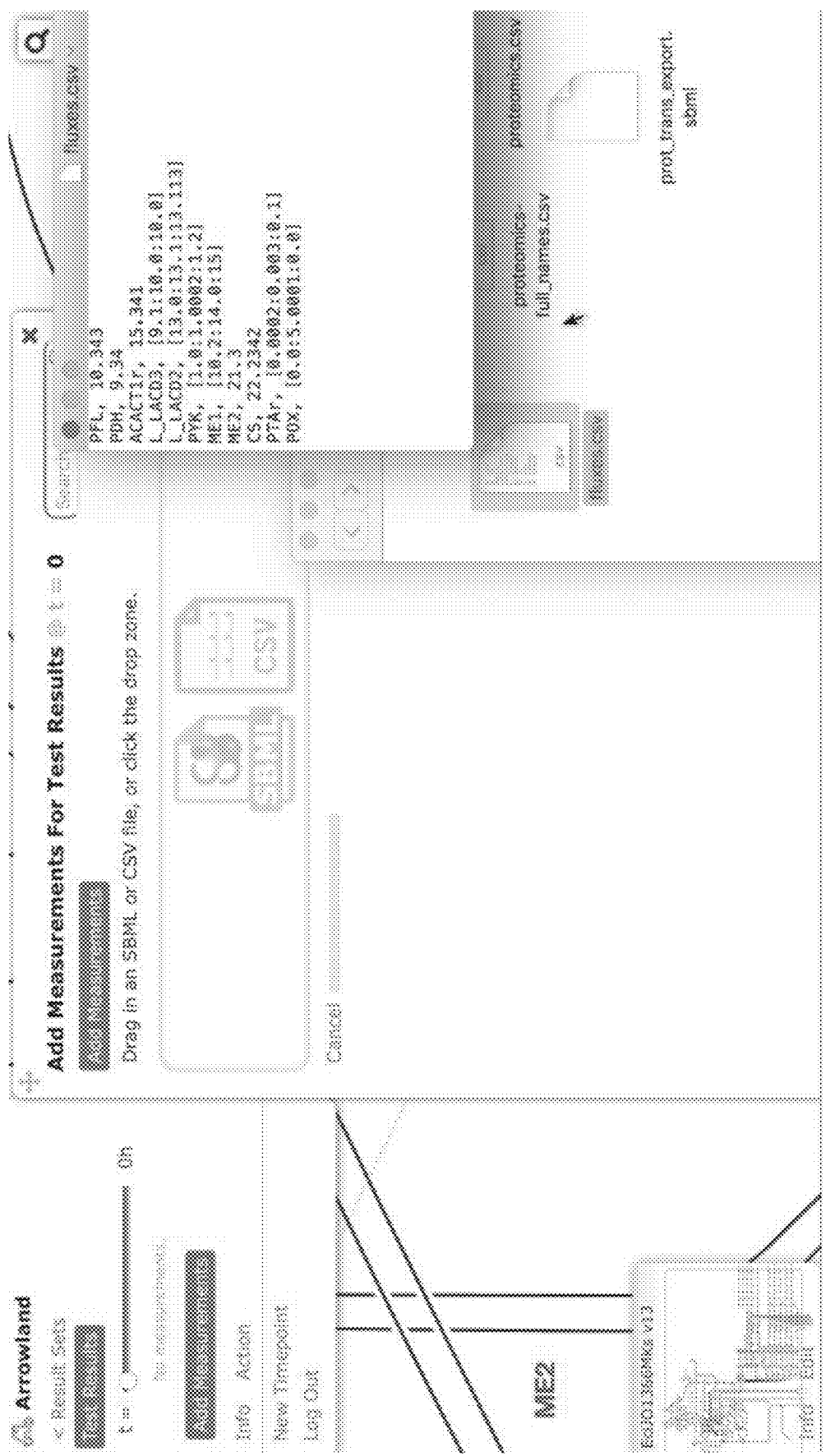
Figure 11L:
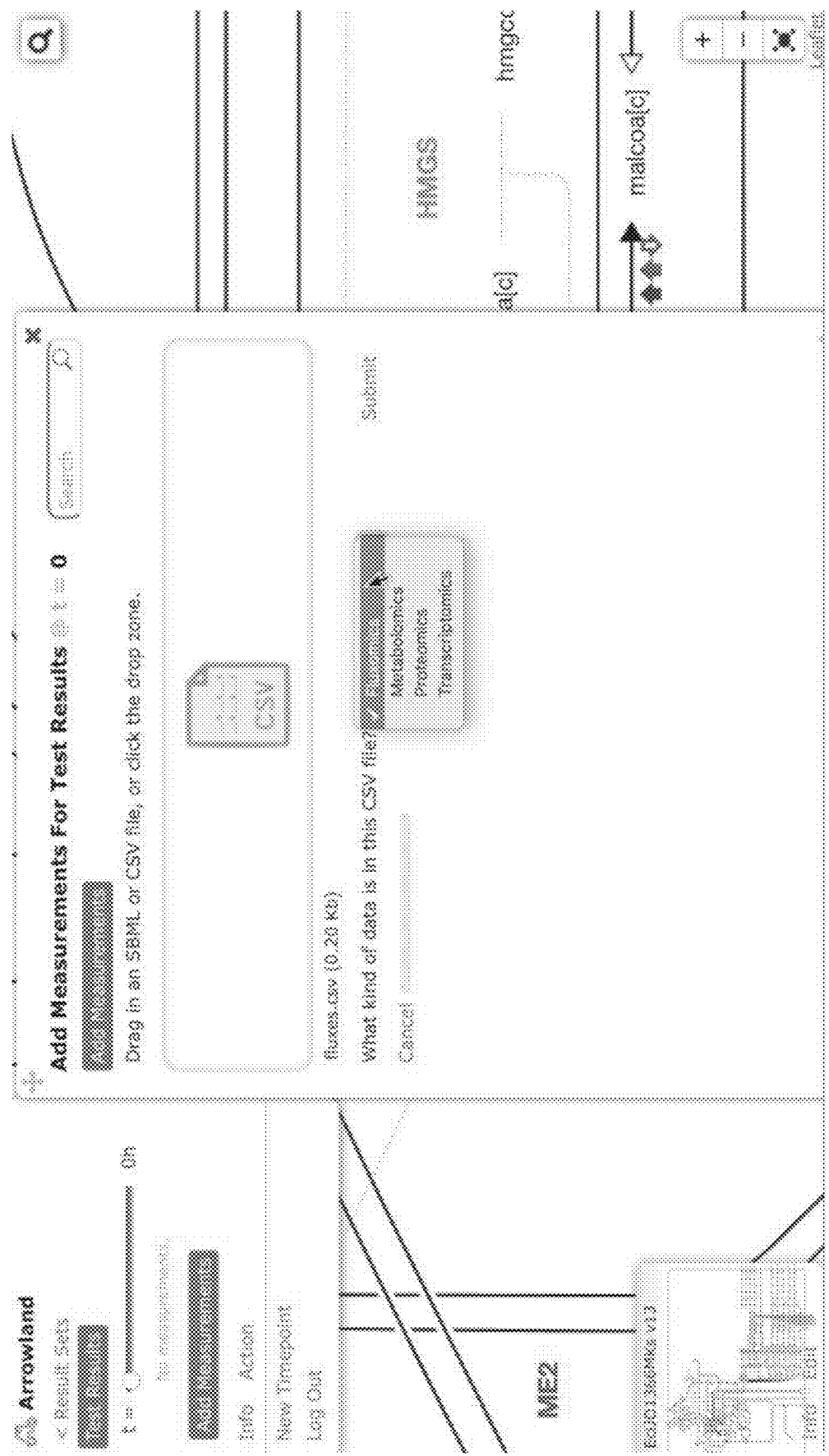
Figure 11M:
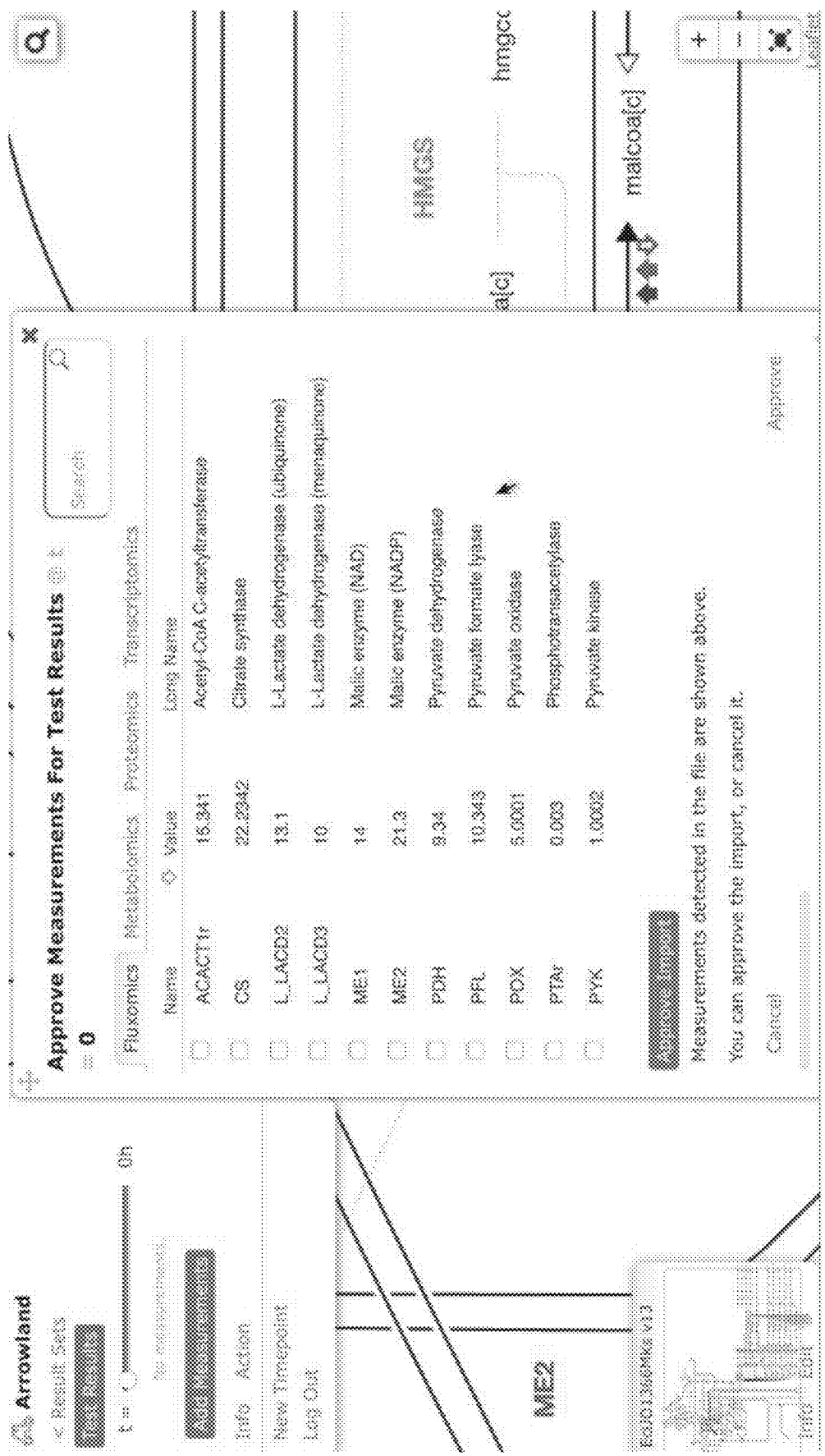
Figure 11N:
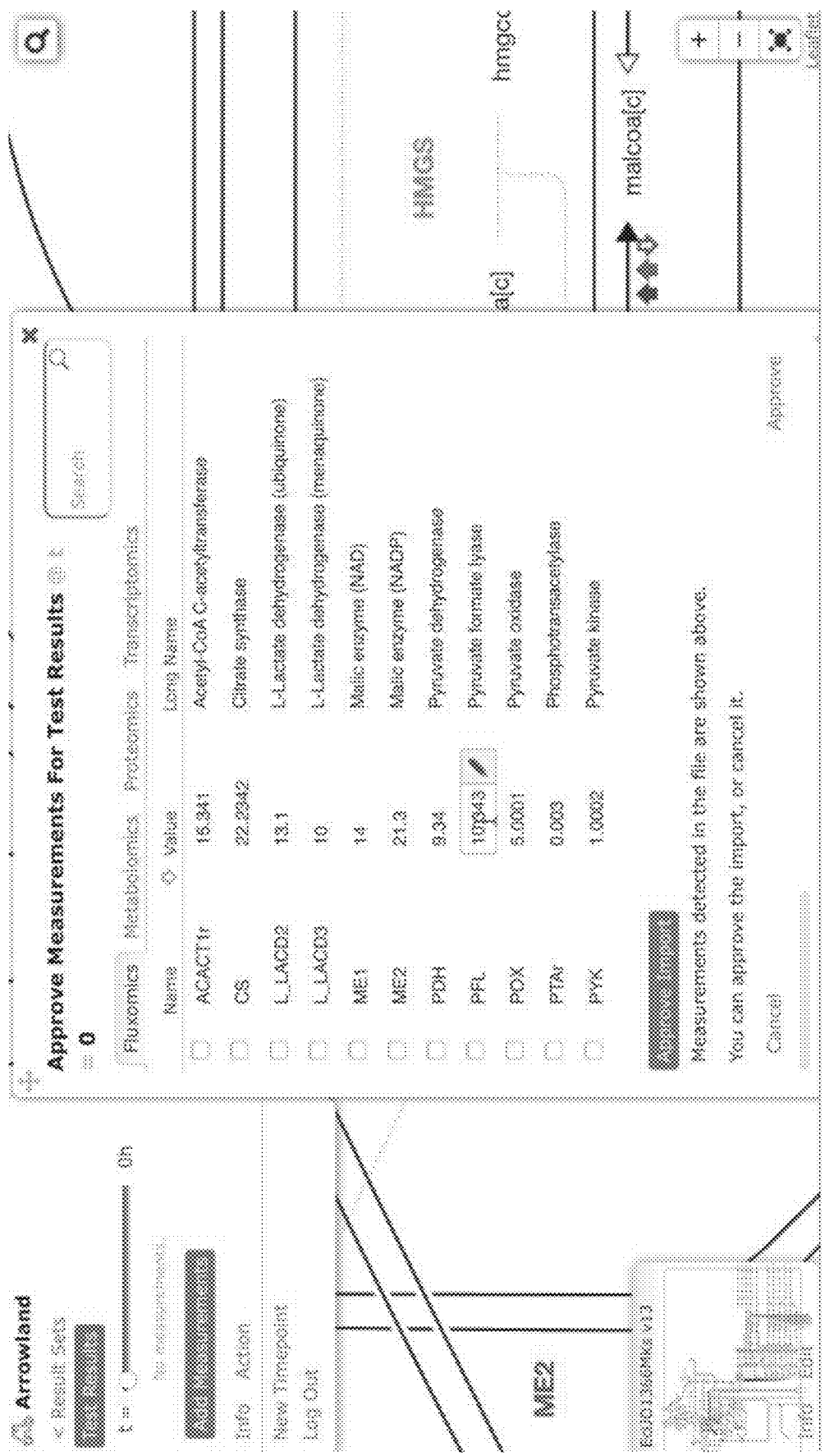
Figure 110:
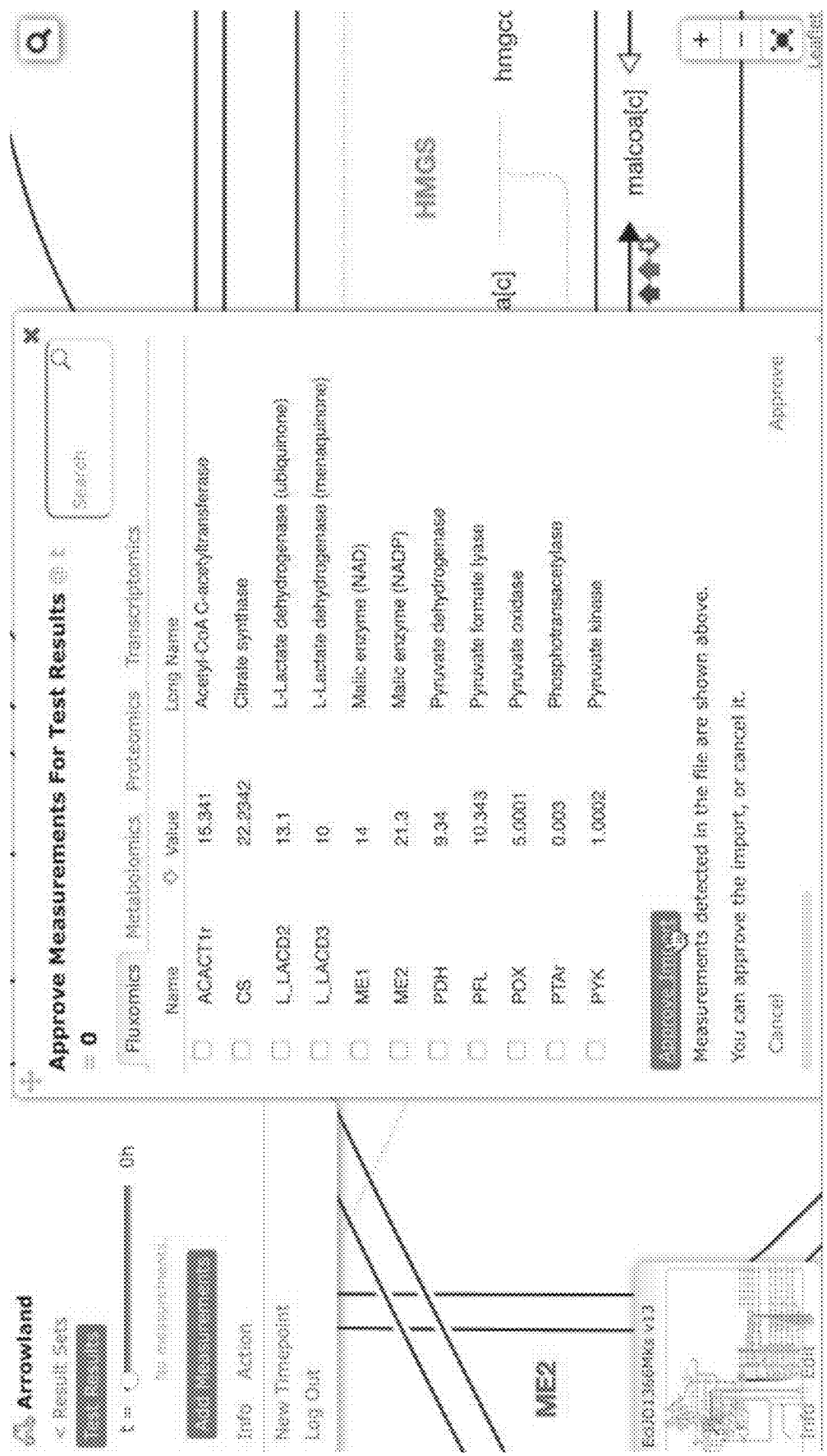
Figure 11P:
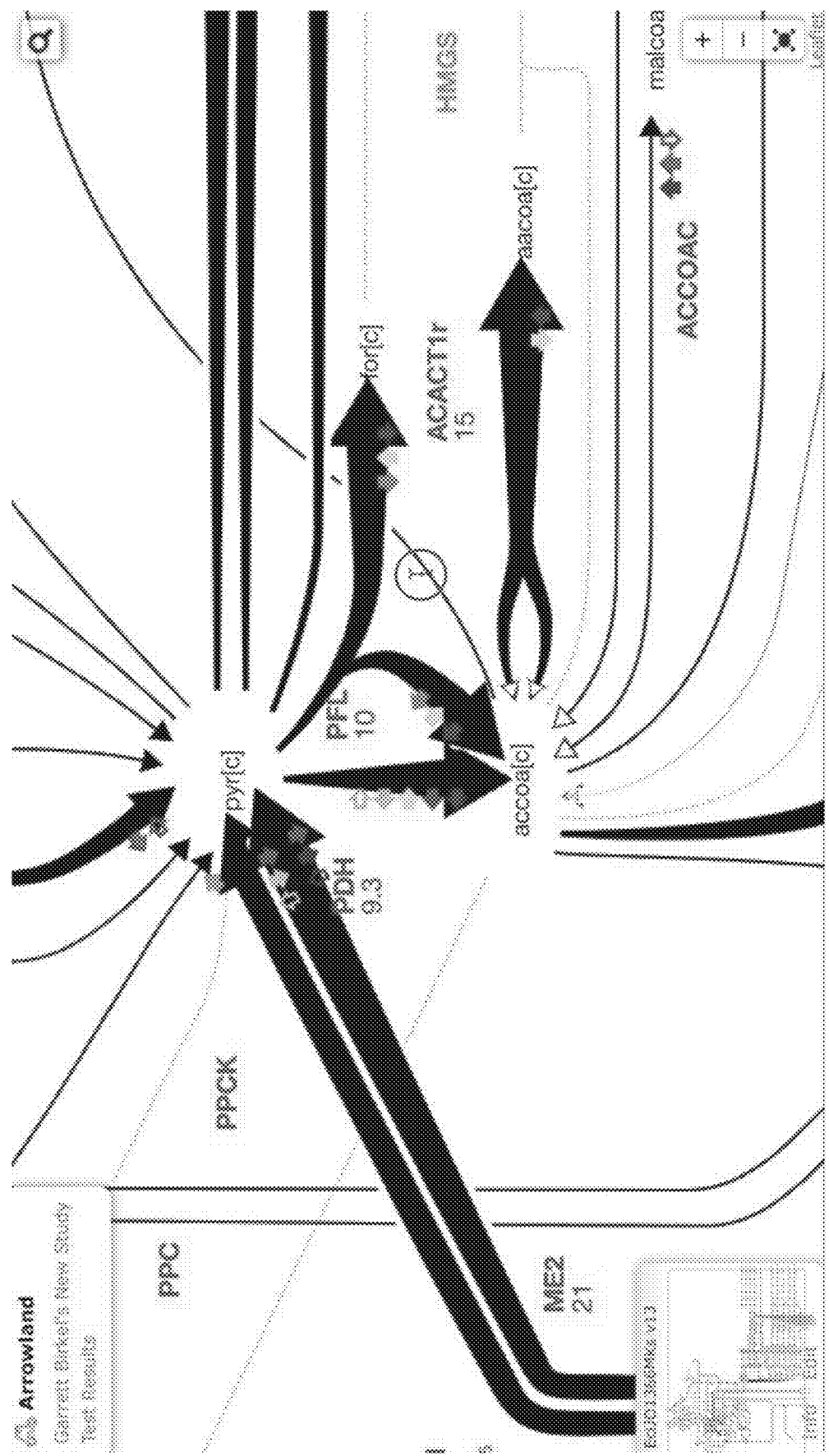
Figure 11Q:
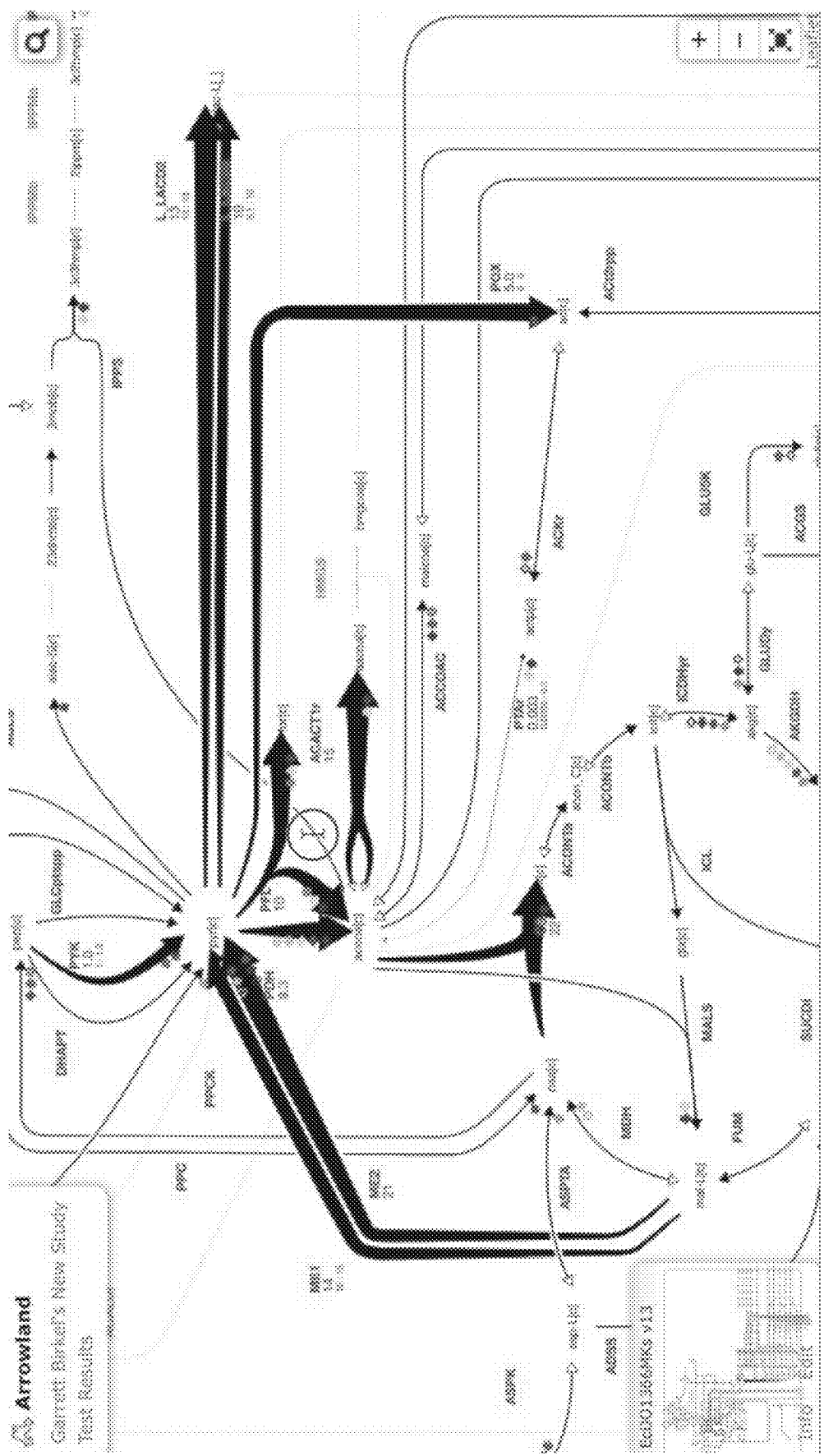
Figure 11R:
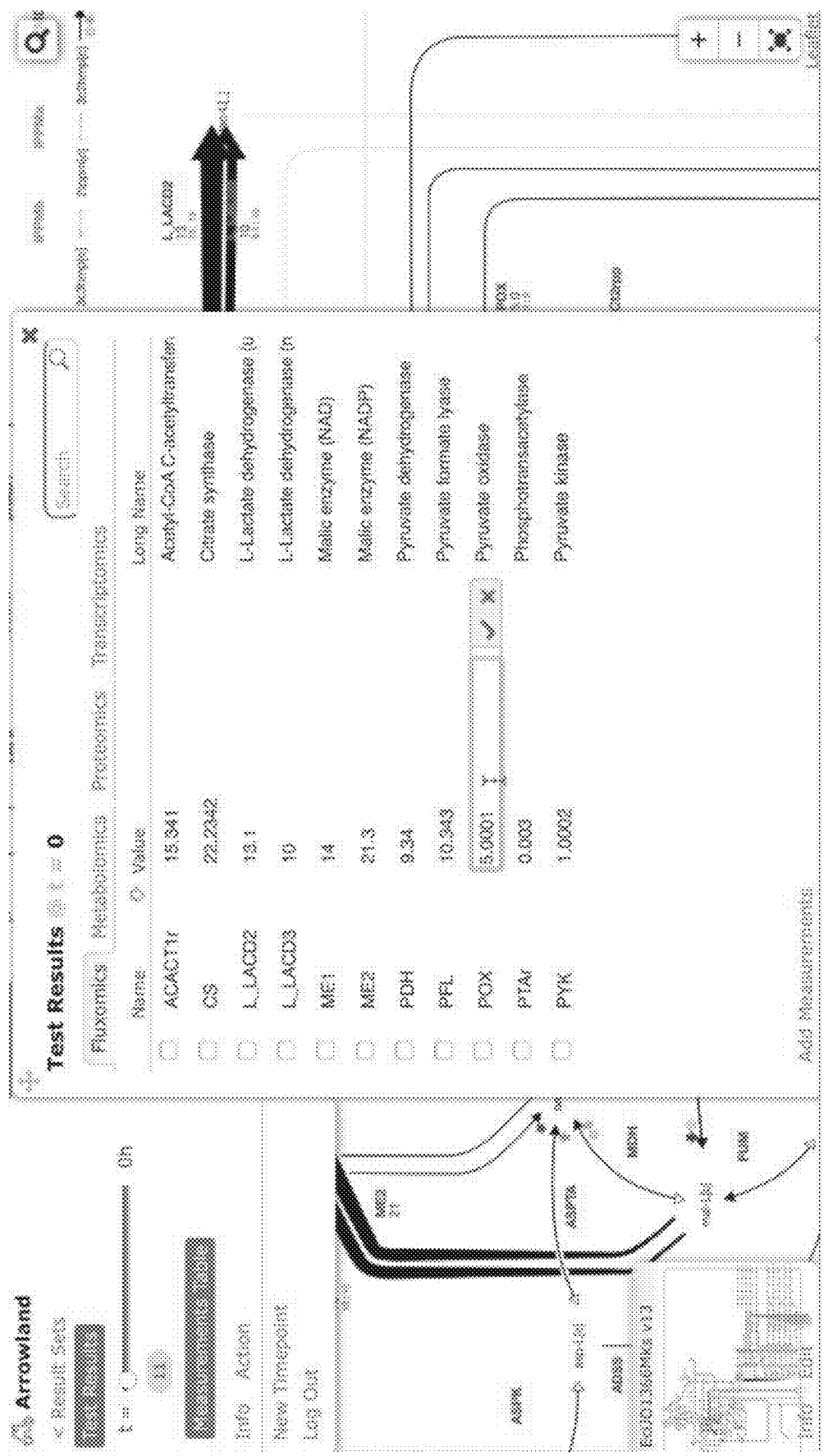
Figure 11S:
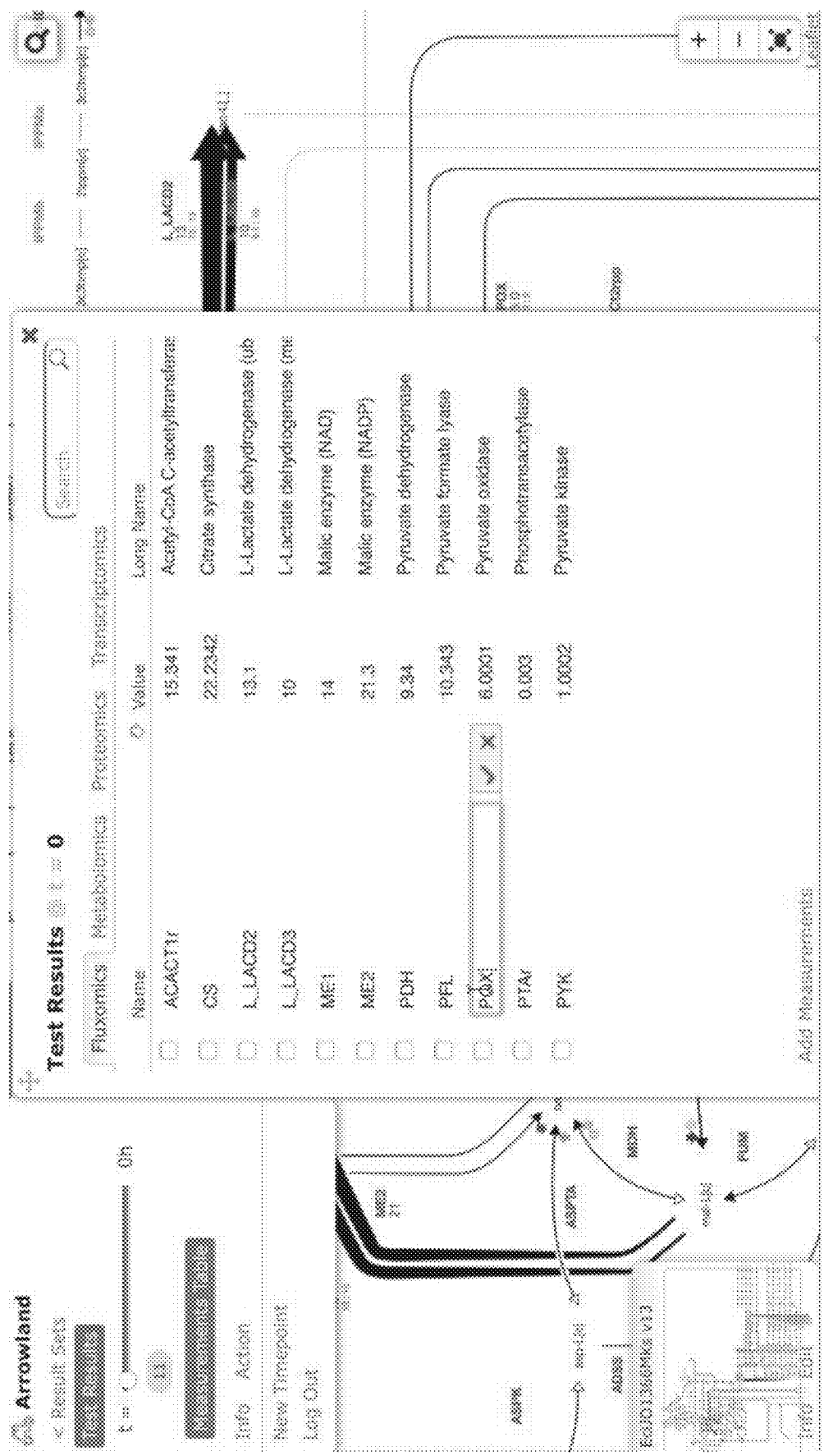
Figure 11T:
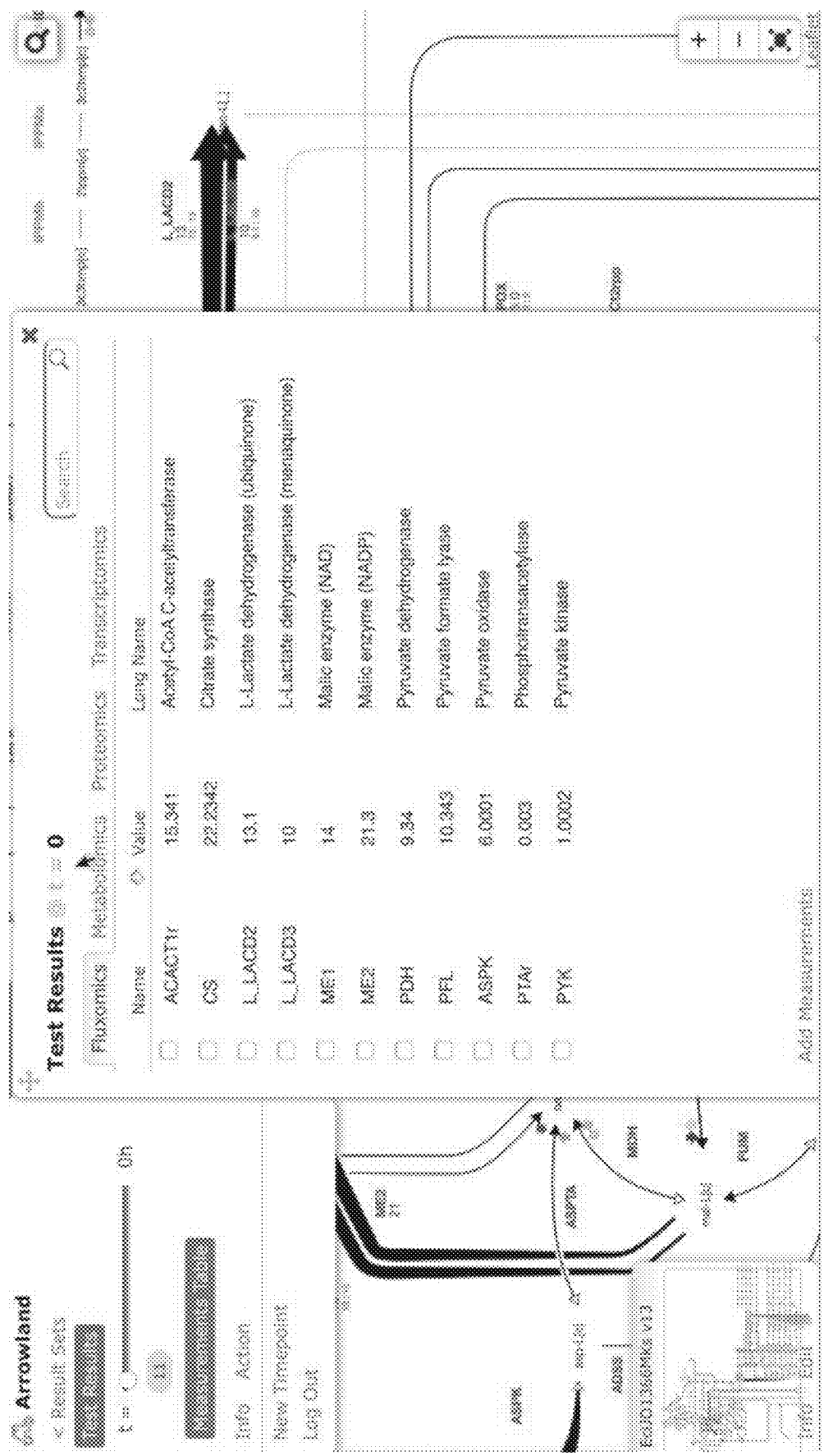
Figure 12B:
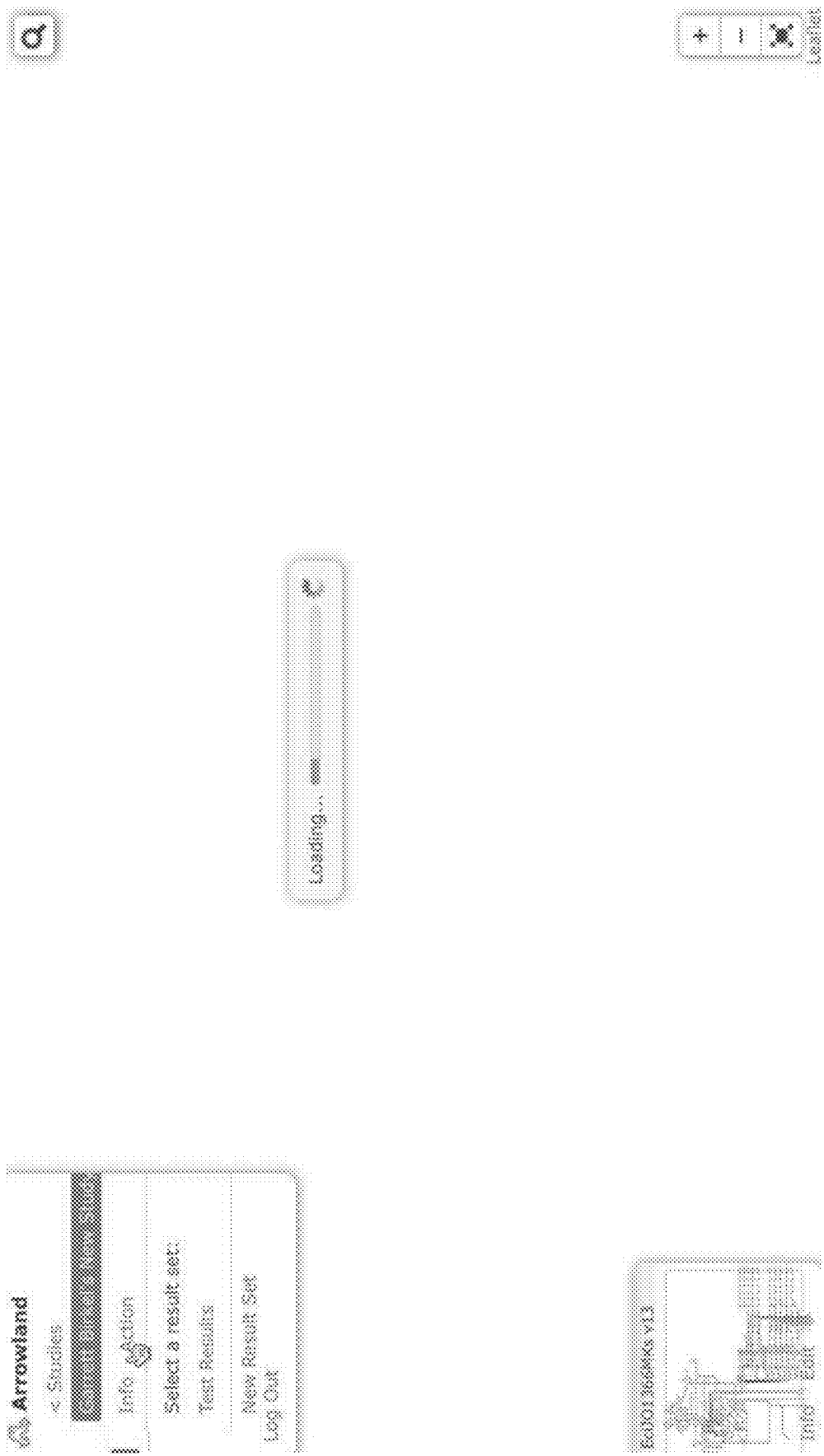
FIGS. 12A-12AA are screenshots showing exemplary importing proteomics data from a CSV file into Arrowland (public-arrowland.jbei.org/static/main/help/proteomics_csv_import.mp4, the content of which is incorporated herein by reference in its entirety). To show proteomics in Arrowland, a user may first create a study and a result set inside the study. The study should have a default map and a default model assigned to it. The result set may then be selected and the user can be ready to import. The user may add measurements to show the import window at the drop zone. The user can drop in a CSV file containing proteomics, which may include names followed by values. Protein names may correspond to the protein names used in the model, or may be in different formats. The user may indicate to Arrowland to look for proteomics measurements. In use, the window changes to show all the measurements Arrowland could find in the file. Identifiers may be translated from one format to their equivalent names used by Arrowland. The user may approve the import by selecting the approve button. Every reaction on the map that has proteomics data has a halo on one side. When the user zooms in, the user can see the individual values for each protein. Note that the proteins are grouped into columns. Each group is capable of catalyzing the reaction separately. If the user wants to see the measurements in tabular format, the measurements table button may be selected. The user can edit the measurement values here or change with protein value belongs to. The results of the edits will be immediately visible on the map.
Figure 12C:
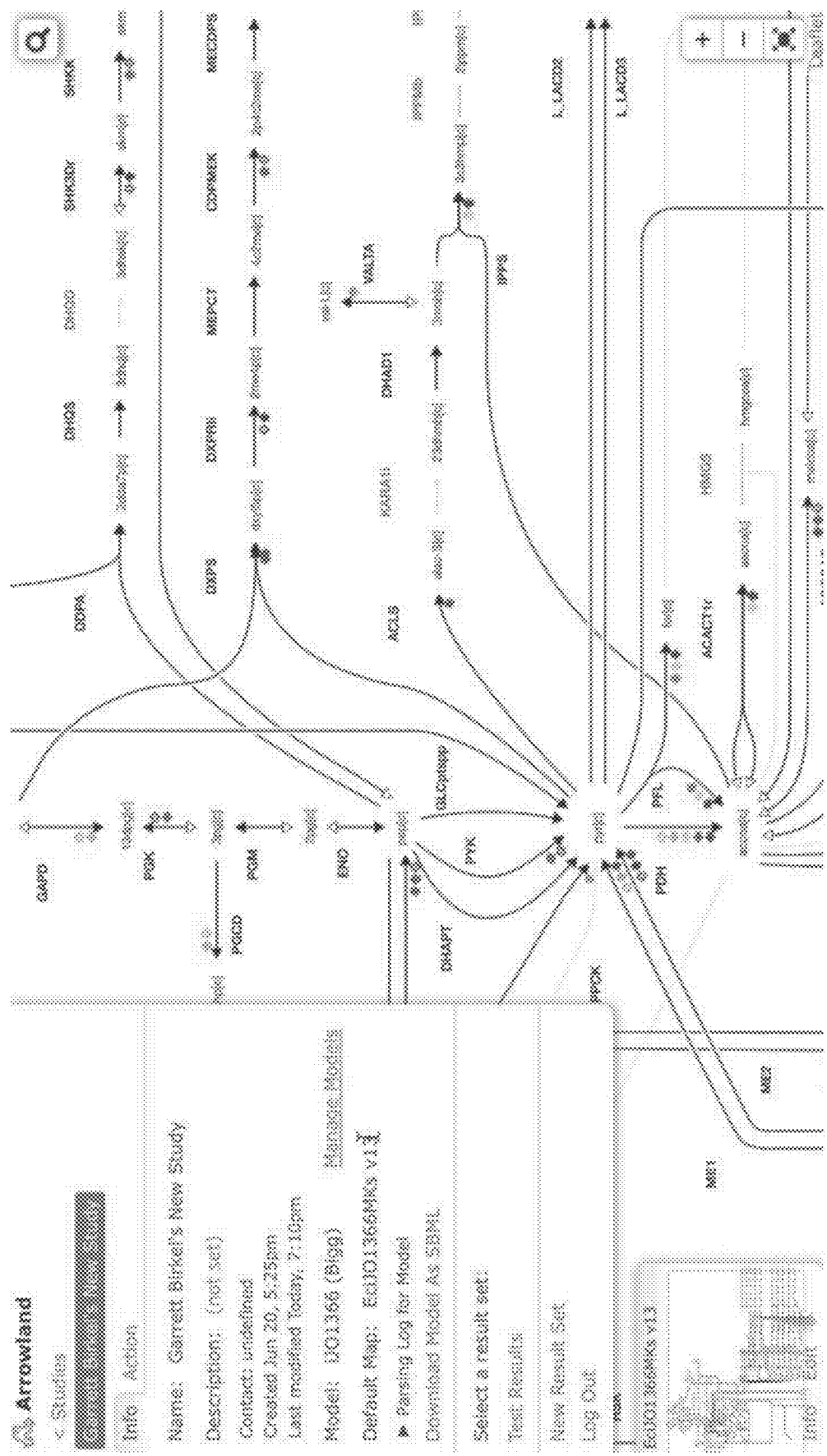
Figure 12D:
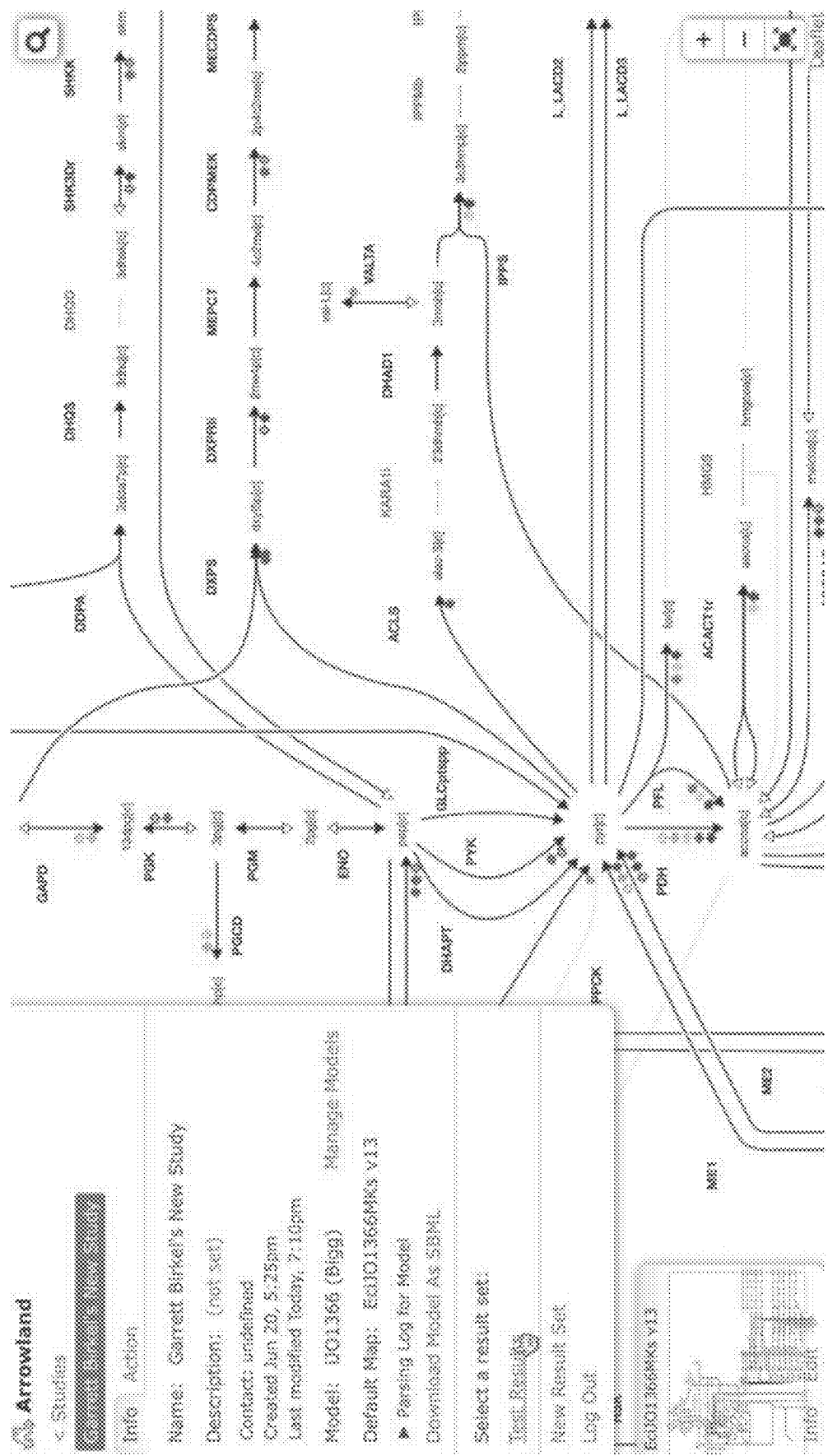
Figure 12E:
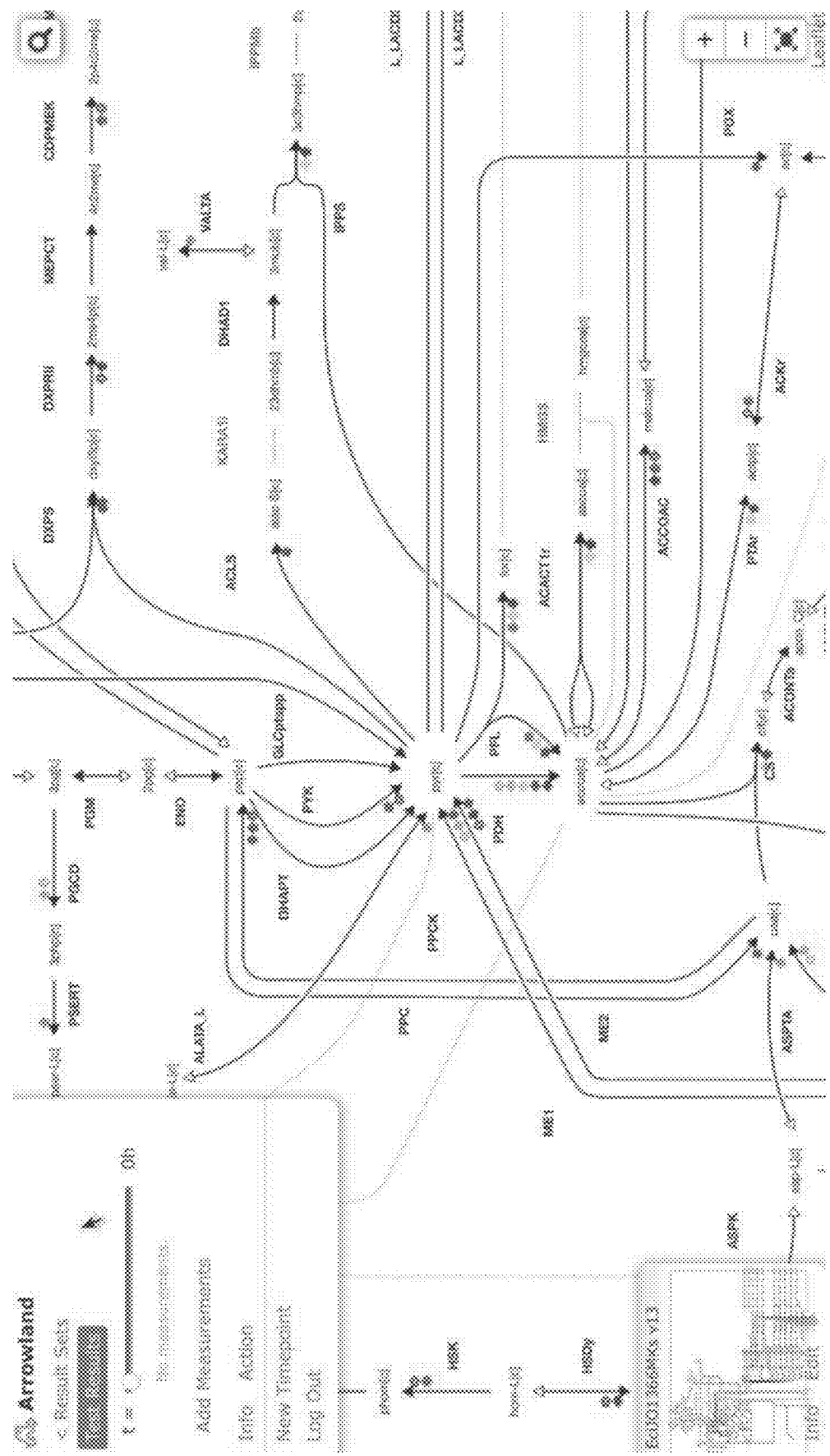
Figure 12F:
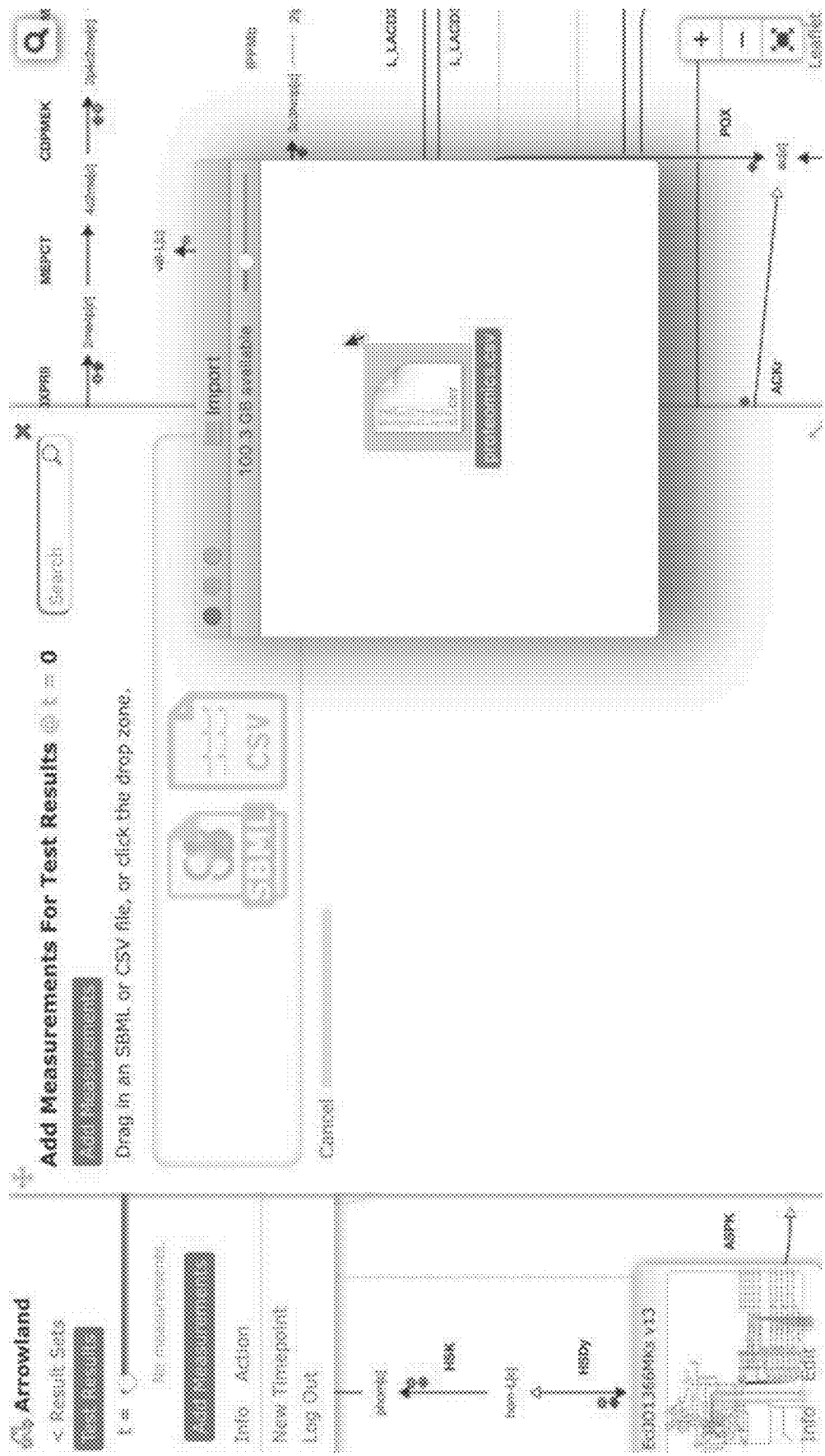
Figure 12G:
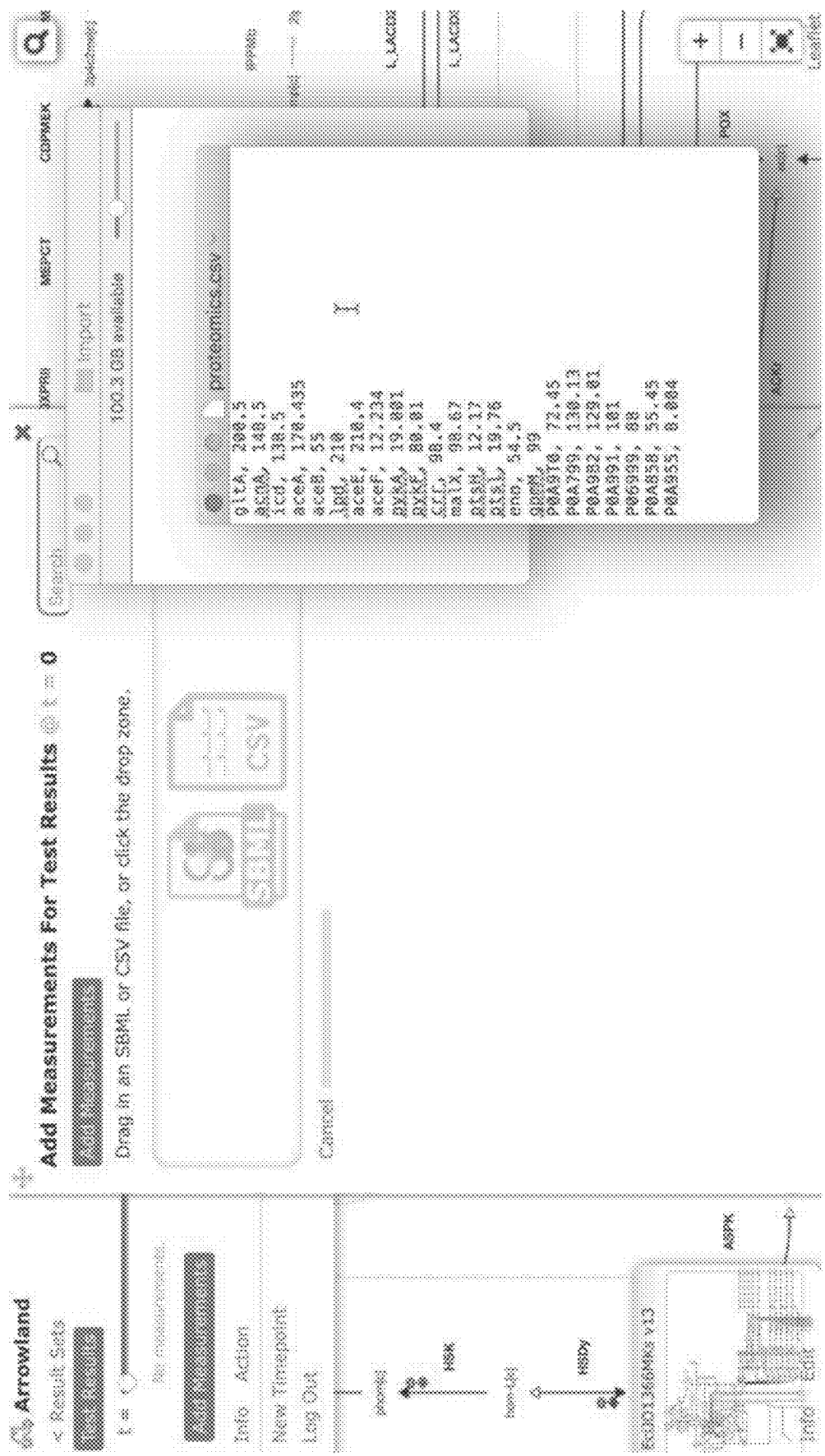
Figure 12H:
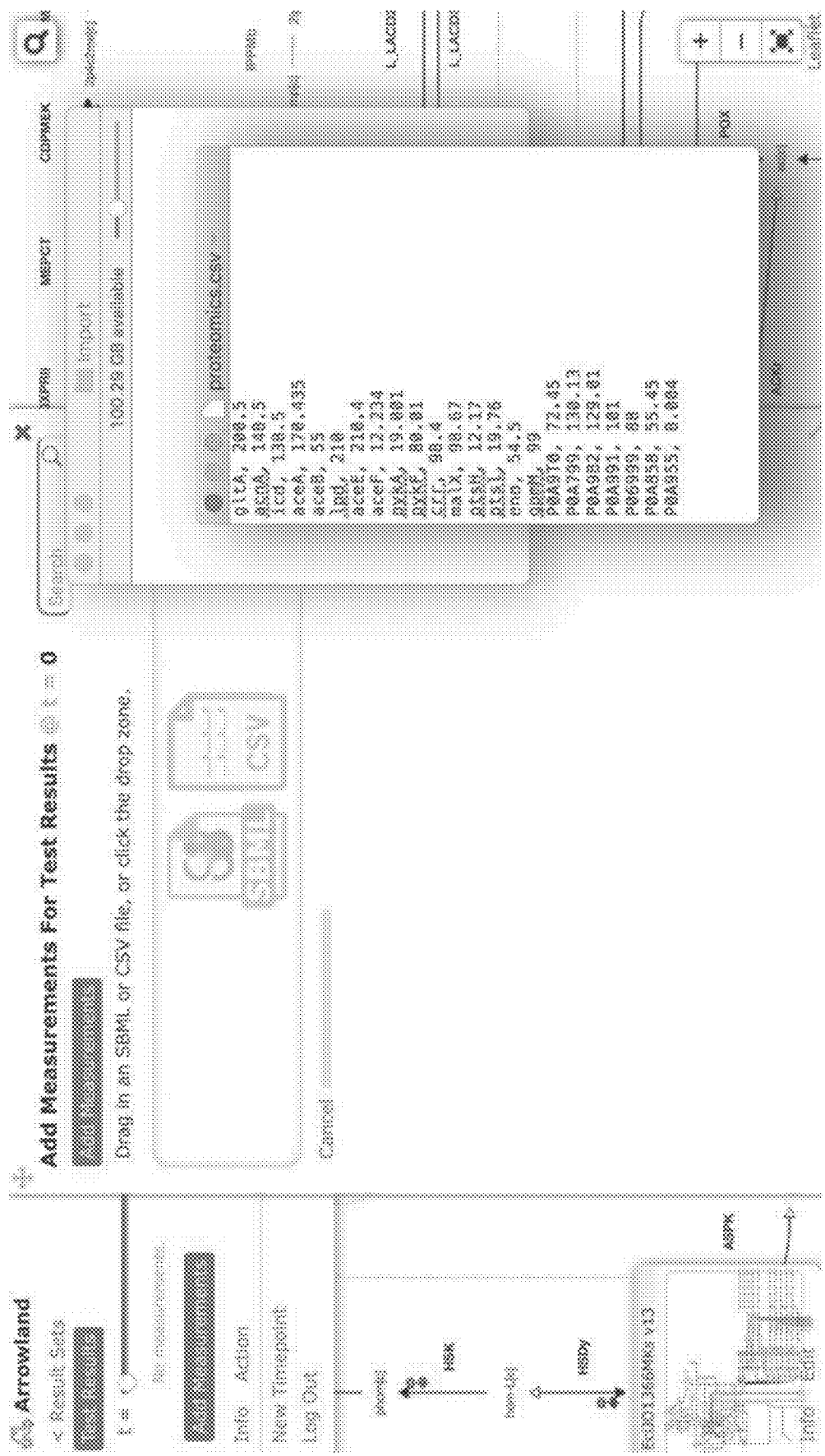
Figure 12I:
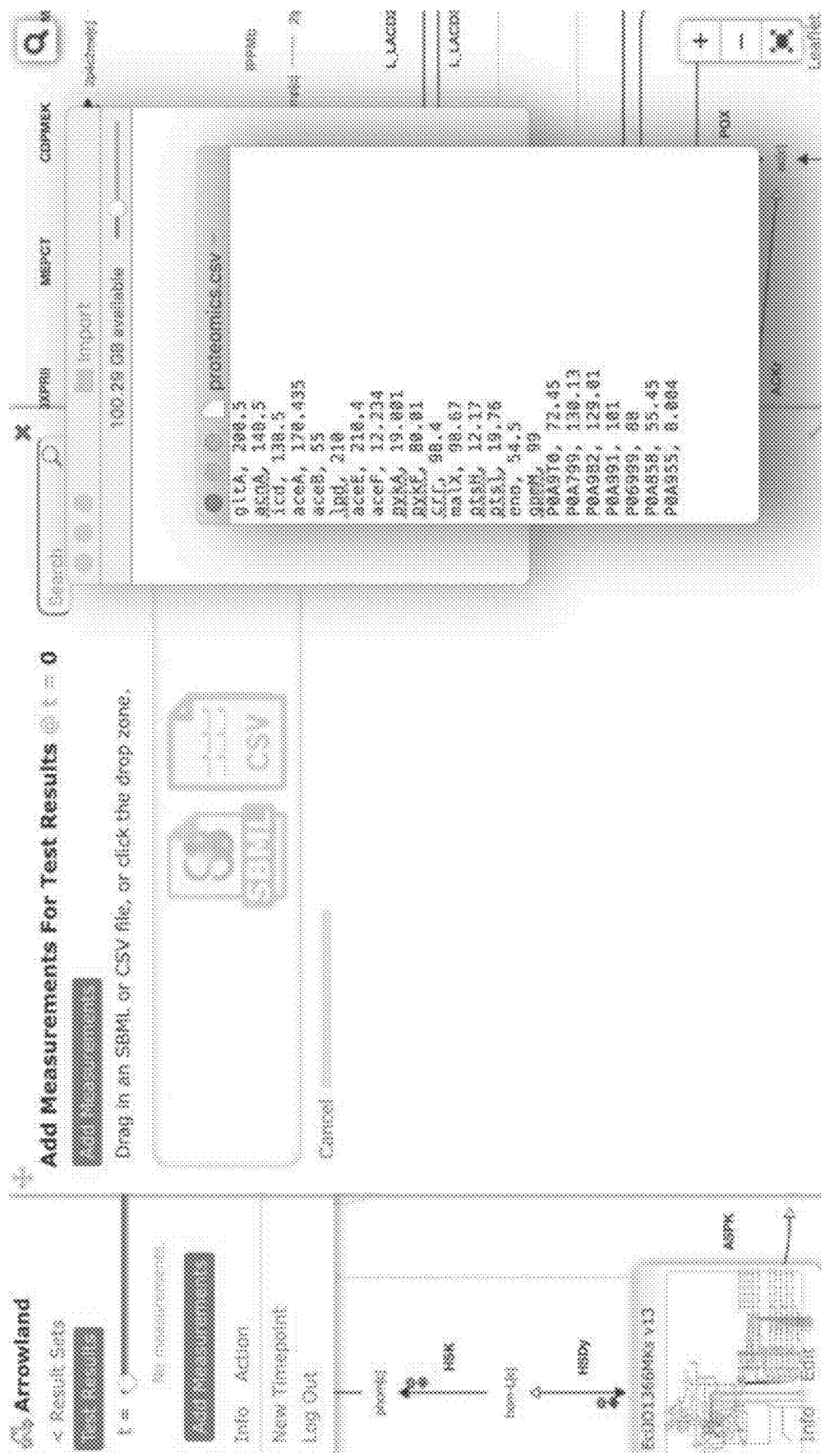
Figure 12J:
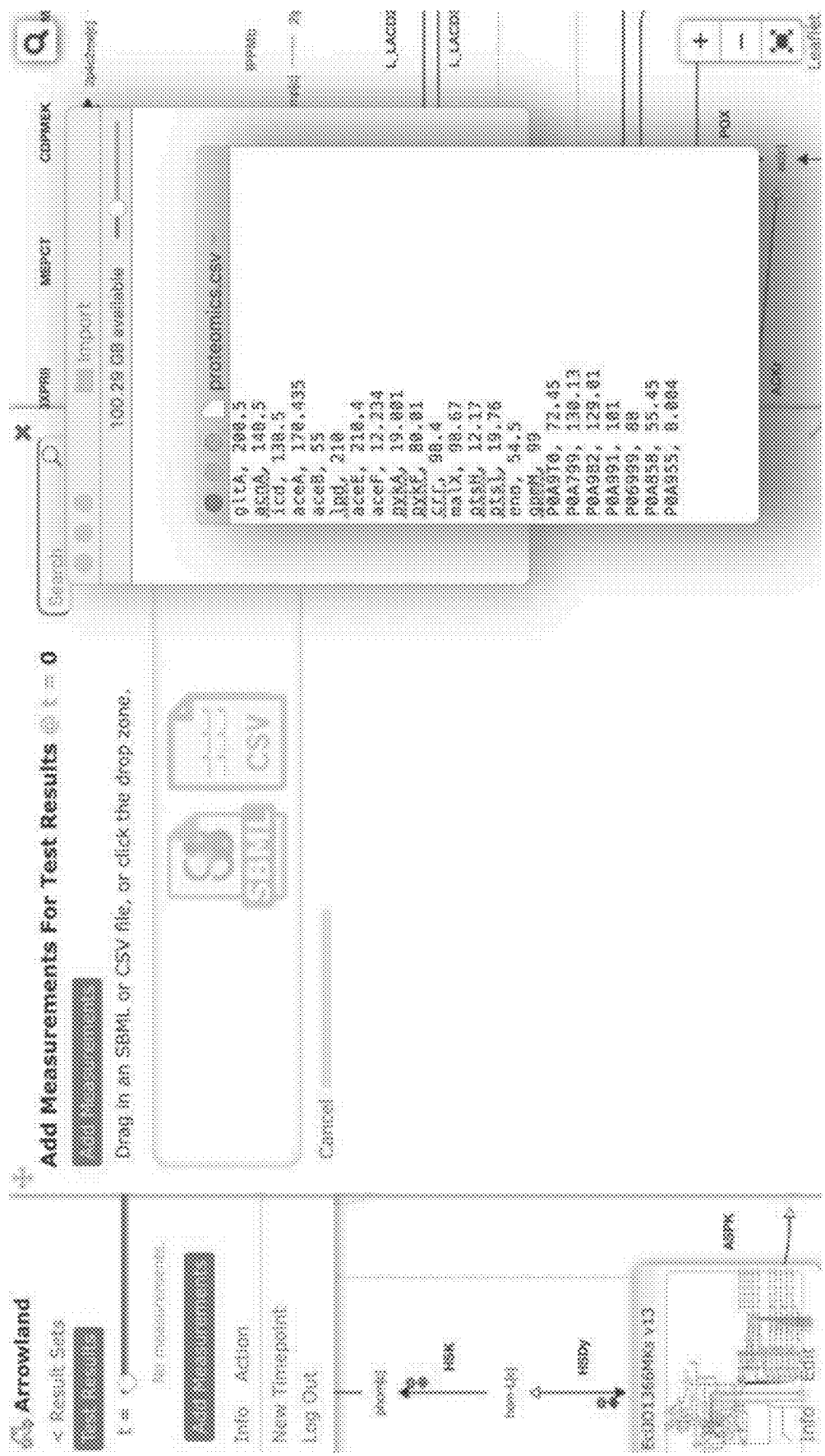
Figure 12K:
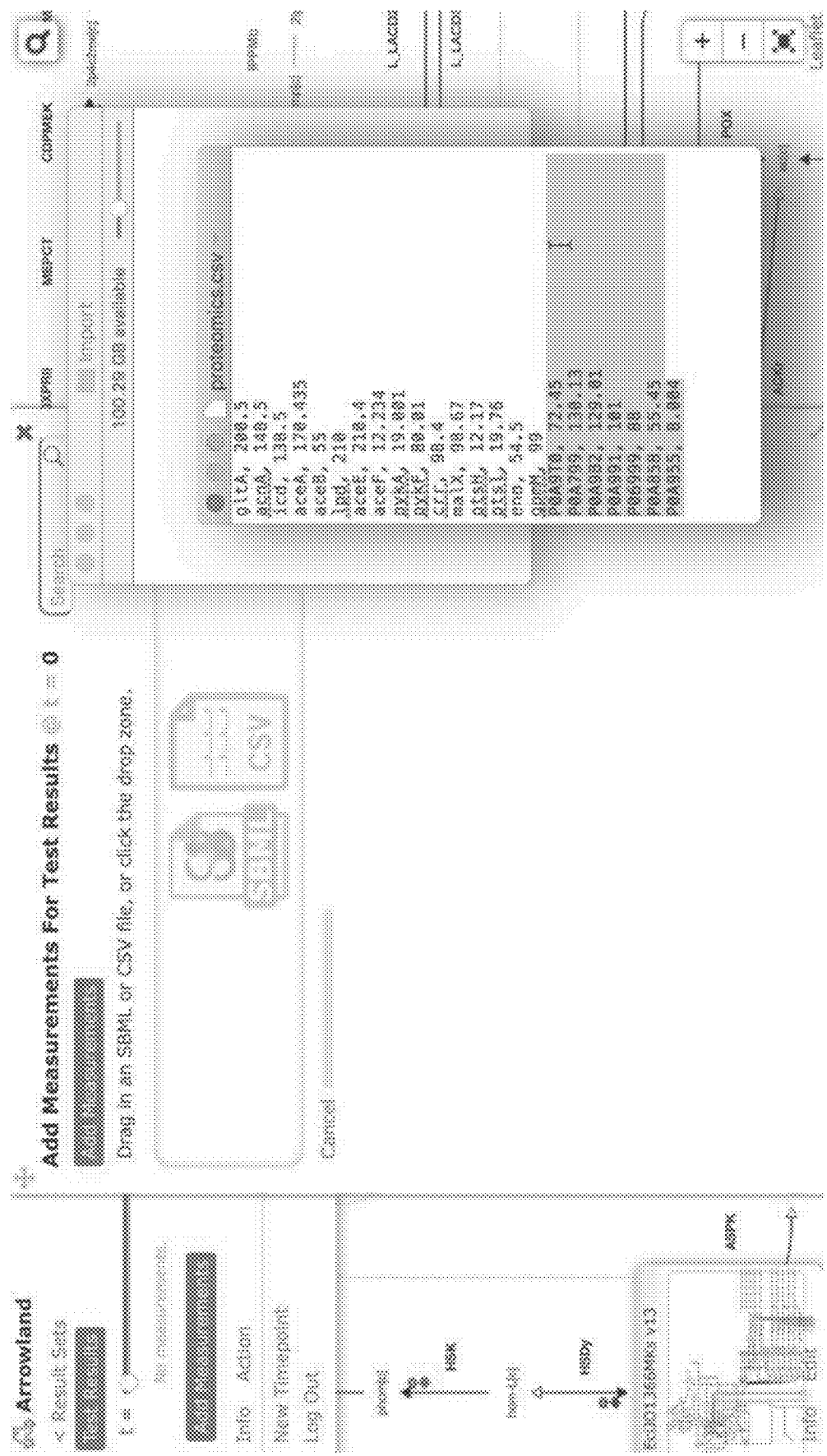
Figure 12L:
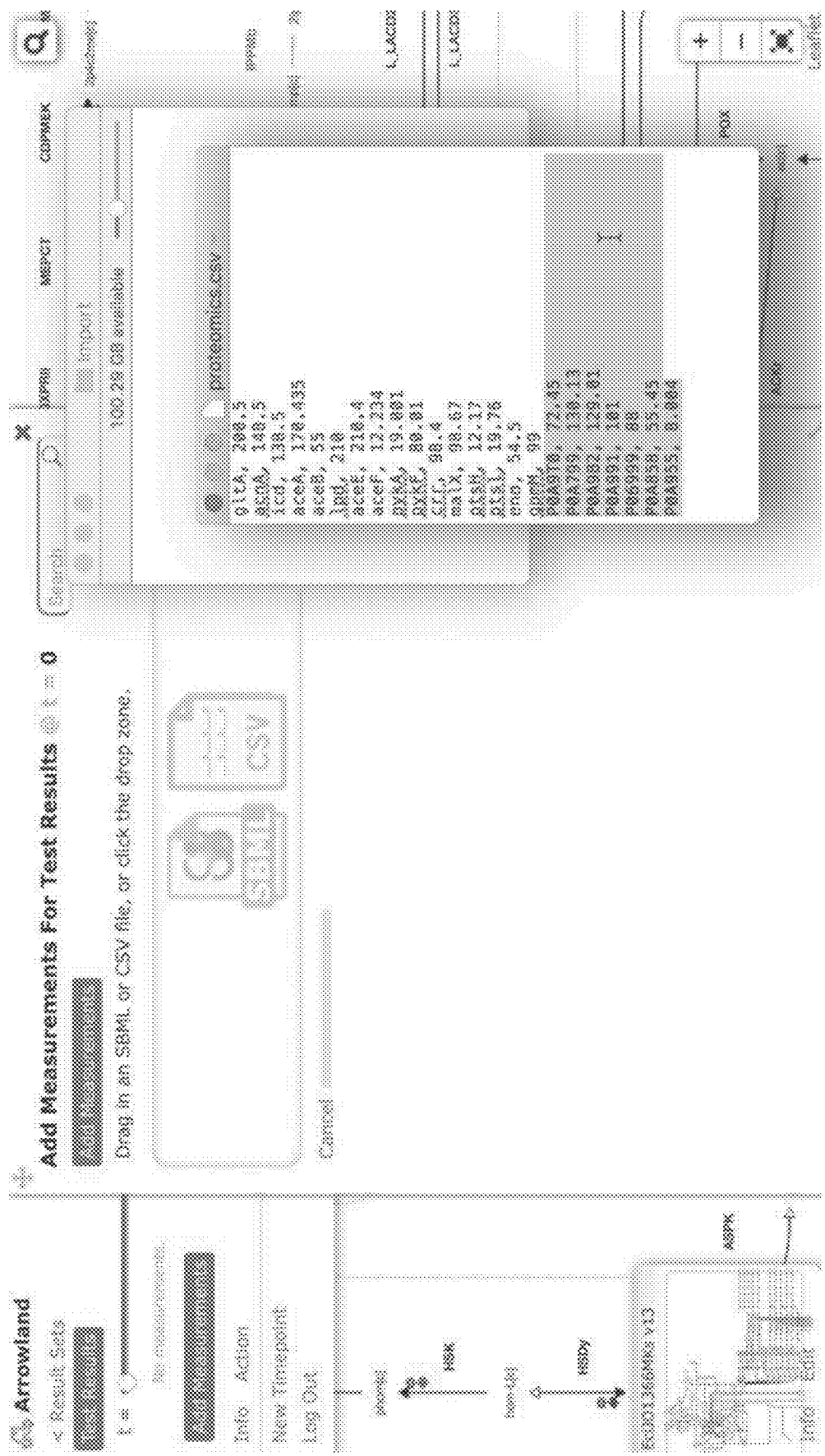
Figure 12M:
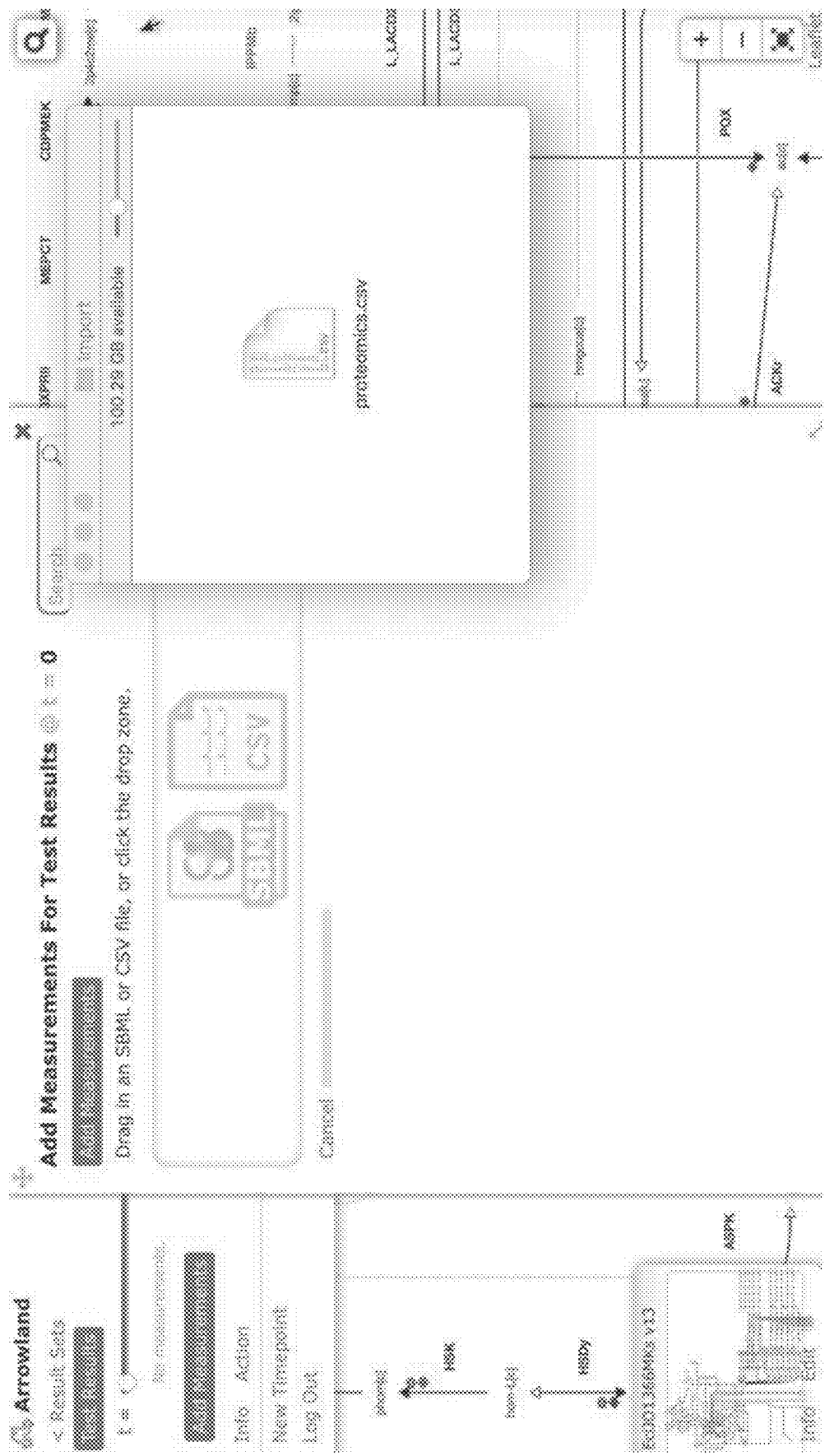
Figure 12N:
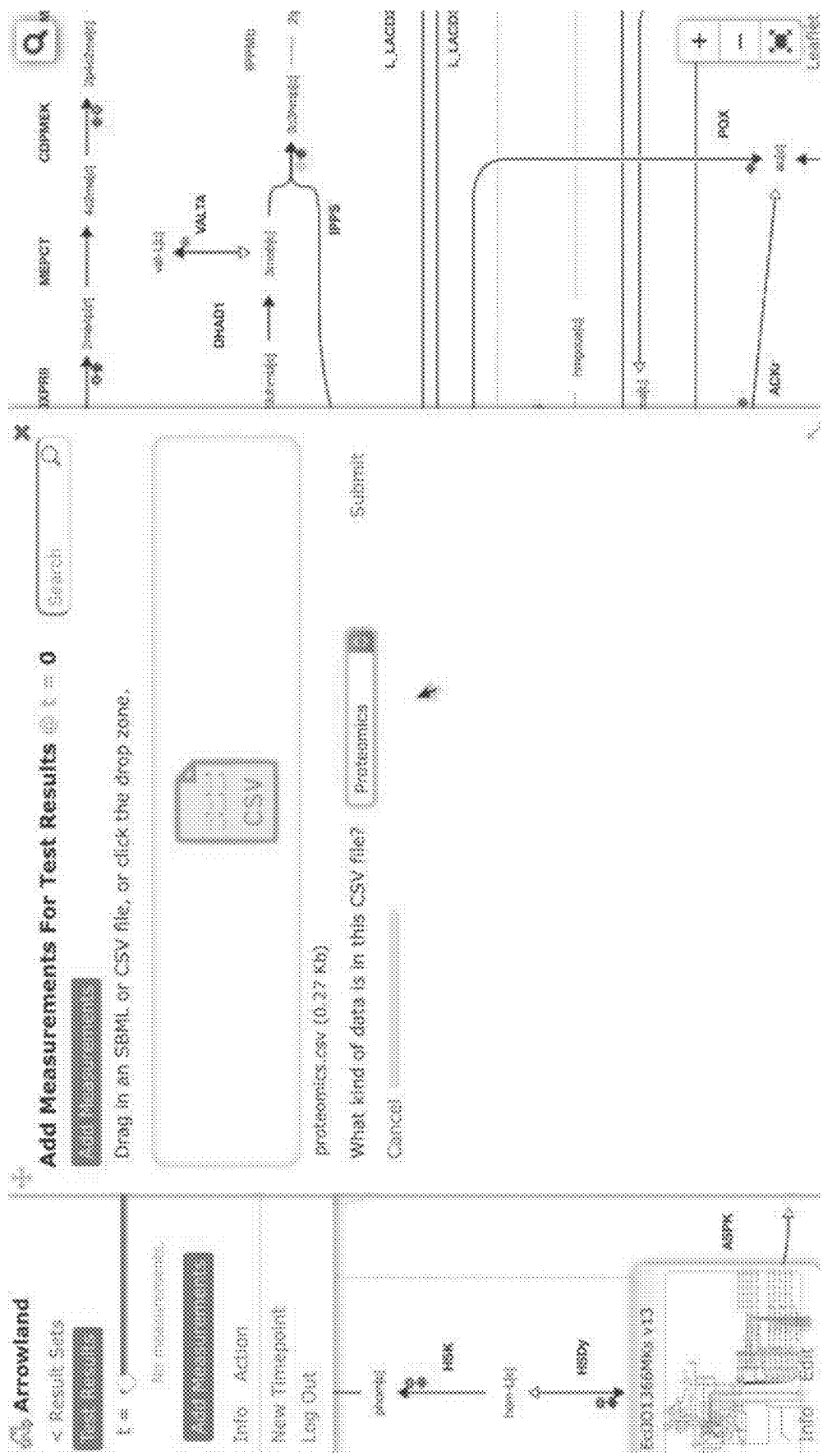
Figure 12O:
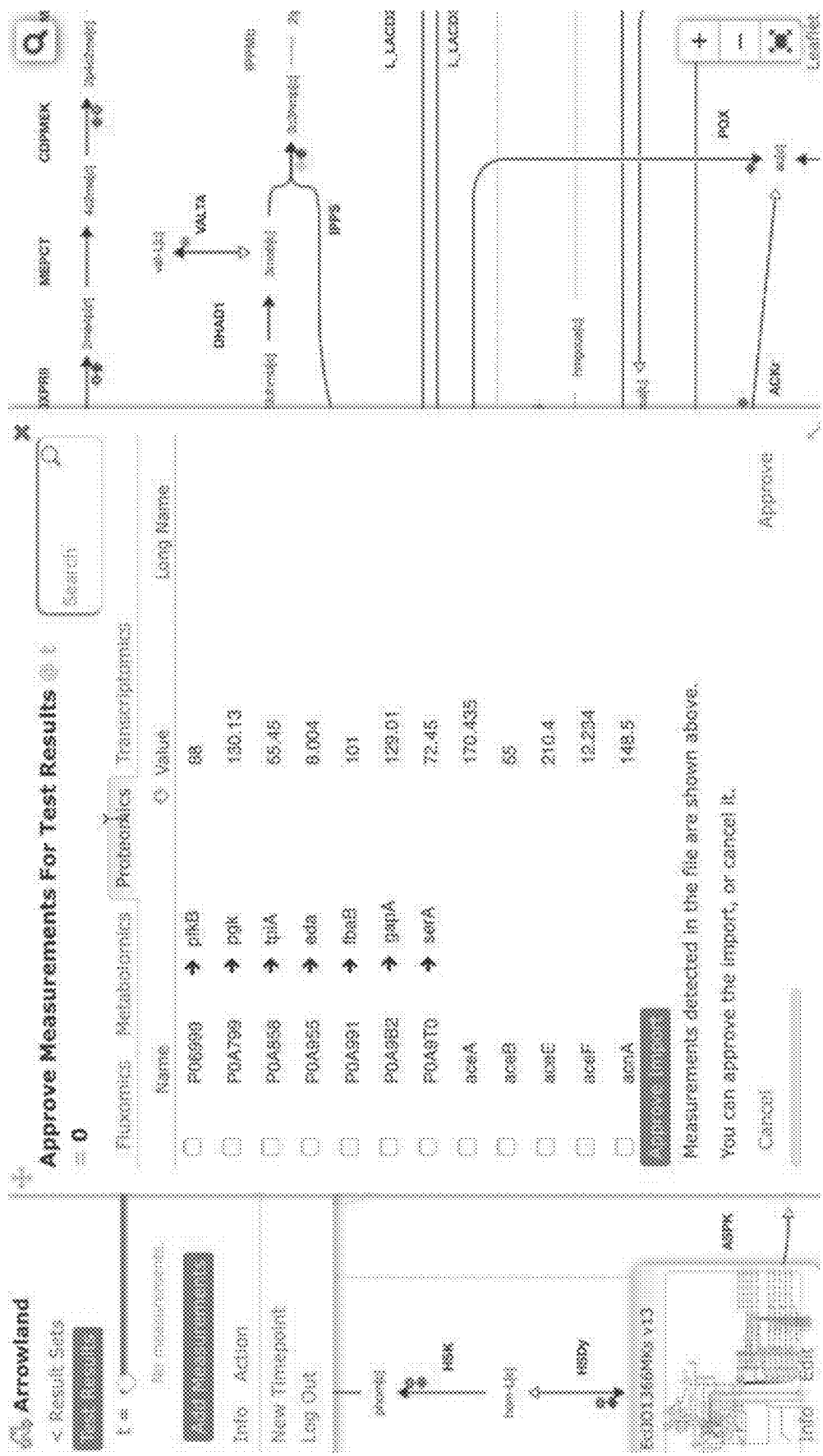
Figure 12P:
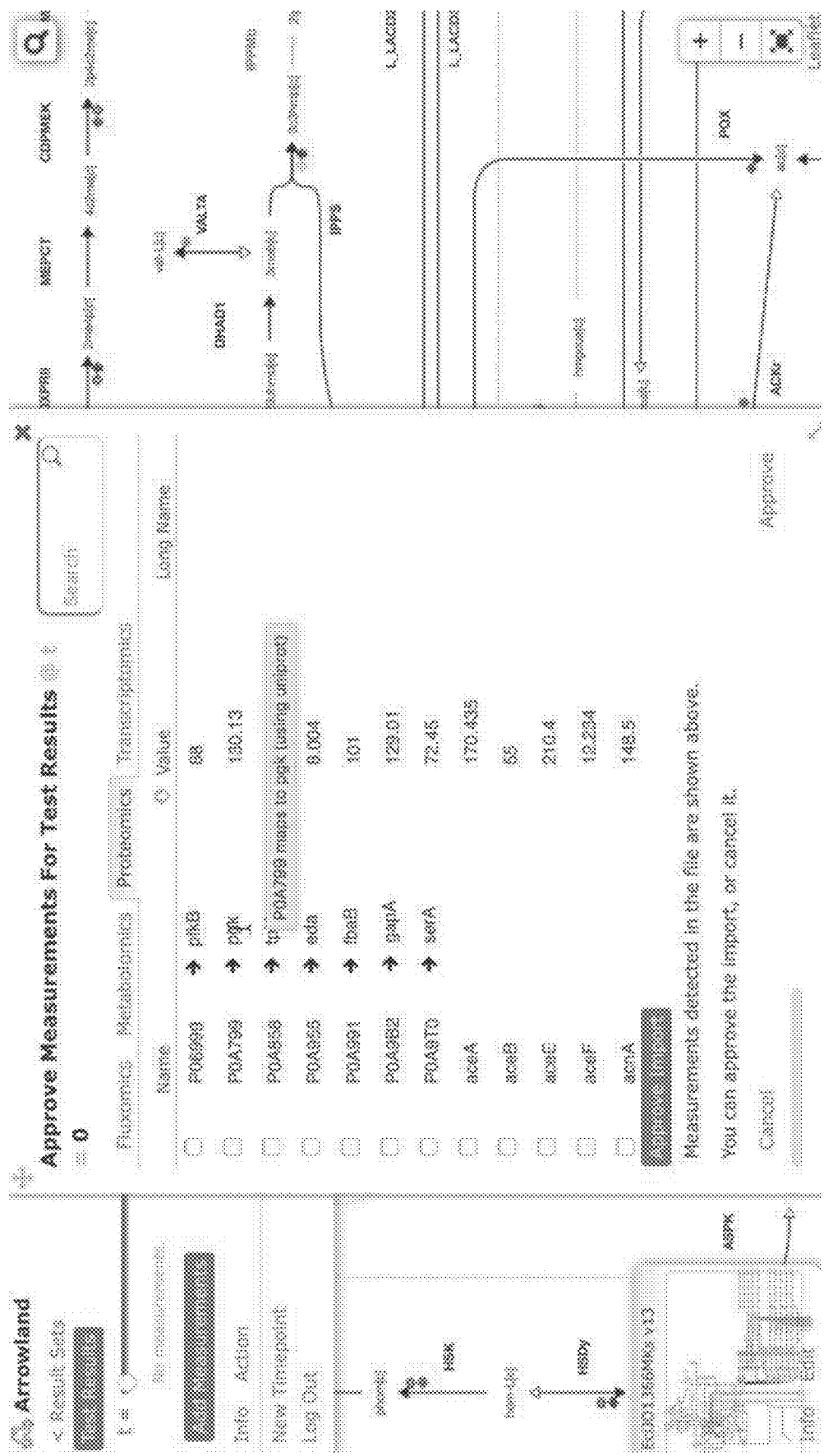
Figure 12Q:
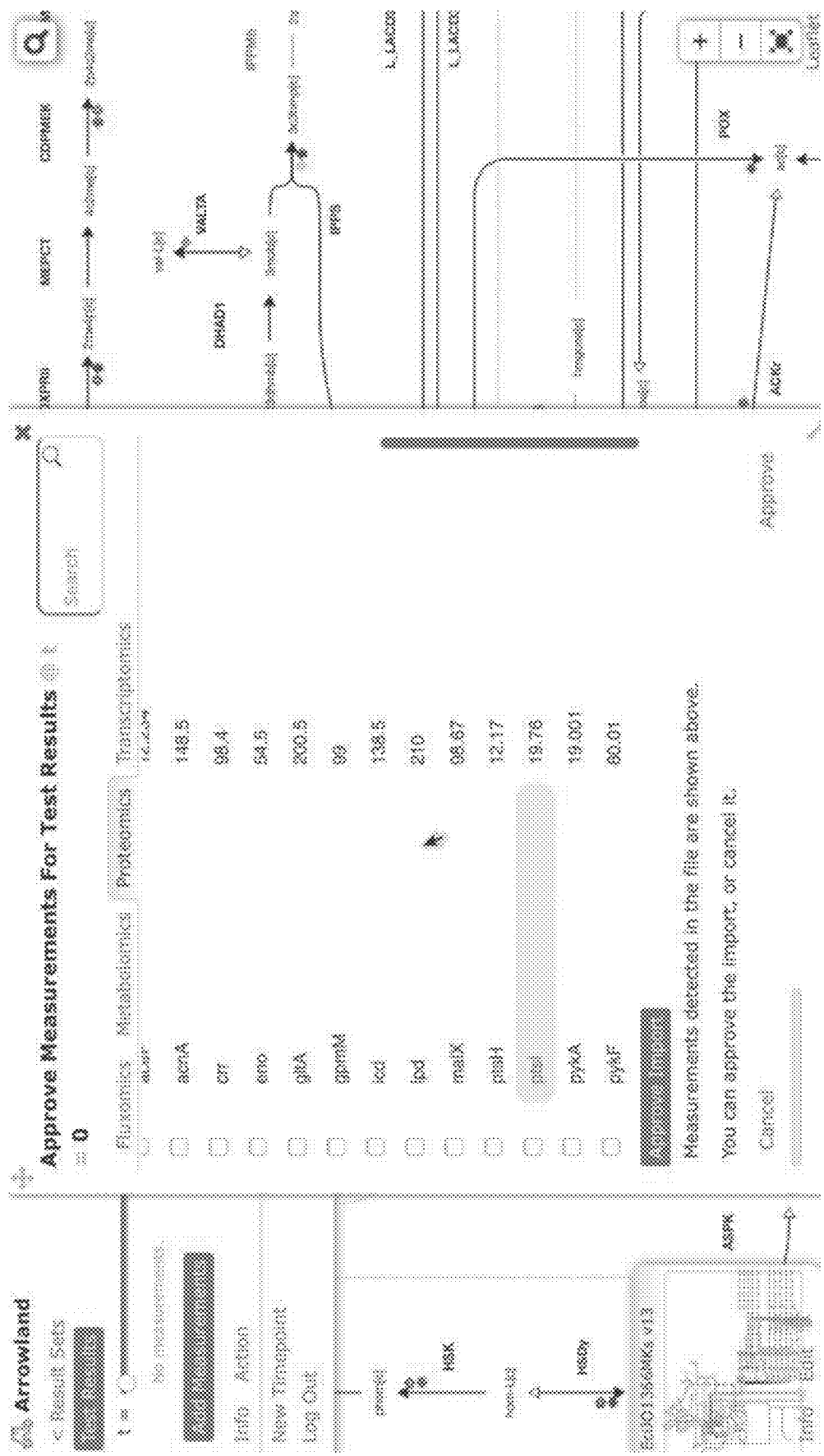
Figure 12R:
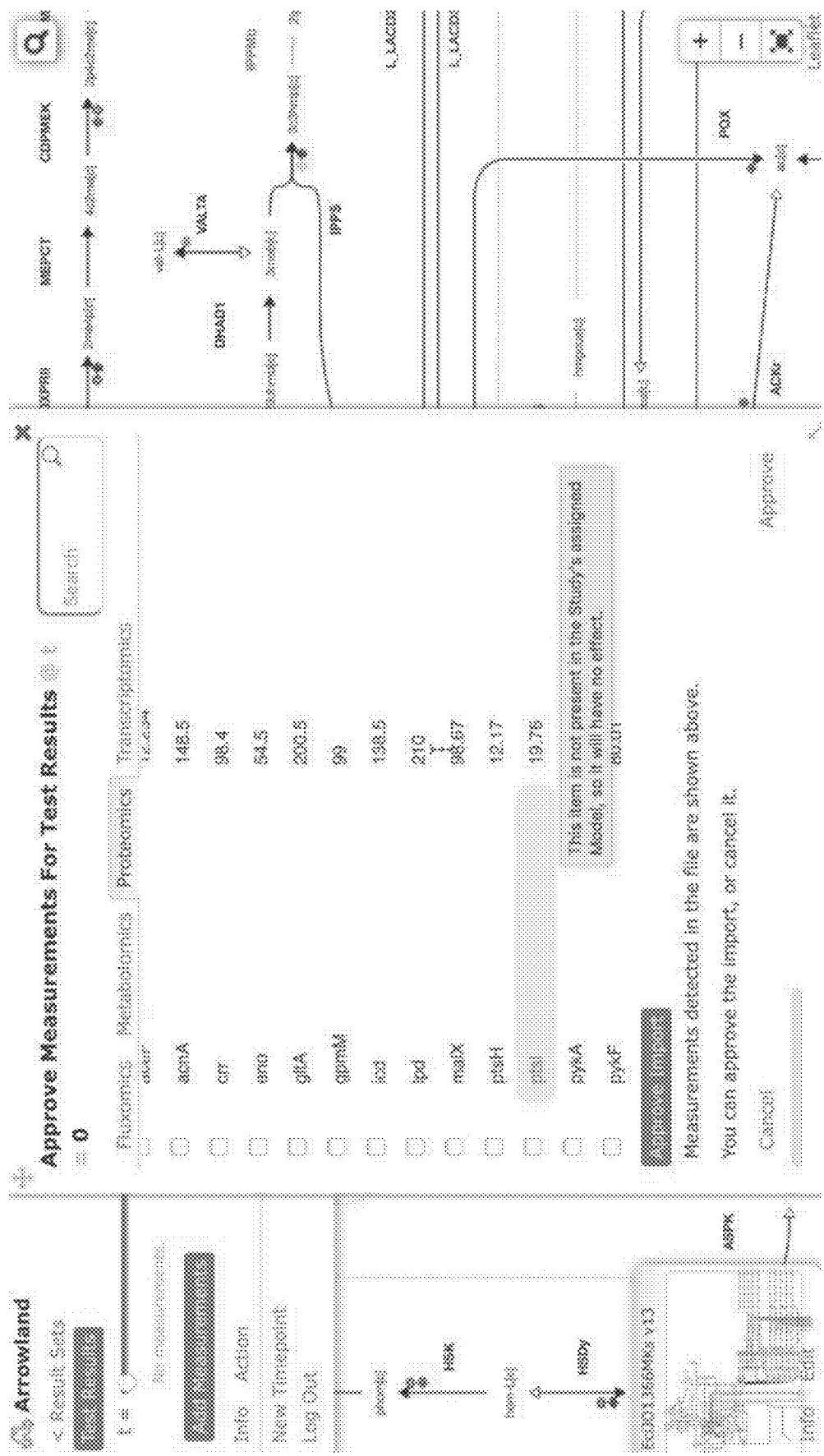
Figure 12T:
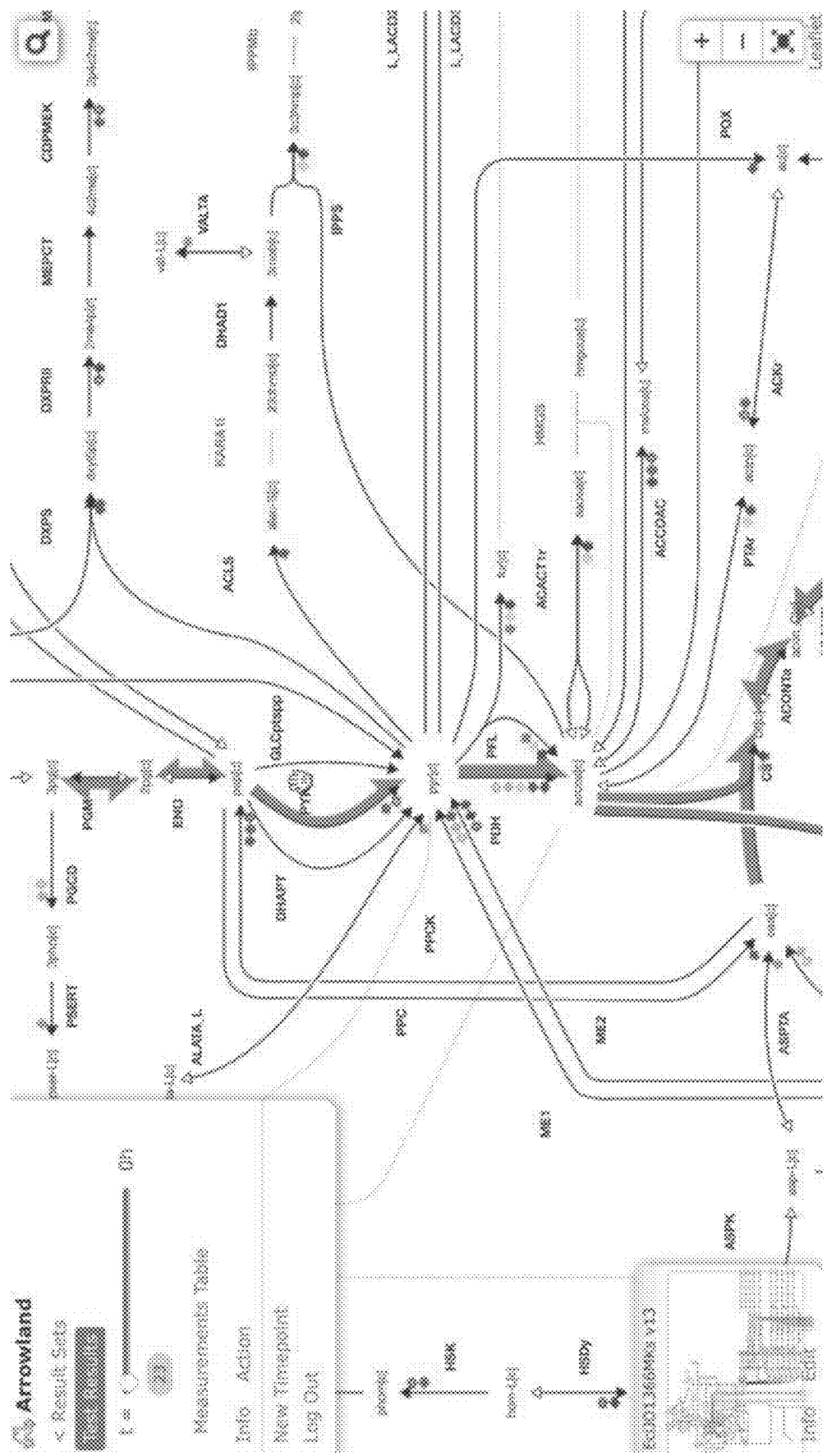
Figure 12U:
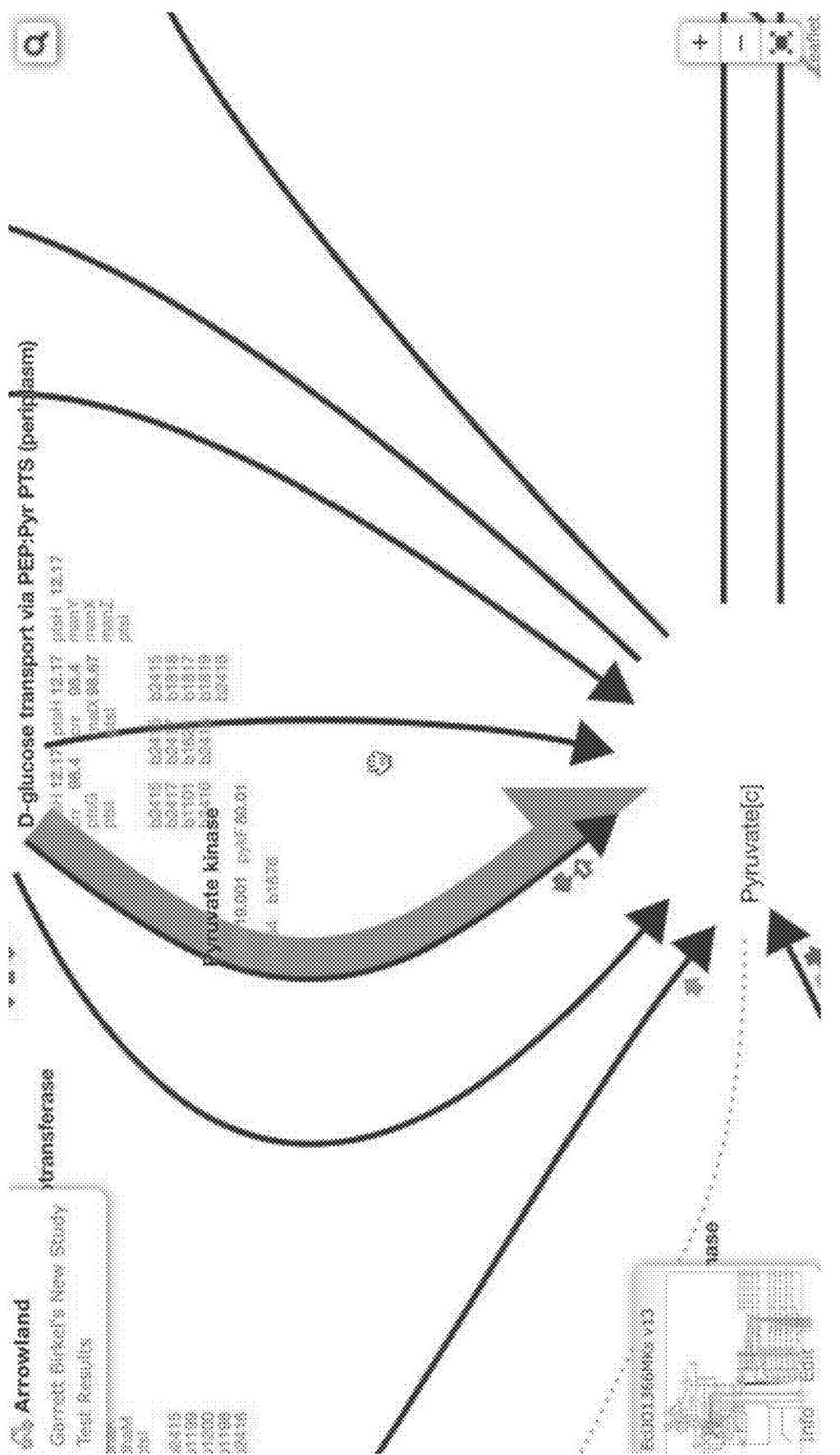
Figure 12V:
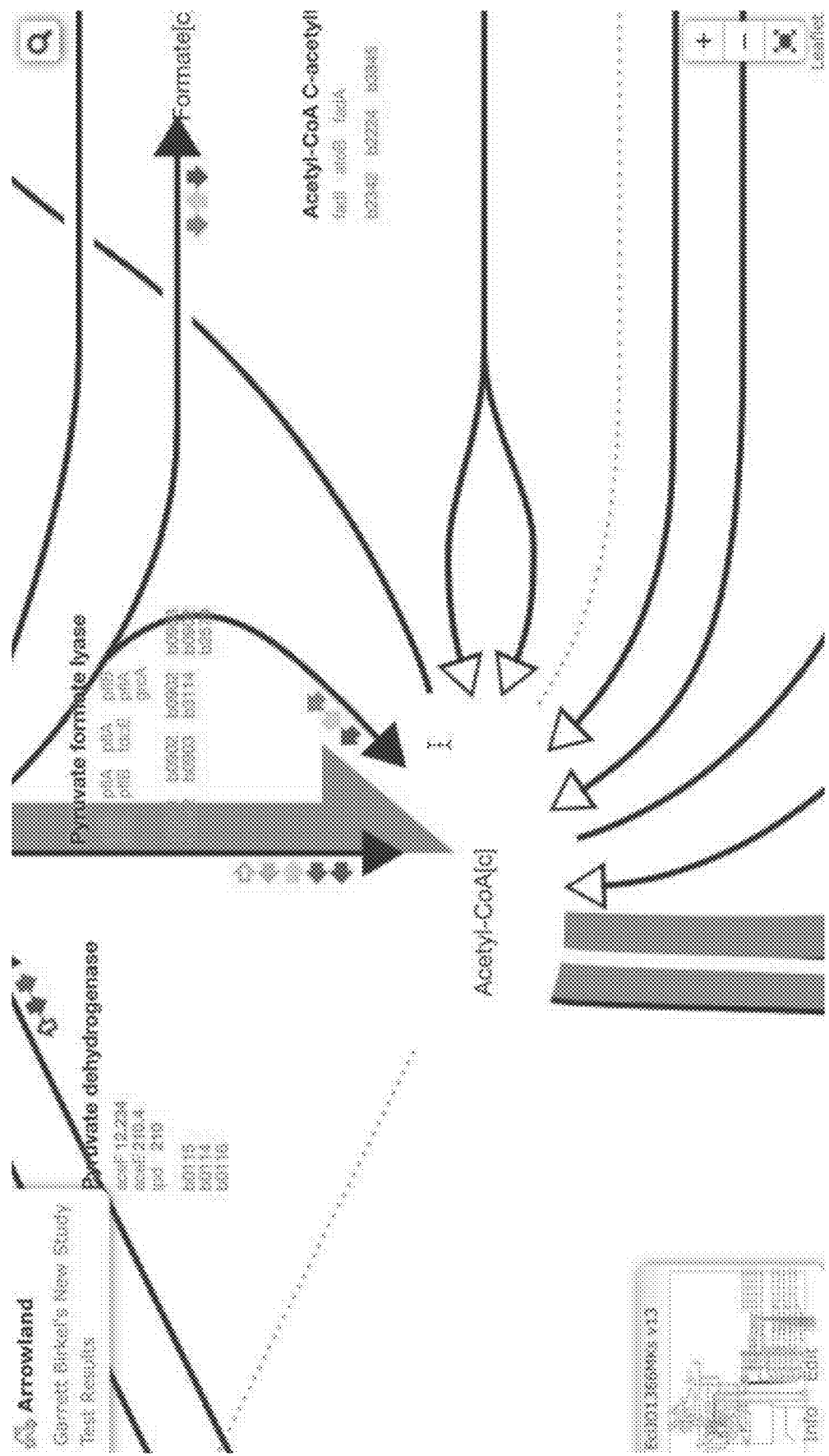
Figure 12W:
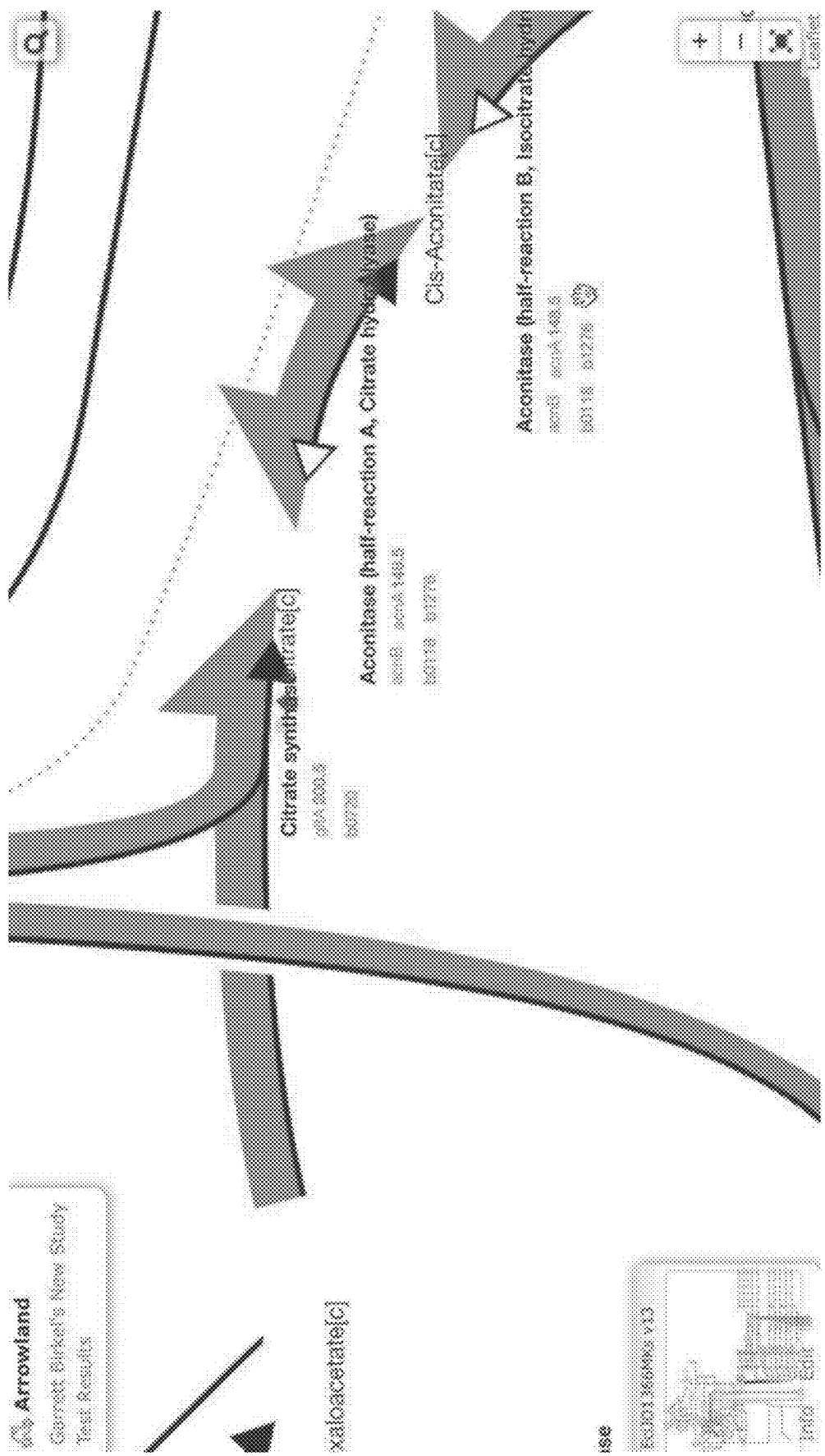
Figure 12X:
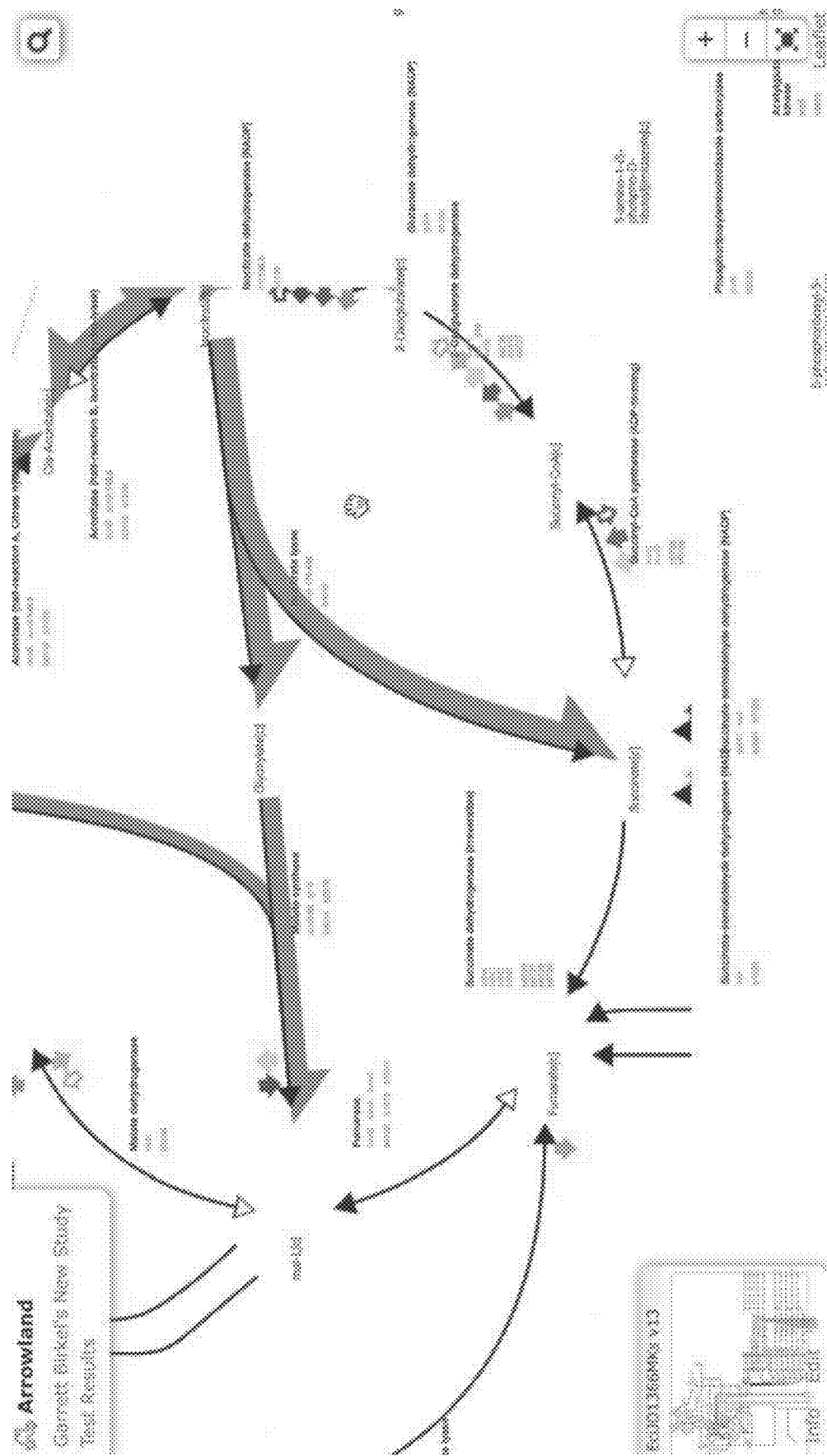
Figure 12Z:
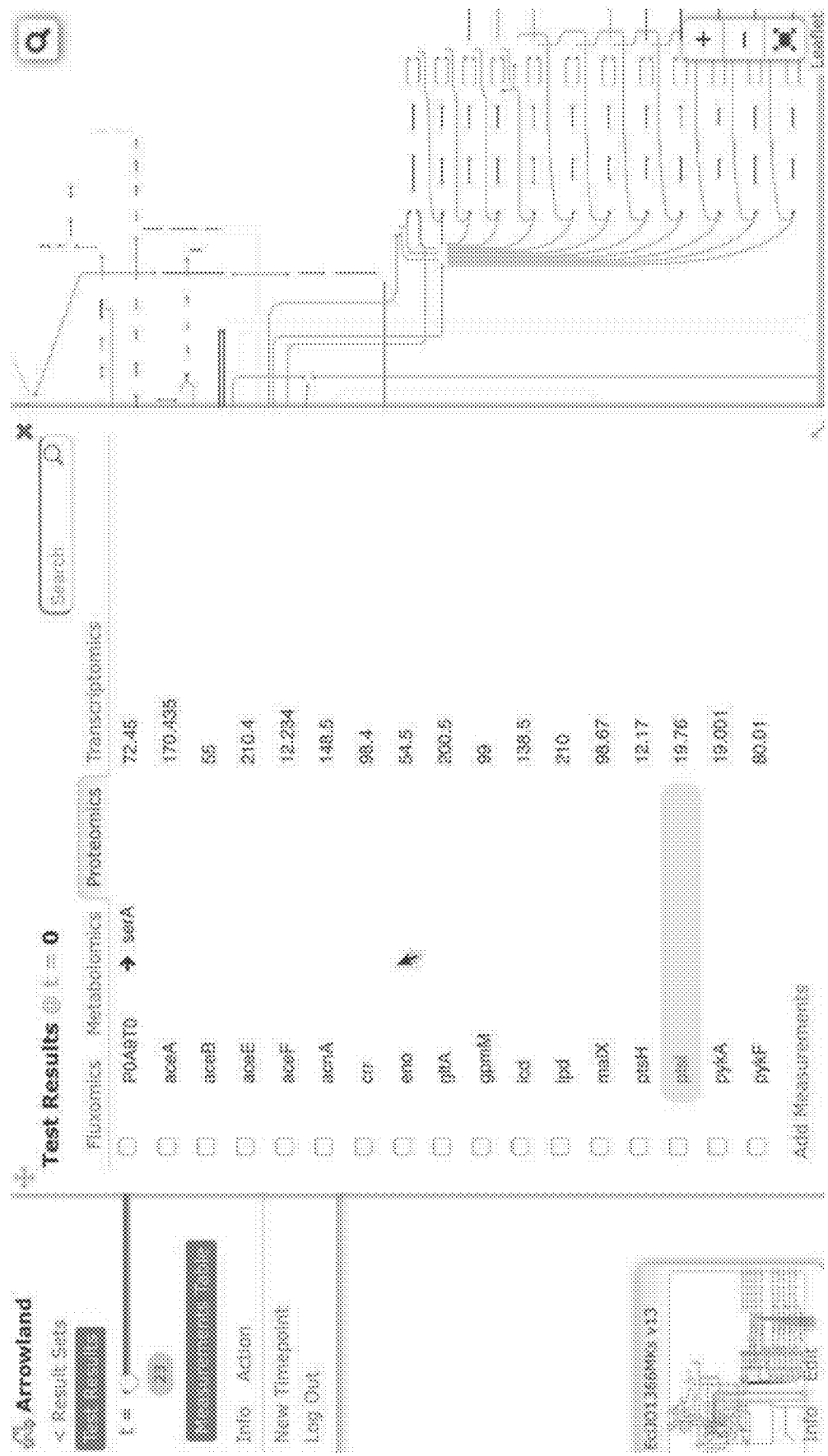
Figure 12A:
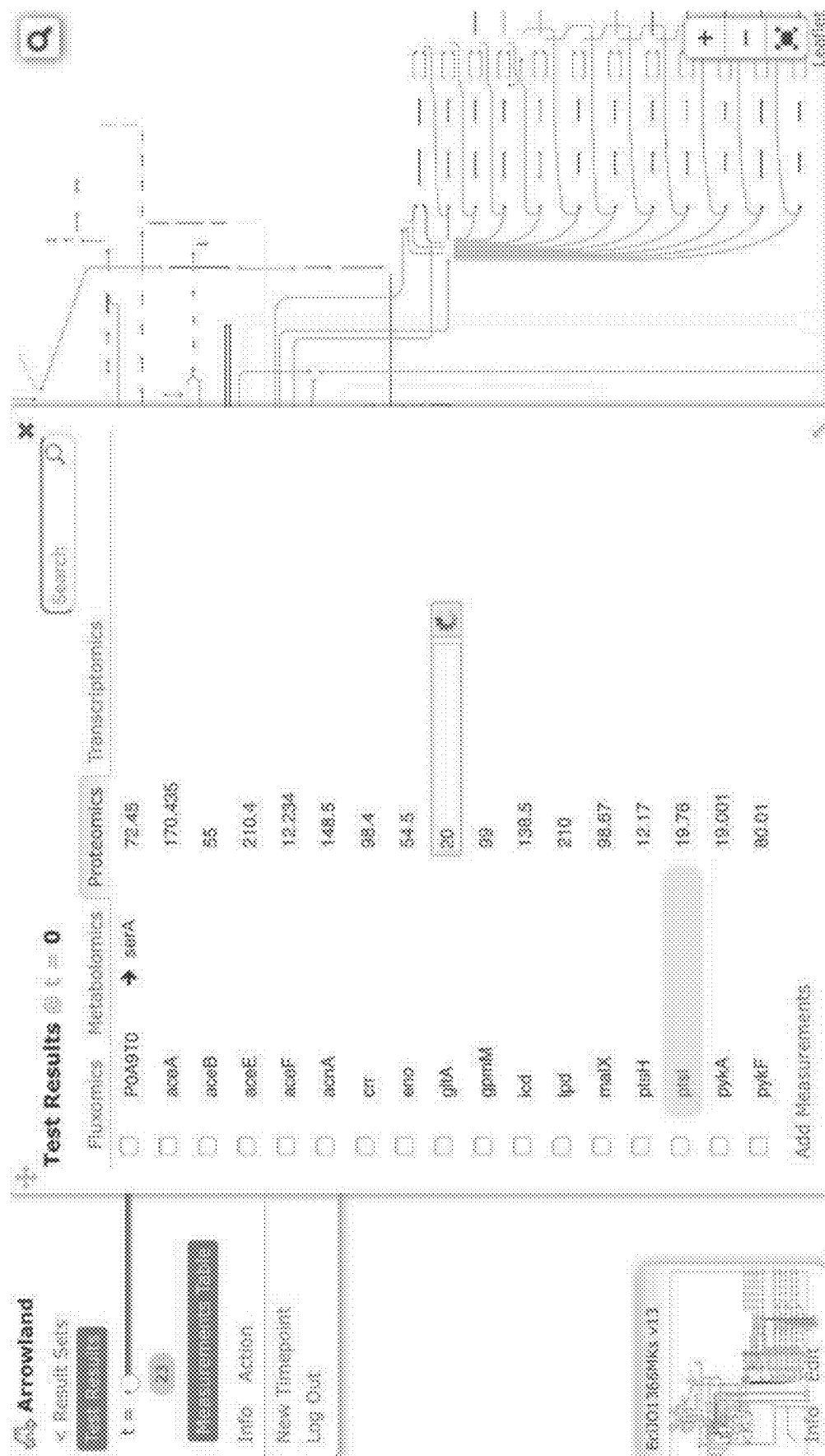
Figure 13B:
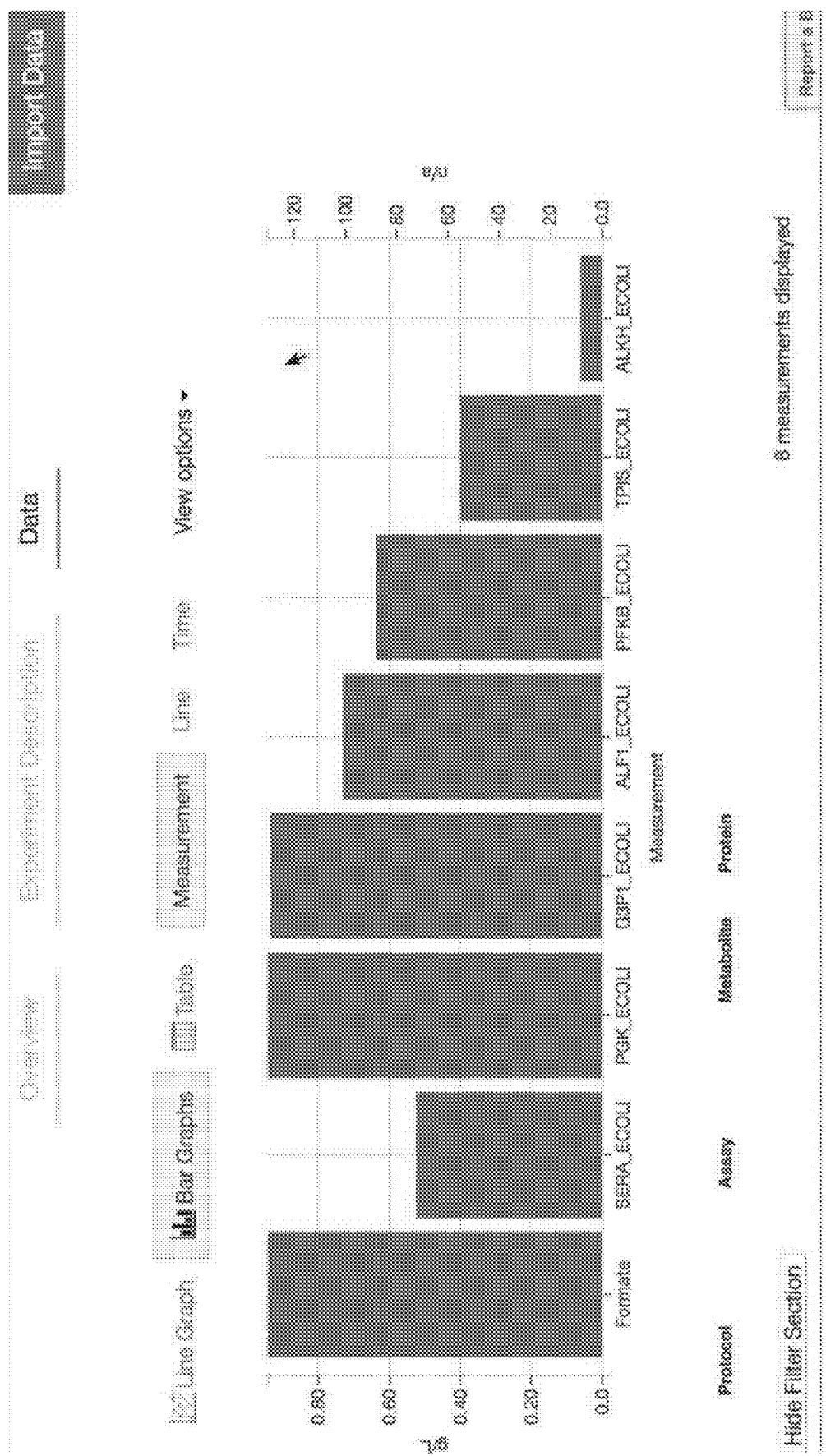
FIGS. 13A-13Q are screenshots showing exemplary importing proteomics data from the Experiment Data Depot (EDD) into Arrowland (public-arrowland.jbei.org/static/ main/help/proteomics_edd_import.mp4, the content of which is incorporated herein by reference in its entirety). To get proteomics data from EDD into Arrowland, a user can first go to his or her study in EDD, view the data in table mode, and find the line or essay containing the proteomics data to export. The user can choose to export data as CSV. On the export page, deselect all the fields, leaving only the measurement type field selected. The user can apply the settings to confirm that the export will contain only protein names and values. Then the user can download the data. The user can then go to the study of interest in Arrowland which may have a default map and model selected. The user can choose the results that the data from EDD will be imported into and the time point in the results set. The user can add data from experiment data depot into Arrowland by dragging the CSV file into the drop zone. The data will appear under the proteomics data. Any reaction that has proteomics data may gain a halo on one side. The user can zoom in to see specific proteomics values of interest.
Figure 10R:
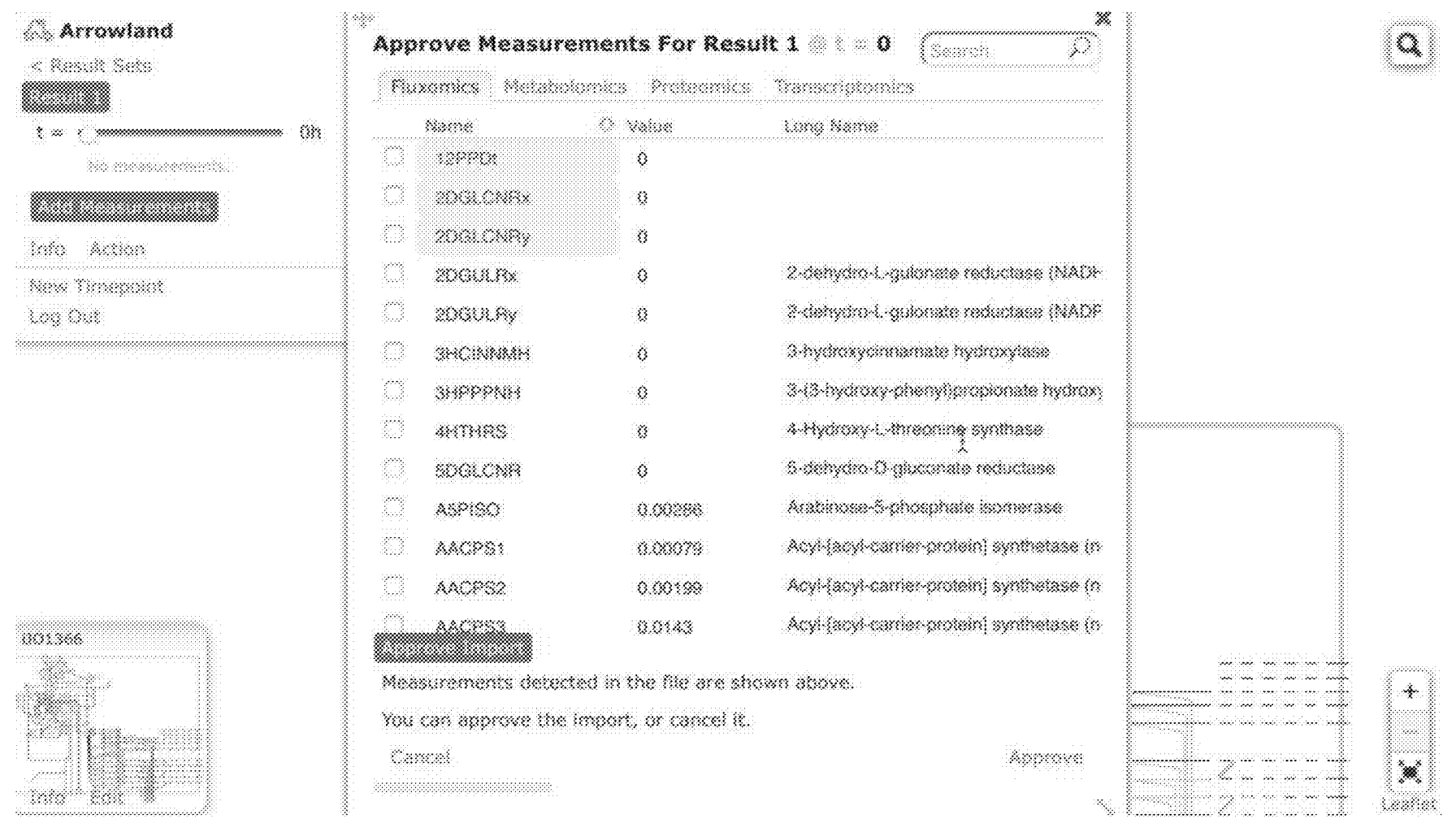
Figure 10S:
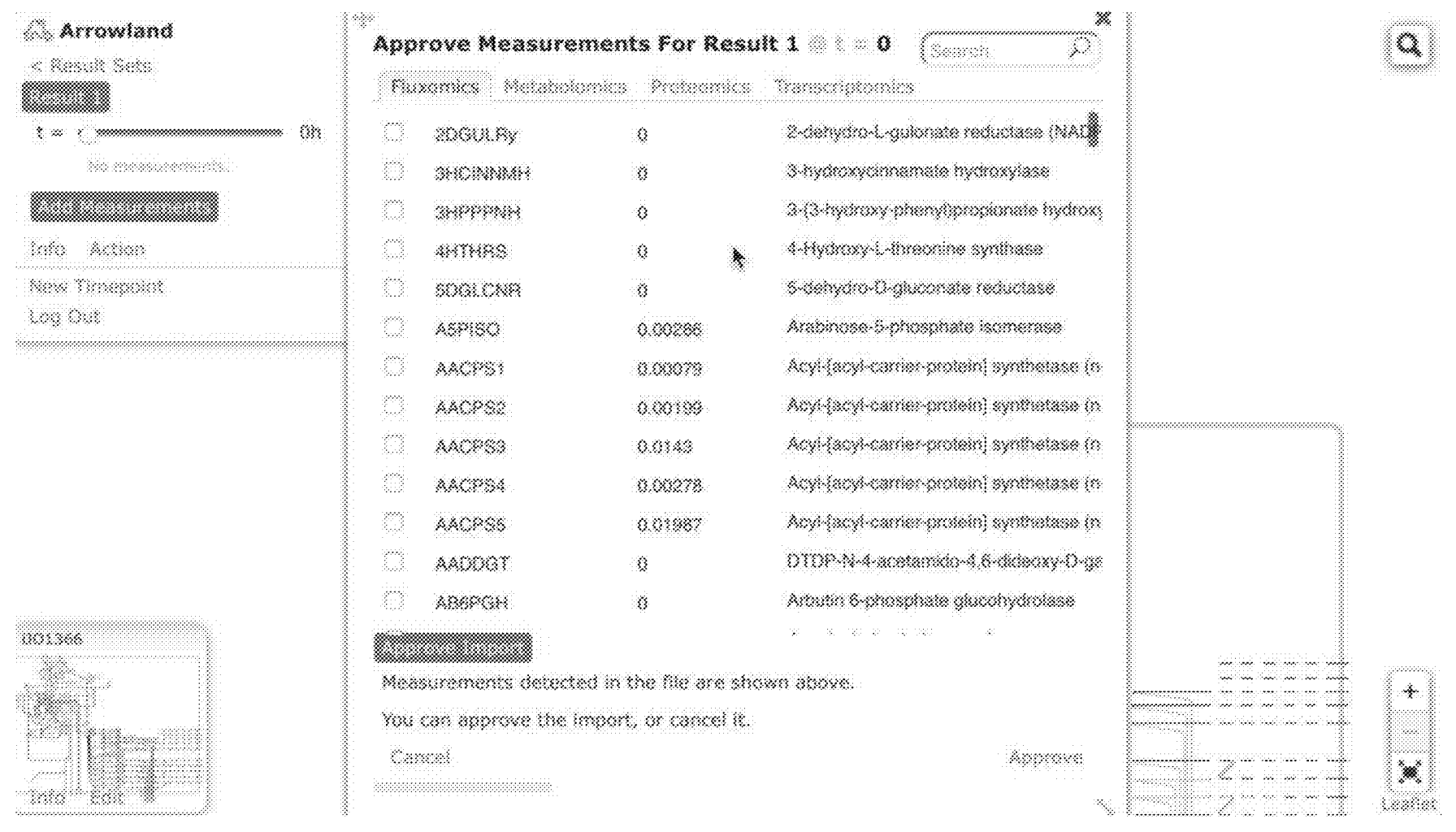
Figure 10V:
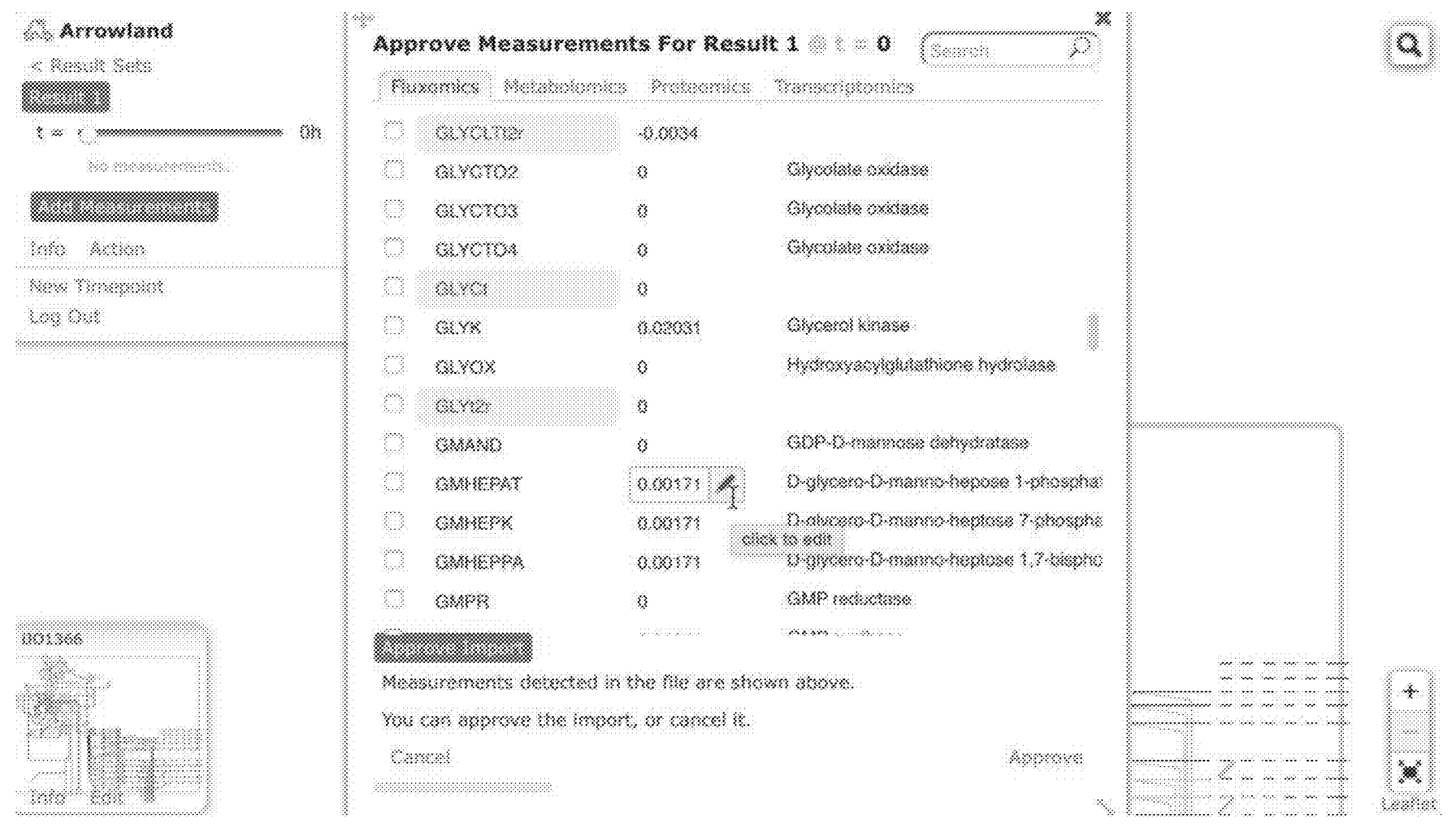
Figure 13A:
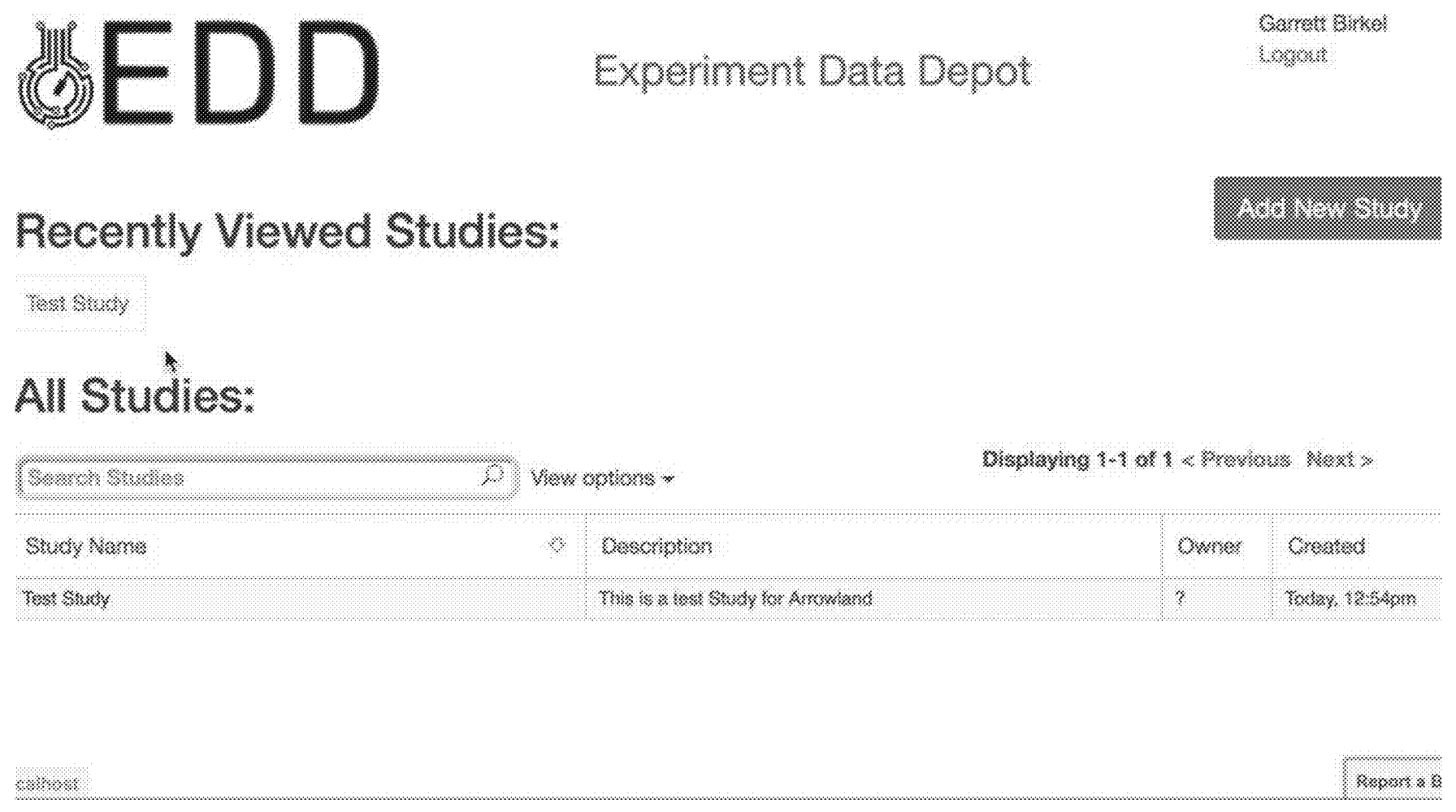
Figure 13D:
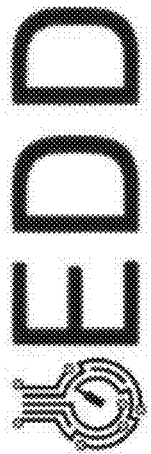
Figure 13E:
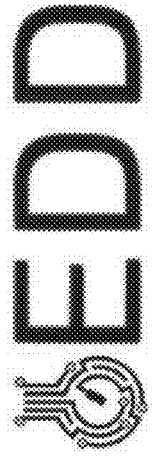
Figure 13F:
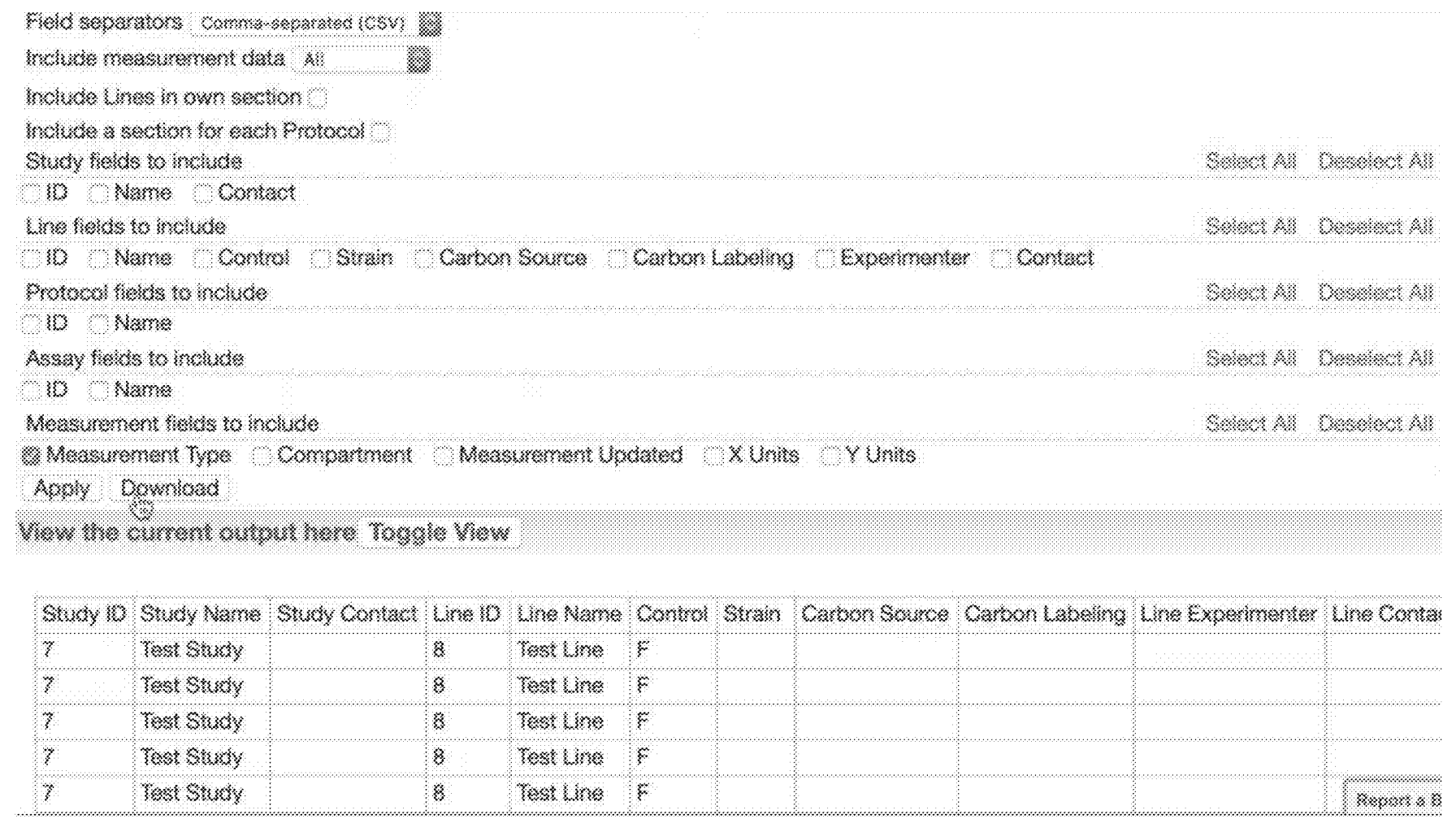
Figure 13H:
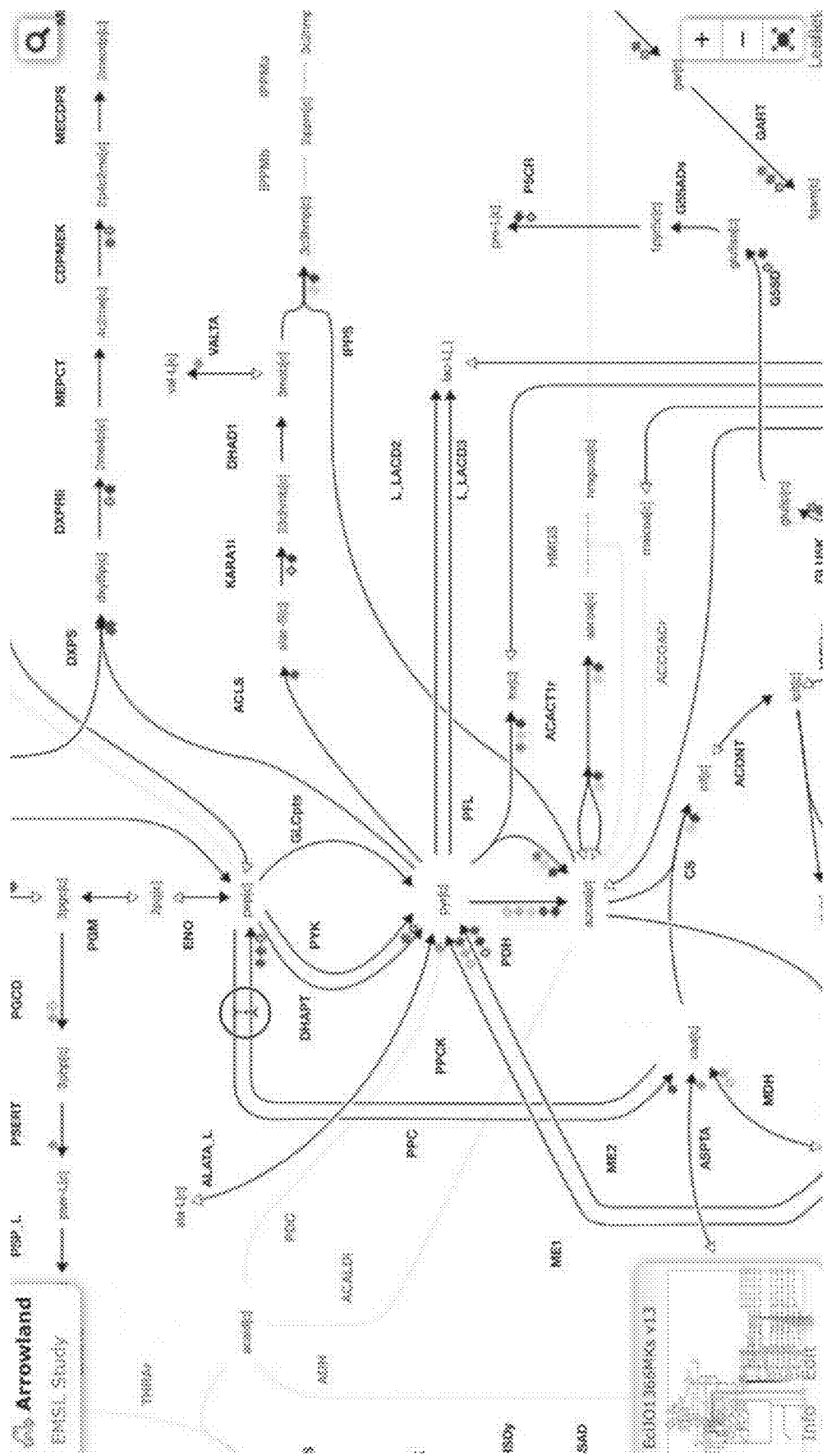
Figure 13I:
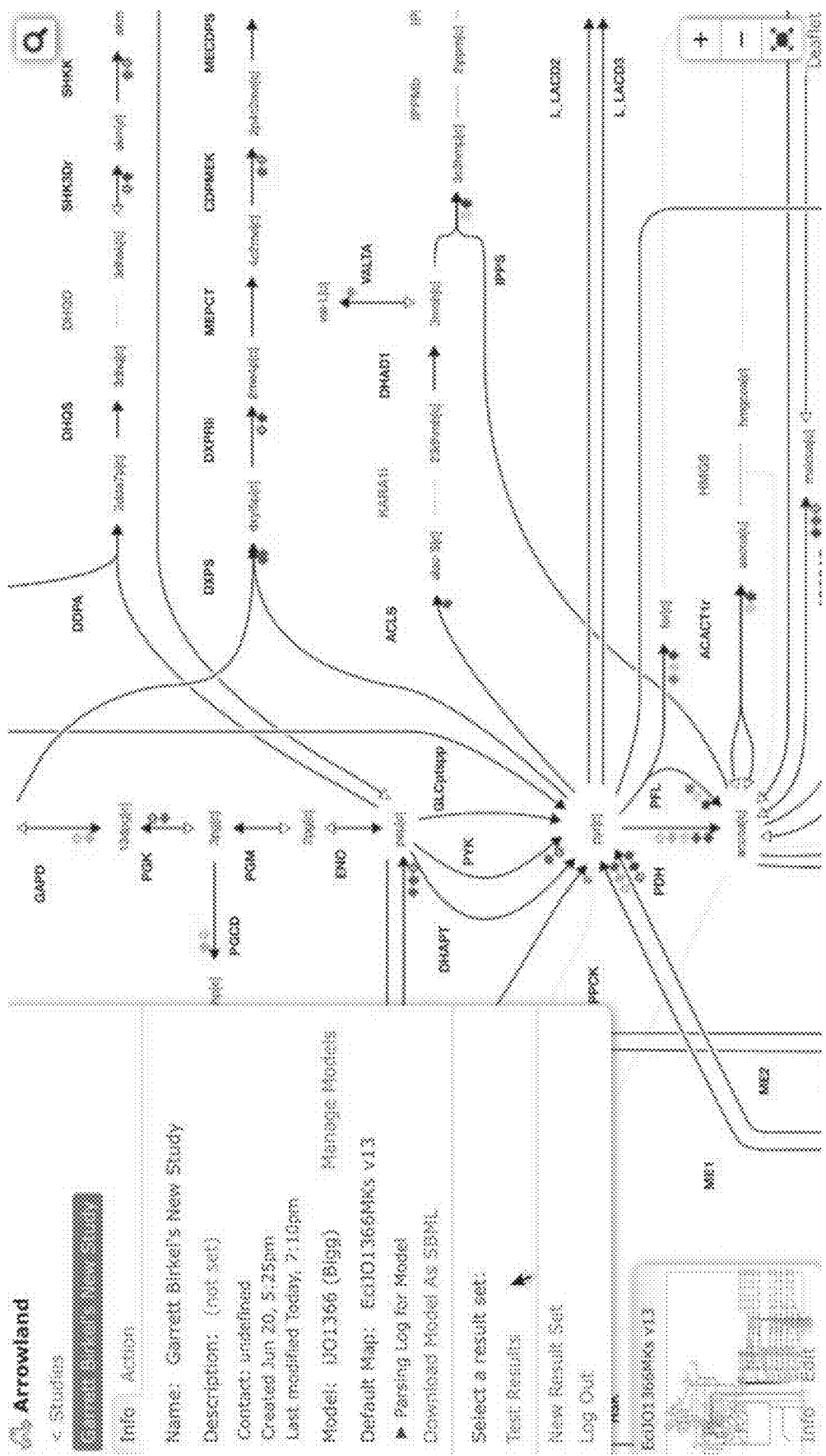
Figure 13J:
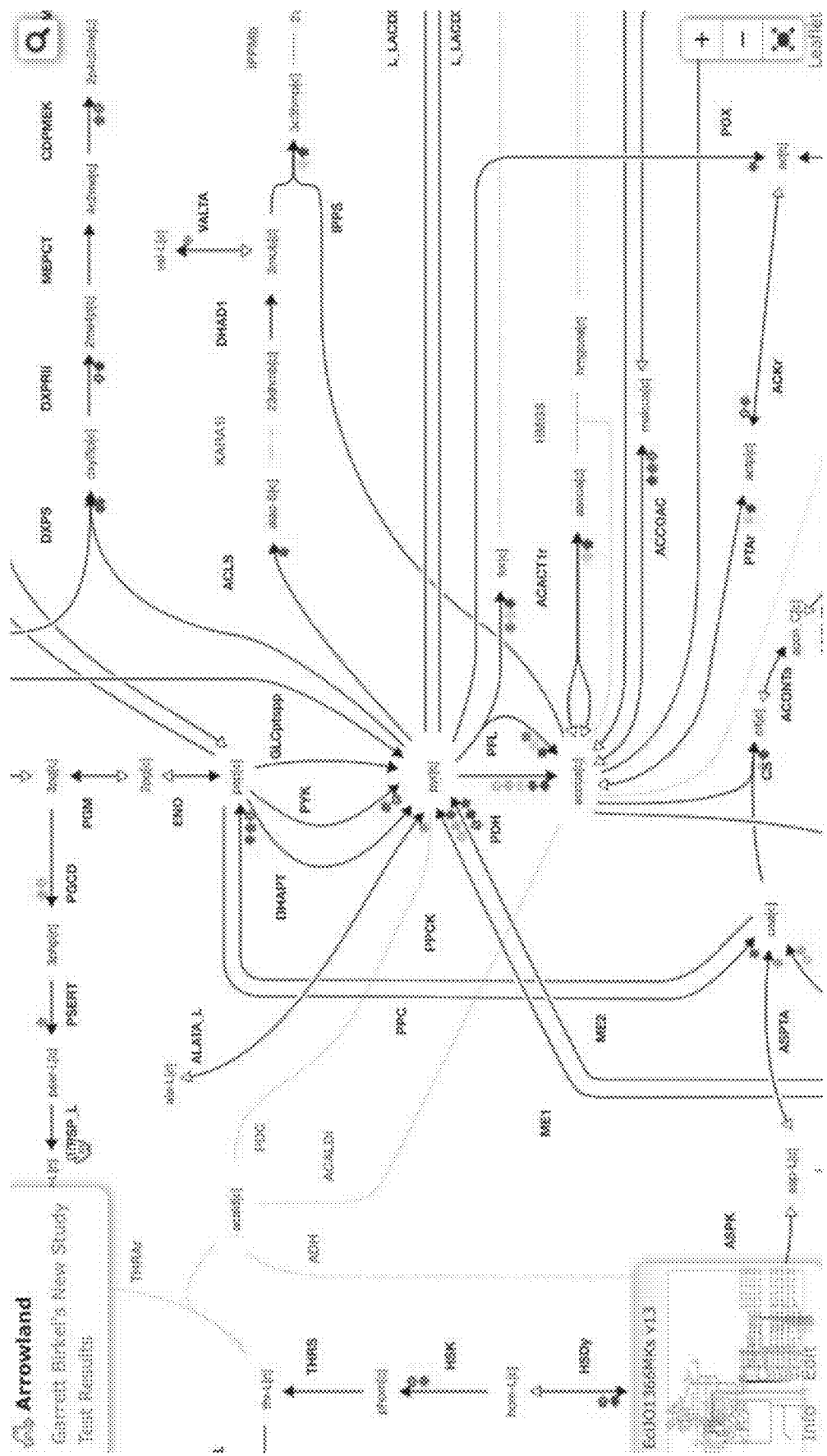
Figure 13K:
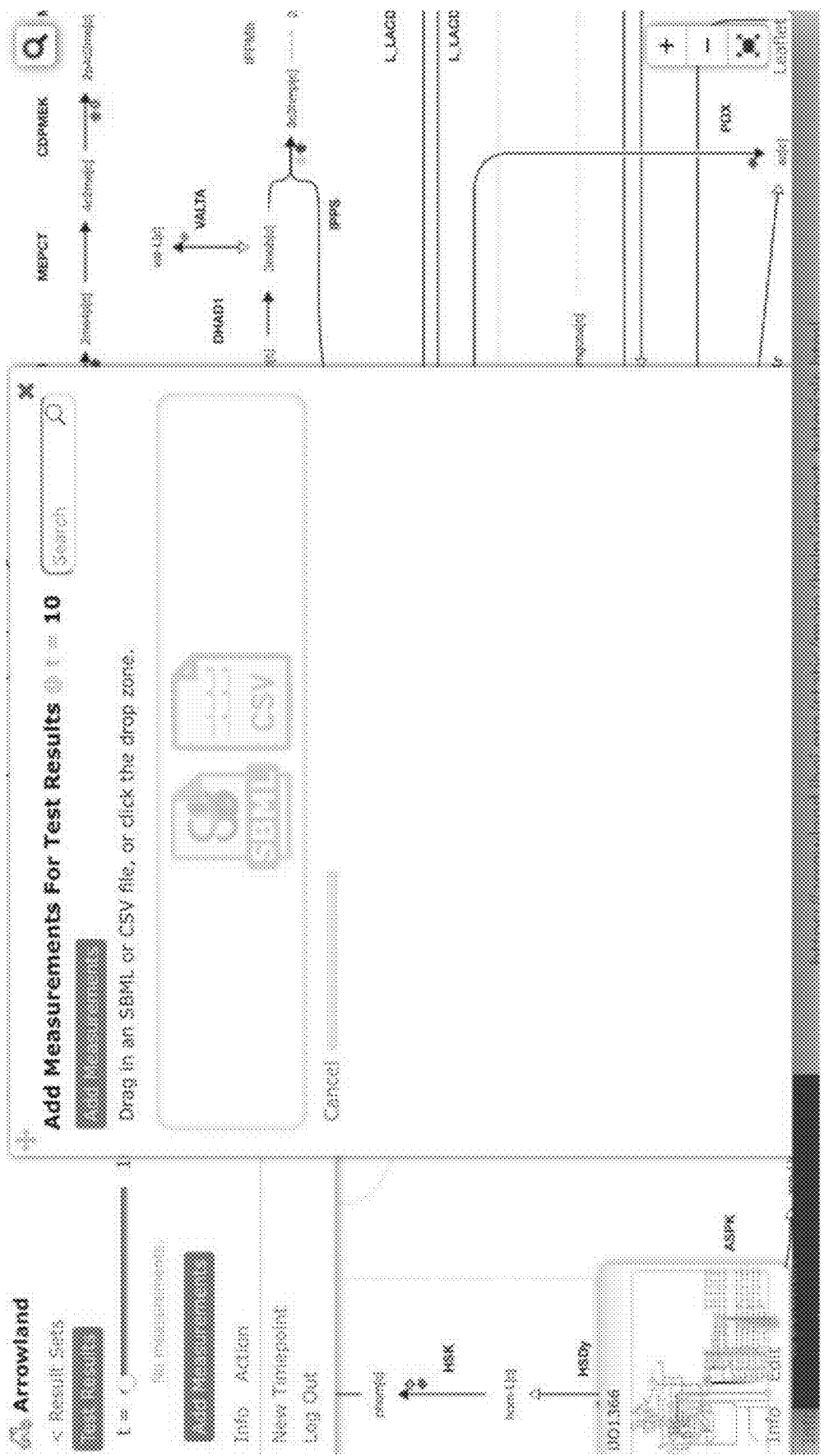
Figure 13L:
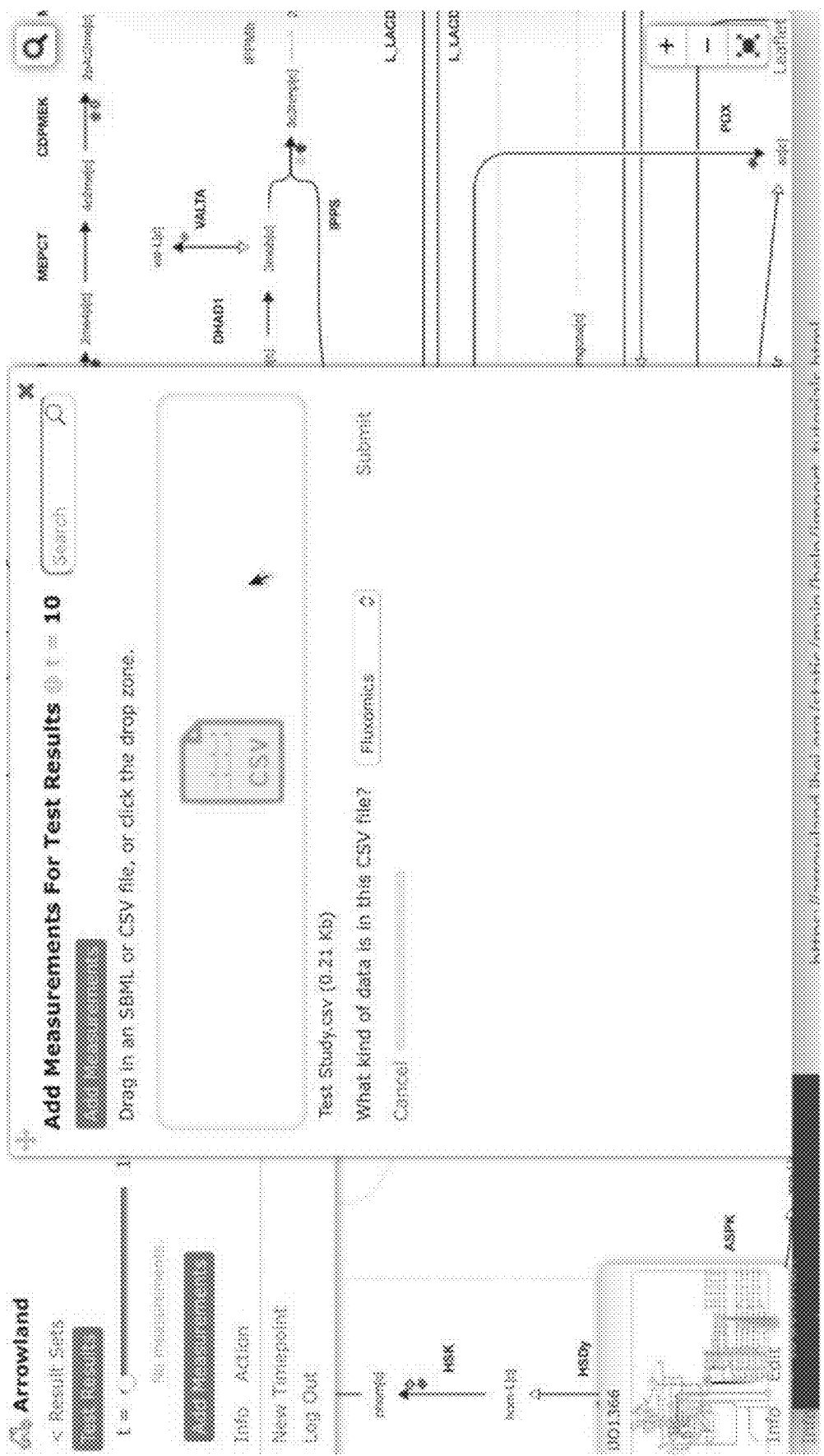
Figure 13M:
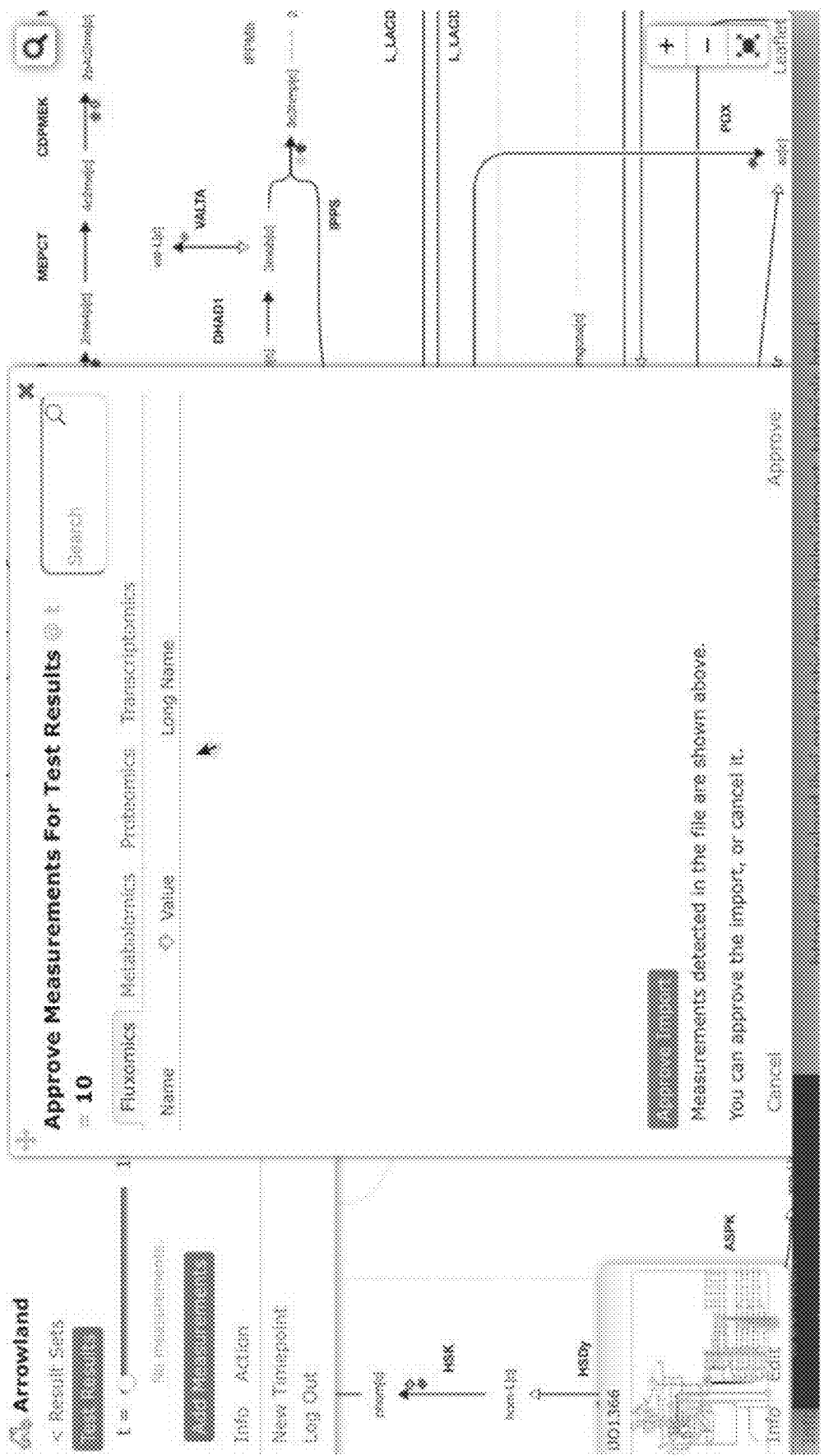
Figure 13N:
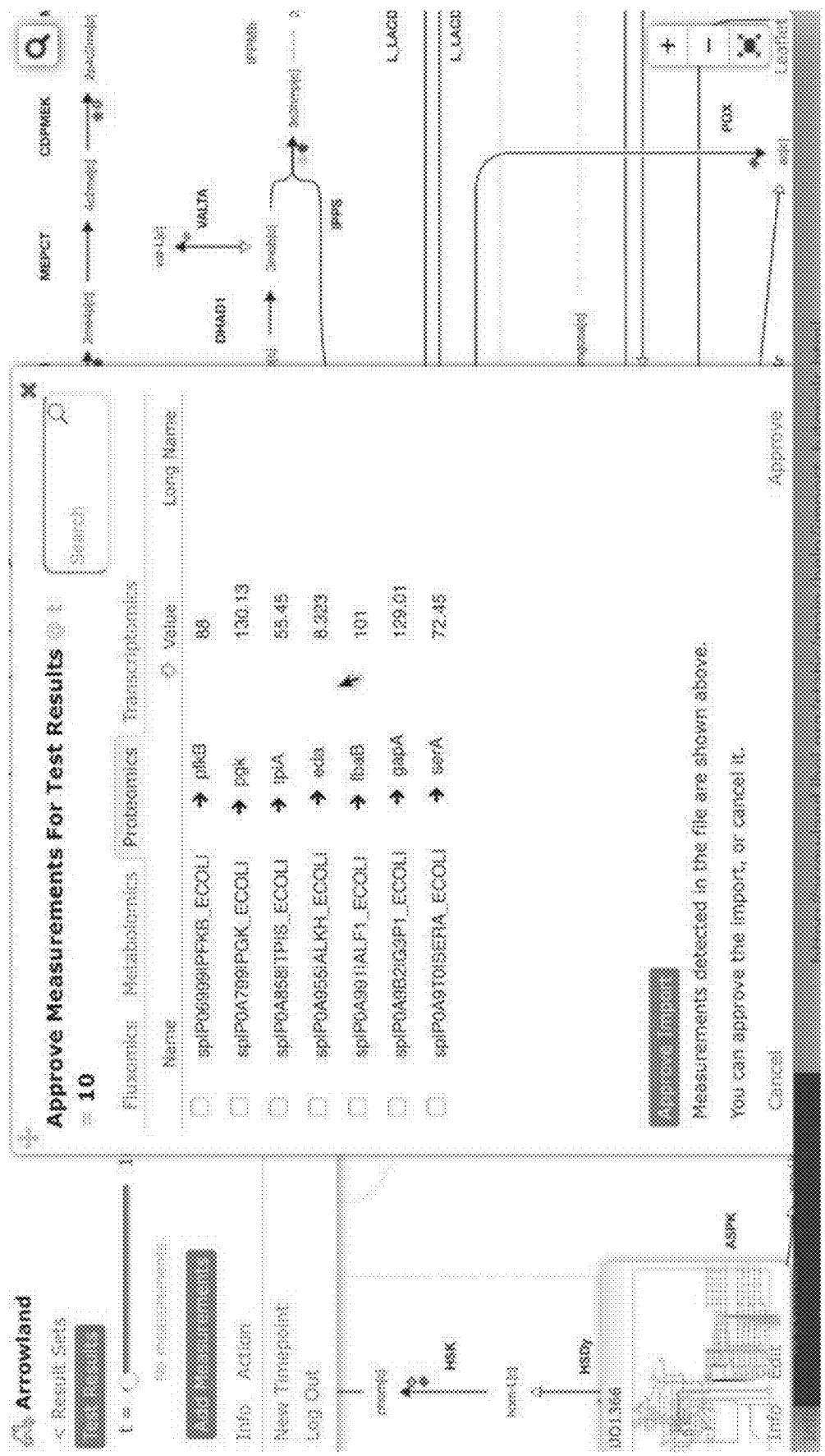
Figure 130:
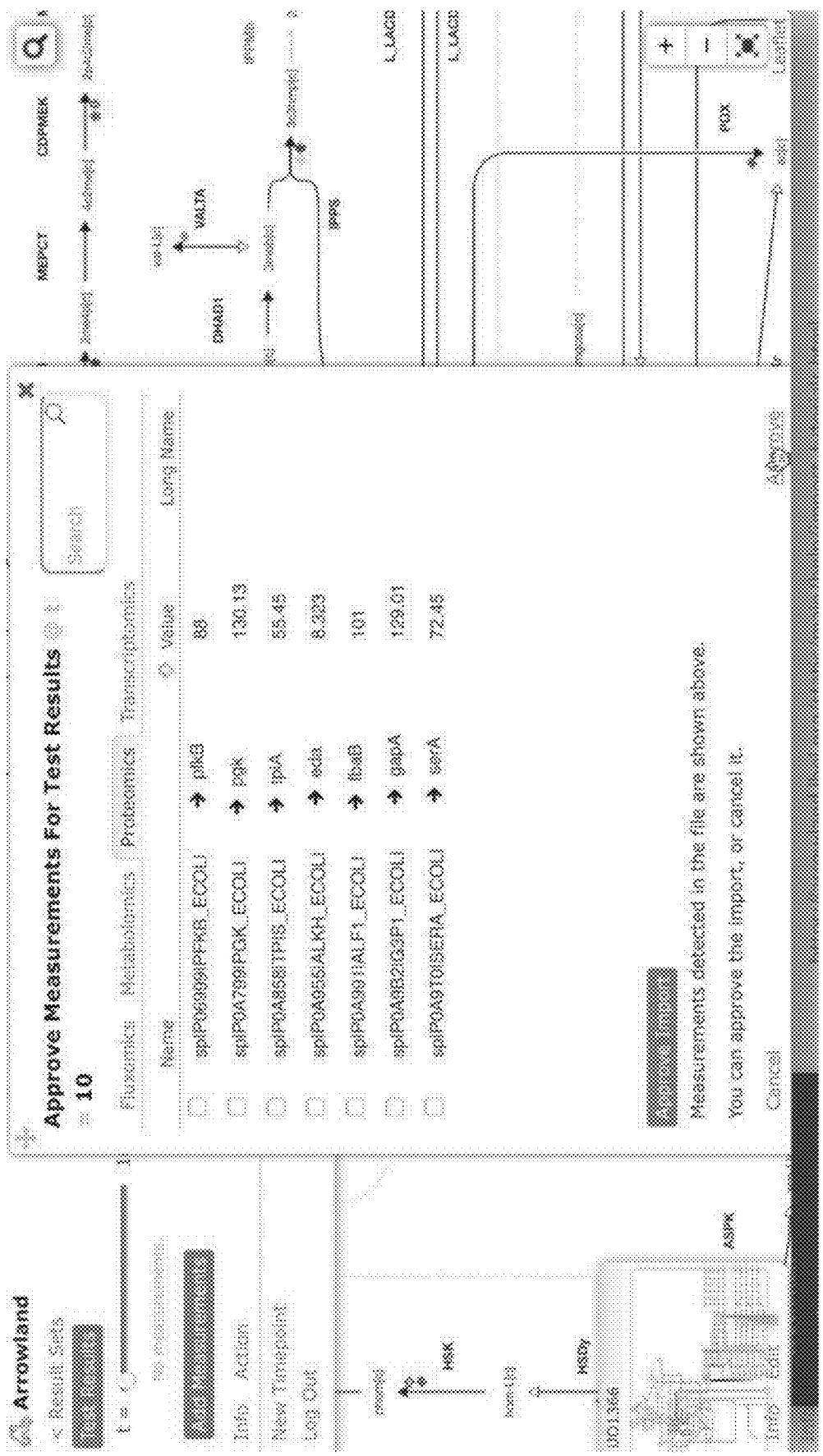
Figure 13P:
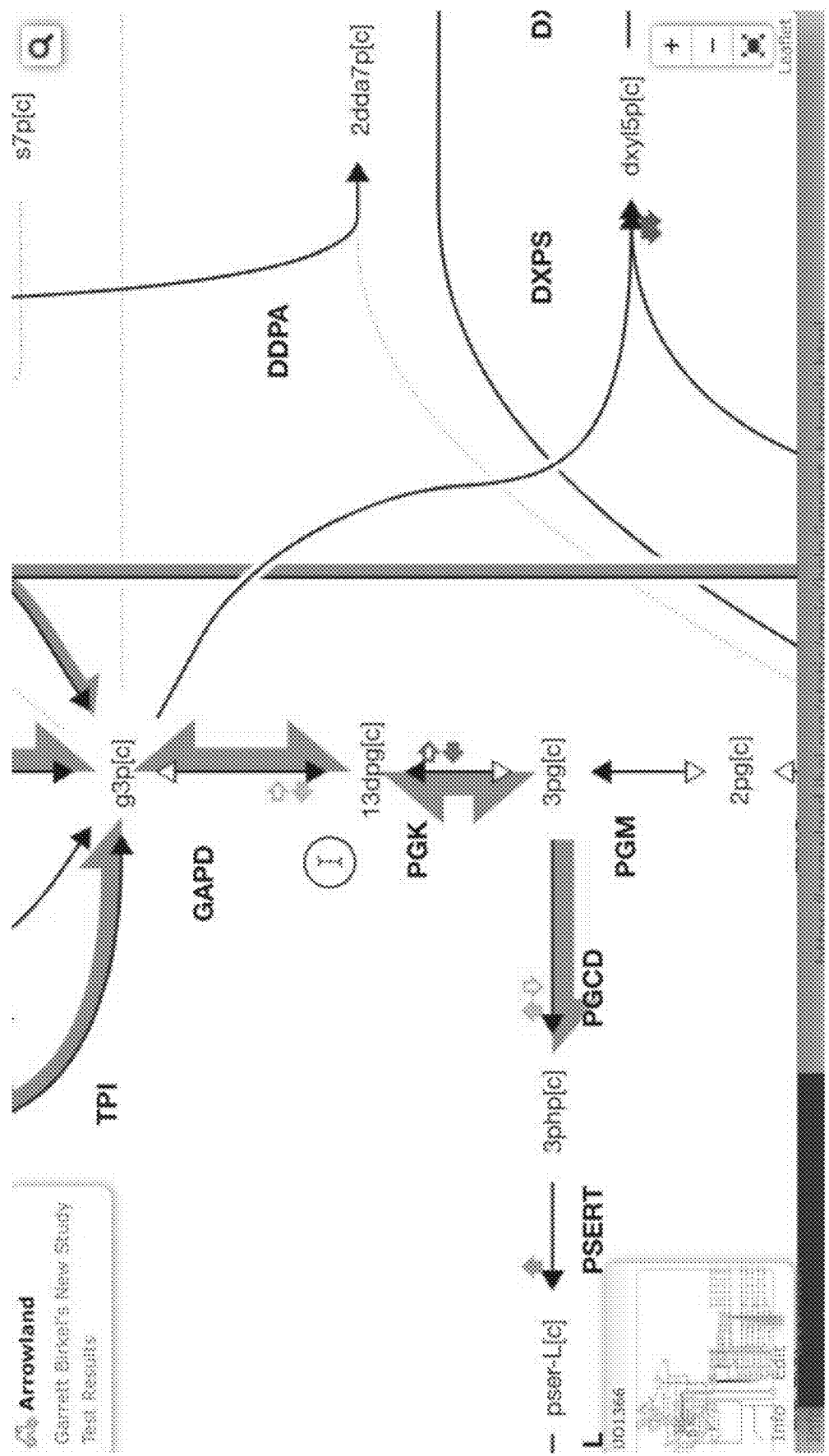
Figure 13Q:
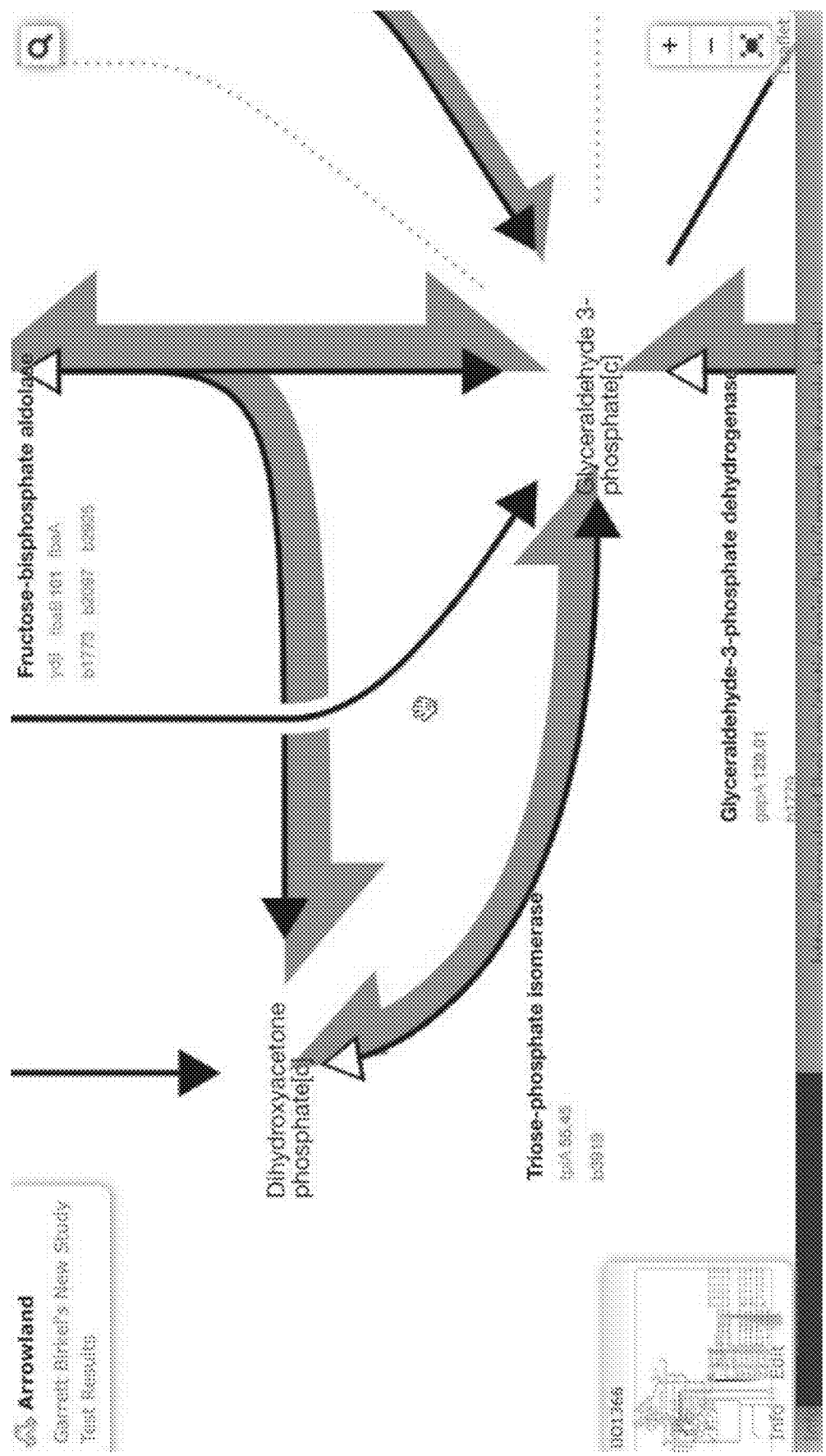

| | Description | Exemplary Usage Illustration |
|---|---|---|
| 1 | Data import | FIGS. 10A-10AP |
| 2 | Fluxomics visualization (CSV) | FIGS. 11A-11T |
| 3 | Transcriptomics visualization (CSV) | FIGS. 14A-14Y |
| 4 | Proteomics visualization (CSV) | FIGS. 12A-12AA |
| 5 | Metabolomics visualization (CSV) | FIGS. 16A-16X |
| 6 | Inline visualization in Jupyter notebook | FIGS. 18A-18K |
| 7 | Transcriptomics visualization (EDD) | FIGS. 15A-15P |
| 8 | Proteomics visualization (EDD) | FIGS. 13A-13Q |
| 9 | Metabolomics visualization (EDD) | |
| 10 | Multiomics visualization (CSV) | |
| 11 | Multiomics visualization (EDD) | |
| 12 | Multiomics dataset comparison | FIGS. 17A-17J |

Single -Omics Visualization

This workflow demonstrates how to upload single -omics data (e.g., transcriptomic, proteomics, metabolomics or fluxomics) so that they can be visualized as shown in FIGS. 2A-2C and 3A-3C.

Initially, a new study may be created by selecting "New Study" on the upper left of the input screen. The study is created with a default genome-scale model and metabolic map associated to it, which can be changed. Within the study click on "New Result Set" and enter the corresponding name. Once the result set is created, click on "Add Measurements". A user can now drag and drop a file into the drop zone. The file can be either a CSV file or a SMBL file. The CSV file should be composed of label and value pairs, where the label is either a Genbank gene id number (transcriptomics), a UniProt unique identifier (UPI, proteomics), a PubChem compound identifier (metabolomics) or a BIGG model reaction name (fluxomics). The value will be either an RPKM value (transcriptomics), the protein count per cell (proteomics), a metabolite concentration in g/l (metabolomics) or a flux in mmol/gdw/hr (fluxomics). Once the file is loaded, a user needs to tell Arrowland what type of data this is (transcriptomics, proteomics, metabolomics or fluxomics) through a pull-down menu. Arrowland then process the file and displays the labels and values it has found for the user to review. Labels not found in the model assigned to the study are greyed out. Values for each label can be changed if needed, and clicking on "Approve" loads the data into Arrowland for visualization. Alternatively, the user can use an SBML obtained from EDD, which takes care standardizing all labels and values.

Each -omics data type is shown differently in the metabolic map: fluxes values are represented through the black arrow thickness (FIGS. 2A-2C), transcriptomics data are shown as a blue halo on the left side of the arrow proportional to the corresponding Reads Per Kilobase of transcript per Million mapped reads (RPKMRPKM), proteomics data uses the same approach but with a red halo on the right side of the arrow, and metabolomics data is represented through a circle of size proportional to the metabolite concentration (FIGS. 3A-3C).

Multiomics Data Visualization

Multiomics data visualization is similar to single -omics visualization. A user can visualize all -omics data types by storing all data in an SBML file obtained from EDD and stacked data by dragging and dropping the file. Alternatively, the different types of -omics data can be uploaded sequentially.

The result is a metabolic map as shown in FIGS. 3A-3C, which shows all -omics data types simultaneously shown. Because the visualization modes used are not overlapping, this allows the user to view all data types simultaneously.

Multiomics Data Set Comparison

The compact visualization of -omics data used in Arrowland allows users to compare multiomics profiles simultaneously.

To do so, a user can set the current multiomics map as a baseline by clicking on the base line button in. The user can then compare with another multiomics data (e.g., from another time point or another condition). This map is shown slightly displaced, transparent and color shifted so as to make it obvious it is not the baseline data.

The same options for multiscale and multiscale inteainteractive viewing are available as for single -omics, so the user can zoom in and get more detail in a specific part of the metabolic map or obtain a general picture by zooming out. These options help digest the deluge of data comfortably.

Embedding in Jupyter Notebooks

The full power of Arrowland is available within a Jupyter notebook, a common tool for workflow exchange among data scientists. This embedding allows for the interlacing of calculations and prediction through e.g., COBRApy or the jQMM library and the -omics data visualization, facilitating an interactive session of predictions and visualization. Arrowland can be viewed in a cell within a Jupyter notebook (FIG. 4) simply by loading the module * and using the function y, as shown in screencast *.

Execution Environment

FIG. 19 depicts a general architecture of an exemplary computing system 1900 configured to generate -omics and multiomics data visualization. The general architecture of the computing device 1900 depicted in FIG. 19 includes an arrangement of computer hardware and software components. The computing system 1900 may include many more (or fewer) elements than those shown in FIG. 19. It is not necessary, however, that all of these generally conventional elements be shown in order to provide an enabling disclosure. As illustrated, the computing system 1900 includes a processing unit 1940, a network interface 1945, a computer readable medium drive 1950, an input/output device interface 1955, a display 1960, and an input device 1965, all of which may communicate with one another by way of a communication bus. The network interface 1945 may provide connectivity to one or more networks or computing systems. The processing unit 1940 may thus receive information and instructions from other computing systems or services via a network. The processing unit 1940 may also communicate to and from memory 1970 and further provide output information for an optional display 1960 via the input/output device interface 1955. The input/output device interface 1955 may also accept input from the optional input device 1965, such as a keyboard, mouse, digital pen, microphone, touch screen, gesture recognition system, voice recognition system, gamepad, accelerometer, gyroscope, or other input device.

The memory 1970 may contain computer program instructions (grouped as modules or components in some embodiments) that the processing unit 1940 executes in order to implement one or more embodiments. The memory 1970 generally includes RAM, ROM and/or other persistent, auxiliary or non-transitory computer-readable media. The memory 1970 may store an operating system 1971 that provides computer program instructions for use by the processing unit 1940 in the general administration and operation of the computing device 1900. The memory 1970 may further include computer program instructions and other information for implementing aspects of the present disclosure. For example, in one embodiment, the memory 1970 includes a transcriptomics visualization module 1972 for generating transcriptomics data visualization, a proteomics visualization module 1973 for generating proteomics data visualization, a metabolomics visualization module 1974 for generating metabolomics data visualization, and a fluxomics visualization module 1975 for generating fluxomics data visualization. The memory 1970 may additionally or alternatively include a multiomics visualization module 1976 for generating multiomics data visualization. In addition, memory 1970 may include or communicate with data store 1990 and/or one or more other data stores that store data for generating -omics and multiomics data visualization and visualization generated.

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

All of the processes described herein may be embodied in, and fully automated via, software code modules executed by a computing system that includes one or more computers or processors. The code modules may be stored in any type of non-transitory computer-readable medium or other computer storage device. Some or all the methods may be embodied in specialized computer hardware.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks and modules described in connection with the embodiments disclosed herein can be implemented or performed by a machine, such as a processing unit or processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

Conditional language such as, among others, "can," "could," "might" or "may," unless specifically stated otherwise, are otherwise understood within the context as used in general to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Further, the term "each", as used herein, in addition to having its ordinary meaning, can mean any subset of a set of elements to which the term "each" is applied.

Any process descriptions, elements or blocks in the flow diagrams described herein and/or depicted in the attached figures should be understood as potentially representing modules, segments, or portions of code which include one or more executable instructions for implementing specific logical functions or elements in the process. Alternate implementations are included within the scope of the embodiments described herein in which elements or functions may be deleted, executed out of order from that shown, or discussed, including substantially concurrently or in reverse order, depending on the functionality involved as would be understood by those skilled in the art.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A system for displaying multiomics data, comprising:
   non-transitory memory configured to store executable instructions, a metabolic model, and a metabolic map, wherein the metabolic map comprises a plurality of metabolites and a plurality of associations between the plurality of metabolites, wherein an association between two metabolites is defined by the metabolic model comprising a metabolic flux between the two metabolites, a transcript of a gene, and a protein encoded by the gene capable of catalyzing one of the two metabolites to the other of the two metabolites; and
   a processor programmed by the executable instructions to perform:
      receiving a selection of the metabolic model and a selection of the metabolic map from a user device;
      receiving a multiomics data set comprising metabolomics data, fluxomics data, transcriptomics data, and proteomics data;
      generating a metabolic network comprising (1) a plurality of geometric shapes corresponding to the plurality of metabolites, (2) a plurality of arrows between the geometric shapes corresponding to the plurality of associations, wherein a size of a geometric shape is determined based on a quantity of the corresponding metabolite in the multiomics data set;
      generating a plurality of vector graphics representing the metabolic network, or a portion thereof; and
      providing the plurality of vector graphics to a user device, thereby the user device:
         rasterizes one or more of the plurality of vector graphics into corresponding one or more tiles using a rendering queue and a pruned cache; and
         displays the metabolic network, of a portion thereof, as the one or more tiles.

2. The system of claim 1, wherein the metabolic network further comprises (3) a plurality first half-arrow shadings associated with the plurality of arrows, and (4) a plurality of second half-arrow shadings associated with the plurality of arrows, and wherein characteristics of an arrow, an associated first half-arrow shading, and an associated second half-arrow shading are determined by quantities of the corresponding metabolic flux, transcript, and protein in the multiomics data set.

3. The system of claim 1, wherein providing the metabolic network to the user device comprises providing label information of the metabolic network and/or providing external links related to the metabolic network to the user device.

4. The system of claim 1, wherein the multiomics data set comprises time series multiomics data comprising a first multiomics data set at a first time and a second multiomics data set at a second time, wherein generating the metabolic network comprises generating a first metabolic sub-network from the first multiomics sub-dataset and a second metabolic sub-network from the second multiomics sub-dataset with an offset from the first metabolic sub-network.

5. The system of claim 4, wherein the processor is programmed by the executable instructions to receive a selection that the first multiomics sub-dataset is used as a baseline in generating the multiomics network.

6. The system of claim 4, wherein the processor is programmed by the executable instructions to perform:
receiving a selection of an area of the metabolic network;
determining metabolite(s), metabolic flux(es), transcript(s), and protein(s) in the area, or reactions thereof;
determining tiles intersecting the metabolite(s), metabolic flux(es), transcript(s), and protein(s), or reactions thereof;
generating updated tiles; and
providing the user device with the updated tiles.

7. The system of claim 4, wherein the metabolic model comprises a first metabolic sub-model and a second metabolic sub-model, wherein the first metabolic sub-model comprises the two metabolites and an associated stoichiometry, and wherein the second metabolic sub-model comprises one or more genes, transcripts thereof, or proteins thereof, capable of catalyzing one of the two metabolites to the other of the two metabolites.

8. A system for displaying multiomics data, comprising:
non-transitory memory configured to store executable instructions; and
a hardware processor programmed by the executable instructions to perform:
providing a selection of a metabolic model and a selection of a metabolic map to a server device;
providing a multiomics data set comprising metabolomics data, fluxomics data, transcriptomics data, and/or proteomics data to the server device;
receiving as (1) a first rasterized tile of a first vector graphic of the metabolic network and (2) a second vector graphic representing a metabolic network, or a portion thereof, from the server device;
generating a second rasterized tile of the second vector graphic;
providing the first rasterized tile and the second rasterized tile to a display application.

9. The system of claim 8, wherein the display application is a web browser or a mobile device application.

10. The system of claim 8, wherein generating the second rasterized tile of the second vector graphic comprises copying the second vector graphic onto a HTML, canvas element.

11. The system of claim 8, wherein the hardware processor is programmed by the executable instructions to perform:
extracting strings from the second vector graphic; and
discarding the second vector graphic after generating the second rasterized tile of the second vector graphic.

12. A computer-implemented method for displaying multiomics data, comprising:
receiving a selection of a metabolic model and a selection of a metabolic map, wherein the metabolic map comprises a plurality of metabolites and a plurality of associations between the plurality of metabolites, wherein an association between two metabolites is defined by the metabolic model comprising a metabolic flux between the two metabolites, a transcript of a gene, and a protein encoded by the gene capable of performing a catalysis from one of the two metabolites to the other of the two metabolites;
receiving a multiomics data set comprising metabolomics data, fluxomics data, transcriptomics data, and/or proteomics data;
generating a metabolic network from the multiomics data, wherein the metabolic network comprises (1) a plurality of geometric shapes corresponding to the plurality of metabolite, (2) a plurality of first arrows between the geometric shapes corresponding to the plurality of associations, (3) a plurality first shading associated with the plurality of first arrows, and/or (4) a plurality of second shading associated with the plurality of first arrows,
wherein a characteristics of a geometric shape is determined based on a quantity of the corresponding metabolite in the multiomics data set, wherein characteristics of a first arrow, an associated first shading, and an associated second shading are determined by quantities of the corresponding metabolic flux, transcript, and protein in the multiomics data set, and
wherein the metabolic network, or a portion thereof, is represented as a plurality of vector graphics;
rasterizing one or more of the plurality of vector graphics into corresponding one or more tiles; and
displaying the metabolic network, or a portion thereof, as the one or more tiles.

13. The method of claim 12, wherein the geometric shapes comprises a circle, an oval, a square, a rectangle, a square, a trapezoid, a parallelogram, or a combination thereof.

14. The method of claim 12, wherein the characteristics of the geometric shape is a size of the geometric shape, wherein a larger size indicates a larger quantity.

15. The method of claim 12, wherein the characteristics of the geometric shape is a color of the geometric shape, wherein a darker color indicates a larger quantity.

16. The method of claim 12, wherein the characteristics of the first arrow is determined by the quantity of the metabolic flux.

17. The method of claim 12, wherein the characteristics of the first arrow is a size of the first arrow, and wherein a larger size indicates a larger quantity.

18. The method of claim 12, wherein the characteristics of the first arrow is a color of the first arrow, and wherein a darker color indicates a larger quantity.

19. The method of claim 12, wherein the characteristics of the first shading is determined by the quantity of the transcript, and wherein the characteristics of the second shading is determined by the quantity of the protein.

20. The method of claim 12, wherein the characteristics of the first shading is a size of the first shading and/or the characteristics of the second shading is a size of the second shading, and wherein a larger size indicates a larger quantity.

21. The method of claim 12, wherein the characteristics of the first shading is a color of the first shading and/or the characteristics of the second shading is a color of the second shading, and wherein a darker color indicates a larger quantity.

22. The method of claim 12, wherein the first shading and/or the second shading is a box, an ellipse, a Bezier curve, or a combination thereof.

23. The method of claim 22, wherein the Bezier curve is defined by four vectors and two intensity multipliers.

24. The method of claim 12, wherein the metabolic model comprises a cofactor for the catalysis, wherein the metabolic network comprises a second arrow corresponding to the cofactor, and wherein the second arrow is not parallel to the first arrow.

25. The method of claim 24, wherein the second arrow is approximately perpendicular to the first arrow.

* * * * *